(12) United States Patent
Ma et al.

(10) Patent No.: US 10,273,280 B2
(45) Date of Patent: Apr. 30, 2019

(54) CHIMERIC ANTIGEN RECEPTORS (CARS), TARGETING HEMATOLOGIC MALIGNANCIES, COMPOSITIONS AND METHODS OF USE THEREOF

(71) Applicant: iCell Gene Therapeutics LLC, Stony Brook, NY (US)

(72) Inventors: Yupo Ma, Stony Brook, NY (US); Kevin Pinz, Stony Brook, NY (US); Xun Jiang, Stony Brook, NY (US); Masayuki Wada, Stony Brook, NY (US); Kevin Chen, Stony Brook, NY (US)

(73) Assignee: ICELL GENE THERAPEUTICS LLC, Stony Brook, NY (US)

( * ) Notice: Subject to any disclaimer, the term of this patent is extended or adjusted under 35 U.S.C. 154(b) by 0 days.

(21) Appl. No.: 15/551,862

(22) PCT Filed: Feb. 26, 2016

(86) PCT No.: PCT/US2016/019953
§ 371 (c)(1),
(2) Date: Aug. 17, 2017

(87) PCT Pub. No.: WO2016/138491
PCT Pub. Date: Sep. 1, 2016

(65) Prior Publication Data
US 2018/0066034 A1    Mar. 8, 2018

Related U.S. Application Data

(60) Provisional application No. 62/121,842, filed on Feb. 27, 2015.

(51) Int. Cl.
| | | |
|---|---|---|
| C07K 14/705 | (2006.01) | |
| C07K 16/28 | (2006.01) | |
| A61K 39/00 | (2006.01) | |
| C07K 14/725 | (2006.01) | |
| A61K 39/39 | (2006.01) | |
| A61K 48/00 | (2006.01) | |
| A61K 35/15 | (2015.01) | |
| C12N 15/113 | (2010.01) | |
| A61K 38/00 | (2006.01) | |

(52) U.S. Cl.
CPC .......... *C07K 14/7051* (2013.01); *A61K 35/15* (2013.01); *A61K 39/0011* (2013.01); *A61K 39/39* (2013.01); *A61K 48/00* (2013.01); *A61K 48/005* (2013.01); *C07K 14/70521* (2013.01); *C07K 14/70578* (2013.01); *C07K 16/2806* (2013.01); *C07K 16/2809* (2013.01); *C07K 16/2812* (2013.01); *C07K 16/2896* (2013.01); *C12N 15/1138* (2013.01); *A61K 38/00* (2013.01); *A61K 2039/505* (2013.01); *A61K 2039/5156* (2013.01); *A61K 2039/5158* (2013.01); *C07K 2317/622* (2013.01); *C07K 2319/00* (2013.01); *C07K 2319/03* (2013.01); *C07K 2319/33* (2013.01); *C12N 2310/20* (2017.05); *C12N 2740/16043* (2013.01)

(58) Field of Classification Search
None
See application file for complete search history.

(56) References Cited

U.S. PATENT DOCUMENTS

| | | | |
|---|---|---|---|
| 2002/0009449 | A1 | 1/2002 | Wallner et al. |
| 2003/0147865 | A1 | 8/2003 | Salomon et al. |
| 2004/0265315 | A1 | 12/2004 | Dingivan et al. |
| 2005/0277587 | A1 | 12/2005 | Chen et al. |
| 2008/0254027 | A1 | 10/2008 | Bernett et al. |
| 2008/0254512 | A1 | 10/2008 | Capon |
| 2008/0299042 | A1 | 12/2008 | Bechtel et al. |
| 2009/0238791 | A1 | 9/2009 | Jacques et al. |
| 2009/0325188 | A1 | 12/2009 | Glass |
| 2012/0058082 | A1 | 3/2012 | Kaplan et al. |
| 2012/0070408 | A1 | 3/2012 | Kaplan et al. |
| 2012/0134970 | A1* | 5/2012 | Yang ............... C12N 15/86 424/93.21 |
| 2012/0258494 | A1 | 10/2012 | Stitz |
| 2013/0058936 | A1 | 3/2013 | Bruenker et al. |
| 2013/0259876 | A1 | 10/2013 | Murphy et al. |
| 2013/0287748 | A1 | 10/2013 | June et al. |
| 2013/0287752 | A1 | 10/2013 | Davila et al. |

(Continued)

FOREIGN PATENT DOCUMENTS

| | | |
|---|---|---|
| WO | WO2014100385 A1 | 6/2014 |
| WO | WO2014127261 A1 | 8/2014 |

(Continued)

OTHER PUBLICATIONS

Maus et al., Antibody-modified T cells: CARs take the front seat for hematologic malignancies Blood. 2014; pp. 2625-2635).*
D'Amore et al. Phase II trial of zanolimumab (HuMax-CD4) in relapsed or refractory non-cutaneous peripheral T cell lymphoma 2010, Br J Haematol 2010; 150: 565-573.*
Shenghui et al., Elevated frequencies of CD41CD251CD127lo regulatory T cells is associated to poor prognosis in patients with acute myeloid leukemia 2011; Int. J. Cancer: 129, 1373-1381.*
Ehninger et al.,Distribution and levels of cell surface expression of CD33 and CD123 in acute myeloid leukemia 2014 Blood Cancer Journal pp. 1-10.*

(Continued)

*Primary Examiner* — Maria G Leavitt
(74) *Attorney, Agent, or Firm* — Hoffmann & Baron, LLP

(57) ABSTRACT

The present disclosure provides chimeric antigen receptor polypeptides having antigen recognition domains for CD2, CD3, CD4, CD5, CD7, CD8, and CD52 antigens, and polynucleotides encoding for the same. The present disclosure also provides for engineered cells expressing the polynucleotide or polypeptides. In some embodiments, the disclosure provides methods for treating diseases associated with CD2, CD3, CD4, CD5, CD7, CD8, and CD52 antigens.

20 Claims, 79 Drawing Sheets
Specification includes a Sequence Listing.

(56) References Cited

U.S. PATENT DOCUMENTS

| | | | |
|---|---|---|---|
| 2014/0099309 A1 | 4/2014 | Powell, Jr. et al. | |
| 2014/0286918 A1* | 9/2014 | Dao .................. | A61K 35/28 424/93.21 |
| 2014/0322183 A1 | 10/2014 | Milone et al. | |
| 2015/0038684 A1 | 2/2015 | Jensen | |
| 2015/0133640 A1 | 5/2015 | Blein et al. | |
| 2015/0307623 A1 | 10/2015 | Abbot et al. | |
| 2015/0342993 A1 | 12/2015 | Kloss et al. | |

FOREIGN PATENT DOCUMENTS

| | | |
|---|---|---|
| WO | WO2014184143 A1 | 11/2014 |
| WO | WO2015120180 A1 | 8/2015 |
| WO | WO2015157399 A9 | 10/2015 |
| WO | WO2015168613 A2 | 11/2015 |
| WO | WO2015172339 A1 | 11/2015 |
| WO | WO2016014553 A1 | 1/2016 |

OTHER PUBLICATIONS

Liu et al., Molecular Therapy vol. 23, Supplement 1, May 2015 Abstract 512.*

Leavitt et al., Concordant Modulation of Neutralization Resistance and High Infectivity of the Primary Human Immunodeficiency Virus Type 1 MN Strain and Definition of a Potential gp41 Binding Site in gp120 Journal of Virology, Jan. 2003, p. 560-570.*

Schreiber et al., Cancer Immunoediting: Integrating Immunity's Roles in Cancer Suppression and Promotion; pp. 1565-1570.*

Marzo et al Fully Functional Memory CD8 T Cells in the Absence of CD4 T Cells J Immunol 2004; 173:969-975.*

Moeller et al Sustained Antigen-Specific Antitumor Recall Response Mediated by Gene-Modified CD4+ T Helper-1 and CD8+ T Cells Cancer Res 2007; 67: (23). Dec. 1 pp. 11428-11437.*

Lai et al International Scholarly Research Network 2011; pp. 1-6.*

Moeller et al Adoptive transfer of gene-engineered CD4 helper T cells induces potent primary and secondary tumor rejection Blood, Nov. 1, 2005 vol. 106, No. 9; pp. 2995-3003.*

Gibson et al Risk of non-Hodgkin lymphoma subtypes in HIV-infected people during the HAART era: a population-based study AIDS. Sep. 24, 2014; 28(15): 2313-2318.*

Grupp et al., "Chimeric Antigen Receptor-Modified T Cells for Acute Lymphoid Leukemia," New England Journal of Medicine, Apr. 18, 2013, vol. 368, No. 16, pp. 1509-1518.

Rowley et al., "Expression of IL-15RA or an IL-15/IL-15RA fusion on CD8+ T cells modifies adoptively transferred T-cell function in cis," Eur J Immunol, Jan. 29, 2009, vol. 39, No. 2, pp. 491-506.

John et al., "Anti-PD-1 Antibody Therapy Potently Enhances the Eradication of Established Tumors by Gene-Modified T Cells," Clin Cancer Res, Oct. 15, 2013, vol. 19, No. 20, pp. 5636-5646.

Penney et al., "Greater frequency of CD5-negative CD8(+) T cells against human immunodeficiency virus type 1 than other viruses is consistent with adaptation to antigenic variation," AIDS Res Ther, Sep. 15, 2014, vol. 11, No. 30, pp. 1-10.

Maus et al., "Antibody-modified T cells: CARs take the front seat for hematologic malignancies," Blood, Apr. 24, 2014, vol. 123, No. 17, pp. 2625-2635.

D'Amore et al., "Phase II trial of zanolimumab (HuMax-CD4) in relapsed or refractory non-cutaneous peripheral T cell lymphoma," Br J Haematol 2010, 150: 565-573.

Shenghui et al., "Elevated frequencies of CD4+CD25+CD127lo regulatory T cells is associated to poor prognosis in patients with acute myeloid leukemia," Int. J. Cancer 2011, 129: 1373-1381.

Ehninger et al., "Distribution and levels of cell surface expression of CD33 and CD123 in acute myeloid leukemia," Blood Cancer Journal 2014, vol. 4, pp. 1-10.

Liu et al., "Tumor_Associated Macrophages via Up-Regulation of PD1 Ligands Protect Neuroblastoma from Immunotherapy With NKT Cells Expressing GD2-Specific Chimeric Antigen Receptor," Molecular Therapy, vol. 23, Supp. 1, May 2015, Abstract 512. p. S205.

Rouce et al., "Equal opportunity CAR T cells," Blood 2017, 129:3275-3277.

Lai et al., "The Roles of CD4+ T Cells in Tumor Immunity," ISRN Immunology, vol. 2011, Article ID 497397, 6 pages, doi:10.5402/2011/497397.

Kebriaei et al., "Phase I trials using Sleeping Beauty to generate CD19-specific CAR T cells," The Journal of Clinical Investigation, vol. 126, No. 9, Sep. 2016, pp. 3363-3376 and Supplemental Tables.

* cited by examiner

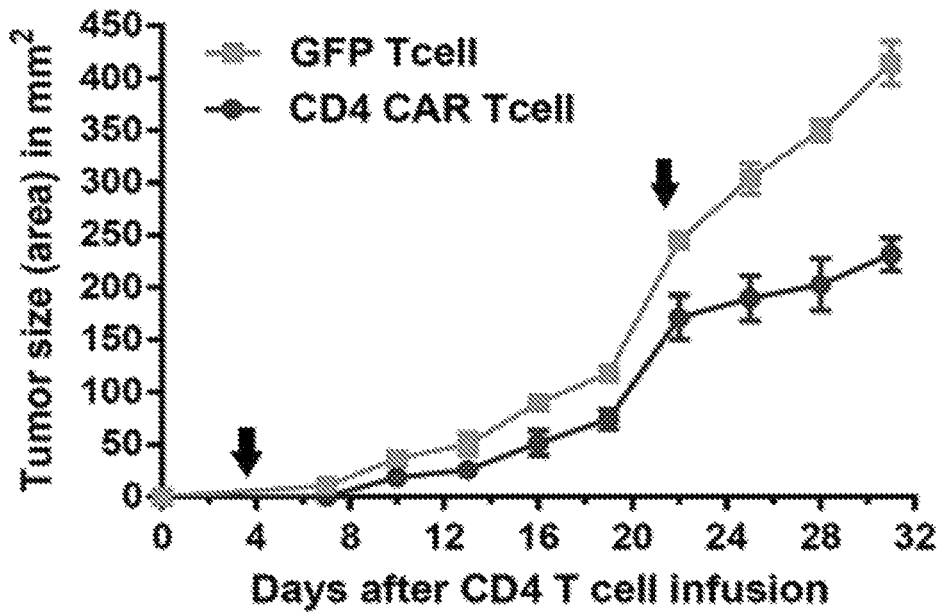
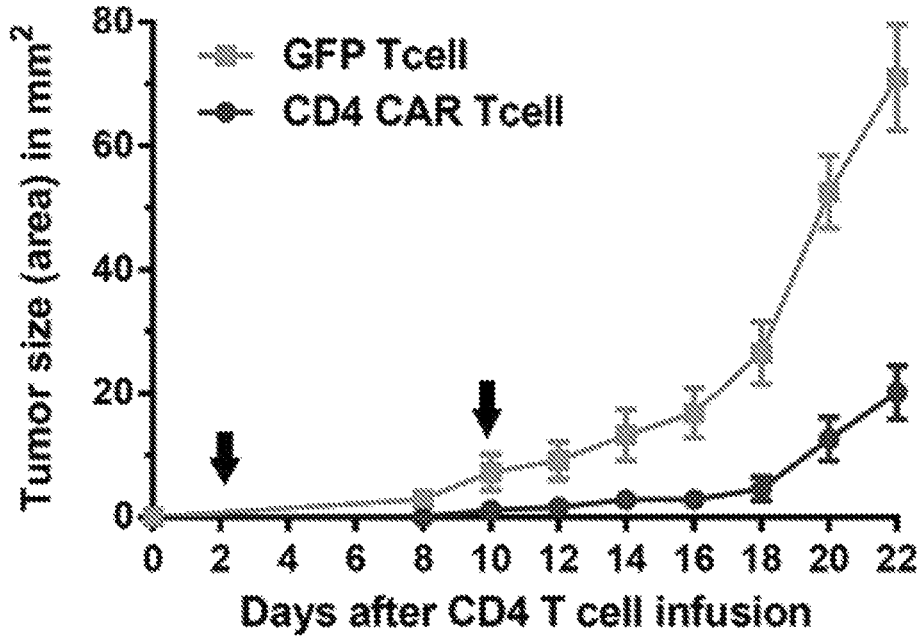

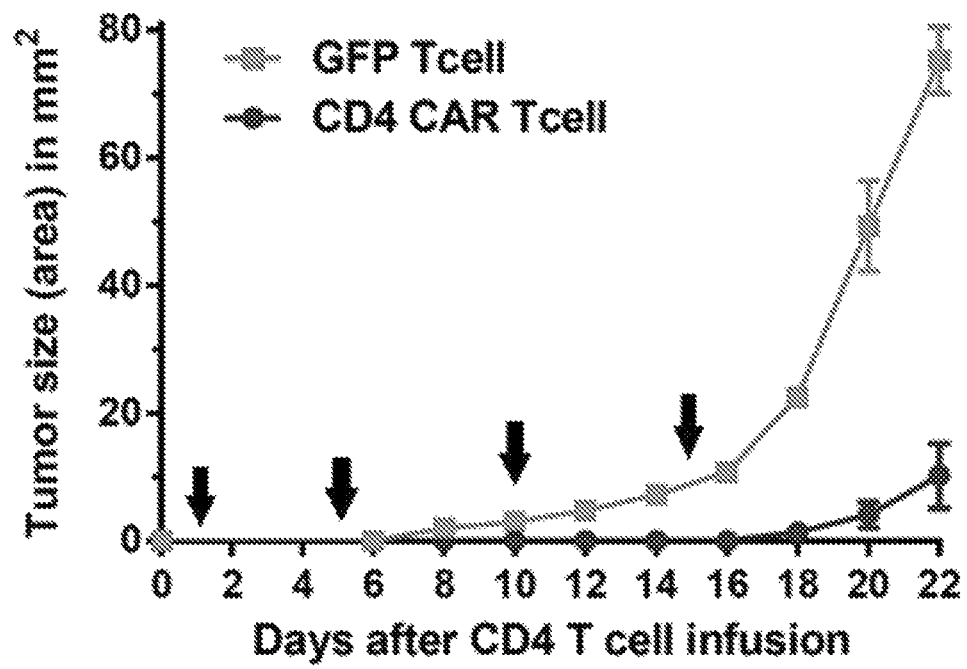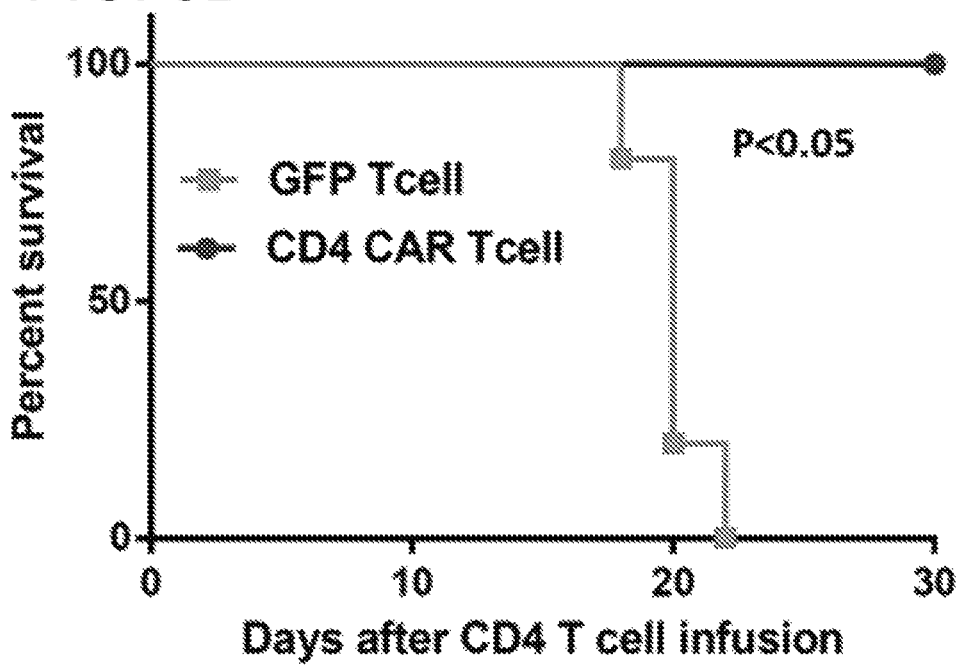

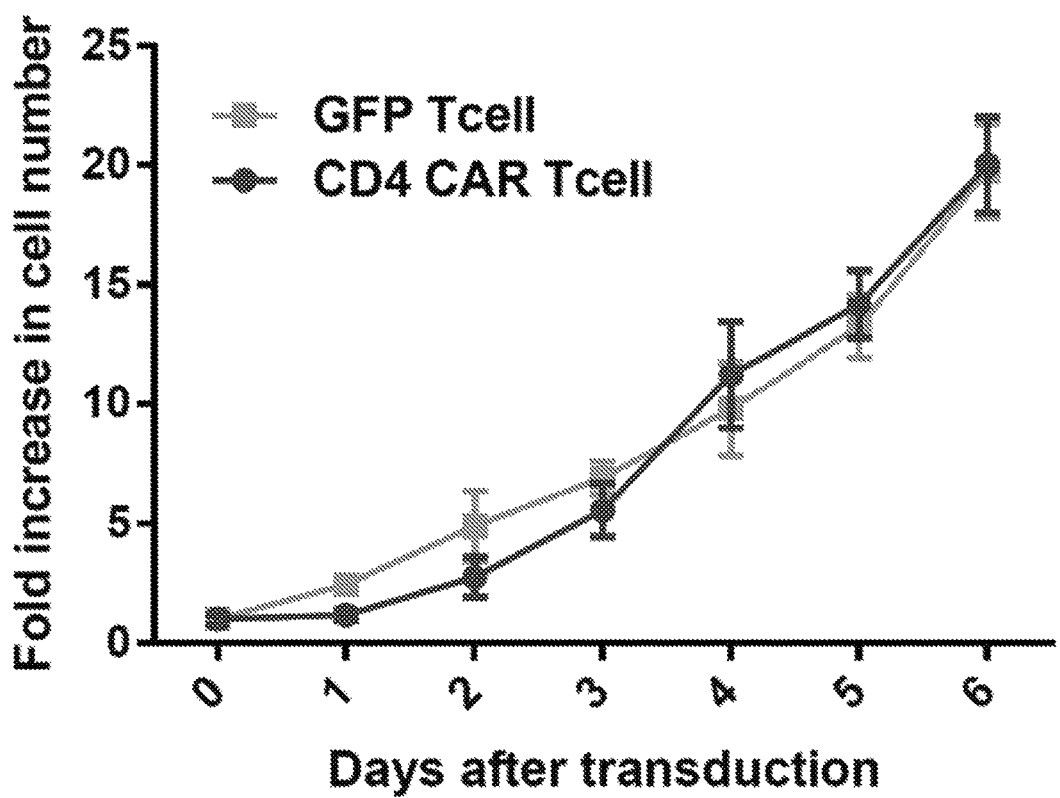

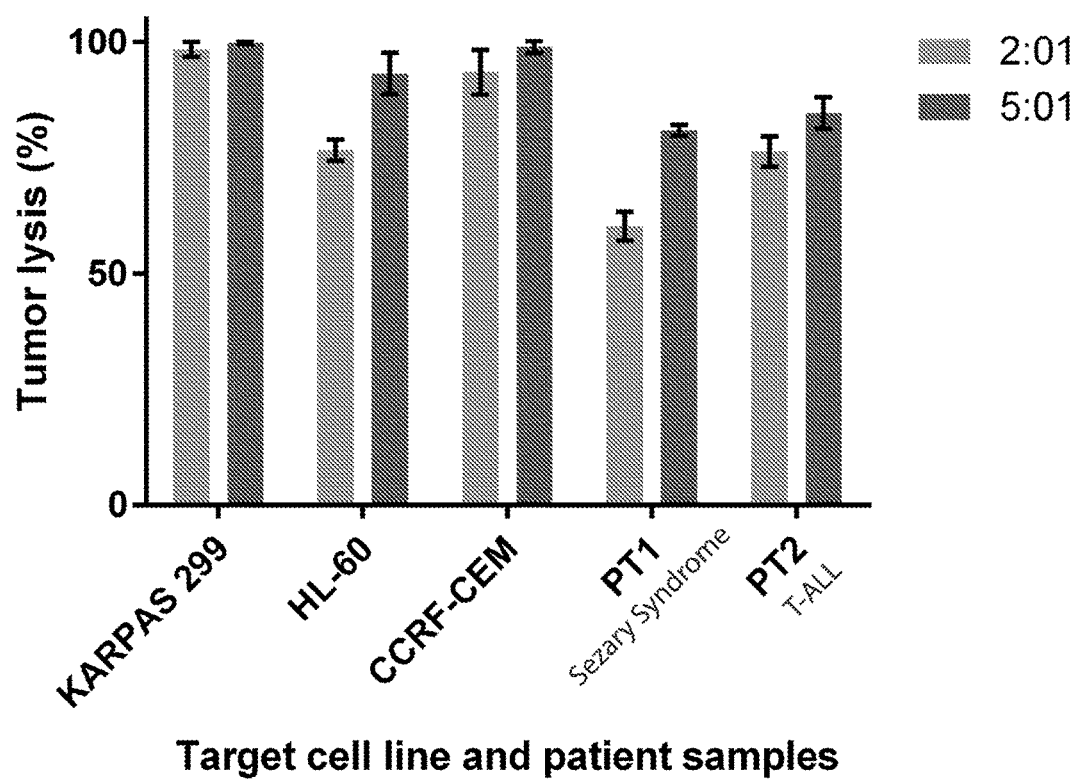

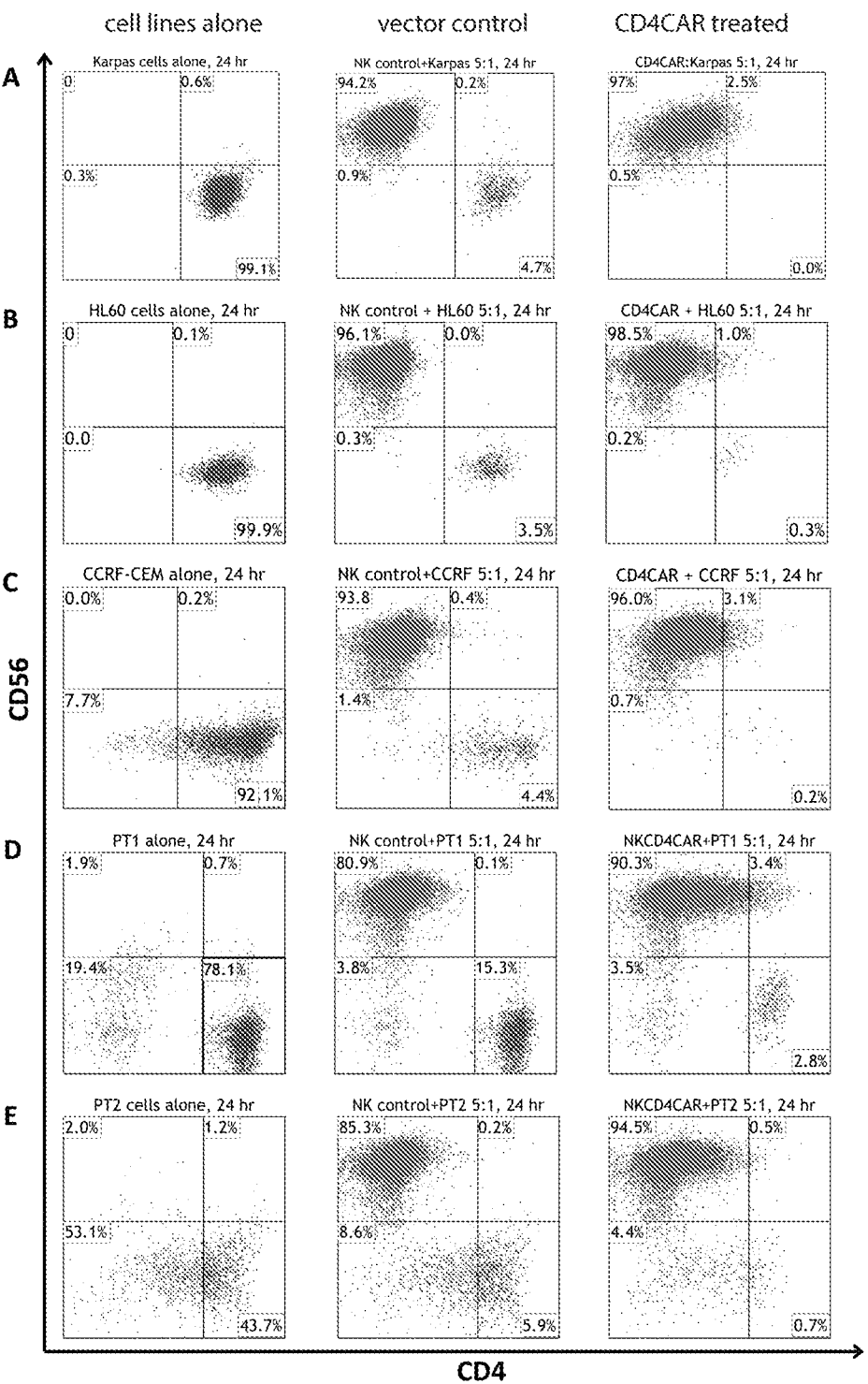

single transduction double transduction

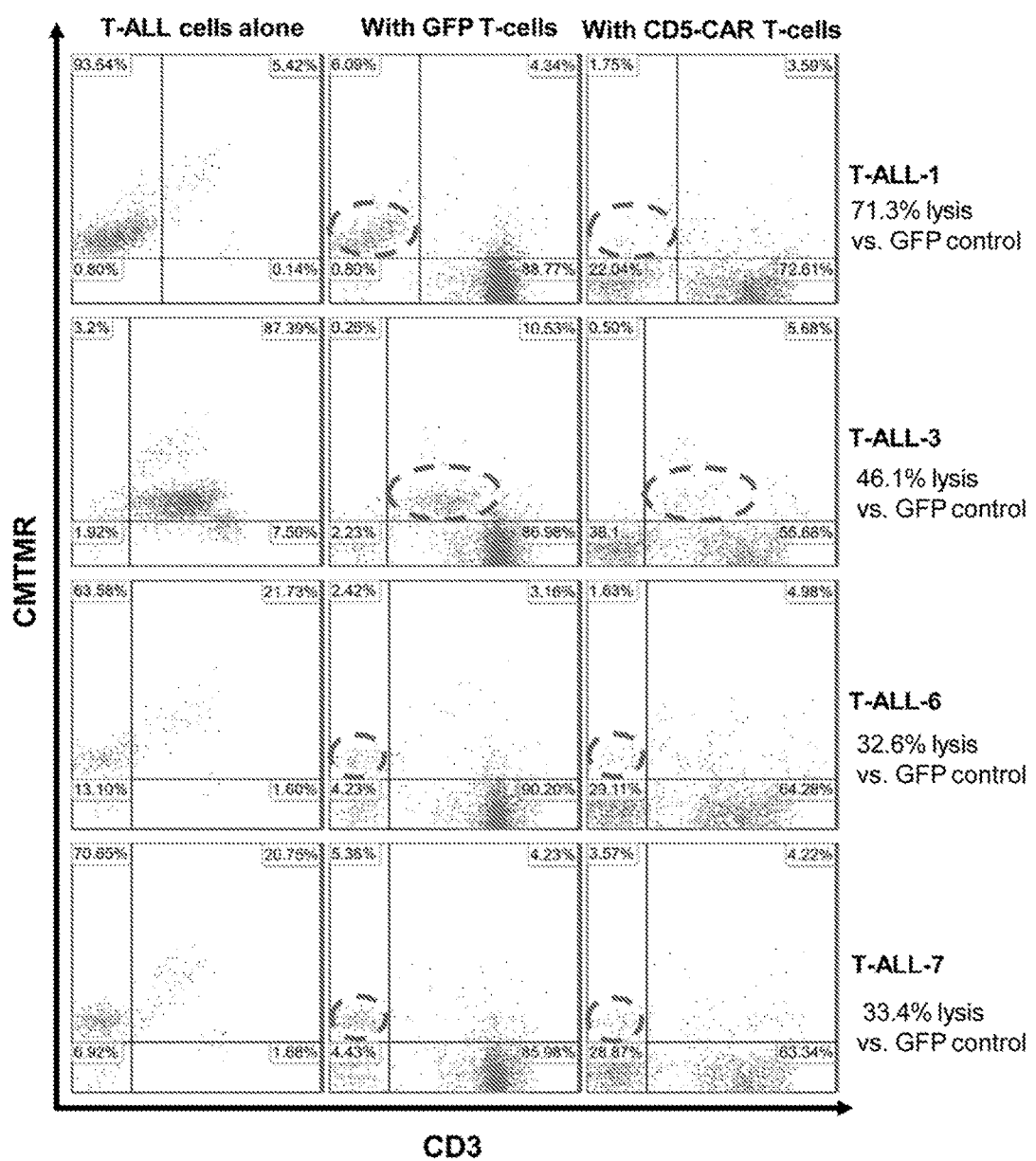

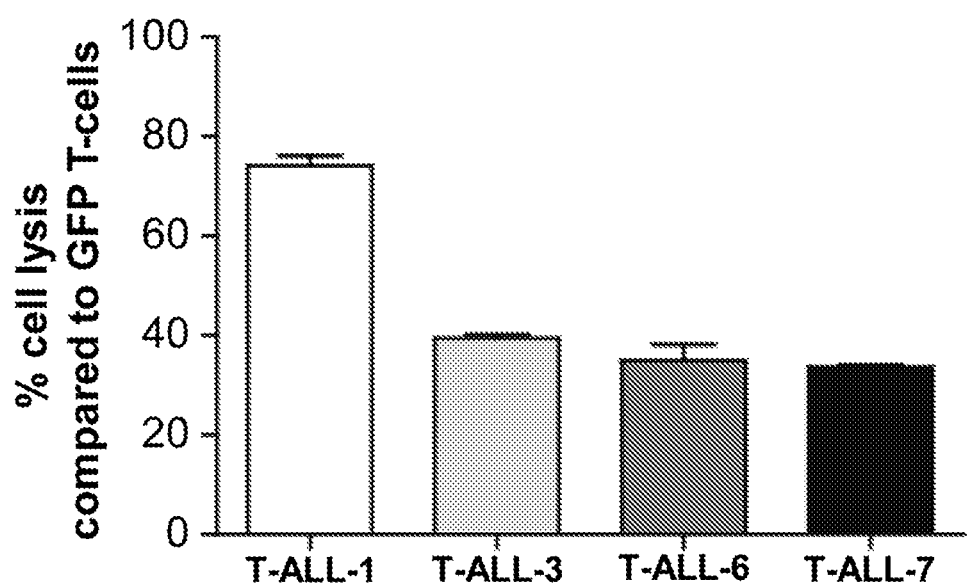

Experimental design

From Day3, GFP-T-cell were co-cultured (1:1)
ratio) for 4 days with following T-cells
1. CD5-CAR
2. Anchored CD5 scFv
3. CD123CAR

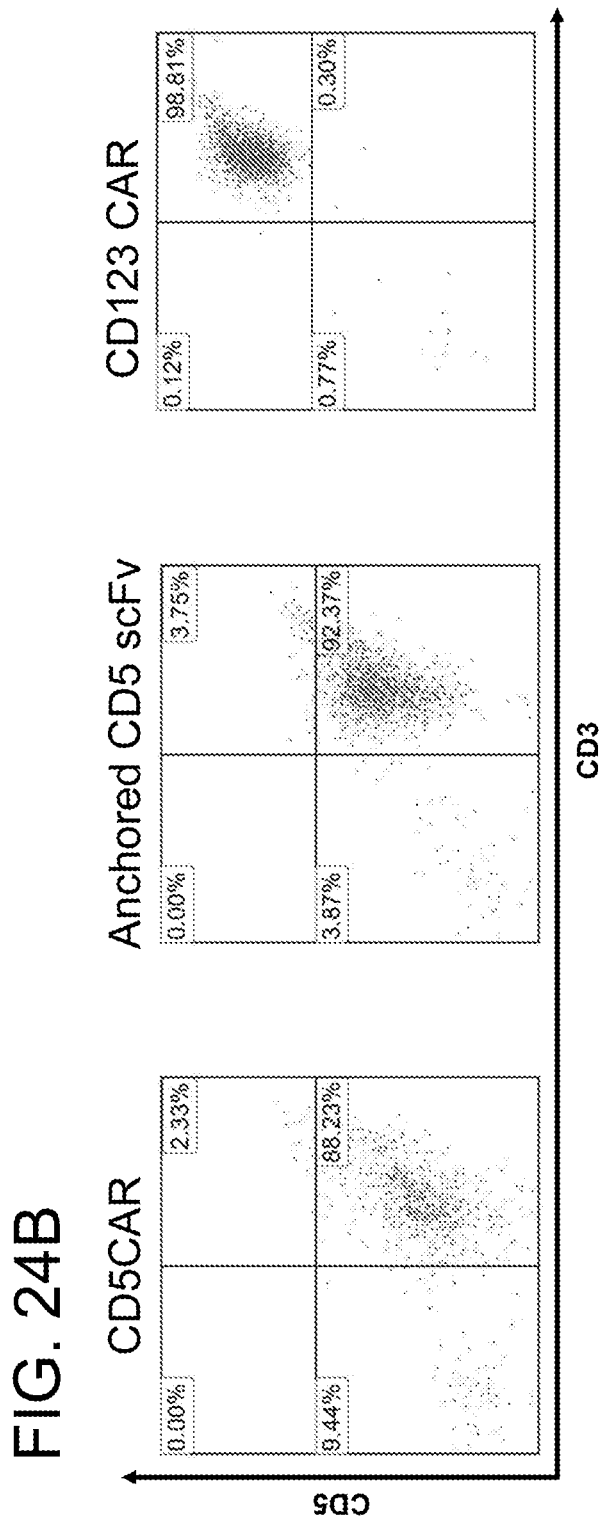

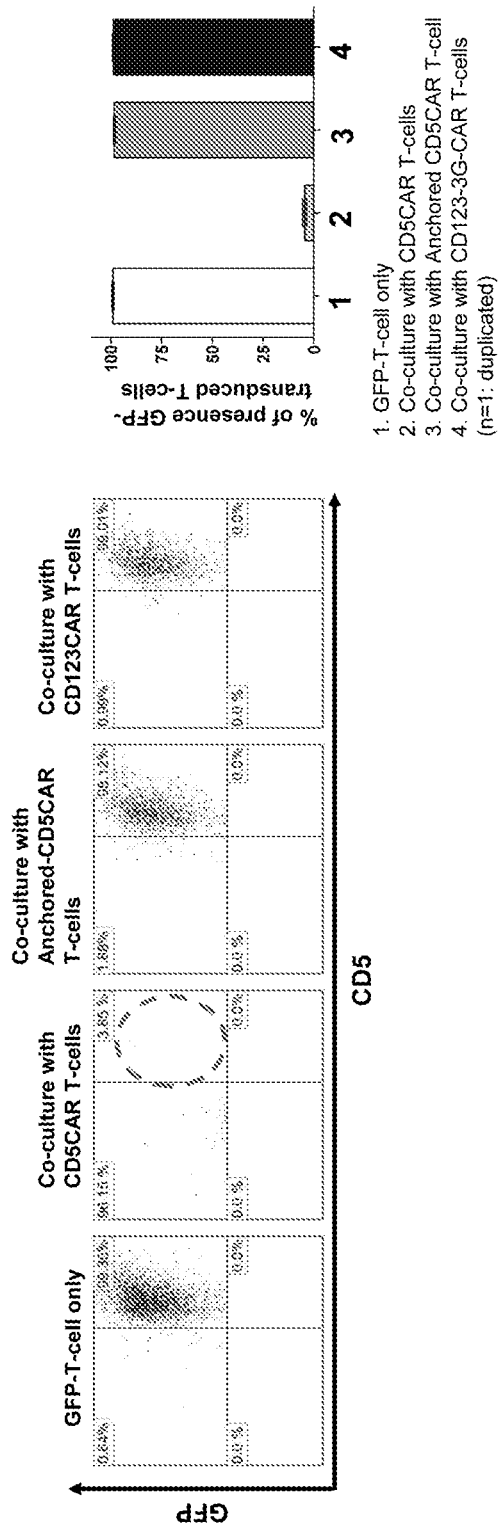

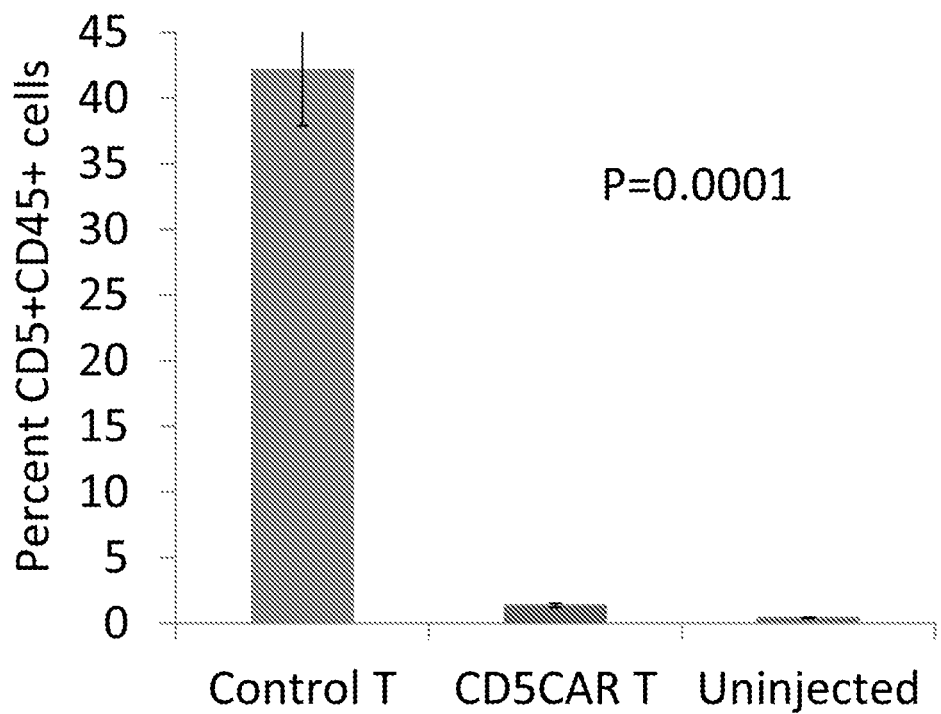

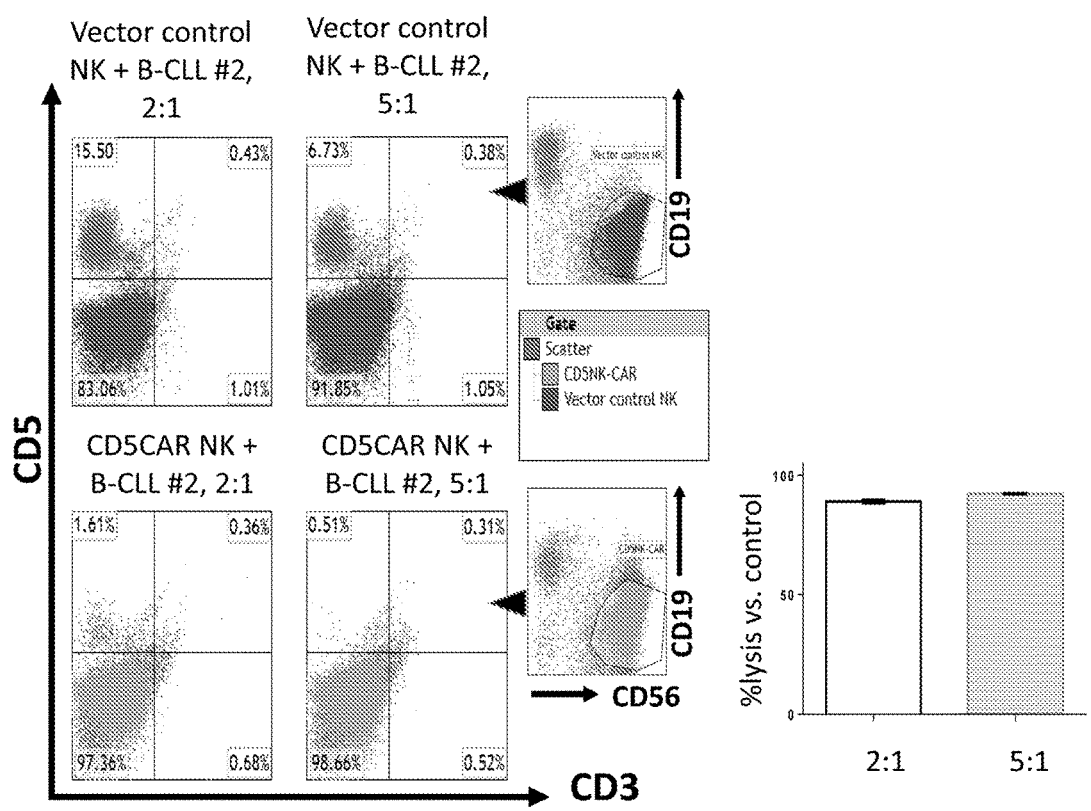

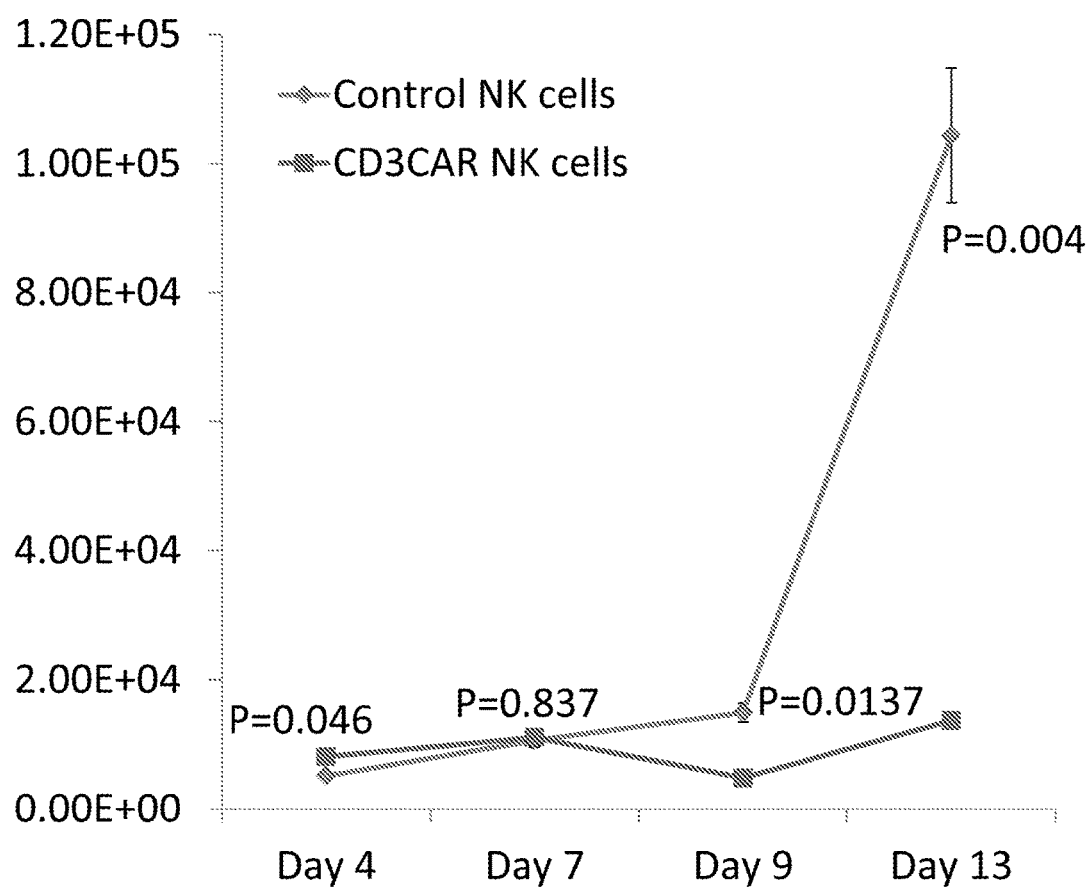

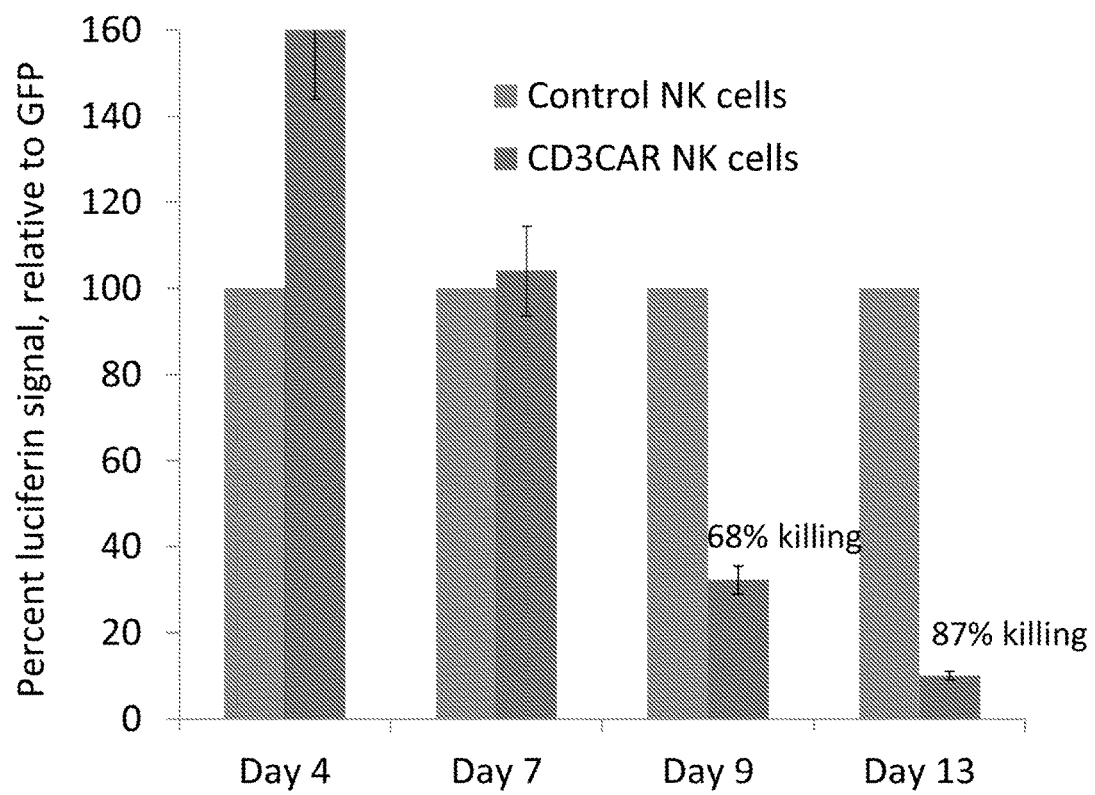

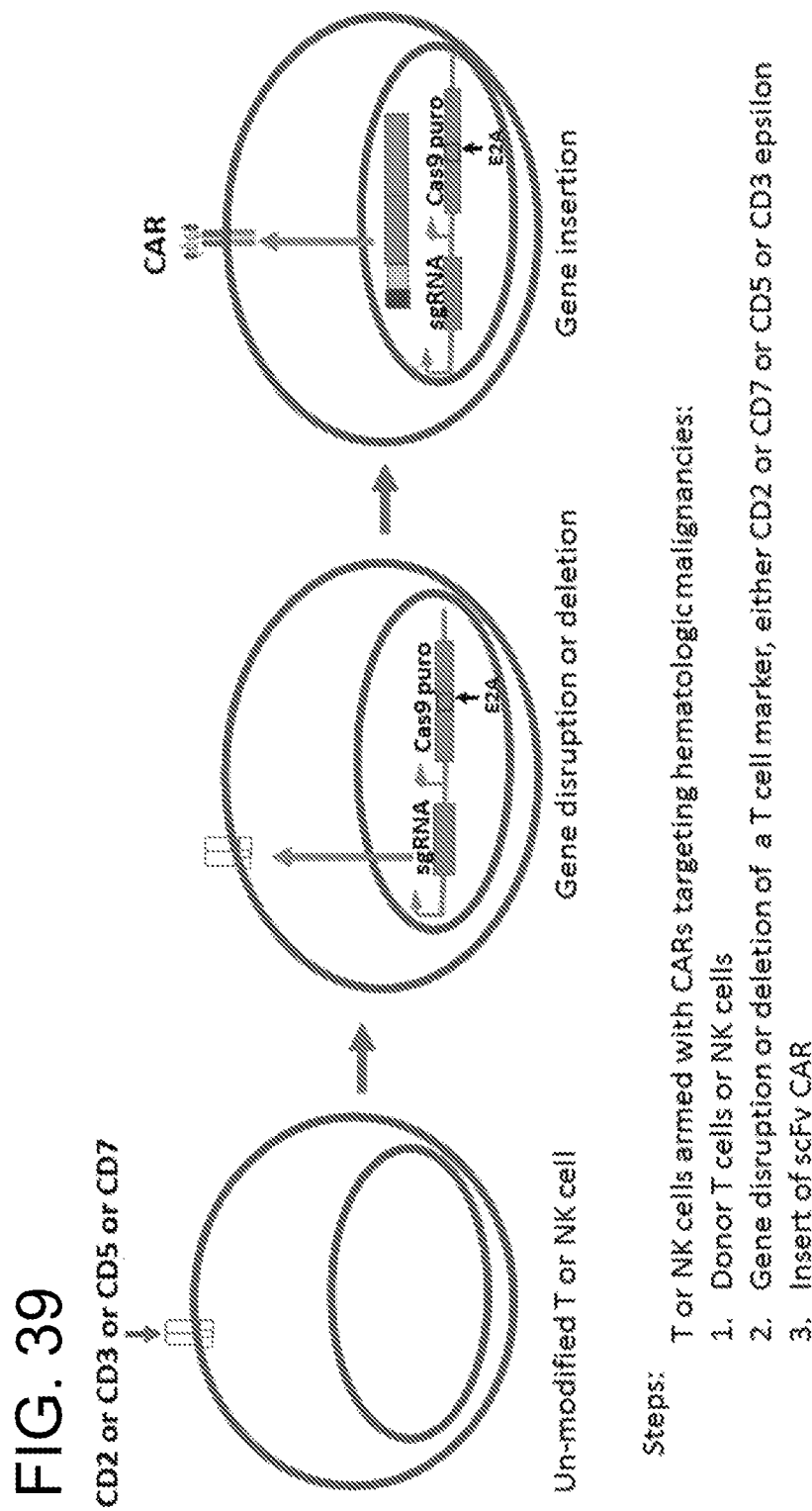

FIG. 40

1. CD2 sgRNA construct:

Lenti-U6-sgCD2a-SFFV-Cas9-puro  GGGTCATCACACACAAG (SEQ ID NO. 27)
Lenti-U6-sgCD2b-SFFV-Cas9-puro  GATGCCCGCCACGCACC (SEQ ID NO. 28)
Lenti-U6-sgCD2c-SFFV-Cas9-puro  GCCACAAAGACCATCAAG (SEQ ID NO. 29)

2. CD3 sgRNA costructs

Lenti-U6-sgCD3E1-SFFV-Cas9puro  GGAGACTTTATATGCTG (SEQ ID NO. 30)
Lenti-U6-sgCD3E2-SFFV-Cas9puro  GGCGTTTGGGGGCAAGA (SEQ ID NO. 31)
Lenti-U6-sgCD3E3-SFFV-Cas9puro  GTCCACTATGACAATTG (SEQ ID NO. 32)

3. CD5 sgRNA constructs:

Lenti-U6-sgCD5a-SFFV-Cas9puro  GCCGGAGCTCCAAGCAG (SEQ ID NO. 33)
Lenti-U6-sgCD5b-SFFV-Cas9puro  GGGGGCCTTGTCGTTGG (SEQ ID NO. 34)
Lenti-U6-sgCD5c-SFFV-Cas9puro  GGGTACCATCAGCTATG (SEQ ID NO. 35)

4. CD7 sgRNA construct:

Lenti-U6-sgCD7a-SFFV-Cas9-puro  GCCAGCGCCAGAAGCAG (SEQ ID NO. 36)
Lenti-U6-sgCD7b-SFFV-Cas9-puro  GGAGACTGCTGCACCTC (SEQ ID NO. 37)
Lenti-U6-sgCD7c-SFFV-Cas9-puro  GCCGCATGACTTCTCA (SEQ ID NO. 38)

Sorted-CCRF-CEM/sgCD5A

SEQUENCE LISTING

```
<160> NUMBER OF SEQ ID NOS: 38

<210> SEQ ID NO 1
<211> LENGTH: 1593
<212> TYPE: DNA
<213> ORGANISM: Artificial Sequence
<220> FEATURE:
<223> OTHER INFORMATION: Synthetic sequence

<400> SEQUENCE: 1
atggccttac cagtgaccgc cttgctcctg ccgctggcct tgctgctcca cgccgccagg      60
ccggacatta tgatgacaca gtcgccatca tctctggctg tgtctgcagg agaaaaggtc     120
actatgacct gtaagtccag tcaaagtgtt ttatacagtt caaatcagaa gaactacttg     180
gcctggtacc agcagaaacc agggcagtct cctaaactac tgatctactg ggcatccact     240
agggaatctg gtgtccctga tcgcttcaca ggcagtggat ctgggacaga ttttactctt     300
accatcagca gtgtgcaacc tgaagacctg gcagtttatt actgtcatca atacctctcc     360
tcgcacacgt tcggagggg gaccaagctg gaaataaaac ggggtggcgg tggctcgggc     420
ggtggtgggt cgggtggcgg cggatctcaa ctgcagcagc ctggggctga gctggtgagg     480
cctgggtctt cagtgaagct gtcctgcaag gcttctggct acaccttcac caggtactgg     540
atacattggg tgaagcagag gcctatacaa ggccttgaat ggattggtaa cattgatcct     600
tctgatagtg aaactcacta caatcaaaag ttcaaggaca aggccacatt gactgtagac     660
aaatcctccg gcacagccta catgcagctc agcagcctga catctgagga ctctgcggtc     720
tattactgtg caacagagga tctttactat gctatggagt actggggtca aggaacctca     780
gtcaccgtct cctctaccac gacgccagcg ccgcgaccac caacaccggc gcccaccatc     840
gcgtcgcagc ccctgtccct gcgcccagag gcgtgccggc cagcggcggg gggcgcagtg     900
cacacgaggg ggctggactt cgcctgtgat atctacatct gggcgccctt ggccgggact     960
tgtggggtcc ttctcctgtc actggttatc acccttact gcaggagtaa gaggagcagg    1020
ctcctgcaca gtgactacat gaacatgact ccccgccgcc ccgggcccac ccgcaagcat    1080 taccagcct atgccccacc acgcgacttc gcagcctatc gctccaaacg gggcagaaag    1140
aaactcctgt atatattcaa acaaccattt atgagaccag tacaaactac tcaagaggaa    1200
gatggctgta gctgccgatt tccagaagaa gaagaggag gatgtgaact gagagtgaag    1260
ttcagcagga gcgcagacgc cccccgcgtac cagcagggcc agaaccagct ctataacgag    1320
ctcaatctag gacgaagaga ggagtacgat gttttggaca gagacgtgg ccgggaccct    1380 gagatggggg gaaagccgca gagaaggaag aaccctcagg aaggcctgta caatgaactg    1440
cagaaagata gatggcgga ggcctacagt gagattggga tgaaaggcga gcgccggagg    1500
ggcaaggggc acgatggcct ttaccagggt ctcagtacag ccaccaagga cacctacgac    1560
gcccttcaca tgcaggccct gccccctcgc taa                                1593
```

<210> SEQ ID NO 2
<211> LENGTH: 1590
<212> TYPE: DNA
<213> ORGANISM: Artificial Sequence
<220> FEATURE:
<223> OTHER INFORMATION: Synthetic sequence

<400> SEQUENCE: 2

```
atggccttac cagtgaccgc cttgctcctg ccgctggcct tgctgctcca cgccgccagg      60
ccggacattg tgatgactca gtctccagcc accctgtctg tgactccagg agatagagtc     120
tctctttcct gcagggccag ccagagtatt agcgactact acactggta tcaacaaaaa     180
tcacatgagt ctccaaggct ctcatcaaa tatgcttccc aatccatctc tgggatcccc     240
tccaggttca gtggcagtgg atcagggtca gatttcactc tcagtatcaa cagtgtggaa     300
cctgaagatg ttggagtgta ttactgtcaa aatggtcaca gctttccgct cacgttcggt     360
gctgggacca agctggagct gagacggggt ggcggtggct cgggcggtgg tgggtcgggt     420
ggcggcggat ctcaggtcca actgcagcag ccagggactg aactggtgag gcctgggtct     480
tcagtgaagc tgtcctgcaa ggcttctggc tacacgttca ccagctactg ggtgaactgg     540
gttaaacaga ggcctgacca aggccttgag tggattggaa ggattgatcc ttacgacagt     600
gaaactcact acaatcagaa gttcacggac aaggccatat cgactattga cacatcctcc     660
aacacagcct acatgcaact cagcaccctg acatctgatg cttctgcggt ctattactgt     720
tcaagatcac cccgagacag ctcgaccaac cttgctgact ggggccaagg gactctggtc     780
actgtctctt ctaccacgac gccagcgccg cgaccaccaa caccggcgcc caccatcgcg     840
tcgcagcccc tgtccctgcg cccagaggcg tgccggccag cggcgggggg cgcagtgcac     900
acgagggggc tggacttcgc ctgtgatatc tacatctggg cgcccttggc cgggacttgt     960
ggggtccttc tcctgtcact ggttatcacc ctttactgca ggagtaagag gagcaggctc    1020
ctgcacagtg actacatgaa catgactccc cgccgcccg ggcccacccg caagcattac    1080
cagccctatg ccccaccacg cgacttcgca gcctatcgct ccaaacgggg cagaaagaaa    1140
ctcctgtata tattcaaaca accatttatg agaccagtac aaactactca agaggaagat    1200
ggctgtagct gccgatttcc agaagaagaa gaaggaggat gtgaactgag agtgaagttc    1260
agcaggagcg cagacgcccc cgcgtaccag cagggccaga accagctcta taacgagctc    1320
aatctaggac gaagagagga gtacgatgtt ttggacaaga cgtggccg ggaccctgag    1380
atgggggaa agccgcagag aaggaagaac cctcaggaag gcctgtacaa tgaactgcag    1440
aaagataaga tggcggaggc ctacagtgag attgggatga aggcgagcg ccggagggc    1500
aaggggcacg atggccttta ccagggtctc agtacagcca ccaaggacac ctacgacgcc    1560
cttcacatgc aggccctgcc ccctcgctaa                                    1590
```

<210> SEQ ID NO 3
<211> LENGTH: 1578
<212> TYPE: DNA
<213> ORGANISM: Artificial Sequence
<220> FEATURE:
<223> OTHER INFORMATION: Synthetic sequence

<400> SEQUENCE: 3

```
atggccttac cagtgaccgc cttgctcctg ccgctggcct tgctgctcca cgccgccagg      60
ccggacatcc agatgaccca gagcccagc agcctgagcg ccagcgtggg cgacagagtg     120
accatcacct gcagcgccag cagcagcgtg agctacatga actggtacca gcagacccc     180
```

```
ggcaaggccc ccaagagatg gatctacgac accagcaagc tggccagcgg cgtgcccagc    240
agattcagcg gcagcggcag cggcaccgac tacaccttca ccatcagcag cctgcagccc    300
gaggacatcg ccacctacta ctgccagcag tggagcagca ccccttcac cttcggccag     360
ggcaccaagc tgcagatcgg cggcggcggc agcggcggcg cggcagcgg cggcggcggc     420
agccaggtgc agctggtgca gagcggcggc ggcgtggtgc agcccggcag aagcctgaga    480
ctgagctgca aggccagcgg ctacaccttc accagataca ccatgcactg ggtgagacag    540
gcccccggca agggcctgga gtggatcggc tacatcaacc ccagcagagg ctacaccaac    600
tacaaccaga aggtgaagga cagattcacc atcagcagag acaacagcaa gaacaccgcc    660
ttcctgcaga tggacagcct gagacccgag gacaccggcg tgtacttctg cgccagatac    720
tacgacgacc actactgcct ggactactgg ggccagggca cccccgtgac cgtgagcagc    780
accacgacgc cagcgccgcg accaccaaca ccggcgccca ccatcgcgtc gcagccctg    840
tccctgcgcc cagaggcgtg ccggccagcg cgggggggcg cagtgcacac gagggggctg    900
gacttcgcct gtgatatcta catctgggcg cccttggccg ggacttgtgg ggtccttctc    960
ctgtcactgg ttatcaccct ttactgcagg agtaagagga gcaggctcct gcacagtgac   1020
tacatgaaca tgactccccg ccgccccggg cccacccgca gcattacca gccctatgcc    1080
ccaccacgcg acttcgcagc ctatcgctcc aaacggggca gaaagaaact cctgtatata    1140
ttcaaacaac catttatgag accagtacaa actactcaag aggaagatgg ctgtagctgc    1200
cgatttccag aagaagaaga aggaggatgt gaactgagag tgaagttcag caggagcgca    1260
gacgccccccg cgtaccagca gggccagaac cagctctata cgagctcaa tctaggacga    1320
agagaggagt acgatgtttt ggacaagaga cgtggccggg accctgagat ggggggaaag    1380
ccgcagagaa ggaagaaccc tcaggaaggc ctgtacaatg aactgcagaa agataagatg    1440
gcggaggcct acagtgagat tgggatgaaa ggcgagcgcc ggaggggcaa ggggcacgat    1500
ggcctttacc agggtctcag tacagccacc aaggacacct cgacgccct tcacatgcag    1560
gccctgcccc ctcgctaa                                                 1578
```

<210> SEQ ID NO 4  
<211> LENGTH: 1608  
<212> TYPE: DNA  
<213> ORGANISM: Artificial Sequence  
<220> FEATURE:  
<223> OTHER INFORMATION: Synthetic sequence

<400> SEQUENCE: 4

```
atggccttac cagtgaccgc cttgctcctg ccgctggcct tgctgctcca cgccgccagg     60
ccggacatcg tgatgaccca agcccccgac agcctggccg tgagcctggg cgagagggtg    120
accatgaact gcaaaagcag ccagtccctg ctgtactcca ccaaccagaa gaactacctg    180
gcttggtatc aacagaagcc cggacagagc cccaagctgc tgatctattg gccagcact    240
agggaaagcg gcgtgcccga taggttcagc ggcagcggga cggcacaga cttcactctg    300
accattagca gcgtgcaggc tgaggatgtg gccgtctact actgccagca gtactacagc    360
tacaggacct ttgggggcgg aactaagctg gagatcaagg agggggggg atccggggga    420
ggaggctccg gcggaggcgg aagccaagtg caactgcagc agagcggccc agaggtggtc    480
aaacctgggg caagcgtgaa gatgagctgc aaggctagcg gctataccct caccagctat    540
gtgatccact gggtgaggca gaaaccagga caggcctgg actggatcgg ctacatcaac    600
ccctacaatg acggcaccga ttatgacgaa aaattcaagg ggaaggccac cctgaccagc    660
```

```
gacaccagca caagcaccgc ctacatggag ctgtccagcc tgaggtccga ggacaccgcc    720
gtgtattact gtgccaggga aaggacaat tacgccaccg gcgcttggtt cgcctactgg     780
ggccagggca cactggtgac agtgagcagc accacgacgc cagcgccgcg accaccaaca    840
ccggcgccca ccatcgcgtc gcagcccctg tccctgcgcc cagaggcgtg ccggccagcg    900 gcgggggggcg cagtgcacac gaggggggctg gacttcgcct gtgatatcta catctgggcg   960
cccttggccg ggacttgtgg ggtccttctc ctgtcactgg ttatcaccct ttactgcagg   1020
agtaagagga gcaggctcct gcacagtgac tacatgaaca tgactccccg ccgccccggg    1080
cccacccgca agcattacca gccctatgcc ccaccacgcg acttcgcagc ctatcgctcc    1140
aaacggggca gaaagaaact cctgtatata ttcaaacaac catttatgag accagtacaa    1200
actactcaag aggaagatgg ctgtagctgc cgatttccag aagaagaaga aggaggatgt    1260
gaactgagag tgaagttcag caggagcgca gacgccccg cgtaccagca gggccagaac    1320
cagctctata cgagctcaa tctaggacga agagaggagt acgatgtttt ggacaagaga    1380
cgtggccggg accctgagat ggggggaaag ccgcagagaa ggaagaaccc tcaggaaggc    1440
ctgtacaatg aactgcagaa agataagatg cggaggcct acagtgagat tgggatgaaa    1500
ggcgagcgcc ggaggggcaa ggggcacgat ggcctttacc agggtctcag tacagccacc    1560
aaggacacct acgacgccct tcacatgcag gccctgcccc ctcgctaa                1608
```

<210> SEQ ID NO 5
<211> LENGTH: 1611
<212> TYPE: DNA
<213> ORGANISM: Artificial Sequence
<220> FEATURE:
<223> OTHER INFORMATION: Synthetic sequence
<400> SEQUENCE: 5

```
atggccttac cagtgaccgc cttgctcctg ccgctggcct tgctgctcca cgccgccagg     60
ccggacatcg tgatgaccca gagccccgac agcctggccg tgagcctggg cgagagggcc    120
accatcaact gcagggccag caagagcgtg agcaccagcg gctacagcta catctactgg    180
taccagcaga agcccggcca gccccccaag ctgctgatct acctggccag catcctggag    240
agcggcgtgc ccgacaggtt cagcggcagc ggcagcggca ccgacttcac cctgaccatc    300
agcagcctgc aggccgagga cgtggccgtg tactactgcc agcacagcag ggagctgccc    360
tggaccttcg gccagggcac caaggtggag atcaagggcg gcggcggcag cggcggcggc    420
ggcagcggcg gcggcggcag cgaggagcag ctggtggaga gcggcggcgg cctggtgaag    480
cccggcggca gcctgaggct gagctgcgcc gccagcggct tcagcttcag cgactgcagg    540
atgtactggt gaggcaggc cccgggcaag gccctggagt ggatcggcgt gatcagcgtg    600
aagagcgaga actacggcgc caactacgcc gagagcgtga gggcaggtt caccatcagc    660 agggacgaca gcaagaacac cgtgtacctg cagatgaaca gcctgaagac cgaggacacc    720
gccgtgtact actgcagcgc cagctactac aggtacgacg tgggcgcctg gttcgcctac    780
tggggccagg gcaccctggt gaccgtgagc agcaccacga cgccagcgcc gcgaccacca    840
acaccggcgc ccaccatcgc gtcgcagccc ctgtccctgc gcccagaggc gtgccggcca    900
gcggcggggg gcgcagtgca cacgaggggg ctggacttcg cctgtgatat ctacatctgg    960
gcgcccttgg ccgggacttg tggggtcctt ctcctgtcac tggttatcac cctttactgc    1020
aggagtaaga ggagcaggct cctgcacagt gactacatga acatgactcc ccgccgcccc   1080
```

| | | |
|---|---|---|
| gggcccaccc gcaagcatta ccagccctat gccccaccac gcgacttcgc agcctatcgc | 1140 | |
| tccaaacggg gcagaaagaa actcctgtat atattcaaac aaccatttat gagaccagta | 1200 | |
| caaactactc aagaggaaga tggctgtagc tgccgatttc cagaagaaga agaaggagga | 1260 | |
| tgtgaactga gagtgaagtt cagcaggagc gcagacgccc ccgcgtacca gcagggccag | 1320 | |
| aaccagctct ataacgagct caatctagga cgaagagagg agtacgatgt tttggacaag | 1380 | |
| agacgtggcc gggaccctga gatgggggga aagccgcaga gaaggaagaa ccctcaggaa | 1440 | |
| ggcctgtaca atgaactgca gaaagataag atggcggagg cctacagtga gattgggatg | 1500 | |
| aaaggcgagc gccggagggg caaggggcac gatggccttt accagggtct cagtacagcc | 1560 | |
| accaaggaca cctacgacgc ccttcacatg caggccctgc ccctcgcta a | 1611 | |

<210> SEQ ID NO 6
<211> LENGTH: 1581
<212> TYPE: DNA
<213> ORGANISM: Artificial Sequence
<220> FEATURE:
<223> OTHER INFORMATION: Synthetic sequence

<400> SEQUENCE: 6

| | |
|---|---|
| atggccttac cagtgaccgc cttgctcctg ccgctggcct tgctgctcca cgccgccagg | 60 |
| ccggacatcc aggtgaccca gagccccagc agcctgagcg ccagcctggg cgagagaatc | 120 |
| agcctgacct gcgaaccag ccaggacatc agcaactacc tgaactggtt ccagcagaag | 180 |
| cccgacggca ccttcaagag actgatctac gccaccagca gcctggacag cggcgtgccc | 240 |
| aagagattca gcggcagcgg cagcggcagc gactacagcc tgaccatcag cagcctggag | 300 |
| agcgaggact tcgccgacta ctactgcctg cagtacgcca gctaccccct caccttcggc | 360 |
| agcggcacca gctggagat caaggggaggg ggggatccg ggggaggagg ctccggcgga | 420 |
| ggcggaagcg aggtgcagct gcaggagagc ggccccggcc tggtgaagcc agccagacc | 480 |
| ctgagcctga cctgcagcgt gaccggctac agcatcacca gcggctacta ctggcactgg | 540 |
| atcagacagt tccccggcaa caagctgcag tggatgggct acatcagcta cagcggcttc | 600 |
| accaactaca gaccagcct gatcaacaga atcagcatca cccacgacac cagcgagaac | 660 |
| cagttcttcc tgaacctgaa cagcgtgacc accgaggaca ccgccaccta ctactgcgcc | 720 |
| ggcgacagaa ccggcagctg gttcgcctac tgggggccagg gcaccctggt gaccgtgagc | 780 |
| gccaccacga cgccagcgcc gcgaccacca caccggcgc ccaccatcgc gtcgcagccc | 840 |
| ctgtccctgc gcccagaggc gtgccggcca cggcggggg gcgcagtgca cacgaggggg | 900 |
| ctggacttcg cctgtgatat ctacatctgg gcgcccttgg ccgggacttg tggggtcctt | 960 |
| ctcctgtcac tggttatcac cctttactgc aggagtaaga ggagcaggct cctgcacagt | 1020 |
| gactacatga acatgactcc ccgccgcccc gggcccaccc gcaagcatta ccagccctat | 1080 |
| gccccaccac gcgacttcgc agcctatcgc tccaaacggg gcagaaagaa actcctgtat | 1140 |
| atattcaaac aaccatttat gagaccagta caaactactc aagaggaaga tggctgtagc | 1200 |
| tgccgatttc cagaagaaga agaaggagga tgtgaactga gagtgaagtt cagcaggagc | 1260 |
| gcagacgccc ccgcgtacca gcagggccag aaccagctct ataacgagct caatctagga | 1320 |
| cgaagagagg agtacgatgt tttggacaag agacgtggcc gggaccctga gatgggggga | 1380 |
| aagccgcaga gaaggaagaa ccctcaggaa ggcctgtaca atgaactgca gaaagataag | 1440 |
| atggcggagg cctacagtga gattgggatg aaaggcgagc gccggagggg caaggggcac | 1500 |
| gatggccttt accagggtct cagtacagcc accaaggaca cctacgacgc ccttcacatg | 1560 |

```
caggccctgc cccctcgctg a                                          1581

<210> SEQ ID NO 7
<211> LENGTH: 993
<212> TYPE: DNA
<213> ORGANISM: Artificial Sequence
<220> FEATURE:
<223> OTHER INFORMATION: Synthetic sequence

<400> SEQUENCE: 7
atggccttac cagtgaccgc cttgctcctg ccgctggcct tgctgctcca cgccgccagg    60
ccggacatcc aggtgaccca gagccccagc agcctgagcg ccagcctggg cgagagaatc   120
agcctgacct gcagaaccag ccaggacatc agcaactacc tgaactggtt ccagcagaag   180
cccgacggca ccttcaagag actgatctac gccaccagca gcctggacag cggcgtgccc   240
aagagattca gcggcagcgg cagcggcagc gactacagcc tgaccatcag cagcctggag   300
agcgaggact cgccgactac tactgcctg cagtacgcca gctacccctt caccttcggc   360
agcggcacca agctggagat caagggaggg gggggatccg ggggaggagg ctccggcgga   420
ggcggaagcg aggtgcagct gcaggagagc ggccccggcc tggtgaagcc cagccagacc   480
ctgagcctga cctgcagcgt gaccggctac agcatcacca gcggctacta ctggcactgg   540
atcagacagt tccccggcaa caagctgcag tggatgggct acatcagcta cagcggcttc   600
accaactaca gaccagcct gatcaacaga atcagcatca cccacgacac cagcgagaac   660
cagttcttcc tgaacctgaa cagcgtgacc accgaggaca ccgccaccta ctactgcgcc   720
ggcgacagaa ccggcagctg gttcgcctac tggggccagg gcaccctggt gaccgtgagc   780
gccaccacga cgccagcgcc gcgaccacca caccggcgc ccaccatcgc gtcgcagccc   840
ctgtccctgc gcccagaggc gtgccggcca gcggcggggg gcgcagtgca cacgaggggg   900
ctggacttcg cctgtgatat ctacatctgg gcgcccttgg ccgggacttg tggggtcctt   960
ctcctgtcac tggttatcac cctttactgc tga                                993

<210> SEQ ID NO 8
<211> LENGTH: 1623
<212> TYPE: DNA
<213> ORGANISM: Artificial Sequence
<220> FEATURE:
<223> OTHER INFORMATION: Synthetic sequence

<400> SEQUENCE: 8
atggccttac cagtgaccgc cttgctcctg ccgctggcct tgctgctcca cgccgccagg    60
ccgggcgccc agcccgccat ggccgcctac aaggacatcc agatgaccca gaccaccagc   120
agcctgagcg ccagcctggg cgacagagtg accatcagct gcagcgccag ccagggcatc   180
agcaactacc tgaactggta ccagcagaag cccgacggca ccaacaagct gctgatctac   240
tacaccagca gcctgcacag cggcgtgccc agcagattca gcggcagcgg cagcggcacc   300
gactacagcc tgcacagcaa cctggagccc gaggacatcg ccacctacta ctgccagcag   360
tacagcaagc tgccctacac cttcggcggc ggcaccaagc tggagatcaa gagaggcggc   420
ggcggcagcg gcggcggcgg cagcggcggc ggcggcagcg gcggcggcgg cagcgaggtg   480
cagctggtgg agagcggcgg cggcctggtg aagcccggcg gcagcctgaa gctgagctgc   540
gccgccagcg gcctgacctt cagcagctac gccatgagct ggaacagaca gaccccgag   600 aagagactgg agtgggtggc cagcatcagc agcggcggct caccctacta ccccgacagc   660
```

| | |
|---|---:|
| aacaagggca gattcaccat cagcagagac aacgccagaa acatcctgta cctgcagatg | 720 |
| agcagcctga aagcgagga caccgccatg tactactgcg ccagagacga ggtgagaggc | 780 |
| tacctggacg tgtggggcgc cggcaccacc gtgaccgtga gcagcaccac gacgccagcg | 840 |
| ccgcgaccac caacaccggc gcccaccatc gcgtcgcagc ccctgtccct gcgcccagag | 900 |
| gcgtgccggc cagcggcggg gggcgcagtg cacacgaggg ggctggactt cgcctgtgat | 960 |
| atctacatct gggcgccctt ggccgggact tgtggggtcc ttctcctgtc actggttatc | 1020 |
| acccttttact gcaggagtaa gaggagcagg ctcctgcaca gtgactacat gaacatgact | 1080 |
| ccccgccgcc ccgggcccac ccgcaagcat taccagccct atgccccacc acgcgacttc | 1140 |
| gcagcctatc gctccaaacg gggcagaaag aaactcctgt atatattcaa acaaccattt | 1200 |
| atgagaccag tacaaactac tcaagaggaa gatggctgta gctgccgatt tccagaagaa | 1260 |
| gaagaaggag gatgtgaact gagagtgaag ttcagcagga gcgcagacgc ccccgcgtac | 1320 |
| cagcagggcc agaaccagct ctataacgag ctcaatctag gacgaagaga ggagtacgat | 1380 |
| gttttggaca agagacgtgg ccgggaccct gagatggggg aaagccgca gagaaggaag | 1440 |
| aaccctcagg aaggcctgta caatgaactg cagaaagata gatggcgga ggcctacagt | 1500 |
| gagattggga tgaaaggcga gcgccggagg ggcaagggga cgatggcct ttaccagggt | 1560 |
| ctcagtacag ccaccaagga cacctacgac gcccttcaca tgcaggccct gccccctcgc | 1620 |
| taa | 1623 |

<210> SEQ ID NO 9
<211> LENGTH: 1590
<212> TYPE: DNA
<213> ORGANISM: Artificial Sequence
<220> FEATURE:
<223> OTHER INFORMATION: Synthetic sequence

<400> SEQUENCE: 9

| | |
|---|---:|
| atggccttac cagtgaccgc cttgctcctg ccgctggcct tgctgctcca cgccgccagg | 60 |
| ccggacatcc agatgaccca gagccccagc agcctgagcg ccagcgtggg cgacagagtg | 120 |
| accatcacct gcaaggccag ccagaacatc gacaagtacc tgaactggta ccagcagaag | 180 |
| cccggcaagg cccccaagct gctgatctac aacaccaaca acctgcagac cggcgtgccc | 240 |
| agcagattca gcggcagcgg cagcggcacc gacttcaccc tcaccatcag cagcctgcag | 300 |
| cccgaggaca tcgccaccta ctactgcctg cagcacatca gcagacccag aaccttcggc | 360 |
| cagggcacca aggtggagat caagggcggc ggcggcagcg gcggcggcgg cagcggcggc | 420 |
| ggcggcagcc aggtgcagct gcaggagagc ggccccggcc tggtgagacc cagccagacc | 480 |
| ctgagcctga cctgcaccgt gagcggcttc accttcaccg acttctacat gaactgggtg | 540 |
| agacagcccc ccggcagagg cctggagtgg atcggcttca tcagagacaa ggccaagggc | 600 |
| tacaccaccg agtacaaccc cagcgtgaag ggcagagtga ccatgctggt ggacaccagc | 660 |
| aagaaccagt tcagcctgag actgagcagc gtgaccgccg ccgacaccgc cgtgtactac | 720 |
| tgcgccagag agggccacac cgccgccccc ttcgactact ggggccaggg cagcctggtg | 780 |
| accgtgagca gcaccgacgc cagcgccgc gaccaccaa caccggcgcc caccatcgcg | 840 |
| tcgcagcccc tgtccctgcg cccagaggcg tgccggccag cggcggggg cgcagtgcac | 900 |
| acgagggggc tggacttcgc ctgtgatatc tacatctggg cgcccttggc cgggacttgt | 960 |
| ggggtccttc tcctgtcact ggttatcacc ctttactgca ggagtaagag gagcaggctc | 1020 |
| ctgcacagtg actacatgaa catgactccc cgccgcccg ggcccacccg caagcattac | 1080 |

```
cagccctatg ccccaccacg cgacttcgca gcctatcgct ccaaacgggg cagaaagaaa    1140
ctcctgtata tattcaaaca accatttatg agaccagtac aaactactca agaggaagat    1200
ggctgtagct gccgatttcc agaagaagaa gaaggaggat gtgaactgag agtgaagttc    1260
agcaggagcg cagacgcccc cgcgtaccag cagggccaga accagctcta taacgagctc    1320
aatctaggac gaagagagga gtacgatgtt ttggacaaga cgtggccg ggaccctgag     1380 atgggggaa agccgcagag aaggaagaac cctcaggaag gcctgtacaa tgaactgcag     1440
aaagataaga tggcggaggc ctacagtgag attgggatga aggcgagcg ccggaggggc    1500 aaggggcacg atggccttta ccagggtctc agtacagcca ccaaggacac ctacgacgcc   1560
cttcacatgc aggccctgcc ccctcgctaa                                      1590
```

<210> SEQ ID NO 10
<211> LENGTH: 530
<212> TYPE: PRT
<213> ORGANISM: Artificial Sequence
<220> FEATURE:
<223> OTHER INFORMATION: Synthetic sequence

<400> SEQUENCE: 10

```
Met Ala Leu Pro Val Thr Ala Leu Leu Leu Pro Leu Ala Leu Leu Leu
1               5                   10                  15

His Ala Ala Arg Pro Asp Ile Met Met Thr Gln Ser Pro Ser Ser Leu
            20                  25                  30

Ala Val Ser Ala Gly Glu Lys Val Thr Met Thr Cys Lys Ser Ser Gln
        35                  40                  45

Ser Val Leu Tyr Ser Ser Asn Gln Lys Asn Tyr Leu Ala Trp Tyr Gln
    50                  55                  60

Gln Lys Pro Gly Gln Ser Pro Lys Leu Leu Ile Tyr Trp Ala Ser Thr
65                  70                  75                  80

Arg Glu Ser Gly Val Pro Asp Arg Phe Thr Gly Ser Gly Ser Gly Thr
                85                  90                  95

Asp Phe Thr Leu Thr Ile Ser Ser Val Gln Pro Glu Asp Leu Ala Val
            100                 105                 110

Tyr Tyr Cys His Gln Tyr Leu Ser Ser His Thr Phe Gly Gly Gly Thr
        115                 120                 125

Lys Leu Glu Ile Lys Arg Gly Gly Gly Ser Gly Gly Gly Gly Ser
    130                 135                 140

Gly Gly Gly Gly Ser Gln Leu Gln Gln Pro Gly Ala Glu Leu Val Arg
145                 150                 155                 160

Pro Gly Ser Ser Val Lys Leu Ser Cys Lys Ala Ser Gly Tyr Thr Phe
                165                 170                 175

Thr Arg Tyr Trp Ile His Trp Val Lys Gln Arg Pro Ile Gln Gly Leu
            180                 185                 190

Glu Trp Ile Gly Asn Ile Asp Pro Ser Asp Ser Glu Thr His Tyr Asn
        195                 200                 205

Gln Lys Phe Lys Asp Lys Ala Thr Leu Thr Val Asp Lys Ser Ser Gly
    210                 215                 220

Thr Ala Tyr Met Gln Leu Ser Ser Leu Thr Ser Glu Asp Ser Ala Val
225                 230                 235                 240

Tyr Tyr Cys Ala Thr Glu Asp Leu Tyr Tyr Ala Met Glu Tyr Trp Gly
                245                 250                 255

Gln Gly Thr Ser Val Thr Val Ser Ser Thr Thr Pro Ala Pro Arg
            260                 265                 270
```

```
Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
        290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Arg Ser
                325                 330                 335

Lys Arg Ser Arg Leu Leu His Ser Asp Tyr Met Asn Met Thr Pro Arg
                340                 345                 350

Arg Pro Gly Pro Thr Arg Lys His Tyr Gln Pro Tyr Ala Pro Pro Arg
                355                 360                 365

Asp Phe Ala Ala Tyr Arg Ser Lys Arg Gly Arg Lys Lys Leu Leu Tyr
370                 375                 380

Ile Phe Lys Gln Pro Phe Met Arg Pro Val Gln Thr Thr Gln Glu Glu
385                 390                 395                 400

Asp Gly Cys Ser Cys Arg Phe Pro Glu Glu Glu Glu Gly Gly Cys Glu
                405                 410                 415

Leu Arg Val Lys Phe Ser Arg Ser Ala Asp Ala Pro Ala Tyr Gln Gln
                420                 425                 430

Gly Gln Asn Gln Leu Tyr Asn Glu Leu Asn Leu Gly Arg Arg Glu Glu
                435                 440                 445

Tyr Asp Val Leu Asp Lys Arg Arg Gly Arg Asp Pro Glu Met Gly Gly
                450                 455                 460

Lys Pro Gln Arg Arg Lys Asn Pro Gln Glu Gly Leu Tyr Asn Glu Leu
465                 470                 475                 480

Gln Lys Asp Lys Met Ala Glu Ala Tyr Ser Glu Ile Gly Met Lys Gly
                485                 490                 495

Glu Arg Arg Arg Gly Lys Gly His Asp Gly Leu Tyr Gln Gly Leu Ser
                500                 505                 510

Thr Ala Thr Lys Asp Thr Tyr Asp Ala Leu His Met Gln Ala Leu Pro
                515                 520                 525

Pro Arg
    530

<210> SEQ ID NO 11
<211> LENGTH: 529
<212> TYPE: PRT
<213> ORGANISM: Artificial Sequence
<220> FEATURE:
<223> OTHER INFORMATION: Synthetic sequence

<400> SEQUENCE: 11

Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Pro Ala Thr Leu
                20                  25                  30

Ser Val Thr Pro Gly Asp Arg Val Ser Leu Ser Cys Arg Ala Ser Gln
            35                  40                  45

Ser Ile Ser Asp Tyr Leu His Trp Tyr Gln Gln Lys Ser His Glu Ser
        50                  55                  60

Pro Arg Leu Leu Ile Lys Tyr Ala Ser Gln Ser Ile Ser Gly Ile Pro
65                  70                  75                  80

Ser Arg Phe Ser Gly Ser Gly Ser Gly Ser Asp Phe Thr Leu Ser Ile
                85                  90                  95
```

```
Asn Ser Val Glu Pro Glu Asp Val Gly Val Tyr Tyr Cys Gln Asn Gly
            100                 105                 110

His Ser Phe Pro Leu Thr Phe Gly Ala Gly Thr Lys Leu Glu Leu Arg
            115                 120                 125

Arg Gly Gly Gly Ser Gly Gly Gly Ser Gly Gly Gly Gly Ser
        130                 135                 140

Gln Val Gln Leu Gln Gln Pro Gly Thr Glu Leu Val Arg Pro Gly Ser
145                 150                 155                 160

Ser Val Lys Leu Ser Cys Lys Ala Ser Gly Tyr Thr Phe Thr Ser Tyr
                165                 170                 175

Trp Val Asn Trp Val Lys Gln Arg Pro Asp Gln Gly Leu Glu Trp Ile
            180                 185                 190

Gly Arg Ile Asp Pro Tyr Asp Ser Glu Thr His Tyr Asn Gln Lys Phe
        195                 200                 205

Thr Asp Lys Ala Ile Ser Thr Ile Asp Thr Ser Ser Asn Thr Ala Tyr
    210                 215                 220

Met Gln Leu Ser Thr Leu Thr Ser Asp Ala Ser Ala Val Tyr Tyr Cys
225                 230                 235                 240

Ser Arg Ser Pro Arg Asp Ser Ser Thr Asn Leu Ala Asp Trp Gly Gln
                245                 250                 255

Gly Thr Leu Val Thr Val Ser Ser Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Arg Ser Lys
                325                 330                 335

Arg Ser Arg Leu Leu His Ser Asp Tyr Met Asn Met Thr Pro Arg Arg
            340                 345                 350

Pro Gly Pro Thr Arg Lys His Tyr Gln Pro Tyr Ala Pro Pro Arg Asp
        355                 360                 365

Phe Ala Ala Tyr Arg Ser Lys Arg Gly Arg Lys Lys Leu Leu Tyr Ile
    370                 375                 380

Phe Lys Gln Pro Phe Met Arg Pro Val Gln Thr Thr Gln Glu Glu Asp
385                 390                 395                 400

Gly Cys Ser Cys Arg Phe Pro Glu Glu Glu Glu Gly Gly Cys Glu Leu
                405                 410                 415

Arg Val Lys Phe Ser Arg Ser Ala Asp Ala Pro Ala Tyr Gln Gln Gly
            420                 425                 430

Gln Asn Gln Leu Tyr Asn Glu Leu Asn Leu Gly Arg Arg Glu Glu Tyr
        435                 440                 445

Asp Val Leu Asp Lys Arg Arg Gly Arg Asp Pro Glu Met Gly Gly Lys
    450                 455                 460

Pro Gln Arg Arg Lys Asn Pro Gln Glu Gly Leu Tyr Asn Glu Leu Gln
465                 470                 475                 480

Lys Asp Lys Met Ala Glu Ala Tyr Ser Glu Ile Gly Met Lys Gly Glu
                485                 490                 495

Arg Arg Arg Gly Lys Gly His Asp Gly Leu Tyr Gln Gly Leu Ser Thr
            500                 505                 510
```

Ala Thr Lys Asp Thr Tyr Asp Ala Leu His Met Gln Ala Leu Pro Pro
            515                 520                 525

Arg

<210> SEQ ID NO 12
<211> LENGTH: 525
<212> TYPE: PRT
<213> ORGANISM: Artificial Sequence
<220> FEATURE:
<223> OTHER INFORMATION: Synthetic sequence

<400> SEQUENCE: 12

Met Ala Leu Pro Val Thr Ala Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Ser Ala Ser Ser
        35                  40                  45

Ser Val Ser Tyr Met Asn Trp Tyr Gln Gln Thr Pro Gly Lys Ala Pro
    50                  55                  60

Lys Arg Trp Ile Tyr Asp Thr Ser Lys Leu Ala Ser Gly Val Pro Ser
65                  70                  75                  80

Arg Phe Ser Gly Ser Gly Ser Gly Thr Asp Tyr Thr Phe Thr Ile Ser
                85                  90                  95

Ser Leu Gln Pro Glu Asp Ile Ala Thr Tyr Tyr Cys Gln Gln Trp Ser
            100                 105                 110

Ser Asn Pro Phe Thr Phe Gly Gln Gly Thr Lys Leu Gln Ile Gly Gly
        115                 120                 125

Gly Gly Ser Gly Gly Gly Ser Gly Gly Gly Ser Gln Val Gln
    130                 135                 140

Leu Val Gln Ser Gly Gly Gly Val Val Gln Pro Gly Arg Ser Leu Arg
145                 150                 155                 160

Leu Ser Cys Lys Ala Ser Gly Tyr Thr Phe Thr Arg Tyr Thr Met His
                165                 170                 175

Trp Val Arg Gln Ala Pro Gly Lys Gly Leu Glu Trp Ile Gly Tyr Ile
            180                 185                 190

Asn Pro Ser Arg Gly Tyr Thr Asn Tyr Asn Gln Lys Val Lys Asp Arg
        195                 200                 205

Phe Thr Ile Ser Arg Asp Asn Ser Lys Asn Thr Ala Phe Leu Gln Met
    210                 215                 220

Asp Ser Leu Arg Pro Glu Asp Thr Gly Val Tyr Phe Cys Ala Arg Tyr
225                 230                 235                 240

Tyr Asp Asp His Tyr Cys Leu Asp Tyr Trp Gly Gln Gly Thr Pro Val
                245                 250                 255

Thr Val Ser Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Arg Ser Lys Arg Ser Arg Leu
                325                 330                 335

Leu His Ser Asp Tyr Met Asn Met Thr Pro Arg Arg Pro Gly Pro Thr

```
              340                 345                 350
Arg Lys His Tyr Gln Pro Tyr Ala Pro Pro Arg Asp Phe Ala Ala Tyr
            355                 360                 365
Arg Ser Lys Arg Gly Arg Lys Lys Leu Leu Tyr Ile Phe Lys Gln Pro
        370                 375                 380
Phe Met Arg Pro Val Gln Thr Thr Gln Glu Glu Asp Gly Cys Ser Cys
385                 390                 395                 400
Arg Phe Pro Glu Glu Glu Glu Gly Gly Cys Glu Leu Arg Val Lys Phe
                405                 410                 415
Ser Arg Ser Ala Asp Ala Pro Ala Tyr Gln Gln Gly Gln Asn Gln Leu
            420                 425                 430
Tyr Asn Glu Leu Asn Leu Gly Arg Arg Glu Glu Tyr Asp Val Leu Asp
        435                 440                 445
Lys Arg Arg Gly Arg Asp Pro Glu Met Gly Gly Lys Pro Gln Arg Arg
    450                 455                 460
Lys Asn Pro Gln Glu Gly Leu Tyr Asn Glu Leu Gln Lys Asp Lys Met
465                 470                 475                 480
Ala Glu Ala Tyr Ser Glu Ile Gly Met Lys Gly Glu Arg Arg Arg Gly
                485                 490                 495
Lys Gly His Asp Gly Leu Tyr Gln Gly Leu Ser Thr Ala Thr Lys Asp
            500                 505                 510
Thr Tyr Asp Ala Leu His Met Gln Ala Leu Pro Pro Arg
        515                 520                 525

<210> SEQ ID NO 13
<211> LENGTH: 535
<212> TYPE: PRT
<213> ORGANISM: Artificial Sequence
<220> FEATURE:
<223> OTHER INFORMATION: Synethic sequence

<400> SEQUENCE: 13

Met Ala Leu Pro Val Thr Ala Leu Leu Leu Pro Leu Ala Leu Leu Leu
1               5                   10                  15
His Ala Ala Arg Pro Asp Ile Val Met Thr Gln Ser Pro Asp Ser Leu
            20                  25                  30
Ala Val Ser Leu Gly Glu Arg Val Thr Met Asn Cys Lys Ser Ser Gln
        35                  40                  45
Ser Leu Leu Tyr Ser Thr Asn Gln Lys Asn Tyr Leu Ala Trp Tyr Gln
    50                  55                  60
Gln Lys Pro Gly Gln Ser Pro Lys Leu Leu Ile Tyr Trp Ala Ser Thr
65                  70                  75                  80
Arg Glu Ser Gly Val Pro Asp Arg Phe Ser Gly Ser Gly Ser Gly Thr
                85                  90                  95
Asp Phe Thr Leu Thr Ile Ser Ser Val Gln Ala Glu Asp Val Ala Val
            100                 105                 110
Tyr Tyr Cys Gln Gln Tyr Tyr Ser Tyr Arg Thr Phe Gly Gly Gly Thr
        115                 120                 125
Lys Leu Glu Ile Lys Gly Gly Gly Gly Ser Gly Gly Gly Gly Ser Gly
    130                 135                 140
Gly Gly Gly Ser Gln Val Gln Leu Gln Gln Ser Gly Pro Glu Val Val
145                 150                 155                 160
Lys Pro Gly Ala Ser Val Lys Met Ser Cys Lys Ala Ser Gly Tyr Thr
                165                 170                 175
Phe Thr Ser Tyr Val Ile His Trp Val Arg Gln Lys Pro Gly Gln Gly
```

```
            180                 185                 190
Leu Asp Trp Ile Gly Tyr Ile Asn Pro Tyr Asn Asp Gly Thr Asp Tyr
        195                 200                 205

Asp Glu Lys Phe Lys Gly Lys Ala Thr Leu Thr Ser Asp Thr Ser Thr
    210                 215                 220

Ser Thr Ala Tyr Met Glu Leu Ser Ser Leu Arg Ser Glu Asp Thr Ala
225                 230                 235                 240

Val Tyr Tyr Cys Ala Arg Glu Lys Asp Asn Tyr Ala Thr Gly Ala Trp
                245                 250                 255

Phe Ala Tyr Trp Gly Gln Gly Thr Leu Val Thr Val Ser Ser Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Arg Ser Lys Arg Ser Arg Leu Leu His Ser Asp Tyr Met
            340                 345                 350

Asn Met Thr Pro Arg Arg Pro Gly Pro Thr Arg Lys His Tyr Gln Pro
        355                 360                 365

Tyr Ala Pro Pro Arg Asp Phe Ala Ala Tyr Arg Ser Lys Arg Gly Arg
    370                 375                 380

Lys Lys Leu Leu Tyr Ile Phe Lys Gln Pro Phe Met Arg Pro Val Gln
385                 390                 395                 400

Thr Thr Gln Glu Glu Asp Gly Cys Ser Cys Arg Phe Pro Glu Glu Glu
                405                 410                 415

Glu Gly Gly Cys Glu Leu Arg Val Lys Phe Ser Arg Ser Ala Asp Ala
            420                 425                 430

Pro Ala Tyr Gln Gln Gly Gln Asn Gln Leu Tyr Asn Glu Leu Asn Leu
        435                 440                 445

Gly Arg Arg Glu Glu Tyr Asp Val Leu Asp Lys Arg Arg Gly Arg Asp
    450                 455                 460

Pro Glu Met Gly Gly Lys Pro Gln Arg Arg Lys Asn Pro Gln Glu Gly
465                 470                 475                 480

Leu Tyr Asn Glu Leu Gln Lys Asp Lys Met Ala Glu Ala Tyr Ser Glu
                485                 490                 495

Ile Gly Met Lys Gly Glu Arg Arg Gly Lys Gly His Asp Gly Leu
            500                 505                 510

Tyr Gln Gly Leu Ser Thr Ala Thr Lys Asp Thr Tyr Asp Ala Leu His
        515                 520                 525

Met Gln Ala Leu Pro Pro Arg
    530                 535

<210> SEQ ID NO 14
<211> LENGTH: 536
<212> TYPE: PRT
<213> ORGANISM: Artificial Sequence
<220> FEATURE:
<223> OTHER INFORMATION: Synthetic sequence

<400> SEQUENCE: 14

Met Ala Leu Pro Val Thr Ala Leu Leu Leu Pro Leu Ala Leu Leu Leu
```

```
1               5                   10                  15
His Ala Ala Arg Pro Asp Ile Val Met Thr Gln Ser Pro Asp Ser Leu
                20                  25                  30

Ala Val Ser Leu Gly Glu Arg Ala Thr Ile Asn Cys Arg Ala Ser Lys
                35                  40                  45

Ser Val Ser Thr Ser Gly Tyr Ser Tyr Ile Tyr Trp Tyr Gln Gln Lys
                50                  55                  60

Pro Gly Gln Pro Pro Lys Leu Leu Ile Tyr Leu Ala Ser Ile Leu Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Leu Gln Ala Glu Asp Val Ala Val Tyr Tyr
                100                 105                 110

Cys Gln His Ser Arg Glu Leu Pro Trp Thr Phe Gly Gln Gly Thr Lys
                115                 120                 125

Val Glu Ile Lys Gly Gly Gly Gly Ser Gly Gly Gly Gly Ser Gly Gly
                130                 135                 140

Gly Gly Ser Glu Glu Gln Leu Val Glu Ser Gly Gly Gly Leu Val Lys
145                 150                 155                 160

Pro Gly Gly Ser Leu Arg Leu Ser Cys Ala Ala Ser Gly Phe Ser Phe
                165                 170                 175

Ser Asp Cys Arg Met Tyr Trp Leu Arg Gln Ala Pro Gly Lys Gly Leu
                180                 185                 190

Glu Trp Ile Gly Val Ile Ser Val Lys Ser Glu Asn Tyr Gly Ala Asn
                195                 200                 205

Tyr Ala Glu Ser Val Arg Gly Arg Phe Thr Ile Ser Arg Asp Asp Ser
                210                 215                 220

Lys Asn Thr Val Tyr Leu Gln Met Asn Ser Leu Lys Thr Glu Asp Thr
225                 230                 235                 240

Ala Val Tyr Tyr Cys Ser Ala Ser Tyr Tyr Arg Tyr Asp Val Gly Ala
                245                 250                 255

Trp Phe Ala Tyr Trp Gly Gln Gly Thr Leu Val Thr Val Ser Ser Thr
                260                 265                 270

Thr Thr Pro Ala Pro Arg Pro Pro Thr Pro Ala Pro Thr Ile Ala Ser
                275                 280                 285

Gln Pro Leu Ser Leu Arg Pro Glu Ala Cys Arg Pro Ala Ala Gly Gly
                290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Arg Ser Lys Arg Ser Arg Leu Leu His Ser Asp Tyr
                340                 345                 350

Met Asn Met Thr Pro Arg Arg Pro Gly Pro Thr Arg Lys His Tyr Gln
                355                 360                 365

Pro Tyr Ala Pro Pro Arg Asp Phe Ala Ala Tyr Arg Ser Lys Arg Gly
                370                 375                 380

Arg Lys Lys Leu Leu Tyr Ile Phe Lys Gln Pro Phe Met Arg Pro Val
385                 390                 395                 400

Gln Thr Thr Gln Glu Glu Asp Gly Cys Ser Cys Arg Phe Pro Glu Glu
                405                 410                 415

Glu Glu Gly Gly Cys Glu Leu Arg Val Lys Phe Ser Arg Ser Ala Asp
                420                 425                 430
```

Ala Pro Ala Tyr Gln Gln Gly Gln Asn Gln Leu Tyr Asn Glu Leu Asn
        435                 440                 445

Leu Gly Arg Arg Glu Glu Tyr Asp Val Leu Asp Lys Arg Arg Gly Arg
    450                 455                 460

Asp Pro Glu Met Gly Gly Lys Pro Gln Arg Arg Lys Asn Pro Gln Glu
465                 470                 475                 480

Gly Leu Tyr Asn Glu Leu Gln Lys Asp Lys Met Ala Glu Ala Tyr Ser
                485                 490                 495

Glu Ile Gly Met Lys Gly Glu Arg Arg Arg Gly Lys Gly His Asp Gly
                500                 505                 510

Leu Tyr Gln Gly Leu Ser Thr Ala Thr Lys Asp Thr Tyr Asp Ala Leu
    515                 520                 525

His Met Gln Ala Leu Pro Pro Arg
    530                 535

<210> SEQ ID NO 15
<211> LENGTH: 526
<212> TYPE: PRT
<213> ORGANISM: Artificial Sequence
<220> FEATURE:
<223> OTHER INFORMATION: Synthetic sequence

<400> SEQUENCE: 15

Met Ala Leu Pro Val Thr Ala Leu Leu Leu Pro Leu Ala Leu Leu Leu
1               5                   10                  15

His Ala Ala Arg Pro Asp Ile Gln Val Thr Gln Ser Pro Ser Ser Leu
            20                  25                  30

Ser Ala Ser Leu Gly Glu Arg Ile Ser Leu Thr Cys Arg Thr Ser Gln
        35                  40                  45

Asp Ile Ser Asn Tyr Leu Asn Trp Phe Gln Gln Lys Pro Asp Gly Thr
    50                  55                  60

Phe Lys Arg Leu Ile Tyr Ala Thr Ser Ser Leu Asp Ser Gly Val Pro
65                  70                  75                  80

Lys Arg Phe Ser Gly Ser Gly Ser Asp Tyr Ser Leu Thr Ile
                85                  90                  95

Ser Ser Leu Glu Ser Glu Asp Phe Ala Asp Tyr Tyr Cys Leu Gln Tyr
                100                 105                 110

Ala Ser Tyr Pro Phe Thr Phe Gly Ser Gly Thr Lys Leu Glu Ile Lys
            115                 120                 125

Gly Gly Gly Gly Ser Gly Gly Gly Ser Gly Gly Gly Ser Glu
        130                 135                 140

Val Gln Leu Gln Glu Ser Gly Pro Gly Leu Val Lys Pro Ser Gln Thr
145                 150                 155                 160

Leu Ser Leu Thr Cys Ser Val Thr Gly Tyr Ser Ile Thr Ser Gly Tyr
                165                 170                 175

Tyr Trp His Trp Ile Arg Gln Phe Pro Gly Asn Lys Leu Gln Trp Met
            180                 185                 190

Gly Tyr Ile Ser Tyr Ser Gly Phe Thr Asn Tyr Lys Thr Ser Leu Ile
        195                 200                 205

Asn Arg Ile Ser Ile Thr His Asp Thr Ser Glu Asn Gln Phe Phe Leu
    210                 215                 220

Asn Leu Asn Ser Val Thr Thr Glu Asp Thr Ala Thr Tyr Tyr Cys Ala
225                 230                 235                 240

Gly Asp Arg Thr Gly Ser Trp Phe Ala Tyr Trp Gly Gln Gly Thr Leu
                245                 250                 255

Val Thr Val Ser Ala Thr Thr Pro Ala Pro Arg Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
        290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Arg Ser Lys Arg Ser Arg
                325                 330                 335

Leu Leu His Ser Asp Tyr Met Asn Met Thr Pro Arg Arg Pro Gly Pro
            340                 345                 350

Thr Arg Lys His Tyr Gln Pro Tyr Ala Pro Pro Arg Asp Phe Ala Ala
            355                 360                 365

Tyr Arg Ser Lys Arg Gly Arg Lys Lys Leu Leu Tyr Ile Phe Lys Gln
        370                 375                 380

Pro Phe Met Arg Pro Val Gln Thr Thr Gln Glu Glu Asp Gly Cys Ser
385                 390                 395                 400

Cys Arg Phe Pro Glu Glu Glu Glu Gly Gly Cys Glu Leu Arg Val Lys
                405                 410                 415

Phe Ser Arg Ser Ala Asp Ala Pro Ala Tyr Gln Gln Gly Gln Asn Gln
            420                 425                 430

Leu Tyr Asn Glu Leu Asn Leu Gly Arg Arg Glu Glu Tyr Asp Val Leu
        435                 440                 445

Asp Lys Arg Arg Gly Arg Asp Pro Glu Met Gly Gly Lys Pro Gln Arg
        450                 455                 460

Arg Lys Asn Pro Gln Glu Gly Leu Tyr Asn Glu Leu Gln Lys Asp Lys
465                 470                 475                 480

Met Ala Glu Ala Tyr Ser Glu Ile Gly Met Lys Gly Glu Arg Arg Arg
                485                 490                 495

Gly Lys Gly His Asp Gly Leu Tyr Gln Gly Leu Ser Thr Ala Thr Lys
            500                 505                 510

Asp Thr Tyr Asp Ala Leu His Met Gln Ala Leu Pro Pro Arg
            515                 520                 525

<210> SEQ ID NO 16
<211> LENGTH: 329
<212> TYPE: PRT
<213> ORGANISM: Artificial Sequence
<220> FEATURE:
<223> OTHER INFORMATION: Synthetic sequence

<400> SEQUENCE: 16

Met Ala Leu Pro Val Thr Ala Leu Leu Leu Pro Leu Ala Leu Leu Leu
1               5                   10                  15

His Ala Ala Arg Pro Asp Ile Gln Val Thr Gln Ser Pro Ser Ser Leu
            20                  25                  30

Ser Ala Ser Leu Gly Glu Arg Ile Ser Leu Thr Cys Arg Thr Ser Gln
        35                  40                  45

Asp Ile Ser Asn Tyr Leu Asn Trp Phe Gln Gln Lys Pro Asp Gly Thr
    50                  55                  60

Phe Lys Arg Leu Ile Tyr Ala Thr Ser Ser Leu Asp Ser Gly Val Pro
65                  70                  75                  80

Lys Arg Phe Ser Gly Ser Gly Ser Gly Ser Asp Tyr Ser Leu Thr Ile
                85                  90                  95

```
Ser Ser Leu Glu Ser Glu Asp Phe Ala Asp Tyr Tyr Cys Leu Gln Tyr
            100                 105                 110

Ala Ser Tyr Pro Phe Thr Phe Gly Ser Gly Thr Lys Leu Glu Ile Lys
            115                 120                 125

Gly Gly Gly Gly Ser Gly Gly Gly Ser Gly Gly Gly Gly Ser Glu
            130                 135                 140

Val Gln Leu Gln Glu Ser Gly Pro Gly Leu Val Lys Pro Ser Gln Thr
145                 150                 155                 160

Leu Ser Leu Thr Cys Ser Val Thr Gly Tyr Ser Ile Thr Ser Gly Tyr
            165                 170                 175

Tyr Trp His Trp Ile Arg Gln Phe Pro Gly Asn Lys Leu Gln Trp Met
            180                 185                 190

Gly Tyr Ile Ser Tyr Ser Gly Phe Thr Asn Tyr Lys Thr Ser Leu Ile
            195                 200                 205

Asn Arg Ile Ser Ile Thr His Asp Thr Ser Glu Asn Gln Phe Phe Leu
            210                 215                 220

Asn Leu Asn Ser Val Thr Thr Glu Asp Thr Ala Thr Tyr Tyr Cys Ala
225                 230                 235                 240

Gly Asp Arg Thr Gly Ser Trp Phe Ala Tyr Trp Gly Gln Gly Thr Leu
            245                 250                 255

Val Thr Val Ser Ala Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
            275                 280                 285

Arg Pro Ala Ala Gly Gly Ala Val His Thr Arg Gly Asp Phe Ala Cys
            290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys
            325

<210> SEQ ID NO 17
<211> LENGTH: 540
<212> TYPE: PRT
<213> ORGANISM: Artificial Sequence
<220> FEATURE:
<223> OTHER INFORMATION: Synthetic sequence

<400> SEQUENCE: 17

Met Ala Leu Pro Val Thr Ala Leu Leu Leu Pro Leu Ala Leu Leu Leu
1               5                   10                  15

His Ala Ala Arg Pro Gly Ala Gln Pro Ala Met Ala Ala Tyr Lys Asp
            20                  25                  30

Ile Gln Met Thr Gln Thr Thr Ser Ser Leu Ser Ala Ser Leu Gly Asp
            35                  40                  45

Arg Val Thr Ile Ser Cys Ser Ala Ser Gln Gly Ile Ser Asn Tyr Leu
        50                  55                  60

Asn Trp Tyr Gln Gln Lys Pro Asp Gly Thr Asn Lys Leu Leu Ile Tyr
65              70                  75                  80

Tyr Thr Ser Ser Leu His Ser Gly Val Pro Ser Arg Phe Ser Gly Ser
                85                  90                  95

Gly Ser Gly Thr Asp Tyr Ser Leu His Ser Asn Leu Glu Pro Glu Asp
            100                 105                 110

Ile Ala Thr Tyr Tyr Cys Gln Gln Tyr Ser Lys Leu Pro Tyr Thr Phe
            115                 120                 125
```

```
Gly Gly Gly Thr Lys Leu Glu Ile Lys Arg Gly Gly Gly Ser Gly
            130                 135                 140
Gly Gly Gly Ser Gly Gly Gly Ser Gly Gly Gly Ser Glu Val
145                 150                 155                 160
Gln Leu Val Glu Ser Gly Gly Gly Leu Val Lys Pro Gly Gly Ser Leu
                    165                 170                 175
Lys Leu Ser Cys Ala Ala Ser Gly Leu Thr Phe Ser Ser Tyr Ala Met
                180                 185                 190
Ser Trp Asn Arg Gln Thr Pro Glu Lys Arg Leu Glu Trp Val Ala Ser
            195                 200                 205
Ile Ser Ser Gly Gly Phe Thr Tyr Tyr Pro Asp Ser Asn Lys Gly Arg
210                 215                 220
Phe Thr Ile Ser Arg Asp Asn Ala Arg Asn Ile Leu Tyr Leu Gln Met
225                 230                 235                 240
Ser Ser Leu Arg Ser Glu Asp Thr Ala Met Tyr Tyr Cys Ala Arg Asp
                245                 250                 255
Glu Val Arg Gly Tyr Leu Asp Val Trp Gly Ala Gly Thr Thr Val Thr
                260                 265                 270
Val Ser Ser Thr Thr Thr Pro Ala Pro Arg Pro Pro Thr Pro Ala Pro
            275                 280                 285
Thr Ile Ala Ser Gln Pro Leu Ser Leu Arg Pro Glu Ala Cys Arg Pro
290                 295                 300
Ala Ala Gly Gly Ala Val His Thr Arg Gly Leu Asp Phe Ala Cys Asp
305                 310                 315                 320
Ile Tyr Ile Trp Ala Pro Leu Ala Gly Thr Cys Gly Val Leu Leu Leu
                325                 330                 335
Ser Leu Val Ile Thr Leu Tyr Cys Arg Ser Lys Arg Ser Arg Leu Leu
                340                 345                 350
His Ser Asp Tyr Met Asn Met Thr Pro Arg Arg Pro Gly Pro Thr Arg
            355                 360                 365
Lys His Tyr Gln Pro Tyr Ala Pro Pro Arg Asp Phe Ala Ala Tyr Arg
370                 375                 380
Ser Lys Arg Gly Arg Lys Lys Leu Leu Tyr Ile Phe Lys Gln Pro Phe
385                 390                 395                 400
Met Arg Pro Val Gln Thr Thr Gln Glu Glu Asp Gly Cys Ser Cys Arg
                405                 410                 415
Phe Pro Glu Glu Glu Glu Gly Gly Cys Glu Leu Arg Val Lys Phe Ser
                420                 425                 430
Arg Ser Ala Asp Ala Pro Ala Tyr Gln Gln Gly Gln Asn Gln Leu Tyr
            435                 440                 445
Asn Glu Leu Asn Leu Gly Arg Arg Glu Glu Tyr Asp Val Leu Asp Lys
450                 455                 460
Arg Arg Gly Arg Asp Pro Glu Met Gly Gly Lys Pro Gln Arg Arg Lys
465                 470                 475                 480
Asn Pro Gln Glu Gly Leu Tyr Asn Glu Leu Gln Lys Asp Lys Met Ala
                485                 490                 495
Glu Ala Tyr Ser Glu Ile Gly Met Lys Gly Glu Arg Arg Arg Gly Lys
                500                 505                 510
Gly His Asp Gly Leu Tyr Gln Gly Leu Ser Thr Ala Thr Lys Asp Thr
            515                 520                 525
Tyr Asp Ala Leu His Met Gln Ala Leu Pro Pro Arg
530                 535                 540
```

<210> SEQ ID NO 18
<211> LENGTH: 529
<212> TYPE: PRT
<213> ORGANISM: Artificial Sequence
<220> FEATURE:
<223> OTHER INFORMATION: Synthetic sequence

<400> SEQUENCE: 18

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Lys Ala Ser Gln
        35                  40                  45

Asn Ile Asp Lys Tyr Leu Asn Trp Tyr Gln Gln Lys Pro Gly Lys Ala
    50                  55                  60

Pro Lys Leu Leu Ile Tyr Asn Thr Asn Asn Leu Gln Thr Gly Val Pro
65                  70                  75                  80

Ser Arg Phe Ser Gly Ser Gly Ser Gly Thr Asp Phe Thr Phe Thr Ile
                85                  90                  95

Ser Ser Leu Gln Pro Glu Asp Ile Ala Thr Tyr Tyr Cys Leu Gln His
            100                 105                 110

Ile Ser Arg Pro Arg Thr Phe Gly Gln Gly Thr Lys Val Glu Ile Lys
        115                 120                 125

Gly Gly Gly Gly Ser Gly Gly Gly Ser Gly Gly Gly Ser Gln
    130                 135                 140

Val Gln Leu Gln Glu Ser Gly Pro Gly Leu Val Arg Pro Ser Gln Thr
145                 150                 155                 160

Leu Ser Leu Thr Cys Thr Val Ser Gly Phe Thr Phe Thr Asp Phe Tyr
                165                 170                 175

Met Asn Trp Val Arg Gln Pro Pro Gly Arg Gly Leu Glu Trp Ile Gly
            180                 185                 190

Phe Ile Arg Asp Lys Ala Lys Gly Tyr Thr Thr Glu Tyr Asn Pro Ser
        195                 200                 205

Val Lys Gly Arg Val Thr Met Leu Val Asp Thr Ser Lys Asn Gln Phe
    210                 215                 220

Ser Leu Arg Leu Ser Ser Val Thr Ala Ala Asp Thr Ala Val Tyr Tyr
225                 230                 235                 240

Cys Ala Arg Glu Gly His Thr Ala Ala Pro Phe Asp Tyr Trp Gly Gln
                245                 250                 255

Gly Ser Leu Val Thr Val Ser Ser Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Arg Ser Lys
                325                 330                 335

Arg Ser Arg Leu Leu His Ser Asp Tyr Met Asn Met Thr Pro Arg Arg
            340                 345                 350

Pro Gly Pro Thr Arg Lys His Tyr Gln Pro Tyr Ala Pro Pro Arg Asp
        355                 360                 365
```

```
Phe Ala Ala Tyr Arg Ser Lys Arg Gly Arg Lys Lys Leu Leu Tyr Ile
    370                 375                 380
Phe Lys Gln Pro Phe Met Arg Pro Val Gln Thr Thr Gln Glu Glu Asp
385                 390                 395                 400
Gly Cys Ser Cys Arg Phe Pro Glu Glu Glu Gly Gly Cys Glu Leu
                405                 410                 415
Arg Val Lys Phe Ser Arg Ser Ala Asp Ala Pro Ala Tyr Gln Gln Gly
                420                 425                 430
Gln Asn Gln Leu Tyr Asn Glu Leu Asn Leu Gly Arg Arg Glu Glu Tyr
            435                 440                 445
Asp Val Leu Asp Lys Arg Arg Gly Arg Asp Pro Glu Met Gly Gly Lys
    450                 455                 460
Pro Gln Arg Arg Lys Asn Pro Gln Glu Gly Leu Tyr Asn Glu Leu Gln
465                 470                 475                 480
Lys Asp Lys Met Ala Glu Ala Tyr Ser Glu Ile Gly Met Lys Gly Glu
                485                 490                 495
Arg Arg Arg Gly Lys Gly His Asp Gly Leu Tyr Gln Gly Leu Ser Thr
                500                 505                 510
Ala Thr Lys Asp Thr Tyr Asp Ala Leu His Met Gln Ala Leu Pro Pro
            515                 520                 525
Arg

<210> SEQ ID NO 19
<211> LENGTH: 185
<212> TYPE: PRT
<213> ORGANISM: Artificial Sequence
<220> FEATURE:
<223> OTHER INFORMATION: Synthetic sequence

<400> SEQUENCE: 19

Lys Glu Ile Thr Asn Ala Leu Glu Thr Trp Gly Ala Leu Gly Gln Asp
1               5                   10                  15
Ile Asn Leu Asp Ile Pro Ser Phe Gln Met Ser Asp Asp Ile Asp Asp
                20                  25                  30
Ile Lys Trp Glu Lys Thr Ser Asp Lys Lys Lys Ile Ala Gln Phe Arg
            35                  40                  45
Lys Glu Lys Glu Thr Phe Lys Glu Lys Asp Thr Tyr Lys Leu Phe Lys
    50                  55                  60
Asn Gly Thr Leu Lys Ile Lys His Leu Lys Thr Asp Asp Gln Asp Ile
65                  70                  75                  80
Tyr Lys Val Ser Ile Tyr Asp Thr Lys Gly Lys Asn Val Leu Glu Lys
                85                  90                  95
Ile Phe Asp Leu Lys Ile Gln Glu Arg Val Ser Lys Pro Lys Ile Ser
                100                 105                 110
Trp Thr Cys Ile Asn Thr Thr Leu Thr Cys Glu Val Met Asn Gly Thr
            115                 120                 125
Asp Pro Glu Leu Asn Leu Tyr Gln Asp Gly Lys His Leu Lys Leu Ser
        130                 135                 140
Gln Arg Val Ile Thr His Lys Trp Thr Thr Ser Leu Ser Ala Lys Phe
145                 150                 155                 160
Lys Cys Thr Ala Gly Asn Lys Val Ser Lys Glu Ser Ser Val Glu Pro
                165                 170                 175
Val Ser Cys Pro Glu Lys Gly Leu Asp
                180                 185
```

-continued

<210> SEQ ID NO 20
<211> LENGTH: 104
<212> TYPE: PRT
<213> ORGANISM: Artificial Sequence
<220> FEATURE:
<223> OTHER INFORMATION: Synthetic sequence

<400> SEQUENCE: 20

```
Asp Gly Asn Glu Glu Met Gly Gly Ile Thr Gln Thr Pro Tyr Lys Val
1               5                   10                  15

Ser Ile Ser Gly Thr Thr Val Ile Leu Thr Cys Pro Gln Tyr Pro Gly
            20                  25                  30

Ser Glu Ile Leu Trp Gln His Asn Asp Lys Asn Ile Gly Gly Asp Glu
        35                  40                  45

Asp Asp Lys Asn Ile Gly Ser Asp Glu Asp His Leu Ser Leu Lys Glu
    50                  55                  60

Phe Ser Glu Leu Glu Gln Ser Gly Tyr Tyr Val Cys Tyr Pro Arg Gly
65                  70                  75                  80

Ser Lys Pro Glu Asp Ala Asn Phe Tyr Leu Tyr Leu Arg Ala Arg Val
                85                  90                  95

Cys Glu Asn Cys Met Glu Met Asp
            100
```

<210> SEQ ID NO 21
<211> LENGTH: 371
<212> TYPE: PRT
<213> ORGANISM: Artificial Sequence
<220> FEATURE:
<223> OTHER INFORMATION: Synthetic sequence

<400> SEQUENCE: 21

```
Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Val Tyr Lys Lys Glu Gly Glu
            180                 185                 190

Gln Val Glu Phe Ser Phe Pro Leu Ala Phe Thr Val Glu Lys Leu Thr
        195                 200                 205
```

Gly Ser Gly Glu Leu Trp Trp Gln Ala Glu Arg Ala Ser Ser Ser Lys
210                 215                 220

Ser Trp Ile Thr Phe Asp Leu Lys Asn Lys Glu Val Ser Val Lys Arg
225                 230                 235                 240

Val Thr Gln Asp Pro Lys Leu Gln Met Gly Lys Lys Leu Pro Leu His
                245                 250                 255

Leu Thr Leu Pro Gln Ala Leu Pro Gln Tyr Ala Gly Ser Gly Asn Leu
            260                 265                 270

Thr Leu Ala Leu Glu Ala Lys Thr Gly Lys Leu His Gln Glu Val Asn
        275                 280                 285

Leu Val Val Met Arg Ala Thr Gln Leu Gln Lys Asn Leu Thr Cys Glu
290                 295                 300

Val Trp Gly Pro Thr Ser Pro Lys Leu Met Leu Ser Leu Lys Leu Glu
305                 310                 315                 320

Asn Lys Glu Ala Lys Val Ser Lys Arg Glu Lys Ala Val Trp Val Leu
                325                 330                 335

Asn Pro Glu Ala Gly Met Trp Gln Cys Leu Leu Ser Asp Ser Gly Gln
            340                 345                 350

Val Leu Leu Glu Ser Asn Ile Lys Val Leu Pro Thr Trp Ser Thr Pro
        355                 360                 365

Val Gln Pro
370

<210> SEQ ID NO 22
<211> LENGTH: 348
<212> TYPE: PRT
<213> ORGANISM: Artificial Sequence
<220> FEATURE:
<223> OTHER INFORMATION: Synthetic sequence

<400> SEQUENCE: 22

Arg Leu Ser Trp Tyr Asp Pro Asp Phe Gln Ala Arg Leu Thr Arg Ser
1               5                   10                  15

Asn Ser Lys Cys Gln Gly Gln Leu Glu Val Tyr Leu Lys Asp Gly Trp
                20                  25                  30

His Met Val Cys Ser Gln Ser Trp Gly Arg Ser Ser Lys Gln Trp Glu
            35                  40                  45

Asp Pro Ser Gln Ala Ser Lys Val Cys Gln Arg Leu Asn Cys Gly Val
        50                  55                  60

Pro Leu Ser Leu Gly Pro Phe Leu Val Thr Tyr Thr Pro Gln Ser Ser
65                  70                  75                  80

Ile Ile Cys Tyr Gly Gln Leu Gly Ser Phe Ser Asn Cys Ser His Ser
                85                  90                  95

Arg Asn Asp Met Cys His Ser Leu Gly Leu Thr Cys Leu Glu Pro Gln
            100                 105                 110

Lys Thr Thr Pro Pro Thr Thr Arg Pro Pro Pro Thr Thr Thr Pro Glu
        115                 120                 125

Pro Thr Ala Pro Pro Arg Leu Gln Leu Val Ala Gln Ser Gly Gly Gln
        130                 135                 140

His Cys Ala Gly Val Val Glu Phe Tyr Ser Gly Ser Leu Gly Gly Thr
145                 150                 155                 160

Ile Ser Tyr Glu Ala Gln Asp Lys Thr Gln Asp Leu Glu Asn Phe Leu
                165                 170                 175

Cys Asn Asn Leu Gln Cys Gly Ser Phe Leu Lys His Leu Pro Glu Thr
            180                 185                 190

```
Glu Ala Gly Arg Ala Gln Asp Pro Gly Glu Pro Arg His Gln Pro
            195                 200                 205

Leu Pro Ile Gln Trp Lys Ile Gln Asn Ser Ser Cys Thr Ser Leu Glu
210                 215                 220

His Cys Phe Arg Lys Ile Lys Pro Gln Lys Ser Gly Arg Val Leu Ala
225                 230                 235                 240

Leu Leu Cys Ser Gly Phe Gln Pro Lys Val Gln Ser Arg Leu Val Gly
                245                 250                 255

Gly Ser Ser Ile Cys Glu Gly Thr Val Glu Val Arg Gln Gly Ala Gln
                260                 265                 270

Trp Ala Ala Leu Cys Asp Ser Ser Ser Ala Arg Ser Ser Leu Arg Trp
            275                 280                 285

Glu Glu Val Cys Arg Glu Gln Gln Cys Gly Ser Val Asn Ser Tyr Arg
290                 295                 300

Val Leu Asp Ala Gly Asp Pro Thr Ser Arg Gly Leu Phe Cys Pro His
305                 310                 315                 320

Gln Lys Leu Ser Gln Cys His Glu Leu Trp Glu Arg Asn Ser Tyr Cys
                325                 330                 335

Lys Lys Val Phe Val Thr Cys Gln Asp Pro Asn Pro
                340                 345

<210> SEQ ID NO 23
<211> LENGTH: 155
<212> TYPE: PRT
<213> ORGANISM: Artificial Sequence
<220> FEATURE:
<223> OTHER INFORMATION: Synthetic sequence

<400> SEQUENCE: 23

Ala Gln Glu Val Gln Gln Ser Pro His Cys Thr Thr Val Pro Val Gly
1               5                   10                  15

Ala Ser Val Asn Ile Thr Cys Ser Thr Ser Gly Gly Leu Arg Gly Ile
                20                  25                  30

Tyr Leu Arg Gln Leu Gly Pro Gln Pro Gln Asp Ile Ile Tyr Tyr Glu
            35                  40                  45

Asp Gly Val Val Pro Thr Thr Asp Arg Arg Phe Arg Gly Arg Ile Asp
50                  55                  60

Phe Ser Gly Ser Gln Asp Asn Leu Thr Ile Thr Met His Arg Leu Gln
65                  70                  75                  80

Leu Ser Asp Thr Gly Thr Tyr Thr Cys Gln Ala Ile Thr Glu Val Asn
                85                  90                  95

Val Tyr Gly Ser Gly Thr Leu Val Leu Val Thr Glu Glu Gln Ser Gln
            100                 105                 110

Gly Trp His Arg Cys Ser Asp Ala Pro Pro Arg Ala Ser Ala Leu Pro
        115                 120                 125

Ala Pro Pro Thr Gly Ser Ala Leu Pro Asp Pro Gln Thr Ala Ser Ala
    130                 135                 140

Leu Pro Asp Pro Pro Ala Ala Ser Ala Leu Pro
145                 150                 155

<210> SEQ ID NO 24
<211> LENGTH: 161
<212> TYPE: PRT
<213> ORGANISM: Artificial Sequence
<220> FEATURE:
<223> OTHER INFORMATION: Synthetic sequence

<400> SEQUENCE: 24
```

Ser Gln Phe Arg Val Ser Pro Leu Asp Arg Thr Trp Asn Leu Gly Glu
1               5                   10                  15

Thr Val Glu Leu Lys Cys Gln Val Leu Leu Ser Asn Pro Thr Ser Gly
            20                  25                  30

Cys Ser Trp Leu Phe Gln Pro Arg Gly Ala Ala Ala Ser Pro Thr Phe
            35                  40                  45

Leu Leu Tyr Leu Ser Gln Asn Lys Pro Lys Ala Ala Glu Gly Leu Asp
        50                  55                  60

Thr Gln Arg Phe Ser Gly Lys Arg Leu Gly Asp Thr Phe Val Leu Thr
65                  70                  75                  80

Leu Ser Asp Phe Arg Arg Glu Asn Glu Gly Tyr Tyr Phe Cys Ser Ala
                85                  90                  95

Leu Ser Asn Ser Ile Met Tyr Phe Ser His Phe Val Pro Val Phe Leu
            100                 105                 110

Pro Ala Lys Pro Thr Thr Thr Pro Ala Pro Arg Pro Pro Thr Pro Ala
            115                 120                 125

Pro Thr Ile Ala Ser Gln Pro Leu Ser Leu Arg Pro Glu Ala Cys Arg
            130                 135                 140

Pro Ala Ala Gly Gly Ala Val His Thr Arg Gly Leu Asp Phe Ala Cys
145                 150                 155                 160

Asp

<210> SEQ ID NO 25
<211> LENGTH: 149
<212> TYPE: PRT
<213> ORGANISM: Artificial Sequence
<220> FEATURE:
<223> OTHER INFORMATION: Synthetic sequence

<400> SEQUENCE: 25

Leu Gln Gln Thr Pro Ala Tyr Ile Lys Val Gln Thr Asn Lys Met Val
1               5                   10                  15

Met Leu Ser Cys Glu Ala Lys Ile Ser Leu Ser Asn Met Arg Ile Tyr
            20                  25                  30

Trp Leu Arg Gln Arg Gln Ala Pro Ser Ser Asp Ser His His Glu Phe
            35                  40                  45

Leu Ala Leu Trp Asp Ser Ala Lys Gly Thr Ile His Gly Glu Glu Val
        50                  55                  60

Glu Gln Glu Lys Ile Ala Val Phe Arg Asp Ala Ser Arg Phe Ile Leu
65                  70                  75                  80

Asn Leu Thr Ser Val Lys Pro Glu Asp Ser Gly Ile Tyr Phe Cys Met
                85                  90                  95

Ile Val Gly Ser Pro Glu Leu Thr Phe Gly Lys Gly Thr Gln Leu Ser
            100                 105                 110

Val Val Asp Phe Leu Pro Thr Thr Ala Gln Pro Thr Lys Lys Ser Thr
            115                 120                 125

Leu Lys Lys Arg Val Cys Arg Leu Pro Arg Pro Glu Thr Gln Lys Gly
            130                 135                 140

Pro Leu Cys Ser Pro
145

<210> SEQ ID NO 26
<211> LENGTH: 12
<212> TYPE: PRT
<213> ORGANISM: Artificial Sequence
<220> FEATURE:

<223> OTHER INFORMATION: Synthetic sequence

<400> SEQUENCE: 26

Gly Gln Asn Asp Thr Ser Gln Thr Ser Ser Pro Ser
1               5                   10

<210> SEQ ID NO 27
<211> LENGTH: 17
<212> TYPE: DNA
<213> ORGANISM: Artificial Sequence
<220> FEATURE:
<223> OTHER INFORMATION: Synthetic sequence

<400> SEQUENCE: 27
gggtcatcac acacaag                                                  17

<210> SEQ ID NO 28
<211> LENGTH: 17
<212> TYPE: DNA
<213> ORGANISM: Artificial Sequence
<220> FEATURE:
<223> OTHER INFORMATION: Synthetic sequence

<400> SEQUENCE: 28
gatgcccgcc acgcacc                                                  17

<210> SEQ ID NO 29
<211> LENGTH: 18
<212> TYPE: DNA
<213> ORGANISM: Artificial Sequence
<220> FEATURE:
<223> OTHER INFORMATION: Synthetic sequence

<400> SEQUENCE: 29
gccacaaaga ccatcaag                                                 18

<210> SEQ ID NO 30
<211> LENGTH: 17
<212> TYPE: DNA
<213> ORGANISM: Artificial Sequence
<220> FEATURE:
<223> OTHER INFORMATION: Synthetic sequence

<400> SEQUENCE: 30
ggagacttta tatgctg                                                  17

<210> SEQ ID NO 31
<211> LENGTH: 17
<212> TYPE: DNA
<213> ORGANISM: Artificial Sequence
<220> FEATURE:
<223> OTHER INFORMATION: Synthetic sequence

<400> SEQUENCE: 31
ggcgtttggg ggcaaga                                                  17

<210> SEQ ID NO 32
<211> LENGTH: 17
<212> TYPE: DNA
<213> ORGANISM: Artificial Sequence
<220> FEATURE:
<223> OTHER INFORMATION: Synthetic sequence

<400> SEQUENCE: 32
gtccactatg acaattg                                                  17

```
<210> SEQ ID NO 33
<211> LENGTH: 17
<212> TYPE: DNA
<213> ORGANISM: Artificial Sequence
<220> FEATURE:
<223> OTHER INFORMATION: Synthetic sequence

<400> SEQUENCE: 33
gccggagctc caagcag                                                  17

<210> SEQ ID NO 34
<211> LENGTH: 17
<212> TYPE: DNA
<213> ORGANISM: Artificial Sequence
<220> FEATURE:
<223> OTHER INFORMATION: Synthetic sequence

<400> SEQUENCE: 34
gggggccttg tcgttgg                                                  17

<210> SEQ ID NO 35
<211> LENGTH: 17
<212> TYPE: DNA
<213> ORGANISM: Artificial Sequence
<220> FEATURE:
<223> OTHER INFORMATION: Synthetic sequence

<400> SEQUENCE: 35
gggtaccatc agctatg                                                  17

<210> SEQ ID NO 36
<211> LENGTH: 17
<212> TYPE: DNA
<213> ORGANISM: Artificial Sequence
<220> FEATURE:
<223> OTHER INFORMATION: Synthetic sequence

<400> SEQUENCE: 36
gccagcgcca gaagcag                                                  17

<210> SEQ ID NO 37
<211> LENGTH: 17
<212> TYPE: DNA
<213> ORGANISM: Artificial Sequence
<220> FEATURE:
<223> OTHER INFORMATION: Synthetic sequence

<400> SEQUENCE: 37
ggagactgct gcacctc                                                  17

<210> SEQ ID NO 38
<211> LENGTH: 17
<212> TYPE: DNA
<213> ORGANISM: Artificial Sequence
<220> FEATURE:
<223> OTHER INFORMATION: Synthetic sequence

<400> SEQUENCE: 38
gccgcatcga cttctca                                                  17
```

CHIMERIC ANTIGEN RECEPTORS (CARS), TARGETING HEMATOLOGIC MALIGNANCIES, COMPOSITIONS AND METHODS OF USE THEREOF

CROSS-REFERENCE TO RELATED APPLICATIONS

This application is a national stage filing under 35 USC § 371 of international application number PCT/US2016/019953, filed on Feb. 26, 2016, which claims benefit of U.S. Provisional Application No. 62/121,842, filed Feb. 27, 2015, which are incorporated herein by reference in their entirety.

BACKGROUND

T cells, a type of lymphocyte, play a central role in cell-mediated immunity. They are distinguished from other lymphocytes, such as B cells and natural killer cells (NK cells), by the presence of a T-cell receptor (TCR) on the cell surface. T helper cells, also called CD4+ T or CD4 T cells, express CD4 glycoprotein on their surface. Helper T cells are activated when exposed to peptide antigens presented by MHC (major histocompatibility complex) class II molecules. Once activated, these cells proliferate rapidly and secrete cytokines that regulate immune response. Cytotoxic T cells, also known as CD8+ T cells or CD8 T cells, express CD8 glycoprotein on the cell surface. The CD8+ T cells are activated when exposed to peptide antigens presented by MHC class I molecules. Memory T cells, a subset of T cells, persist long term and respond to their cognate antigen, thus providing the immune system with "memory" against past infections and/or tumor cells.

T cells can be genetically engineered to produce special receptors on their surface called chimeric antigen receptors (CARs). CARs are proteins that allow the T cells to recognize a specific protein (antigen) on tumor cells. These engineered CAR T cells are then grown in the laboratory until they number in the billions. The expanded population of CAR T cells is then infused into the patient.

Clinical trials to date have shown chimeric antigen receptor (CAR) T cells to have great promise in hematologic malignancies resistant to standard chemotherapies. Most notably, CD19-specific CAR (CD19CAR) T-cell therapies have had remarkable results including long-term remissions in B-cell malignancies (Kochenderfer, Wilson et al. 2010, Kalos, Levine et al. 2011, Porter, Levine et al. 2011, Davila, Riviere et al. 2013, Grupp, Frey et al. 2013, Grupp, Kalos et al. 2013, Kalos, Nazimuddin et al. 2013, Kochenderfer, Dudley et al. 2013, Kochenderfer, Dudley et al. 2013, Lee, Shah et al. 2013, Park, Riviere et al. 2013, Maude, Frey et al. 2014).

Despite the success of CAR therapy in B-cell leukemia and lymphoma, the application of CAR therapy to T-cell malignancies has not yet been well established. Given that T-cell malignancies are associated with dramatically poorer outcomes compared to those of B-cell malignancies (Abramson, Feldman et al. 2014), CAR therapy in this respect has the potential to further address a great clinical need.

CD5 is expressed in more than 80% of T-cell acute lymphoblastic leukemia (T-ALL). One treatment option is to treat patients with anti-CD5 antibodies as T-cell leukemias or T-cell lymphomas expressing the CD5 surface molecule. However attempts have met limited success.

Therefore, there remains a need for improved chimeric antigen receptor-based therapies that allow for more effective, safe, and efficient targeting of T-cell associated malignancies.

SUMMARY OF THE INVENTION

The present disclosure provides chimeric antigen receptors (CARS) targeting hematologic malignancies, compositions and methods of use thereof.

In one embodiment, the disclosure provides an engineered chimeric antigen receptor polypeptide, the polypeptide comprising: a signal peptide, a CD2 antigen recognition domain, a hinge region, a transmembrane domain, at least one co-stimulatory domain, and a signaling domain.

In another embodiment, the disclosure provides an engineered chimeric antigen receptor polypeptide, the polypeptide comprising: a signal peptide, a CD3 antigen recognition domain, a hinge region, a transmembrane domain, at least one co-stimulatory domain, and a signaling domain.

In another embodiment, the disclosure provides an engineered chimeric antigen receptor polypeptide, the polypeptide comprising: a signal peptide, a CD4 antigen recognition domain, a hinge region, a transmembrane domain, at least one co-stimulatory domain, and a signaling domain.

In another embodiment, the disclosure provides an engineered chimeric antigen receptor polypeptide, the polypeptide comprising: a signal peptide, a CD5 antigen recognition domain, a hinge region, a transmembrane domain, at least one co-stimulatory domain, and a signaling domain.

In another embodiment, the disclosure provides an engineered chimeric antigen receptor polypeptide, the polypeptide comprising: a signal peptide, a CD7 antigen recognition domain, a hinge region, a transmembrane domain, at least one co-stimulatory domain, and a signaling domain.

In another embodiment, the disclosure provides an engineered chimeric antigen receptor polypeptide, the polypeptide comprising: a signal peptide, a CD8 antigen recognition domain, a hinge region, a transmembrane domain, at least one co-stimulatory domain, and a signaling domain.

In another embodiment, the disclosure provides an engineered chimeric antigen receptor polypeptide, the polypeptide comprising: a signal peptide, a CD52 antigen recognition domain, a hinge region, a transmembrane domain, at least one co-stimulatory domain, and a signaling domain.

In one embodiment, the disclosure provides an engineered chimeric antigen receptor polynucleotide that encodes for a chimeric antigen receptor polypeptide having an antigen recognition domain selective for CD2.

In another embodiment, the disclosure provides an engineered chimeric antigen receptor polynucleotide that encodes for a chimeric antigen receptor polypeptide having an antigen recognition domain selective for CD3.

In another embodiment, the disclosure provides an engineered chimeric antigen receptor polynucleotide that encodes for a chimeric antigen receptor polypeptide having an antigen recognition domain selective for CD4.

In another embodiment, the disclosure provides an engineered chimeric antigen receptor polynucleotide that encodes for a chimeric antigen receptor polypeptide having an antigen recognition domain selective for CD5.

In another embodiment, the disclosure provides an engineered chimeric antigen receptor polynucleotide that encodes for a chimeric antigen receptor polypeptide having an antigen recognition domain selective for CD7.

In another embodiment, the disclosure provides an engineered chimeric antigen receptor polynucleotide that encodes for a chimeric antigen receptor polypeptide having an antigen recognition domain selective for CD8.

In another embodiment, the disclosure provides an engineered chimeric antigen receptor polynucleotide that encodes for a chimeric antigen receptor polypeptide having an antigen recognition domain selective for CD52.

In one embodiment, the disclosure provides an engineered cell expressing any of the chimeric antigen receptor polypeptides described above.

In another embodiment, the disclosure provides an engineered cell expressing any of the chimeric antigen receptor polynucleotides described above.

In another embodiment, the disclosure provides a method of producing an engineered cell expressing a chimeric antigen receptor polypeptide or polynucleotide having an antigen recognition domain selective for CD2, CD3, CD4, CD5, CD7, CD8, or CD52. The method includes (i) providing peripheral blood cells or cord blood cells; (ii) introducing the aforementioned polynucleotide into the aforementioned cells; (iii) expanding the cells of step (ii); and isolating the cells of step (iii) to provide said engineered cell.

In another embodiment, the disclosure provides a method of producing an engineered cell expressing a chimeric antigen polypeptide or polynucleotide having an antigen recognition domain selective for CD2, CD3, CD4, CD5, CD7, CD8, or CD52. The method includes (i) providing placental cells, embryonic stem cells, induced pluripotent stem cells, or hematopoietic stem cells; (ii) introducing the aforementioned polynucleotide into the cells of step (i); (iii) expanding the cells of step (ii); and (iv) isolating the cells of step (iii) to provide said engineered cell.

In one embodiment, the disclosure provides a method of conferring anti-leukemia or anti lymphoma immunity to CD4 positive T-cell leukemia or CD4 positive T-cell lymphoma in a patient in need thereof. The method includes (i) administering to a patient in need thereof a therapeutically effective amount of an engineered cell expressing a CAR polypeptide having a CD4 antigen recognition domain; and (ii) optionally, assaying for immunity to T-cell leukemia or T-cell lymphoma in the patient.

In another embodiment, the disclosure provides a method of reducing the number of CD4 positive T-cell leukemia cells or CD4 positive T-cell lymphoma cells. The method includes (i) contacting CD4 positive T-cell leukemia cells or CD4 positive T-cell lymphoma cells with an effective amount of an engineered cell expressing a CAR polypeptide having a CD4 antigen recognition domain; and (ii) optionally, assaying for CD4 positive T-cell leukemia cells or CD4 positive T-cell lymphoma cells.

In another embodiment, the disclosure provides a method of reducing the number of immunoregulatory cells having a CD2 antigen. The method includes (i) contacting said immunoregulatory cells with an effective amount of an engineered cell expressing a CAR polypeptide having a CD2 antigen recognition domain; and (ii) optionally, assaying for the reduction in the number of immunoregulatory cells.

In another embodiment, the disclosure provides a method of reducing the number of immunoregulatory cells having CD3. The method includes (i) contacting said immunoregulatory cells with an effective amount of an engineered cell expressing a CAR polypeptide having a CD3 antigen recognition domain; and (ii) optionally, assaying for the reduction in the number of immunoregulatory cells.

In another embodiment, the disclosure provides a method of reducing the number of immunoregulatory cells having CD4. The method includes (i) contacting said immunoregulatory cells with an effective amount of an engineered cell expressing a CAR polypeptide having a CD4 antigen recognition domain; and (ii) optionally, assaying for the reduction in the number of immunoregulatory cells.

In another embodiment, the disclosure provides a method of reducing the number of immunoregulatory cells having CD5. The method includes (i) contacting said immunoregulatory cells with an effective amount of an engineered cell expressing a CAR polypeptide having a CD5 antigen recognition domain; and (ii) optionally, assaying for the reduction in the number of immunoregulatory cells.

In another embodiment, the disclosure provides a method of reducing the number of immunoregulatory cells having CD7. The method includes (i) contacting said immunoregulatory cells with an effective amount of an engineered cell expressing a CAR polypeptide having a CD7 antigen recognition domain; and (ii) optionally, assaying for the reduction in the number of immunoregulatory cells.

In another embodiment, the disclosure provides method of reducing the number of immunoregulatory cells having a CD8 antigen. The method includes (i) contacting said immunoregulatory cells with an effective amount of an engineered cell expressing a CAR polypeptide having a CD8 antigen recognition domain; and (ii) optionally, assaying for the reduction in the number of immunoregulatory cells.

In another embodiment, the disclosure provides a method of reducing the number of immunoregulatory cells having CD52. The method includes (i) contacting said immunoregulatory cells with an effective amount of an engineered cell expressing a CAR polypeptide having a CD52 antigen recognition domain; and (ii) optionally, assaying for the reduction in the number of immunoregulatory cells.

In one embodiment, the disclosure provides a method of treating a cell proliferative disease. The method includes (i) administering to a patient in need thereof a therapeutically effective amount of an engineered cell expressing a CAR polypeptide having a CD2, CD3, CD4, CD5, CD7, CD8, or CD52 antigen recognition domain.

In one embodiment, the disclosure provides a method of treating an autoimmune disease. The method includes (i) administering to a patient in need thereof a therapeutically effective amount of an engineered cell expressing a CAR polypeptide having a CD2, CD3, CD4, CD5, CD7, CD8, or CD52 antigen recognition domain.

In one embodiment, the disclosure provides engineered cells expressing a CAR polypeptide having a CD2, CD3, CD4, CD5, CD7, CD8, or CD52 antigen recognition domain for use in the treatment of a cell proliferative disease. The use includes administering said engineered cells to a patient in need thereof.

In some embodiments, CARs typically include at least one of intracellular signaling, hinge and/or transmembrane domains. First-generation CARs include CD3z as an intracellular signaling domain, whereas second-generation CARs include a single co-stimulatory domain derived from, for example, without limitation, CD28 or 4-1BB. Third generation CARs include two co-stimulatory domains, such as, without limitation, CD28, 4-1BB (also known CD137) and OX-40, and any other co-stimulatory molecules.

In some embodiments, CAR having a CD2, CD3, CD4, CD5, CD7, CD8, or CD52 antigen recognition domain is part of an expression cassette. In a preferred embodiment, the expressing gene or the cassette may include an accessory gene or a tag or a part thereof. The accessory gene may be an inducible suicide gene or a part thereof, including, but not limited to, caspase 9 gene. The "suicide gene" ablation approach improves safety of the gene therapy and kills cells only when activated by a specific compound or a molecule.

In some embodiments, the epitope tag is a c-myc tag, streptavidin-binding peptide (SBP), truncated EGFR gene (EGFRt) or a part or a combination thereof.

BRIEF DESCRIPTION OF DRAWINGS

FIG. 5. CD4CAR T cells efficiently mediate anti-leukemic effects in vivo with different modes. NSG mice received 2.5 Gy for sub-lethal irradiation. Twenty-four hours after irradiation, mice were injected subcutaneously with either $1\times10^6$ (in A) or $0.5\times10^6$ (in B and C) KARPAS 299 cells. Injected mice were treated with different courses and schedules of CD4CAR T cells or control T cells. N=5 for each group of injected mice. (A), a low dose of $2\times10^6$ of CD4CAR T cells was injected on day 3 followed by a large dose, $8\times10^6$, of CD4CAR T cells on day 22 after upon observed acceleration of tumor growth. (B), two large doses of CD4CAR T cells, $8\times10^6$ and $5.5\times10^6$ were injected on day 3 and 10 respectively. (C), a repeat low dose ($2.5\times10^6$) of CD4CAR T cells was injected every 5 days for a total of four administrations. (D), overall survival of mice treated with the indicated CD4CAR T cells or control GFP T cells. N=10.

FIG. 7. Comparison of cell growth between activated PMBC buffy coat cells transduced with lenti-GFP and CD4CAR viruses. The activated PMBC buffy coat cells were transduced with either GFP control or CD4-CAR lentiviral supernatant on Day 0. Cells were washed on Day 1, and media was added on days 3 and 5.

FIG. 14. CD4 CAR NK cells ablate CD4 positive leukemia and lymphoma cells in co-culture assays. All co-culture assays shown were performed at an effector to target ratio of 5:1 for 24 hours, after which, cells were stained with mouse anti-human CD56 and CD4 antibodies. Each assay consists of NK cells transduced with either vector control (center) or CD4CAR (right) lentiviral supernatant and incubated with target cells, as well as target cells incubated alone as a control (left). CD4CAR NK cells eliminated Karpas 299 leukemic T-cells (A), HL-60 T-cells (B), and CCRF-CEM cells (C). CD4CAR NK cells eliminated primary T-cell leukemia cells from patients with CD4 expressing T-cell leukemia/Sézary syndrome (E) and CD4 expressing pediatric T-cell ALL (F).

FIG. 39. Steps for generation of CAR T or NK cell targeting T-cell lymphomas or T-cell leukemias.

FIG. 40. Three pairs of sgRNA per gene are designed with CHOPCHOP to target CD2, CD3, CD5 and CD7. Three pairs of sgRNA were designed with CHOPCHOP to target the gene of interest. Gene-specific sgRNAs were then cloned into the lentiviral vector (Lenti U6-sgRNA-SFFV-Cas9-puro-wpre) expressing a human Cas9 and puromycin resistance genes linked with an E2A self-cleaving linker. The U6-sgRNA cassette is in front of the Cas9 element. The expression of sgRNA and Cas9puro is driven by the U6 promoter and SFFV promoter, respectively.

DETAILED DESCRIPTION

Figure 1A:
FIG. 1. CD4CAR expression. (A), Schematic representation of recombinant lentiviral vectors encoding CD4CAR. CD4CAR expression is driven by a SFFV (spleen focus-forming virus) promoter. The third generation of CD4 CAR contains a leader sequence, the anti-CD4scFv, a hinge domain (H), a transmembrane domain (TM) and intracellular signaling domains as follows: CD28, 4-1BB (both co-stimulators), and CD3 zeta. (B), 293FT cells were transfected with lentiviral plasmids for GFP (lane 1) and CD4CAR (lane 2) for Western blot analysis at 48 h post transfection and probed with mouse anti-human CD3z antibody. (C), Illustration of the components of third-generation chimeric antigen receptor T cells targeting CD4 expressing cells.

The disclosure provides chimeric antigen receptor (CAR) compositions, methods and making thereof, and methods of using the CAR compositions.

Compositions

Chimeric Antigen Receptor Polypeptides

In one embodiment the disclosure provides a chimeric antigen receptor (CAR) polypeptide having a signal peptide, an antigen recognition domain, a hinge region, a transmembrane domain, at least one co-stimulatory domain, and a signaling domain.

As used herein, the terms "peptide," "polypeptide," and "protein" are used interchangeably, and refer to a compound having amino acid residues covalently linked by peptide bonds. A protein or peptide must contain at least two amino acids, and no limitation is placed on the maximum number of amino acids that can include a protein's or peptide's sequence. Polypeptides include any peptide or protein having two or more amino acids joined to each other by peptide bonds. As used herein, the term refers to both short chains, which also commonly are referred to in the art as peptides, oligopeptides, and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

A "signal peptide" includes a peptide sequence that directs the transport and localization of the peptide and any attached polypeptide within a cell, e.g. to a certain cell organelle (such as the endoplasmic reticulum) and/or the cell surface.

The signal peptide is a peptide of any secreted or transmembrane protein that directs the transport of the polypeptide of the disclosure to the cell membrane and cell surface, and provides correct localization of the polypeptide of the present disclosure. In particular, the signal peptide of the present disclosure directs the polypeptide of the present disclosure to the cellular membrane, wherein the extracellular portion of the polypeptide is displayed on the cell surface, the transmembrane portion spans the plasma membrane, and the active domain is in the cytoplasmic portion, or interior of the cell.

In one embodiment, the signal peptide is cleaved after passage through the endoplasmic reticulum (ER), i.e. is a cleavable signal peptide. In an embodiment, the signal peptide is human protein of type I, II, III, or IV. In an embodiment, the signal peptide includes an immunoglobulin heavy chain signal peptide.

The "antigen recognition domain" includes a polypeptide that is selective for an antigen, receptor, peptide ligand, or protein ligand of the target; or a polypeptide of the target.

The target specific antigen recognition domain preferably includes an antigen binding domain derived from an antibody against an antigen of the target, or a peptide binding an antigen of the target, or a peptide or protein binding an antibody that binds an antigen of the target, or a peptide or protein ligand (including but not limited to a growth factor, a cytokine, or a hormone) binding a receptor on the target, or a domain derived from a receptor (including but not limited to a growth factor receptor, a cytokine receptor or a hormone receptor) binding a peptide or protein ligand on the target. The target includes CD2, CD3, CD4, CD5, CD7, CD8, and CD52. In another embodiment, the target includes any portion of CD2, CD3, CD4, CD5, CD7, CD8, and CD52. In one embodiment, the target includes surface exposed portions of the CD2, CD3, CD4, CD5, CD7, CD8, and CD52 polypeptides.

In another embodiment, the target is the extracellular domain of CD2 (SEQ ID NO. 19). In another embodiment, the target is the CD3 epsilon chain extracellular domain (SEQ ID NO. 20). In another embodiment, the target is the CD4 extracellular domain (SEQ ID NO. 21). In another embodiment, the target is the CD5 extracellular domain (SEQ ID NO. 22). In another embodiment, the target is the CD7 extracellular domain (SEQ ID NO. 23). In another embodiment, the target is the CD8 alpha chain extracellular domain (SEQ ID NO. 24). In another embodiment, the target is the CD8 beta chain extracellular domain (SEQ ID NO. 25). In another embodiment, the target is the CD52 CAMPATH-1 antigen (SEQ ID NO. 26).

In one embodiment, the antigen recognition domain includes the binding portion or variable region of a monoclonal or polyclonal antibody directed against (selective for) the target.

In one embodiment, the antigen recognition domain includes fragment antigen-binding fragment (Fab). In another embodiment, the antigen recognition domain includes a single-chain variable fragment (scFV). scFV is a fusion protein of the variable regions of the heavy (VH) and light chains (VL) of immunoglobulins, connected with a short linker peptide.

In another embodiment, the antigen recognition domain includes Camelid single domain antibody, or portions thereof. In one embodiment, Camelid single-domain antibodies include heavy-chain antibodies found in camelids, or VHH antibody. A VHH antibody of camelid (for example camel, dromedary, llama, and alpaca) refers to a variable fragment of a camelid single-chain antibody (See Nguyen et al, 2001; Muyldermans, 2001), and also includes an isolated VHH antibody of camelid, a recombinant VHH antibody of camelid, or a synthetic VHH antibody of camelid.

In another embodiment, the antigen recognition domain includes ligands that engage their cognate receptor. In another embodiment, the antigen recognition domain is humanized.

It is understood that the antigen recognition domain may include some variability within its sequence and still be selective for the targets disclosed herein. Therefore, it is contemplated that the polypeptide of the antigen recognition domain may be at least 95%, at least 90%, at least 80%, or at least 70% identical to the antigen recognition domain polypeptide disclosed herein and still be selective for the targets described herein and be within the scope of the disclosure.

In another embodiment, the antigen recognition domain is selective for SEQ ID NO. 19, SEQ ID NO. 20, SEQ ID NO. 21, SEQ ID NO. 22, SEQ ID NO. 23, SEQ ID NO. 24, or SEQ ID NO. 25, or SEQ ID NO. 26.

The hinge region is a sequence positioned between for example, including, but not limited to, the chimeric antigen receptor, and at least one co-stimulatory domain and a signaling domain. The hinge sequence may be obtained including, for example, from any suitable sequence from any genus, including human or a part thereof. Such hinge regions are known in the art. In one embodiment, the hinge region includes the hinge region of a human protein including CD-8 alpha, CD28, 4-1BB, OX40, CD3-zeta, T cell receptor α or β chain, a CD3 zeta chain, CD28, CD3ε, CD45, CD4, CD5, CD8, CD9, CD16, CD22, CD33, CD37, CD64, CD80, CD86, CD134, CD137, ICOS, CD154, functional derivatives thereof, and combinations thereof.

In one embodiment the hinge region includes the CD8 a hinge region.

In some embodiments, the hinge region includes one selected from, but is not limited to, immunoglobulin (e.g. IgG1, IgG2, IgG3, IgG4, and IgD).

The transmembrane domain includes a hydrophobic polypeptide that spans the cellular membrane. In particular, the transmembrane domain spans from one side of a cell membrane (extracellular) through to the other side of the cell membrane (intracellular or cytoplasmic).

The transmembrane domain may be in the form of an alpha helix or a beta barrel, or combinations thereof. The transmembrane domain may include a polytopic protein, which has many transmembrane segments, each alpha-helical, beta sheets, or combinations thereof.

In one embodiment, the transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex.

For example, a transmembrane domain includes a transmembrane domain of a T-cell receptor α or β chain, a CD3 zeta chain, CD28, CD3ε, CD45, CD4, CD5, CD8, CD9, CD16, CD22, CD33, CD37, CD64, CD80, CD86, CD134, CD137, ICOS, CD154, functional derivatives thereof, and combinations thereof.

The artificially designed transmembrane domain is a polypeptide mainly comprising hydrophobic residues such as leucine and valine. In one embodiment, a triplet of phenylalanine, tryptophan and valine is found at each end of the synthetic transmembrane domain.

In one embodiment, the transmembrane domain is the CD8 transmembrane domain. In another embodiment, the transmembrane domain is the CD28 transmembrane domain. Such transmembrane domains are known in the art.

The signaling domain and co-stimulatory domain include polypeptides that provide activation of an immune cell to stimulate or activate at least some aspect of the immune cell signaling pathway.

In an embodiment, the signaling domain includes the polypeptide of a functional signaling domain of CD3 zeta, common FcR gamma (FCER1G), Fc gamma RIIa, FcR beta (Fc Epsilon Rib), CD3 gamma, CD3 delta, CD3 epsilon, CD79a, CD79b, DNAX-activating protein 10 (DAP10), DNAX-activating protein 12 (DAP12), active fragments thereof, functional derivatives thereof, and combinations thereof. Such signaling domains are known in the art.

In an embodiment, the CAR polypeptide further includes one or more co-stimulatory domains. In an embodiment, the co-stimulatory domain is a functional signaling domain from a protein including OX40, CD27, CD28, CD30, CD40, PD-1, CD2, CD7, CD258, Natural killer Group 2 member C (NKG2C), Natural killer Group 2 member D (NKG2D), B7-H3, a ligand that binds to CD83, ICAM-1, LFA-1 (CD1 la/CD18), ICOS and 4-1BB (CD137), active fragments thereof, functional derivatives thereof, and combinations thereof.

In one embodiment, the CAR polypeptide is CD2CAR, and includes SEQ ID NO. 10 or SEQ ID NO. 11. In one embodiment, the CAR polypeptide is CD3CAR, and includes SEQ ID NO. 12. In one embodiment, the CAR polypeptide is CD4CAR, and includes SEQ ID NO. 13 or SEQ ID NO. 14. In one embodiment, the CAR polypeptide is CD5CAR, and includes SEQ ID NO. 15. In one embodiment, the CAR polypeptide is CD7CAR, and includes SEQ ID NO. 17. In one embodiment, the CAR polypeptide is CD52CAR, and includes SEQ ID NO. 18.

Polynucleotide Encoding Chimeric Antigen Receptor

The present disclosure further provides a polynucleotide encoding the chimeric antigen receptor polypeptide described above. The polynucleotide encoding the CAR is easily prepared from an amino acid sequence of the specified CAR by any conventional method. A base sequence encoding an amino acid sequence can be obtained from the aforementioned NCBI RefSeq IDs or accession numbers of GenBenk for an amino acid sequence of each domain, and the nucleic acid of the present disclosure can be prepared using a standard molecular biological and/or chemical procedure. For example, based on the base sequence, a polynucleotide can be synthesized, and the polynucleotide of the present disclosure can be prepared by combining DNA fragments which are obtained from a cDNA library using a polymerase chain reaction (PCR).

In one embodiment, the polynucleotide disclosed herein is part of a gene, or an expression or cloning cassette.

The term "polynucleotide" as used herein is defined as a chain of nucleotides. Polynucleotides includes DNA and RNA. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and polymerase chain reaction (PCR), and the like, and by synthetic means.

In one embodiment, the polynucleotide includes the CD2CAR polynucleotide of SEQ ID NO. 1 or SEQ ID NO. 2. In one embodiment, the polynucleotide includes the CD3CAR polynucleotide of SEQ ID NO. 3. In one embodiment, the polynucleotide includes the CD4CAR polynucleotide of SEQ ID NO. 4 or SEQ ID NO. 5. In one embodiment, the polynucleotide includes the CD5CAR polynucleotide of SEQ ID NO. 6. In one embodiment, the polynucleotide includes the CD7CAR polynucleotide of SEQ ID NO. 8. In one embodiment, the polynucleotide includes the CD52CAR polynucleotide of SEQ ID NO. 9.

Polynucleotide Vector

The polynucleotide described above can be cloned into a vector. A "vector" is a composition of matter which includes an isolated polynucleotide and which can be used to deliver the isolated polynucleotide to the interior of a cell. Numerous vectors are known in the art including, but not limited to, linear polynucleotides, polynucleotides associated with ionic or amphiphilic compounds, plasmids, phagemid, cosmid, and viruses. Viruses include phages, phage derivatives. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

In one embodiment, vectors include cloning vectors, expression vectors, replication vectors, probe generation vectors, integration vectors, and sequencing vectors.

In an embodiment, the vector is a viral vector. In an embodiment, the viral vector is a retroviral vector or a lentiviral vector. In an embodiment, the engineered cell is virally transduced to express the polynucleotide sequence.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Viral vector technology is well known in the art and is described, for example, in Sambrook et al, (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endomiclease sites, and one or more selectable markers, (e.g., WO 01/96584; WO 01/29058; and U.S. Pat. No. 6,326,193).

Expression of chimeric antigen receptor polynucleotide may be achieved using, for example, expression vectors including, but not limited to, at least one of a SFFV or human elongation factor 11α (EF) promoter, CAG (chicken beta-actin promoter with CMV enhancer) promoter human elongation factor 1α (EF) promoter. Examples of less-strong/lower-expressing promoters utilized may include, but is not limited to, the simian virus 40 (SV40) early promoter, cytomegalovirus (CMV) immediate-early promoter, Ubiquitin C (UBC) promoter, and the phosphoglycerate kinase 1 (PGK) promoter, or a part thereof. Inducible expression of chimeric antigen receptor may be achieved using, for example, a tetracycline responsive promoter, including, but not limited to, TRE3GV (Tet-response element, including all generations and preferably, the 3rd generation), inducible promoter (Clontech Laboratories, Mountain View, Calif.) or a part or a combination thereof.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1 a (EF-1 a). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the disclosure should not be limited to the use of constitutive promoters, inducible promoters are also contemplated as part of the disclosure. The use of an inducible promoter provides a molecular switch capable of turning on expression of the polynucleotide sequence which it is operatively linked when such expression is desired, or turning off the expression when expression is not desired. Examples of inducible promoters include, but are not limited to a metalothionine promoter, a glucocorticoid promoter, a progesterone promoter, and a tetracycline promoter.

"Expression vector" refers to a vector comprising a recombinant polynucleotide comprising expression control sequences operatively linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide, Additional promoter elements, e.g., enhancers, regulate the frequency of transcriptional initiation. Typically, these are located in the region 30-100 bp upstream of the start site, although a number of promoters have recently been shown to contain functional elements downstream of the start site as well. The spacing between promoter elements frequently is flexible, so that promoter function is preserved when elements are inverted or moved relative to one another, in the thymidine kinase (tk) promoter, the spacing between promoter elements can be increased to 50 bp apart before activity begins to decline. Depending on the promoter, it appears that individual elements can function either cooperatively or independently to activate transcription, In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors, in other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyi phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyi phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol.

"Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 19 1 Glycobiology 5; 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous polynucleotides into a host cell or otherwise expose a cell to the polynucleotide of the present disclosure, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the disclosure.

Engineered Cell

In another embodiment, the disclosure provides an engineered cell expressing the chimeric antigen receptor polypeptide described above or polynucleotide encoding for the same, and described above.

An "engineered cell" means any cell of any organism that is modified, transformed, or manipulated by addition or modification of a gene, a DNA or RNA sequence, or protein or polypeptide. Isolated cells, host cells, and genetically engineered cells of the present disclosure include isolated immune cells, such as NK cells and T cells that contain the DNA or RNA sequences encoding a chimeric antigen receptor or chimeric antigen receptor complex and express the chimeric receptor on the cell surface. Isolated host cells and engineered cells may be used, for example, for enhancing an NK cell activity or a T lymphocyte activity, treatment of cancer, and treatment of infectious diseases.

Any cell capable of expressing and/or capable of integrating the chimeric antigen receptor polypeptide, as disclosed herein, into its membrane may be used.

In an embodiment, the engineered cell includes immunoregulatory cells. Immunoregulatory cells include T-cells, such as CD4 T-cells (Helper T-cells), CD8 T-cells (Cytotoxic T-cells, CTLs), and memory T cells or memory stem cell T cells. In another embodiment, T-cells include Natural Killer T-cells (NK T-cells).

In an embodiment, the engineered cell includes Natural Killer cells. Natural killer cells are well known in the art. In one embodiment, natural killer cells include cell lines, such as NK-92 cells. Further examples of NK cell lines include NKG, YT, NK-YS, HANK-1, YTS cells, and NKL cells.

NK cells mediate anti-tumor effects without the risk of GvHD and are short-lived relative to T-cells. Accordingly, NK cells would be exhausted shortly after destroying cancer cells, decreasing the need for an inducible suicide gene on CAR constructs that would ablate the modified cells.

In one embodiment, the engineered cell may include more than one type chimeric antigen receptor polypeptide described herein. Embodiments wherein the engineered cell includes at least two of a CD2CAR, CD3CAR, CD4CAR, CD5CAR, CD7CAR, CD8CAR, and CD52CAR have been contemplated. For example, the engineered cell may include a CD4 chimeric antigen receptor polypeptide (CD4CAR) and a CD5 chimeric antigen receptor polypeptide (CDX-CAR).

As used herein, CDXCAR refers to a chimeric antigen receptor having a CDX antigen recognition domain. As used herein CDX may be any one of CD2, CD3, CD4, CD5, CD7, CD8, and CD52.

TCR Deficient T Cells Used to Carry CAR

In one embodiment, engineered cells, in particular allogeneic T cells obtained from donors can be modified to inactivate components of TCR (T cell receptor) involved in MHC recognition. As a result, TCR deficient T cells would not cause graft versus host disease (GVHD).

T-Antigen Deficient T and NK Cells

T cell lymphomas or T cell leukemias express specific antigens, which may represent useful targets for these diseases. For instance, T cell lymphomas or leukemias express CD7, CD2, CD3 and CD5. However, CD7, CD2, CD3, and CD5 are also expressed in CAR T or NK cells (except for CD3 and CD5), which offset their ability of targeting these antigens. The self-killing might occur in T cells or NK cells armed with CARs targeting any one of these antigens. This makes generation of CARs targeting these antigens difficult.

Therefore, it may be necessary to inactivate an endogenous antigen in a T or NK cell when it is used as a target to arm CARs.

In another embodiment, the engineered cell is further modified to inactivate cell surface polypeptide to prevent engineered cells from acting on other engineered cells. For example, one or more of the endogenous CD2, CD3, CD4, CD5, and CD7 genes of the engineered cells may be knocked out or inactivated. In a preferred embodiment, the engineered cell is a natural killer cell having at least one of the endogenous CD2 and CD7 genes knocked out or inactivated.

In another preferred embodiment, the engineered cell is a T-cell having at least one of the endogenous CD2, CD3, CD4, CD5, CD7, and CD8 genes knocked out or inactivated. In another preferred embodiment, the engineered cell is a NK cell having at least one of the endogenous CD2 and CD7 genes knocked out or inactivated.

In one embodiment, the engineered cell expressing a CAR having a particular antigen recognition domain will have the gene expressing that antigen inactivated or knocked out. For example, a T-cell having a CD2 CAR will have an inactivated or knocked out CD2 antigen gene. In another embodiment, an engineered cell (e.g. NK cell or T-cell) having a CAR with a CD4 antigen recognition domain will be modified so that the CD4 antigen is not expressed on its cell surface. In another embodiment, an engineered cell (e.g. NK cell or T-cell) having one CAR with a CD2 antigen recognition domain and another CAR with a CD7 antigen recognition domain may have both the CD2 antigen gene and the CD7 antigen gene knocked out or inactivated.

TABLE 1 cell surface antigens of Natural Killer cells and T-cells.

| | Natural Killer cells | T-cells |
|---|---|---|
| CD2 | + | + |
| CD4 | − | + |
| CD3 | − | + |
| CD5 | − | + |
| CD7 | + | + |
| CD8 | − | + |

Methods to knock out or inactivate genes are commonly known in the art. For example, CRISPR/Cas9 system, zinc finger nuclease (ZFNs) and TALE nucleases (TALENs) and meganucleases may be used to knock out or inactivate the CD2, CD3, CD4, CD5, CD7, CD8, and CD52 genes of the engineered cells.

Sources of Cells

The engineered cells may be obtained from peripheral blood, cord blood, bone marrow, tumor infiltrating lymphocytes, lymph node tissue, or thymus tissue. The host cells may include placental cells, embryonic stem cells, induced pluripotent stem cells, or hematopoietic stem cells. The cells may be obtained from humans, monkeys, chimpanzees, dogs, cats, mice, rats, and transgenic species thereof. The cells may be obtained from established cell lines.

The above cells may be obtained by any known means. The cells may be autologous, syngeneic, allogeneic, or xenogeneic to the recipient of the engineered cells.

The term "autologous" refer to any material derived from the same individual to whom it is later to be re-introduced into the individual.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "xenogeneic" refers to a graft derived from an animal of a different species.

The term "syngeneic" refers to an extremely close genetic similarity or identity especially with respect to antigens or immunological reactions. Syngeneic systems include for example, models in which organs and cells (e.g. cancer cells and their non-cancerous counterparts) come from the same individual, and/or models in which the organs and cells come from different individual animals that are of the same inbred strain.

Suicide System

The engineered cells of the present disclosure may also include a suicide system. Suicide systems provide a mechanism whereby the engineered cell, as described above, may be deactivated or destroyed. Such a feature allows precise therapeutic control of any treatments wherein the engineered cells are used. As used herein, a suicide system provides a mechanism by which the cell having the suicide system can be deactivated or destroyed. Suicide systems are well known in the art.

In one embodiment, a suicide system includes a gene that can be pharmacologically activated to eliminate the containing cells as required. In specific aspects, the suicide gene is not immunogenic to the host harboring the polynucleotide or cell. In one example, the suicide system includes a gene that causes CD20 to be expressed on the cell surface of the engineered cell. Accordingly, administration of rituximab may be used to destroy the engineered cell containing the gene.

In some embodiments, the suicide system includes an epitope tag. Examples of epitope tags include a c-myc tag, streptavidin-binding peptide (SBP), and truncated EGFR gene (EGFRt). In this embodiment, the epitope tag is expressed in the engineered cell. Accordingly, administration of an antibody against the epitope tag may be used to destroy the engineered cell containing the gene.

In another embodiment, the suicide system includes a gene that causes truncated epidermal growth factor receptor to be expressed on the surface of the engineered cell. Accordingly, administration of cetuximab may be used to destroy the engineered cell containing the gene.

In another embodiment, the suicide gene may include caspace 8 gene, caspase 9 gene, thymidine kinase, cytosine deaminase (CD), or cytochrome P450.

Examples of further suicide systems include those described by Jones et al. (Jones B S, Lamb L S, Goldman F and Di Stasi A (2014) Improving the safety of cell therapy products by suicide gene transfer. *Front. Pharmacol.* 5:254. doi: 10.3389/fphar.2014.00254), which is herein incorporated by reference in its entirety.

CD2CAR

The CD2 adhesion molecule is a cell surface antigen expressed by all peripheral blood T cells and natural killer cells, but not on B lymphocytes. The extracellular domain of CD2 contains immunoglobulin-like domains which can mediate homodimerization. Ligation of CD2 by CD58 (LFA-3) or CD48 helps T cells adhere to antigen-presenting cells, and triggers signal transduction pathways that enhance signaling through the T cell receptor for antigen. CD2 knockout mice exhibit normal immune function, and it is thought that CD2 is similar functionally with other T cell co-stimulatory receptors such as CD28.

CD2 is expressed in T-ALL, T cell lymphoma/leukemia, acute promyelocytic leukemia (microgranular variant), systemic mastocytosis, mast cell disease, thymoma and acute myeloid lymphoma (MO) and NK cell leukemia.

In one embodiment, the disclosure provides a chimeric antigen receptor polypeptide having an antigen recognition domain specific for a CD2 antigen, and engineered cells expressing the same.

In another embodiment, the disclosure provides a chimeric antigen receptor polypeptide having a variant of the sequence of an antigen recognition domain specific for a CD2 antigen, and engineered cells expressing the same.

In one embodiment, the CD2 CAR includes at least one co-stimulatory domain. In another embodiment, the CD2CAR includes at least two co-stimulatory domains.

In one embodiment, the CD2CAR includes SEQ ID NO. 10 and SEQ ID NO. 11.

CD3CAR

CD3 consists of a protein complex and is composed of four distinct chains as described the figure above. The complex contains, a CD3δ chain, a CD3γ chain, and two CD3ε chains. These chains associate with the T-cell receptor (TCR) composing of αβ chains.

The TCR/CD3 complex is a unique marker for T lineage cells. There is a variety of monoclonal antibodies against this complex that have been developed. One such monoclonal antibody is the murine monoclonal antibody OKT3 against the surface CD3. CD3 is the common marker for T cells and T cell malignancies. OKT3 against CD3 epsilon is the common antibody used for identifying T cells. Anti-CD3 monoclonal antibodies as treatments include: (1) acute renal, cardiac or hepatic allograft rejection; (2) depletion of T cells from donor marrow prior to transplant; (3) new onset of type I diabetes. CD3 against CD3 epsilon chain is the most specific T cell antibody used to identify T cells in benign and malignant disorders. CD3 is found in 86% of peripheral T cell lymphomas.

In some embodiments, the disclosure includes a method for generation of CD3CAR. In further embodiments, CD3CAR includes a scFv antibody which specifically binds to the surface protein of CD3.

In some embodiments, CD3CAR includes an scFv molecule, which specifically binds to the TCR/CD3 complexes.

In some embodiments, the scFv in the CAR may be a molecule specifically binding to the extracellular domains of αβTCR associated with CD3.

CD4CAR

In one embodiment, chimeric antigen receptor of the present disclosure includes a CD4 antigen recognition domain, CD4CAR.

In one embodiment, the CD4 CAR includes at least one co-stimulatory domain. In another embodiment, the CD4CAR includes at least two co-stimulatory domains.

In one embodiment, CD4CAR includes SEQ ID NO. 13 and SEQ ID NO. 14.

CD5CAR

In another embodiment, the disclosure provides a chimeric antigen receptor polypeptide having an antigen recognition domain specific for CD5, and engineered cells expressing the same.

In one embodiment, the CD5CAR includes at least one-costimulatory domain. In another embodiment, the CD5CAR includes at least two co-stimulatory domains.

CD7CAR

CD7 is a transmembrane protein which is a member of the immunoglobulin superfamily. This protein is expressed on the surface of mature T cells. It is the earliest surface antigen expressed on T cell lineage cells.

CD7 is a very good marker for T-ALL and more than 90% of T-ALL express CD7. CD7 is also expressed in NK lymphoma, T cell lymphoma/leukemia, chronic myeloid leukemia, acute myeloid leukemia, and lymphocyte rich thymoma In one embodiment, the disclosure provides a chimeric antigen receptor polypeptide having an antigen recognition domain specific for a CD7 antigen, and engineered cells expressing the same.

In one embodiment, the CD7CAR includes at least one co-stimulatory domain. In another embodiment, the CD7CAR includes at least two co-stimulatory domains Methods Method of Making Engineered Cells In one embodiment, the disclosure also provides methods of making the engineered cells described above.

In this embodiment, the cells described above are obtained or isolated. The cells may be isolated by any known means. The cells include peripheral blood cells or cord blood cells. In another embodiment, the cells are placental cells, embryonic stem cells, induced pluripotent stem cells, or hematopoietic stem cells.

The polynucleotide encoding for the chimeric antigen receptor polypeptide described above is introduced into the peripheral blood cells or cord blood cells by any known means. In one example, the polynucleotide encoding for the chimeric antigen receptor polypeptide described above is introduced into the cell by way of viral vector.

The polynucleotide encoding for the chimeric antigen receptor polypeptide described above is introduced into the placental cells, embryonic stem cells, induced pluripotent stem cells, or hematopoietic stem cells by any known means. In one example, the polynucleotide encoding for the chimeric antigen receptor polypeptide described above is introduced into the cell by way of viral vector.

In other embodiments, the chimeric antigen receptor polynucleotide may be constructed as a transient RNA-modified "biodegradable derivatives". The RNA-modified derivatives may be electroporated into a T cell or NK cell. In a further embodiment, chimeric antigen receptor described herein may be constructed in a transposon system also called a "Sleeping Beauty", which integrates the chimeric antigen receptor polynucleotide into the host genome without a viral vector.

Once the polynucleotide described above is introduced into the cell to provide an engineered cell, the engineered cells are expanded. The engineered cells containing the polynucleotide described above are expanded by any known means.

The expanded cells are isolated by any known means to provide isolated engineered cells according to the present disclosure.

Methods of Using

The disclosure provides methods to kill, reduce the number of, or deplete immunoregulatory cells. In another embodiment, the disclosure provides a method to kill, reduce the number of, or deplete cells having at least one of CD2, CD3, CD4, CD5, CD7, CD8, and CD52.

As used herein, "reduce the number of" includes a reduction by at least 5%, at least 10%, at least 25%, at least 50%, at least 75%, at least 80%, at least 90%, at least 99%, or 100%.

As used herein, "deplete" includes a reduction by at least 75%, at least 80%, at least 90%, at least 99%, or 100%.

In one embodiment, the disclosure includes a method of reducing the number of immunoregulatory cells having CD2 by contacting the immunoregulatory cells with an effective amount of the engineered cells described above expressing a chimeric antigen receptor peptide having a CD2 antigen recognition domain. Optionally, the reduction in the number of immunoregulatory cells having CD2 may be determined by any cell death assay known in the art.

As used herein, the immunoregulatory cells may be in a patient, in cell culture, or isolated.

As used herein, "patient" includes mammals. The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

In certain embodiments, the patient is a human 0 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old.

The terms "effective amount" and "therapeutically effective amount" of an engineered cell as used herein mean a sufficient amount of the engineered cell to provide the desired therapeutic or physiological or effect or outcome. Such, an effect or outcome includes reduction or amelioration of the symptoms of cellular disease. Undesirable effects, e.g. side effects, are sometimes manifested along with the desired therapeutic effect; hence, a practitioner balances the potential benefits against the potential risks in determining what an appropriate "effective amount" is. The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation. Generally, the engineered cell or engineered cells is/are given in an amount and under conditions sufficient to reduce proliferation of target cells.

In one embodiment, the disclosure includes a method of reducing the number of immunoregulatory cells having CD2 by contacting the immunoregulatory cells with an effective amount of the engineered cells described above expressing a chimeric antigen receptor peptide having a CD2 antigen recognition domain. Optionally, the reduction in the number of immunoregulatory cells having CD2 may be determined by any cell death assay known in the art.

In one embodiment, the disclosure includes a method of reducing the number of immunoregulatory cells having CD3 by contacting the immunoregulatory cells with an effective amount of the engineered cells described above expressing a chimeric antigen receptor peptide having a CD3 antigen recognition domain. Optionally, the reduction in the number of immunoregulatory cells having CD3 may be determined by any cell death assay known in the art.

In one embodiment, the disclosure includes a method of reducing the number of immunoregulatory cells having CD4 by contacting the immunoregulatory cells with an effective amount of the engineered cells described above expressing a chimeric antigen receptor peptide having a CD4 antigen recognition domain. Optionally, the reduction in the number of immunoregulatory cells having CD4 may be determined by any cell death assay known in the art.

In one embodiment, the disclosure includes a method of reducing the number of immunoregulatory cells having CD5 by contacting the immunoregulatory cells with an effective amount of the engineered cells described above expressing a chimeric antigen receptor peptide having a CD5 antigen recognition domain. Optionally, the reduction in the number of immunoregulatory cells having CD5 may be determined by any cell death assay known in the art.

In one embodiment, the disclosure includes a method of reducing the number of immunoregulatory cells having CD7 by contacting the immunoregulatory cells with an effective amount of the engineered cells described above expressing a chimeric antigen receptor peptide having a CD7 antigen recognition domain. Optionally, the reduction in the number of immunoregulatory cells having CD7 may be determined by any cell death assay known in the art.

In one embodiment, the disclosure includes a method of reducing the number of immunoregulatory cells having a CD8 antigen by contacting the immunoregulatory cells with an effective amount of the engineered cells described above expressing a chimeric antigen receptor peptide having a CD8 antigen recognition domain. Optionally, the reduction in the number of immunoregulatory cells having CD8 may be determined by any cell death assay known in the art.

In one embodiment, the disclosure includes a method of reducing the number of immunoregulatory cells having CD52 by contacting the immunoregulatory cells with an effective amount of the engineered cells described above expressing a chimeric antigen receptor peptide having a CD52 antigen recognition domain. Optionally, the reduction in the number of immunoregulatory cells having CD52 may be determined by any cell death assay known in the art.

Method of Treatment

In another embodiment, the disclosure provides methods for the treatment of a cell proliferative disease. The method includes administration of a therapeutically effective amount of the engineered cells described above to a patient in need thereof.

Cell proliferative disease is any one of cancer, neoplastic disease or any disease involving uncontrolled cell proliferation (e. g. formation of cell mass) without any differentiation of those cells into specialized and different cells.

Cell proliferative diseases as also include a malignancy, or a precancerous condition such as a myelodysplasia syndrome or a preleukemia, or prelymphoma.

With respect to the disclosed methods, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., meduUoblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma), lymphoma, malignant mesothelioma, mastocytoma, melanoma, multiple myeloma, nasopharynx cancer, non-Hodgkin lymphoma, B-chronic lymphocytic leukemia, hairy cell leukemia, acute lymphoblastic leukemia (ALL), T-cell acute lymphocytic leukemia, and Burkitt's lymphoma, extranodal NK/T cell lymphoma, NK cell leukemia/lymphoma, post-transplant lymphoproliferative disorders, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, stomach cancer, testicular cancer, thyroid cancer, and ureter cancer. Preferably, the cancer is a hematological malignancy (e.g., leukemia or lymphoma, including but not limited to Hodgkin lymphoma, non-Hodgkin lymphoma, chronic lymphocytic leukemia, acute lymphocytic cancer, acute myeloid leukemia, B-chronic lymphocytic leukemia, hairy cell leukemia, acute lymphoblastic leukemia (ALL), and Burkitt's lymphoma), thymic carcinoma, diffuse large cell lymphoma, mantle cell lymphoma, small lymphocytic lymphoma (SLL), and chronic lymphoid leukemia (CLL), T-cell lymphoma, and peripheral T-cell lymphoma.

The disclosure provides a method for the treatment of acute organ rejection by depletion of T and NK cells that are associated with CD2, CD3, CD4, CD5, CD7, CD8, and CD52.

In one embodiment, the disclosure includes a method for the treatment of acute or chronic graft versus host disease (GVHD) by depletion of T cells and NK cells that are associated with at least one of CD2, CD3, CD4, CD5, CD7, CD8, and CD52.

In one embodiment, the disclosure provides a method to prevent organ rejection by administering to a patient who has undergone organ transplant or will undergo an organ transplant an effective amount of an engineered cell having CD3CAR.

In another embodiment, the disclosure provides a method to prevent or treat GVHD by administering to a patient in need thereof an effective amount of an engineered cell having CD3CAR.

In one embodiment, the disclosure includes a method for the depletion or reduction of donor and host T or NK cells using CAR T or NK cells in vivo for stem cell transplant. This could be accomplished by administration of CAR T or NK cells to a patient immediately before the infusion of the bone marrow stem cell graft.

The disclosure provides a method of immunotherapy as a conditioning or bridge-to-transplant strategy or stand-alone for the treatment of cell proliferative diseases that are associated with at least one of CD2, CD3, CD4, CD5, CD7, CD8, and CD52.

The disclosure provides a method for the treatment of cell proliferative diseases that are associated with at least one of CD2, CD3, CD4, CD5, CD7, CD8, and CD52.

In another embodiment, the disclosure provides a method for the treatment of non-cancer related diseases that are associated with the expression of at least one of CD2, CD3, CD4, CD5, CD7, CD8, and CD52.

In some embodiments, CAR having a CD2, CD3, CD4, CD5, CD7, CD8, or CD52 antigen recognition domain for use in the treatment of a cell proliferative disease is combined with a checkpoint blockade, such as CTLA-4 and PD1/PD-L1. This may lead to enhanced tumor eradication.

The presence of the immunosuppressive microenvironments can limit the full functions of CAR T/NK cells. In some embodiments, the combination of CD4CAR with checkpoint blockade such as CTLA-4 and PD1/PD-L1 can lead to enhanced tumor eradication. Currently checkpoint blockade is being tested in clinical trials in combination with CAR T cells.

In some embodiments, CARs having a CD2, CD3, CD4, CD5, CD7, CD8, or CD52 antigen recognition domain are used as a strategy to deepen, remove, reduce, resist and/or prolong responses to initial chemotherapy, or when combined with other adjunct therapies. All available adjunct therapies to treat or prevent the disease condition are considered to be part of this disclosure and are within the scope of the present disclosure In some embodiments, NK cell CARs having a CD2, CD3, CD4, CD5, CD7, CD8, or CD52 antigen recognition domain, are administrated "off-the-shelf" to any mammal with cancer and/or autoimmune disorders.

CD3CAR

In some embodiments, the NK cell bearing the CD3 CAR exhibits an antitumor immunity and exerts the efficacy of killing leukemias/lymphomas expressing CD3

The disclosure provides methods for deleting or reducing abnormal or malignant T cells in bone marrow, blood and organs using CD3CAR NK cells. In some embodiments, CD3 positive malignancies may include, but is not limited to precursor T lymphoblastic leukemia/lymphoma, mature T cell lymphomas/leukemias, EBV-positive T-cell lymphoproliferative disorders, adult T-cell leukemia/lymphoma, mycosis fungoides/sezary syndrome, primary cutaneous CD30-positive T-cell lymphoproliferative disorders, peripheral T-cell lymphoma (not otherwise specified), angioimmunoblastic T-cell lymphoma and anaplastic large cell lymphoma.

In some embodiments, CD3CAR NK cells can be used to treat patients with T-leukemias/lymphomas, who are not eligible for stem cell therapy or never achieved a remission despite many intensive chemotherapy regimens. In further embodiments, CD3CAR NK cells may be used as a component of conditioning regimen for a bone marrow transplant or a bridge to the bone marrow transplant.

CD4CAR

In one embodiment, the engineered cell having the CD4CAR exhibits an antitumor immunity when the antigen recognition domain of the CAR binds to its corresponding antigen. In a preferred embodiment, the CD8 T cell comprising the CAR exerts the efficacy of killing leukemias/lymphomas cells expressing CD4.

The present disclosure includes methods for deleting, reducing, treating, preventing or eliminating abnormal or malignant T cells found in, including, but not limited to, bone marrow, blood, and/or organs. In some embodiments, malignant CD4 expressing cells are present in patients with precursor T lymphoblastic leukemia/lymphoma, mature T-cell lymphomas/leukemias cells such as, for example, T-cell prolymphocytic leukemia, EBV-positive T cell lymphoproliferative disorders, adult T-cell leukemia/lymphoma, mycosis fungoides/sezary syndrome, primary cutaneous CD30-positive T-cell lymphoproliferative disorders, peripheral T-cell lymphoma (not otherwise specified), angioimmunoblastic T-cell lymphoma, and anaplastic large cell lymphoma.

In some embodiments, CD4CAR cells are used to treat T-leukemias/lymphomas cells in patients not eligible for stem cell therapy or patients that have never achieved a remission despite many chemotherapy regimens.

In some embodiments, CD4CAR cells are used to treat CD4 expressing acute myelomonocytic leukemia, acute monoblastic leukemia, monocytic leukemia, and chronic myelomonocytic leukemia.

In some embodiments, the CD4CAR T cells can be expanded in the T cell culture medium and the subpopulations such central memory T cells or naïve T cells can be isolated and used to improved engraftment. These cells may persist and support memory T cell functions, which would make them ideal candidates for long-term control of cancers The presence of the immunosuppressive microenvironments can limit the full functions of CAR T/NK cells. In some embodiments, the combination of CD4CAR with checkpoint blockade such as CTLA-4 and PD1/PD-L1 can lead to enhanced tumor eradication.

In some embodiments, CD4CAR cells are used as a strategy to deepen, remove, reduce, resist and/or prolong responses to initial chemotherapy, or when combined with other adjunct therapies. All available adjunct therapies to treat or prevent the disease condition are considered to be part of this disclosure and are within the scope of the present disclosure. Chemotherapy includes, but is not limited to, CHOP (cyclophosphamide, doxorubicin, vincristie, prednisone), EPOCH (etoposide, vincristine, doxorubicin, cyclophosphamide, prednisone), or any other multidrug regimens. In a preferred embodiment, CD4CAR cells are utilized for treating or preventing a residual disease after stem cell transplant and/or chemotherapy.

In one embodiment, the cell including the CD4CAR exhibits depletion of immunoregulatory cells when the antigen recognition domain of the CAR binds to its corresponding antigen. For example, the cells including CD4CAR include, but are not limited to, at least one of CD8 T cell, NK cell, or NK-92 cell. Any other suitable cell having CD4CAR that exhibit and/or exerts the high efficacy of deletion of CD4 helper cells when encountering them, whereby organ transplant rejections can be prevented or autoimmune diseases can be controlled or relieved is considered to be part of this disclosure and within the scope of the present disclosure.

There is no concern about persisting CAR-associated side effects observed in CAR T cells. In some embodiments, CD4CAR NK cells may be administrated to patients with autoimmune disorders in an acute or critical clinical setting to rapidly deplete immunoregulatory cells such as CD4 helper T cells, and thereby enable or allow new or non-memory CD4 helper T cells to regenerate.

The disclosure includes a method of generating CD4CAR. In some embodiments, CD4CAR is generated using T-cells. In other embodiments, CD4CAR is generated using NK cells or NK-92 cells, such that they are administered "off-the-shelf" to any mammal with cancer and/or autoimmune disorders. In some embodiments, CD4CAR NK-92 or NK cells are able to kill cells, reduce, deplete, and/or prevent particular CD4+ T cells or cancer cells expressing CD4.

In some embodiments, CD4CAR NK-92 cells can be generated having a high level of expression of CD4CAR by flow cytometry using goat-anti-mouse Fab antibodies or a part thereof. Any other type of antibody generated using any other genus is considered to be part of this disclosure and is within the scope of the present disclosure.

In some embodiments, CD4CAR NK-92 cells can be utilized for one therapy at a time when there is minimal residual disease after a stem cell transplant or chemotherapy.

In some embodiments, the CD4CAR is part of an expressing gene or a cassette. In a preferred embodiment, the expressing gene or the cassette may include an accessory gene or a epitope tag or a part thereof, in addition to the CD4CAR. The accessory gene may be an inducible suicide gene or a part thereof, including, but not limited to, caspase 9 gene, thymidine kinase, cytosine deaminase (CD) or cytochrome P45029. The "suicide gene" ablation approaches improves safety of the gene therapy and kill cells only when activated by a specific compound or a molecule. In some embodiments, the suicide gene is inducible and is activated using a specific chemical inducer of dimerization (CID).

In some embodiments, the accessory tag is a c-myc tag, truncated EGFR gene (EGFRt) or a part or a combination thereof. The accessory tag may be used as a nonimmunogenic selection tool or for tracking markers.

In some embodiments, the host cells expressing CD4CAR can be administrated with one or more additional therapeutic agents to a mammal (e.g., a human). In this regard, the composition including the host cells or the vector comprising CD4CAR can be administered first, and the one or more additional therapeutic agents can be administered second, or vice versa.

The present disclosure includes within its scope administering a typical amount of host cells expressing CD4CAR to a mammal, which for example may be in the range from about 0.5 million to about 1 billion cells. All sub-ranges and ranges outside the above-indicated range are considered to be part of the disclosure and is within the scope of the present disclosure.

In a preferred embodiment, a SFFV promoter is used to redirect CD8 T cells to target cells expressing CD4 and to drive CD4CAR expression. In some embodiments, the CAR includes functional characteristics such as, extracellular expression of scFv and exertion of a strong immune response when encountering with the CD4 expressing cells.

In one embodiment, the cell comprising the CD4CAR is selected from a group including a cytotoxic T lymphocyte (CTL), and a Natural Killer (NK) cell. In a preferred embodiment, the cells having the CAR include, but are not limited to, CD8 T cells, NK cells, and NK-92 cells.

In some embodiments, CD4CAR may be used with drug conjugates, including DNA/nucleic acid conjugates, peptides, chemical entities and/or small molecules to provide enhanced efficacy and safety.

Control of HIV-1 infection can be achieved in HIV patients using a combination of antiretroviral therapies, however, the viral load increases after discontinuation. The source or reservoir of re-emergent HIV-1 is memory CD4 T cells. In one embodiment, the CD4CAR of the present disclosure is used to deplete memory CD4 T cells, whereby a sterilizing cure is accomplished for the HIV infection. In another embodiment, the CD4CAR assists in blocking HIV viral entrance, whereas CD4CAR binds to the CD4 protein, a protein essential for HIV entry.

Accordingly, the disclosure provides a method prevent organ transplant rejections by depleting CD4 T cells. The method includes administering to a patient in need thereof a therapeutically effective amount of an engineered cell having a chimeric antigen receptor polypeptide having a CD4 antigen recognition domain.

CD5CAR

In another embodiment, administration of a CAR polypeptide having a CD5 antigen recognition domain (CD5CAR) is used to treat rheumatoid arthritis. In another embodiment, CD5CAR may be used as a prophylaxis for graft-versus-host disease following bone marrow transplantation therapy (BMT) therapy. In another embodiment, CD5CAR may be used to modify of CD5 expression in treatment of autoimmune disorders and malignancies.

In some embodiments, the disclosure of engineered cell having a chimeric antigen receptor selective for CD5 may act as a bridge to bone marrow transplant for those patients who are not longer responding to chemotherapy or have minimal residual diseases and are not eligible for bone marrow transplant. In further embodiments, CD5CAR can eliminate CD5 positive leukemic cells followed by bone marrow stem rescues to support lymphopenia.

In particular embodiments, CD5CAR a T or NK cell targets cells that express CD5. Target cells may be, but is not limited to cancer cells, such as T-cell lymphoma or T-cell leukemia, precursor acute T-cell lymphoblastic leukemia/lymphoma, B cell chronic lymphocytic leukemia/small lymphocytic lymphoma, mantle cell lymphoma, CD5 positive diffuse large B cell lymphoma, and thymic carcinoma.

In one embodiment, CD5CAR may be used for treating non-hematologic disorders including, but not limited to, rheumatoid arthritis, graft-versus-host-disease and autoimmune diseases.

The engineered or modified T cells may be expanded in the presence of IL-2 or/and both IL-7 and IL-15, or using other molecules.

The introduction of CARs can be fulfilled before or after the inactivation of CD5 by expanding in vitro engineered T cells prior to administration to a patient.

In particular embodiments, the inactivation of CD5 can be achieved by one of the following means:

(1) Expressing anti-CD5 scFv on T cell surface linked to a transmembrane domain via a hinge region. This may result in the conversion of CD5-positive T cells to CD5 negative T cells.

(2). Expressing anti-CD5 scFv that specifically binds to CD5 protein or negative modulators of CD5 thereof, or fragments or domains thereof.

In some embodiments, a scFv (single-chain antibody) against CD5 is derived from a monoclonal or polyclonal antibody binding to intracellular CD5 and blocks the transport of CD5 protein to the cell surface. In a preferred embodiment, anti-CD5 scFv includes an ER (endoplasmic reticulum) retention sequence, KDEL. When it is expressed intracellularly and retained to the ER or Golgi, the anti-CD5 scFv entraps CD5 within the secretion pathway, which results in the prevention of CD5 proper cell surface location in a T cell.

In some embodiments, CD5CAR T cells are co-administrated with immunomodulatory drugs, such as, but not limited to CTLA-4 and PD-1/PD-L1 blockades, or cytokines, such as IL-2 and IL12 or inhibitors of colony stimulating factor-1 receptor (CSF1R), such as FPA008, which lead to better therapeutic outcomes.

In another embodiment, the disclosure provides a method of imparting, aiding, increasing, or boosting anti-leukemia or anti-lymphoma immunity.

The therapeutic agent including the engineered cell expressing the CAR as an active ingredient can be administered intradermally, intramuscularly, subcutaneously, intraperitoneally, intranasally, intraarterially, intravenously, intratumorally, or into an afferent lymph vessel, by parenteral administration, for example, by injection or infusion, although the administration route is not limited.

Any method of the disclosure may further includes the step of delivering to the individual an additional cancer therapy, such as surgery, radiation, hormone therapy, chemotherapy, immunotherapy, or a combination thereof.

Chemotherapy includes, but is not limited to, CHOP (cyclophosphamide, doxorubicin, vincristie, prednisone), EPOCH (etoposide, vincristine, doxorubicin, cyclophosphamide, prednisone), or any other multidrug regimens. In a preferred embodiment, CD54CAR cells are utilized for treating or preventing a residual disease after stem cell transplant and/or chemotherapy.

In another embodiment, any method of the disclosure may further include antiviral therapy, cidofovir and interleukin-2, Cytarabine (also known as ARA-C) or natalizumab treatment for MS patients or efalizumab treatment for psoriasis patients or other treatments for PML patients. In further aspects, the T cells of the disclosure may be used in a treatment regimen in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation. Drugs that inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993) can also be used. In a further aspect, the cell compositions of the present disclosure are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In one aspect, the cell compositions of the present disclosure are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present disclosure. In an additional embodiment, expanded cells are administered before or following surgery.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia greata, ankylosing spondylitis, autoimmune hepatitis, autoimmune parotitis, Crohn's disease, diabetes (Type 1), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, and ulcerative colitis.

The present disclosure may be better understood with reference to the examples, set forth below. The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure.

Following administration of the delivery system for treating, inhibiting, or preventing a cancer, the efficacy of the therapeutic engineered cell can be assessed in various ways well known to the skilled practitioner. For instance, one of ordinary skill in the art will understand that a therapeutic engineered cell delivered in conjunction with the chemo-adjuvant is efficacious in treating or inhibiting a cancer in a subject by observing that the therapeutic engineered cell reduces the cancer cell load or prevents a further increase in cancer cell load. Cancer cell loads can be measured by methods that are known in the art, for example, using polymerase chain reaction assays to detect the presence of certain cancer cell nucleic acids or identification of certain cancer cell markers in the blood using, for example, an antibody assay to detect the presence of the markers in a sample (e.g., but not limited to, blood) from a subject or patient, or by measuring the level of circulating cancer cell antibody levels in the patient.

Throughout this specification, quantities are defined by ranges, and by lower and upper boundaries of ranges. Each lower boundary can be combined with each upper boundary to define a range. The lower and upper boundaries should each be taken as a separate element.

Reference throughout this specification to "one embodiment," "an embodiment," "one example," or "an example" means that a particular feature, structure or characteristic described in connection with the embodiment or example is included in at least one embodiment of the present embodiments. Thus, appearances of the phrases "in one embodiment," "in an embodiment," "one example," or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

As used herein, the terms "comprises," "comprising," "includes," "including," "has," "having," or any other variation thereof, are intended to cover a non-exclusive inclusion. For example, a process, article, or apparatus that comprises a list of elements is not necessarily limited to only those elements but may include other elements not expressly listed or inherent to such process, article, or apparatus.

Further, unless expressly stated to the contrary, "or" refers to an inclusive "or" and not to an exclusive "or". For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of any term or terms with which they are utilized. Instead, these examples or illustrations are to be regarded as being described with respect to one particular embodiment and as being illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," and "in one embodiment."

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any one, two, three, or four of the members, e.g., a and c; a, d, and e; b, c, d, and e; etc.

Examples

Targeting of Human T Cell Malignancies Using CD4-Specific Chimeric Antigen Receptor (CAR)-Engineered T Cells Materials and Methods Blood Donors, Primary Tumor Cells and Cell Lines Human lymphoma cells and peripheral blood mononuclear cells were obtained from residual samples. Umbilical cord blood cells were obtained from donors at Stony Brook University Hospital. SP53 and KARPAS 299 lymphoma cell lines were obtained from ATCC (Manassas, Va.).

Lentivirus Production and Transduction of T Cells

To produce viral supernatant, 293FT cells were co-transfected with pMD2G and pSPAX viral packaging plasmids, and with either pRSC.CD4.3G or GFP Lentiviral vector, using Lipofectamine 2000 (Life Technologies, Carlsbad, Calif.) per manufacturer's protocol. Prior to lentiviral transduction, umbilical cord or peripheral blood mononuclear buffy coat cells were activated for two days in the presence of 300 IU/mL IL-2 and 1 μg/mL anti-human CD3 (Miltenyi Biotec, Germany).

T Cell Expansion

CAR-transduced T cells were expanded for 7 days in T cell media (50% AIM-V, 40% RPMI 1640, 10% FBS and 1× penicillin/streptomycin; all Gibco) supplemented with IL-2. Cells were counted every day and media was added every 2-3 days in order to maintain T cell counts below $2 \times 10^6$ cells/mL.

CAR Immunophenotype

For the analysis of CAR cell immunophenotype, following 7 days of expansion, CD4CAR T cells and GFP control cells were stained with CD45RO, CD45RA, CD62L and CD8 (all from BD Biosciences) for flow cytometry analysis.

Co-Culture Target Cell Ablation Assays

CD4CAR T cells or GFP T cells (control) were incubated with target cells at ratios of 2:1, 5:1 and 10:1 (200,000, 500,000 or 1 million effector cells to 100,000 target cells, respectively) in 1 mL T cell culture media, without IL-2 for 24 h. Target cells were KARPAS 299 cells (anaplastic large T cell lymphoma expressing CD4), leukemia cells from a patient with CD4+ T cell leukemia—Sezary syndrome—and from a patient with CD4+ PTCL lymphoma. As a negative control, CD4CAR T cells and GFP T cells were also incubated with SP53 (mantle cell lymphoma) cells, which do not express CD4, in the same ratios in 1 mL separate reactions. After 24 hours of co-culture, cells were stained with mouse anti-human CD8 and CD4 antibodies. In the experiments with SP53 cells, SP53 cells were labeled with CMTMR (Life Technologies) prior to co-culture with T cells, and T cells were labeled with mouse anti-human CD3 (PerCp) after co-culture incubation.

In Vivo Mouse Xenogenic Model

NSG mice (NOD.Cg-Prkdc$^{scid}$ Il2rg$^{tm1Wjl}$/SzJ) from the Jackson Laboratory were used under a Stony Brook University IACUC-approved protocol. Mice were all male and between 8 and 12 weeks old. Three sets of in vivo experiments were performed with no blinding. For each set, 10 mice were irradiated with a sublethal (2.5 Gy) dose of gamma irradiation and assigned randomly to the treatment or control group. 24 h later, mice were given one intradermal injection of $0.5\times10^6$ or $1.0\times10^6$ KARPAS 299 cells in order to form a measurable subcutaneous tumor within 7 days. Tumor size area was measured every other day. In the first set, three days after the injection of 1 million KARPAS 299 cells, 2 million CD4CAR T (5 mice) or 2 million GFP T control cells (5 mice) were administered to the mice intravenously (by tail vein injection). A second dose of 8 million cells was injected intravenously on Day 22. In the second set, 10 NSG mice was irradiated and injected with $0.5\times10^6$ KARPAS 299 cells. On day 2, mice were injected intravenously with one course of 8 million CD4CAR T cells (5 mice) and 8 million GFP T control cells (5 mice). A second dose of 5.5 million cells was injected intravenously on Day 10. In the third set, 10 NSG mice were irradiated and injected with $0.5\times10^6$ KARPAS 299 cells. On day 1, mice were intravenously injected with $2.5\times10^6$ CD4CAR T cells or with GFP T control cells (5 mice per group). Intravenous injections were repeated every 5 days for a total of four courses.

Results

Generation of the Third Generation of CD4CAR

The scFv (single-chain variable fragment) nucleotide sequence of the anti-CD4 molecule was derived from humanized monoclonal ibalizumab (also known as Hu5A8 or TNX-355). This monoclonal antibody has been used in a variety of Phase I or II clinical trials. To improve signal transduction through the CD4CAR, the intracellular domains of CD28 and 4-1BB co-stimulators were fused to the CD3 zeta signaling domain. Additionally, the leader sequence of CD8 was introduced for efficient expression of the CD4CAR molecule on the cell surface. Indeed, the anti-CD4 scFv is linked to the intracellular signaling domains by a CD8-derived hinge (H) and transmembrane (TM) regions (FIG. 1A). The CD4CAR DNA molecule was sub-cloned into a lentiviral plasmid. Because of the presence of two co-stimulatory domains (CD28 and 4-1BB), CD4CAR is considered to be a third generation CAR. CD4CAR expression is controlled under a strong SFFV (spleen focus-forming virus) promoter and is well suited for hematological applications.

Characterization of CD4CAR

Figure 1B:
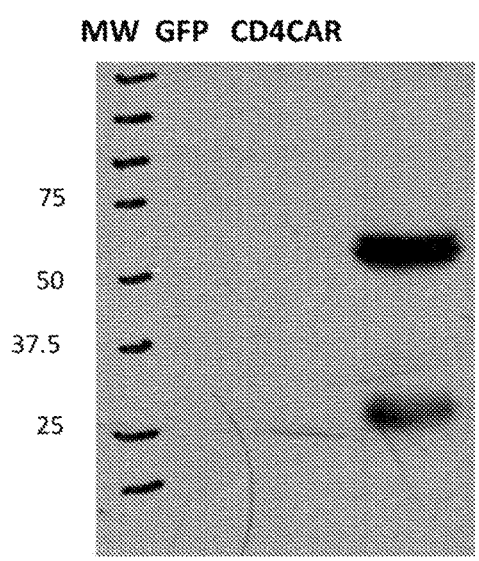
Figure 1C:
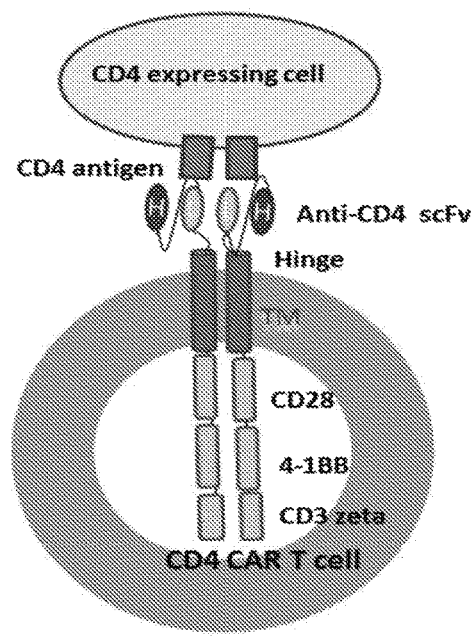
Figure 6:
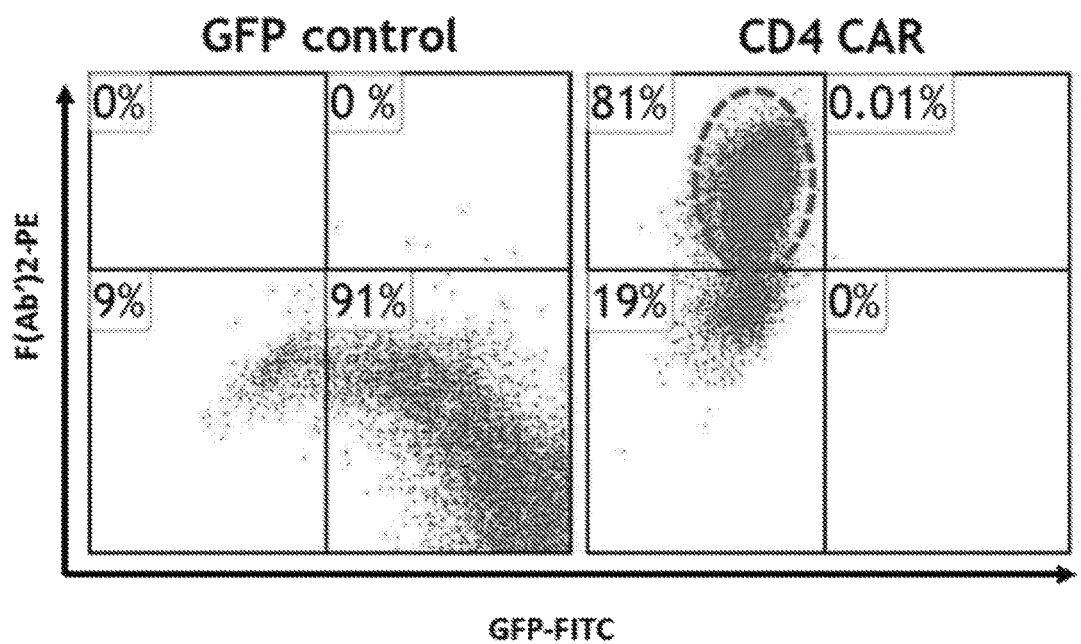
FIG. 6. CD4CAR is expressed on the surface in HEK-293 cells. HEK-293 cells were transduced for 6 hours with CD4CAR or GFP control viral supernatant. Following a 3 day incubation, cells were analyzed by flow cytometry.

In order to verify the CD4CAR construct, transfected 293-FT cells were subjected to Western blot analysis. Immunoblotting with an anti-CD3zeta monoclonal antibody showed bands of predicted size for the CD4CAR CD3zeta fusion protein (FIG. 1B). As expected, no CD3zeta expression was observed for the GFP control vector (FIG. 1B). The generated CD4CAR lentiviruses were also tested for transduction efficiency in HEK293 cells via flow cytometry for scFv (FIG. 6). Therefore, we confirmed that our generated third-generation CD4CAR contained the CD3zeta intracellular domain on the intracellular end and the scFv on the extracellular end, implying that all other elements were present: CD8 hinge and transmembrane domains, and CD28 and 4-1BB co-stimulatory domains (FIG. 1C). For preclinical characterization of CD4CAR expression and function in T cells, human T cells were activated with anti-CD3 antibodies and IL-2, then transduced respectively with CD4CAR and GFP control lentiviral supernatants. The T cells were then expanded for 7 days after transduction.

Cord Blood-Derived CD4CAR T Cells are Highly Enriched for CD8+ T Cells and Most of them Bear a Central Memory T Cell Like Immunophenotype.

Figure 2A:
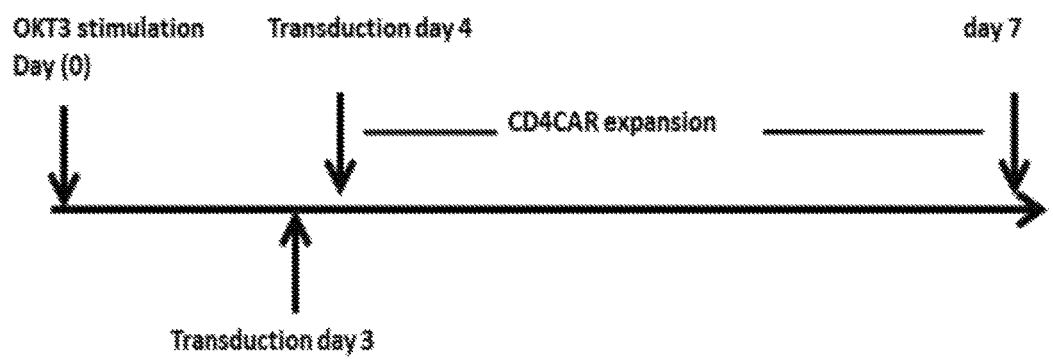
FIG. 2. Production of CD4CAR T cells. (A), experimental design. (B), CB buffy coat cells were activated 2 days with anti-CD3 antibody and IL-2. Cells were transduced with either GFP (middle) or CD4CAR (right) lentiviral supernatant. After 7 days of incubation, cells were analyzed by flow cytometry with goat anti-mouse Fab2 or goat IgG antibodies conjugated with biotin and followed by streptavidin-PE. Non-transduced, labeled CB cells are shown on the left. (C), CD4CAR T cells deplete the CD4+ population during T cell expansion. CB buffy coat cells were activated for 2 days with anti-CD3 antibody and IL-2. CB buffy coat contains two subsets of T cells, CD8+ cytotoxic T cells and CD4+ helper T cells (left). Cells were transduced with either GFP (middle) or CD4CAR (right) lentiviral supernatant. After 3 day culture, cells were analyzed by flow cytometry with mouse-anti-human CD4 (FITC) and CD8 (APC) antibodies. Non-transduced PMBCs were also labeled (left). (D), Most CD4CAR T cells have a central memory-like phenotype. CB buffy coat cells were activated 2 days with anti-CD3 antibody. Cells were transduced with CD4CAR lentiviral supernatant. After 6 day expansion, CD8+ cells were analyzed for CD62L, CD45RO and CD45RA phenotypes by flow cytometry (N=3).
Figure 2B:
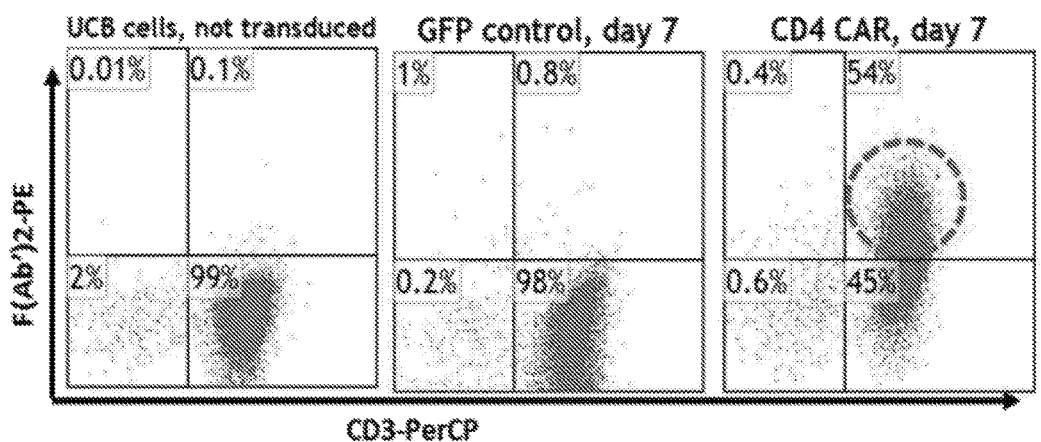
Figure 2C:
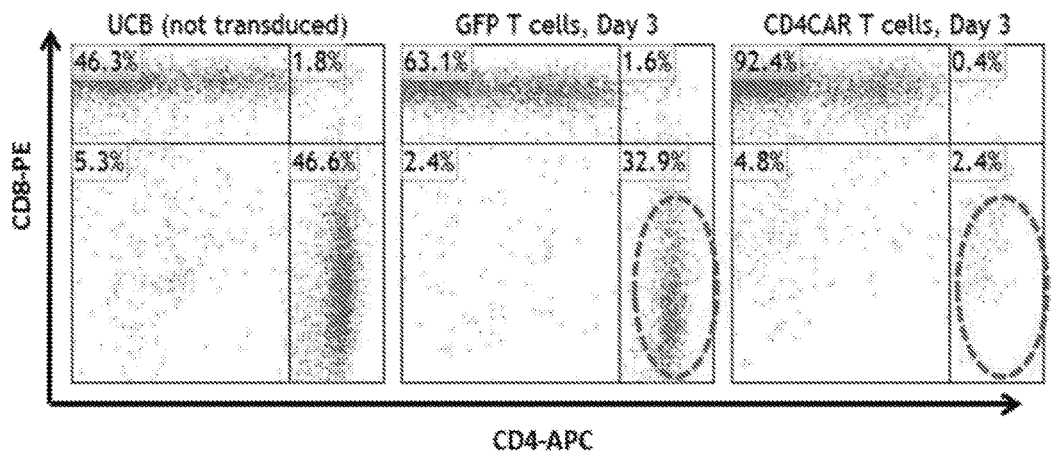

Human umbilical cord blood (CB) is an alternate source for allogeneic T cell therapy. Human CB buffy coat cells were activated and transduced with either CD4CAR or control (GFP) lentiviruses. After transduction, CD4CAR T cells and GFP T cells were expanded for 7 days, with a 20-fold increase in cell count observed for both CD4CAR and GFP T cells (FIG. 7). At day 7, cells were analyzed by flow cytometry for T-cell subsets (FIG. 2A). Flow cytometry analysis showed that ~54% of T-cells expressed the CD4CAR (FIG. 2B). Furthermore, we analyzed the CD4 and CD8 subsets during the course of T expansion following CD4CAR transduction. Consistent with previous findings, a small subset of CD8 cells was induced to express CD4 during T-cell activation with anti-CD3 and costimulatory molecules (FIG. 2C). As expected, the CD4+ T subset was almost completely depleted within 3 or 4 days following CD4CAR transduction as compared to GFP control, in which ~33% of cells remained CD4+(FIG. 2C). These data indicate that CD4CAR T cells exhibit potent anti-CD4 activity in vitro during T cell expansion.

Figure 2D:
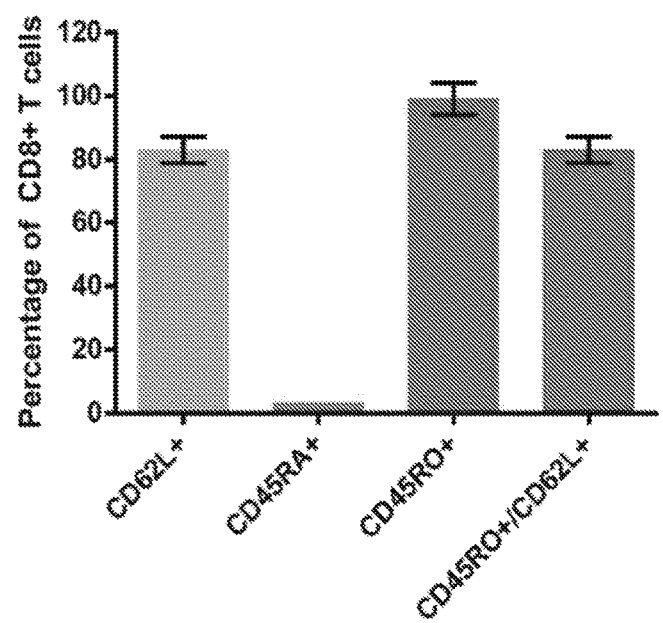

We also evaluated the immunophenotype of CD4CAR T cells at the end of each culture. Following stimulation, naïve T-cells lose CD45RA and gain CD45RO in order to become central memory T-cells. Flow cytometry analysis from 3 representative experiments showed that 96% of the expanded T cells were CD45RO+, ~83% were CD62L+ and ~80% were CD8+CD45RO+CD62L+ whereas fewer than 4% were CD45RA+ (FIG. 2D). The CD8+CD45RO+CD62L+ immunophenotype is consistent with the acquisition of a central memory-like phenotype, and low CD45RA+ expression confirms loss of naïve T cell status.

CD4CAR T Cells Derived from Cord Blood Specifically Kill CD4-Expressing Leukemia/Lymphoma Including Anaplastic Large Cell Lymphoma, Sezary Syndrome and Unclassified PTCL Lymphoma.

Figure 3A:
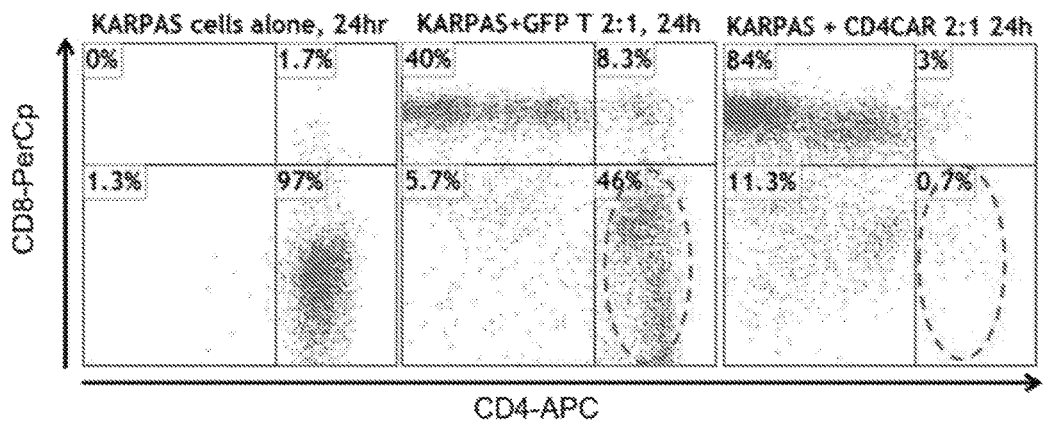
FIG. 3. CD4CAR T cells eliminate T-cell leukemic cells in co-culture assays. (A), CD4CAR T cells eliminate KARPAS 299 T-cell leukemic cells in co-culture. Activated human CB buffy coat cells transduced with either GFP (middle) or CD4CAR (right) lentiviral supernatant were incubated with KARPAS 299 cells at a ratio of 2:1. After 24 hours co-culture, cells were stained with mouse-anti-human CD4 (APC) and CD8 (PerCp) antibodies and analyzed by flow cytometry for T cell subsets (N=3). (B) and (C), CD4CAR T cells eliminate primary T-cell leukemic cells in co-culture. Activated human CB buffy coat cells transduced with either GFP (middle) or CD4CAR (right) lentiviral supernatant were incubated with primary T-cell leukemia cells from Sezary syndrome (B) and PTCLs (C) at a ratio of 2:1. After 24 hours of co-culture, cells were analyzed by flow cytometry with mouse-anti-human CD4 (FITC) and CD8 (APC) antibodies (N=3). Human primary cells alone are also labeled (left). (D) CD4CAR T cells were unable to lyse CD4-negative lymphoma cells (SP53, a B-cell lymphoma cell line). Activated human CB buffy coat cells transduced with either GFP (middle) or CD4CAR (right) lentiviral supernatant were incubated with SP53 mantle cell lymphoma cells which were pre-stained with the membrane dye CMTMR, at a ratio of 2:1. After 24 hours co-culture, cells were stained with mouse-anti-human CD3 (PerCp) and then analyzed by flow cytometry (N=2). SP53 cells alone, pre-stained with CMTMR were also labeled (left).
Figure 3B:
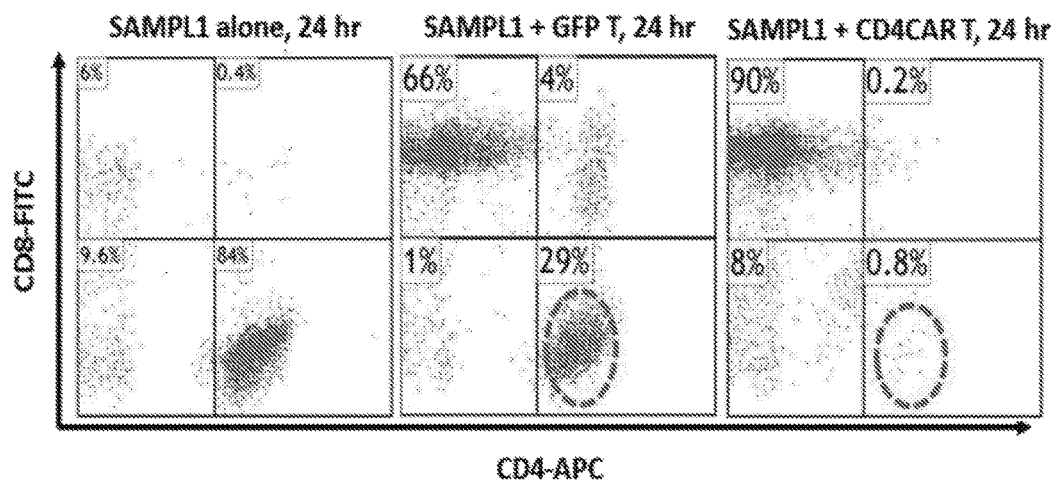
Figure 3C:
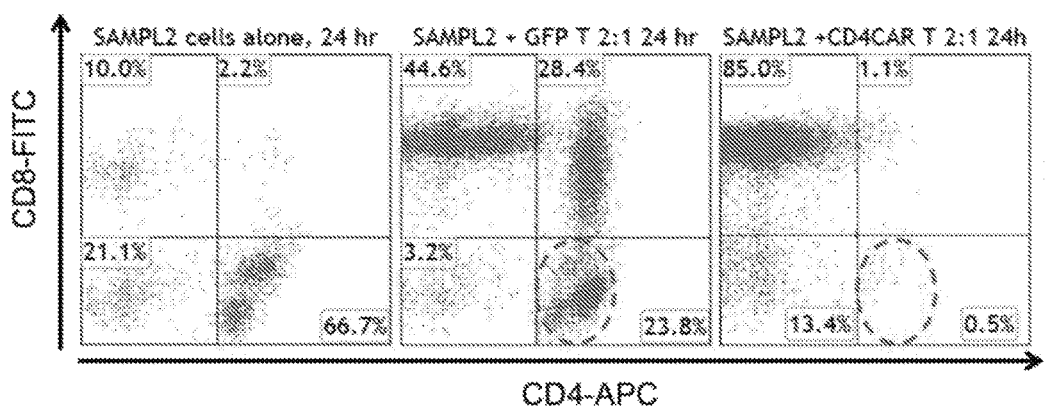
Figure 3D:
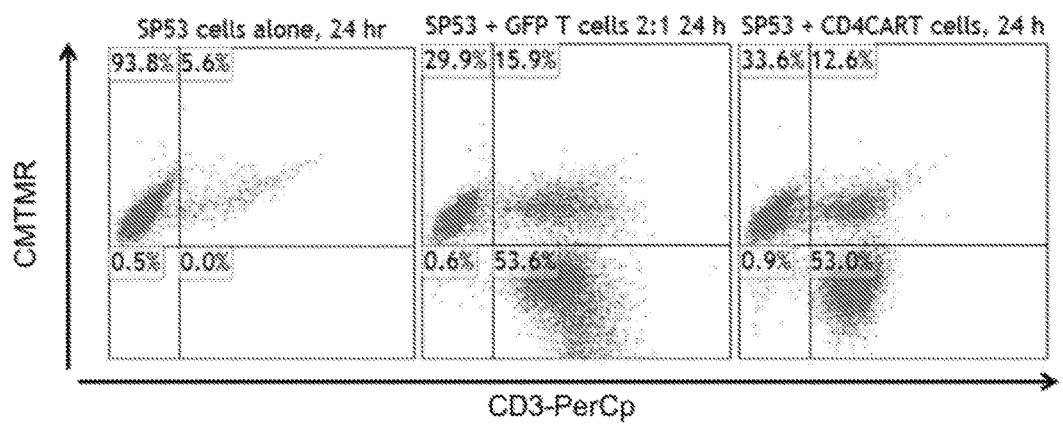

CD4CAR T cells highly enriched for CD8+ T cells were generated (FIG. 2C). The cells were then tested in vitro for anti-leukemic functions using the KARPAS 299 cell line. The KARPAS 299 cell line was initially established from the peripheral blood of a patient with anaplastic large T cell lymphoma expressing CD4. Cytogenetic analysis has previously shown that KARPAS 299 cells have many cytogenetic abnormalities. During co-culture experiments, CD4CAR cells exhibited profound leukemic cell killing abilities (FIG. 3A). First, CB-derived CD4CAR T cells were tested for their ability to ablate KARPAS 299 cells. Indeed, at 24 h incubation and at a low E:T (effector: target) ratio of 2:1, CD4CAR cells successfully eliminated KARPAS 299 cells. As a control, the CD4CAR T cells were also tested for their ability to ablate CD4 negative lymphoma cells. SP53 mantle cell lymphoma cell line is a human B-cell lymphoma cell line that does not express CD4. Flow cytometry analysis showed that CD4CAR T cells were unable to lyse or eliminate SP53 mantle cell lymphoma (FIG. 3D).

Studies were also conducted using patient samples. Patient 1 presented with an aggressive form of CD4+ T cell leukemia, Sezary syndrome, which did not respond to standard chemotherapy. Patient 2 presented with an unspecified CD4+ PTCL lymphoma. Flow cytometry analysis of both patient samples revealed strong and uniform CD4 expression, with almost all leukemic cells expressing CD4 (FIGS. 3B and C). As visualized by flow cytometry analysis, co-culture of patient samples with CD4CAR for 24 hours resulted in rapid and definitive ablation of CD4+ malignancies, with, once again, approximately 98% ablation observed for both Sezary syndrome and PTCL co-cultures, consistent with the ablation of KARPAS previously shown (FIGS. 3B and 3C). Therefore, we show that, in a co-culture assay, CD4CAR T cells efficiently eliminate two different types of aggressive CD4+ lymphoma/leukemia cells directly from patient samples even at the low E:T ratio of 2:1 (FIGS. 3B and 3C). These data support that CD4 is a promising therapeutic target for CD4 positive T-cell leukemias and lymphomas, analogous to the role of CD19 in the targeting of B-cell malignancies via anti-CD19 CAR. Therefore, our patient sample and CD4CAR co-culture assay extends the notion of using CAR to target CD4 positive malignancies.
CD4CAR T Cells Derived from PBMCs Specifically Kill CD4-Expressing the Tumor Cell Line.

Figure 4A:
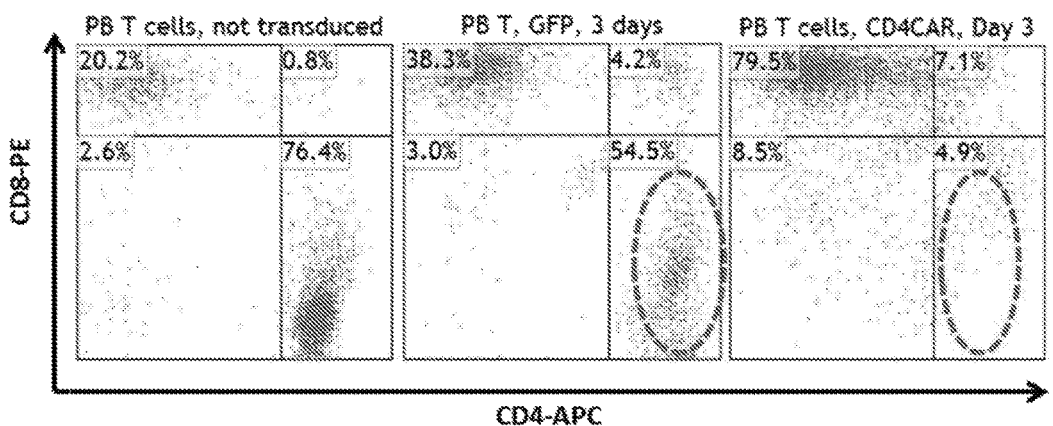
FIG. 4. CD4CAR T cells derived from PBMCs are highly enriched for CD8+ T and specifically kill CD4-expressing leukemic cell lines. (A) CD4CAR T cells derived from PBMCs are highly enriched for CD8+ T cells. PMBC buffy coat cells constituting T cells, CD8+ and CD4+(left) were activated for 2 days with anti-CD3 antibody and IL-2, then transduced with either GFP (middle) or CD4CAR (right) lentiviral supernatant. After 3 days of culture, cells were labeled and analyzed by flow cytometry for T cell subsets. Non-transduced PMBCs were also labeled (left). (B) CD4CAR T cells specifically kill KARPAS 299 cells. PMBC T cells transduced with either GFP control or CD4CAR lentiviral supernatant were incubated with CFSE-stained KARPAS 299 at the ratios of 2:1, 5:1 and 10:1, respectively. After overnight incubation at 37° C., dye 7AAD was added, and the cells were analyzed by flow cytometry. Percent killing of target cells is measured by comparing survival of target cells relative to the survival of negative control cells (SP53 cells, a B-cell lymphoma cell line stained with CMTMR).
Figure 4B:
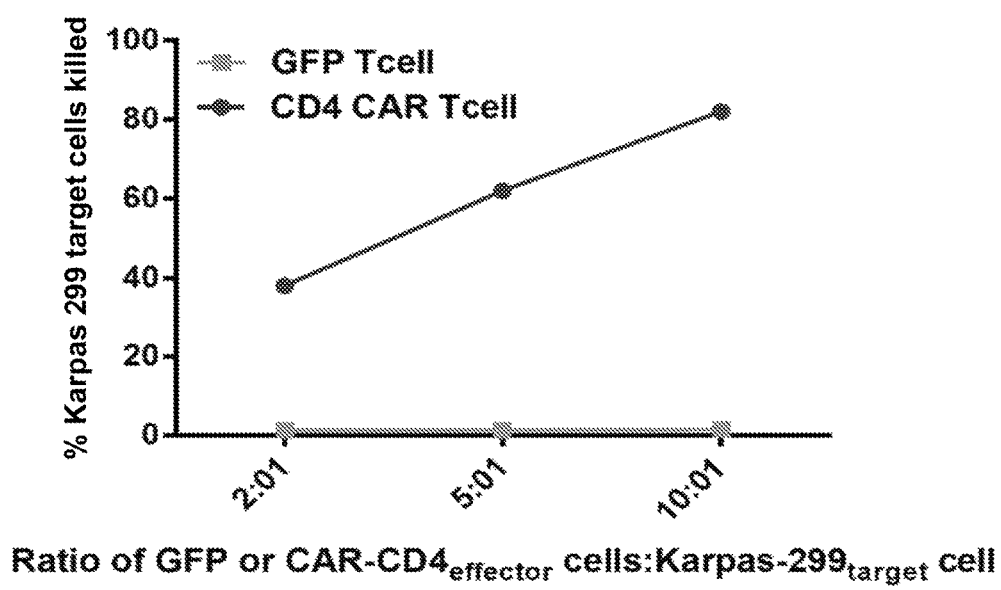

Since autologous adoptive CAR T therapy is commonly used in the clinic, we then tested CD4CAR T cells derived from PBMCs (peripheral blood mononuclear cells). PBMCs were activated and transduced with CD4CAR lentiviruses. The CD4 and CD8 sets were monitored by flow cytometry during cell expansion, and compared to that of cells transduced with control GFP. The PBMCs derived CD4CAR T cells were highly enriched for CD8+ T cells as observed with CD4CAR T cells derived from CB (FIG. 4A), indicative of the role of CD4CAR in the depletion of CD4+. PBMC derived CD4CAR cells were subsequently tested in their ability to ablate CD4 positive leukemia/lymphoma cells, using the KARPAS 299 cell line. The ablation assay involved the co-culture of CD4CAR T cells or GFP T cells, with KARPAS 299 cells, and with the SP53 mantle cell lymphoma cell line negative control. Reactions were stopped after 24 hours: dead cells were stained with 7-AAD (7-aminoactinomycin D) and live cells were analyzed by flow cytometry. KARPAS 299 cells incubated with CD4CAR T cells overnight were eliminated at a rate of 38%, 62%, and 85%, at E:T ratios of 2:1, 5:1, and 10:1, respectively (FIG. 4B). Combined, these data demonstrate a strong dose-response relationship. When target cells were incubated with GFP control T cells, no killing of KARPAS 299 cells was observed. These results demonstrate that CD4CAR T cell ablation is specific to CD4+ targeting.
CD4CAR T Cells Exhibit Significant Anti-Tumor Activity In Vivo.

In order to evaluate in vivo anti-tumor activities, we developed a xenogeneic mouse model using the KARPAS 299 cell line. Multiple different settings were used to test CD4CAR T cell efficacy in vivo. We first tested ability of the CD4CAR T cells to delay the appearance of leukemia in the NSG mice with a single low dose. Prior to the injection, modified T cells displayed ~40 to 50% of cells expressing CD4CAR as demonstrated by flow cytometry analysis. Mice received intradermal injections of KARPAS 299 cells and then a low dose (2 million) of single systemic injection (intravenous administration) of CD4CAR T cells was given. A single low dose of systemic CD4CART cells administration to leukemia-bearing mice caused only transient regression or delayed the appearance of leukemic mass (FIG. 5A). When leukemia growth started to accelerate, an additional course of administration of $8 \times 10^6$ CD4CAR T cells remarkably arrested the leukemic growth (FIG. 5A).

To further test the efficacy of CD4CAR anti-leukemia activity, we administered two courses of relatively large doses of CD4CAR T cells. Similarly, two injections totaling $13.5 \times 10^6$ CD4CAR T cells caused more pronounced leukemia growth arrest as compared to a lower CD4CAR dose but eventually the leukemic cell population recovered (FIG. 5B). Finally, we investigated the efficacy of multiple course injections of a low dose of CD4CAR T cells (each $2.5 \times 10^6$ cells). We treated the mice bearing subcutaneous leukemia with repeat intravenous injections of CD4CAR T cells, once every 4 or 5 days for total of 4 injections. After four courses of CD4CAR T cell administration, one of four treated mice was tumor free and exhibited no toxic appearance. Multiple dose CD4CAR T cell-treated mice displayed more significant anti-leukemic effect compared to single dose (FIGS. 5C and 5A). Moreover, treatment with CD4CAR T cells significantly prolonged the survival of mice bearing KARPAS 299 lymphoma as compared to treatment with the GFP-transduced control T cells (FIG. 5D).
Anti-CD4 Chimeric Antigen Receptor (CD4CAR) NK Cells Efficiently Target T-Cell Malignancies in Preclinical Models
Methods Materials
Primary Tumor Cells and Cell Lines Human leukemia cells were obtained from residual samples on a protocol approved by the Institutional Review Board of Stony Brook University. Cord blood cells were also obtained under protocol from donors at Stony Brook University Hospital. Written, informed consent was obtained from all donors. Karpas 299, HL-60, CCRF-CEM, MOLT4 and NK-92 cell lines were obtained from ATCC (Manassas, Va.). NK-92 cells were cultured in filtered NK cell media, defined as alpha-MEM without ribonucleosides and deoxyribonucleosides with 2 mM L-glutamine, 1.5 g/L sodium bicarbonate, 12.5% heat-inactivated horse serum, 12.5% heat-inactivated FBS, 1× Pen/Strep, 0.2% inositol, 0.02% folic acid, and 50 µM beta-mercaptoethanol, supplemented with IL-2 (300 IU/mL), unless otherwise specified. Karpas 299, CCRF-CEM, and MOLT4 cell lines were cultured in RPMI, 10% FBS, 1× Pen/Strep (Gibco, Waltham, Mass., USA). HL-60 cells were cultured in IMDM, 10% FBS, 1× Pen/Strep (Gibco, Waltham, Mass., USA).
CAR Construct Generation The CD4-specific CAR (pRSC.SFFV.CD4.3G) was designed to contain an intracellular CD28 domain upstream of 4-1BB and CD3zeta domains, thereby making the construct a third-generation CAR.
Lentivirus Production and Transduction To produce viral supernatant, 293FT-cells were co-transfected with pMD2G and pSPAX viral packaging plasmids containing either pRSC.SFFV.CD4.3G or GFP lentiviral vector control, using Lipofectamine 2000 (Life Technologies, Carlsbad, Calif.) per manufacturer's protocol.

NK cells were cultured for a minimum of 2 days in the presence of 300 IU/mL IL-2 prior to transduction with viral supernatant. Transfection and transduction procedures are further described in Supplemental Data.
CAR Detection on Transduced NK Cells In order to determine CAR expression, NK cells were washed and suspended in FACs buffer (0.2% BSA in DPBS) 3 days after transduction. Normal goat IgG (Jackson Immunoresearch, West Grove, Pa.) was used to block nonspecific binding. Each NK cell sample was probed with Biotin-labeled polyclonal goat anti-mouse F(Ab')$^2$ (1:250, Jackson Immunoresearch, West Grove, Pa.) for 30 minutes at 4° C. Cells were washed once, and resuspended in FACs buffer. Cells were then stained with PE-labeled streptavidin (1:250, Jackson Immuno Research, West Grove, Pa.) for 30 minutes at 4° C. Cells were washed with FACs buffer, and resuspended in 2% formalin. Flow cytometry was performed using a FACS Calibur instrument (Becton Dickinson, Franklin Lakes, N.J.), and results were analyzed using Kaluza software (Beckman Coulter, Brea, Calif.).
Co-Culture Assays CD4CAR or vector control NK cells were incubated with CD4 expressing Karpas 299 cells (anaplastic large T-cell lymphoma), HL-60 cells (acute promyelocytic leukemia), CCRF-CEM cells (T-cell acute lymphoblastic leukemia: T-ALL), CD4$^+$ T-cells isolated from human cord blood, or CD4 expressing primary human leukemic cells (adult Sézary syndrome and pediatric T-ALL) at ratios of 2:1 and 5:1

(200,000 and 500,000 effector cells to 100,000 target cells, respectively) in 1 mL of NK-cell culture media, without IL-2. After 24 hours of co-culture, remaining live cells were harvested and stained with mouse anti-human CD56 and CD4 antibodies, and were incubated at 4° C. for 30 minutes. CD56$^+$ single positive denoted NK cells, and CD4$^+$ single positive denoted target cells. All cells were washed with FACs buffer, suspended in 2% formalin, and analyzed by flow cytometry.

Cytotoxicity Assay

CD4CAR or vector control NK cells were incubated with a 50:50 mix of on-target cells (CFSE-stained Karpas 299 cells and CMTMR-stained CCRF-CEM cells) and off-target CMTR-labelled MOLT4 cells at effector: target ratios of 1:1, 1:2, and 1:4 ratios in 1 mL of NK-cell culture media, without IL-2. After 24 hours, cells were stained with 7-AAD (BioLegend, San Diego, Calif.), washed with FACS buffer, and live 7-AAD negative cells were analyzed by flow cytometry.

Colony Forming Unit (CFU) Assay

CD4CAR NK cells were incubated at co-culture effector: target ratios of 2:1 and 5:1 respectively with 500 CD34+CB cells for 24 hours in NK cell media supplemented with IL-2. Controls used were CD34+ cells alone, and non-transduced NK cells co-cultured at 2:1 and 5:1 effector:target ratios with CD34+CB cells. Hematopoietic compartment output was assessed via formation of erythroid burst-forming units (BFU-E) and number of granulocyte/monocyte colony-forming units (CFU-GM) at Day 16. CFU statistical analysis was performed via 2-way ANOVA with alpha set at 0.05.

Xenogeneic Mouse Model

Male 12-week-old NSG mice (NOD.Cg-Prkdcsid Il2rgtm1Wjl/SzJ) were purchased from the Jackson Laboratory (Bar Harbor, Me.) and used under a Stony Brook University IACUC-approved protocol. NSG mice were irradiated with a sublethal (2.5 Gy) dose of gamma irradiation. Twenty-four hours later, mice were intradermally injected with $0.5 \times 10^6$ Karpas 299 cells that had been stably transduced to express luciferase, in order to cause a measurable subcutaneous tumor to form. On day 1, twenty-four hours following Karpas 299 cell injection, mice were intravenously injected via tail vein with $5 \times 10^6$ CD4CAR NK cells or vector control NK cells (N=4 per group). Intravenous injections were repeated every 5 days for 6 courses total. Tumor size area was measured every other day. On days 7, 14, and 21 following Karpas 299 cell injection, mice were injected subcutaneously with 100 μL RediJect D-Luciferin (Perkin Elmer, Waltham, Mass.) and subjected to IVIS imaging (PerkinElmer, Waltham, Mass.). Images were analyzed using Caliper Life Sciences software (PerkinElmer, Waltham, Mass.).

Statistics

Xenogeneic model sample sizes were estimated using 2-sample, 2-sided equality power analysis (90% power and <5% significance). Unpaired Student T tests were used to determine significance of tumor size area and light intensity. Survival curves were constructed using the Kaplan-Meier method and statistical analyses of survival was performed using a log-rank (Mantel-Cox) test with P<0.05 considered significant. Statistical analyses were performed using GraphPad Prism 6 software. Variance was determined to be similar between the treatment and control group prior to unpaired student-test.

Results

Generation of the Third Generation CD4CAR

Figure 8A:
FIG. 8. CD4CAR construct. (A) Schematic representation of lentiviral vector encoding third generation CD4CAR, driven by spleen focus-forming virus (SFFV) promoter. The construct contains a leader sequence, anti-CD4 scFv, hinge domain (H), transmembrane (TM) and signaling domains CD28, 4-1BB, and CD3 zeta. (B) HEK293FT cells were transfected with GFP vector control (lane 1) and CD4CAR (lane 2) lentiviral plasmids. Forty-eight hours after transfection, cells were removed and subsequently used for Western blot analysis with mouse anti-human CD3z antibody. (C) Illustration of third-generation CAR NK cells targeting CD4 expressing cells.
Figure 8B:
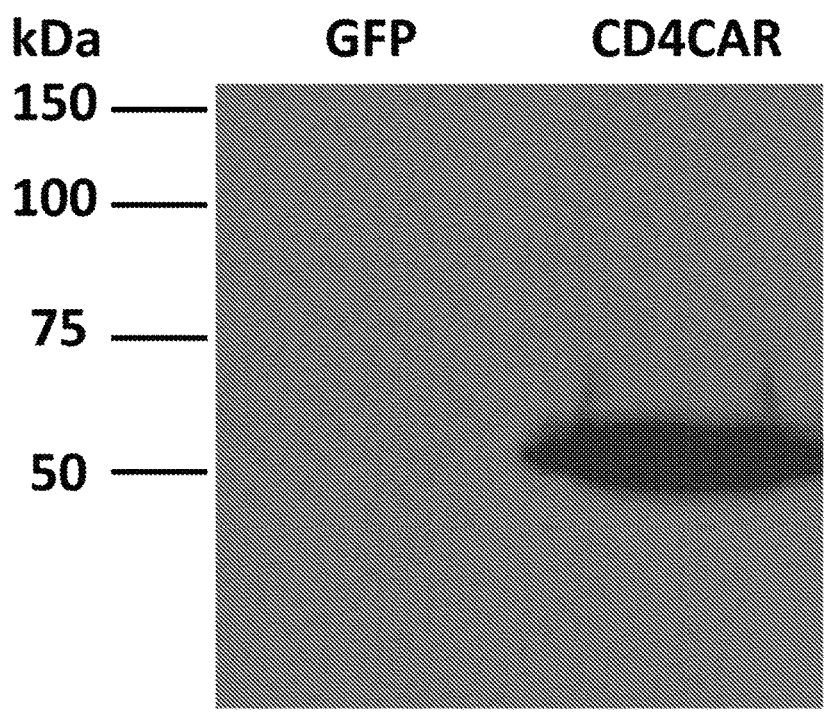
Figure 8C:
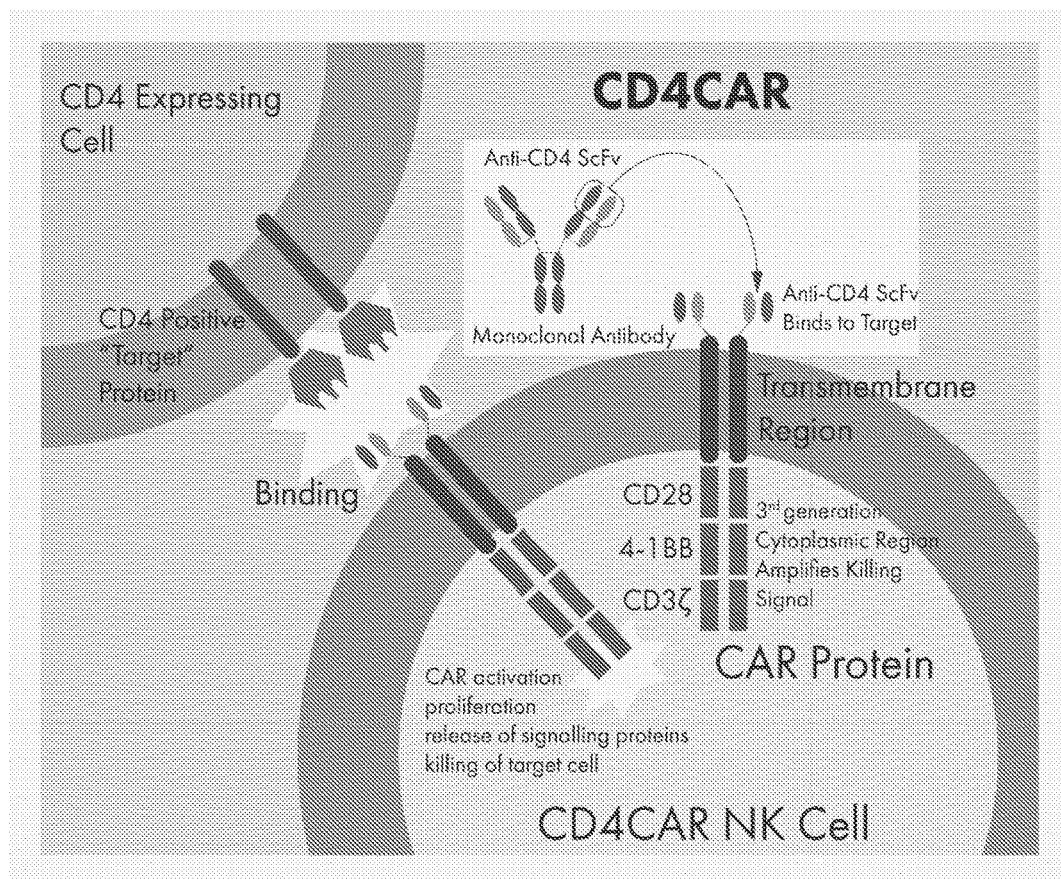

The single-chain variable fragment (scFv) nucleotide sequence of the anti-CD4 molecule was derived from the humanized monoclonal antibody ibalizumab (Hu5A8 or TNX-355)—the safety and efficacy of which have been well studied in clinical trials for HIV. To improve signal transduction, the CD4CAR was designed with CD28 and 4-1BB domains fused to the CD3zeta signaling domain, making it a third generation CAR. CD19-targeting third generation CAR T-cells have previously been used in clinical trials, with great efficacy. For efficient expression of the CD4CAR molecule on the NK cell surface, a strong spleen focus-forming virus promoter (SFFV) was used and the leader sequence of CD8 was incorporated in the construct. The anti-CD4 scFv was separated from the intracellular signaling domains by CD8-derived hinge (H) and transmembrane (TM) regions (FIGS. 8A and 8C). The CD4CAR DNA molecule was subsequently sub-cloned into a lentiviral plasmid.

Characterization of CD4CAR

In order to validate the CD4CAR construct, HEK293-FT cells were transfected with the CD4CAR lentiviral plasmid or vector control plasmid, and 48 hours later were harvested for Western blot analysis. Immunoblotting with an anti-CD3zeta monoclonal antibody showed bands of predicted size for the CD4CAR-CD3zeta fusion protein (FIG. 8B). As expected, no CD3zeta expression was observed for the GFP vector control protein (FIG. 8B).

Generation of CD4CAR NK Cells

Figure 9:
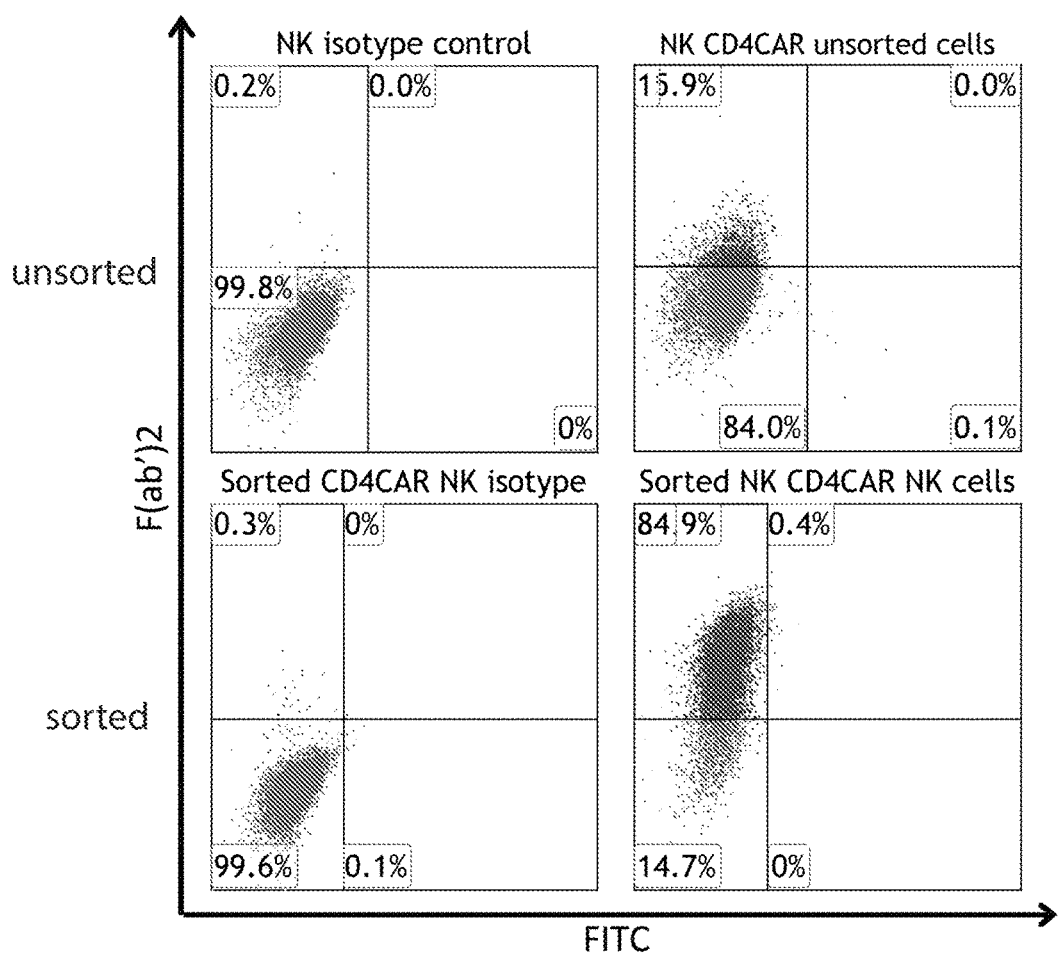
FIG. 9. CD4CAR NK cell production. (A, upper panel) CD4CAR expression levels on NK cells prior to being sorted by FACS (N=3); (A, lower panel) CD4CAR expression on NK cells after sorting and expansion, prior to co-culture experiments (N=3)
Figure 15:
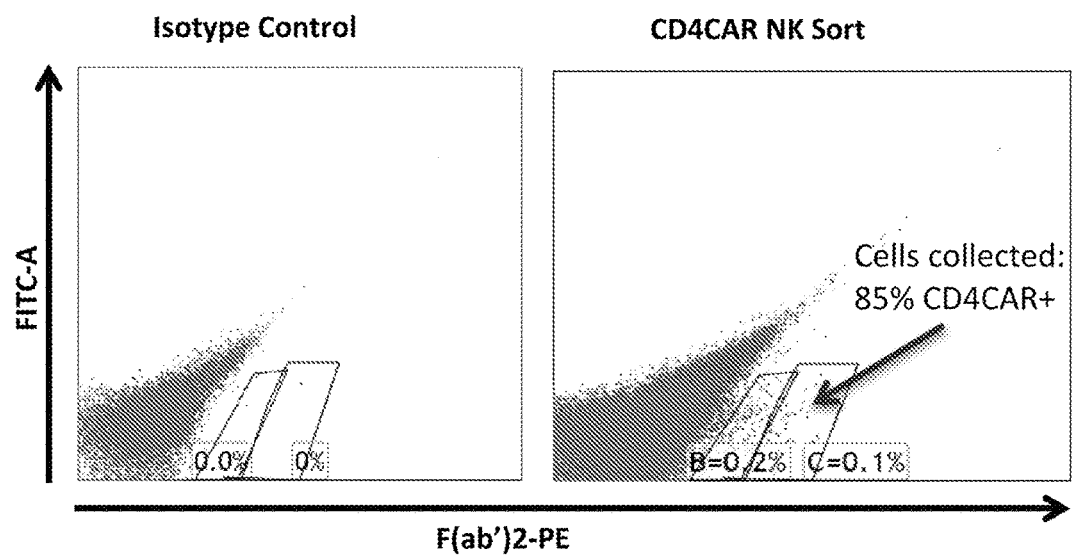
FIG. 15. NK cells were transduced with either vector control or CDCAR lentiviral supernatant, or cultured for non-transduced control. After 7 days of incubation, cells were harvested and analyzed by flow cytometry with Biotin-labeled goat anti-mouse F(Ab')2 followed by streptavidin-PE. NK cells were >85% CD4CAR+ after sorting.

CD4CAR NK transduction efficiency was determined to be 15.9%, as determined by flow cytometry (FIG. 9A upper panel). Next, fluorescence-activated cell sorting (FACS) was used in order to further enrich for CD4CAR$^+$ NK cells. Following sorting, collected CD4CAR$^{high}$ NK cells were confirmed to be more than 85% CD4CAR positive (FIG. 15). After FACS collection of CD4CAR$^{high}$ cells, CD4CAR expression levels remained consistently stable at 75-90% on NK cells during expansion of up to 10 passages, and following cryopreservation. Indeed, at the onset of co-culture experiments, expanded CD4CAR$^{high}$ NK cells expressed CAR at 85% (FIG. 9A lower panel).

CD4CAR NK Cells Specifically Lyse CD4$^+$ Blood Cancer Cells Including Anaplastic Large T-Cell Lymphoma (Karpas 299), Acute Myeloid Leukemia (HL-60) and T-Cell Acute Lymphoblastic Leukemia (CCRF-CEM)

CD4CAR NK cells were tested for anti-lymphoma activity in vitro using the following CD4$^+$ cell lines: Karpas 299, HL-60, and CCRF-CEM. The Karpas 299 cell line was established from the peripheral blood of a 25-year-old patient with anaplastic large T-cell lymphoma. The HL-60 cell line was established from the peripheral blood of a 36-year-old patient with acute promyelocytic leukemia. The CCRF-CEM cell line was established from the peripheral blood of a 4-year-old patient with T-cell acute lymphoblastic leukemia (T-ALL).

Figure 10A:
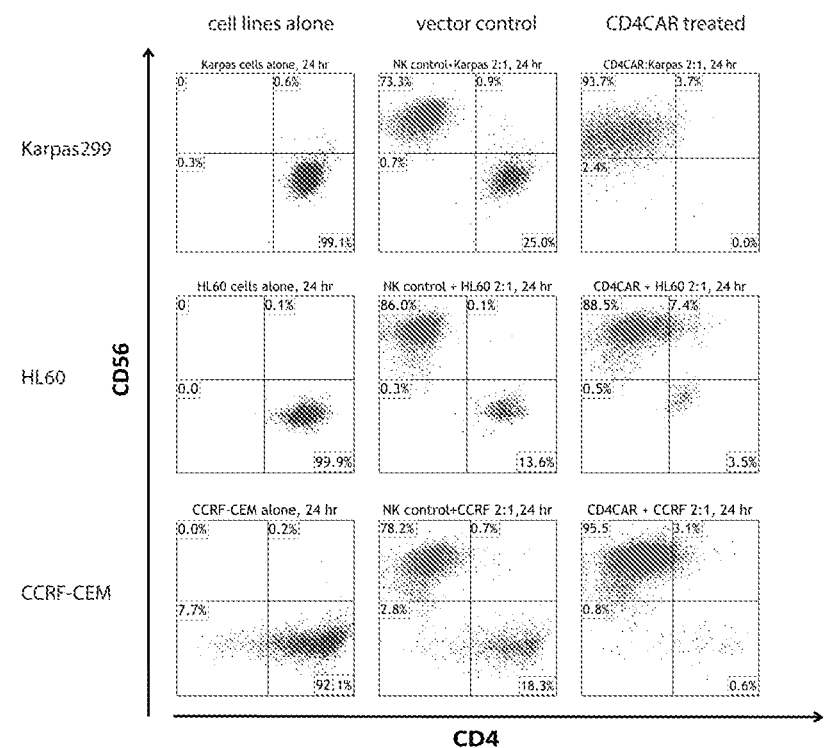
FIG. 10. CD4 CAR NK cells ablate CD4+ leukemia and lymphoma cells in co-culture assays. Co-culture experiments were performed at an effector to target ratio of 2:1 for 24 hours and were directly analyzed by flow cytometry for CD56 and CD4 (panels A and B). Each assay consists of target cells alone control (left), and target cells incubated with NK cells transduced with vector control (center) or CD4CAR (right) lentiviral supernatant. Top row, panel A: Karpas 299 (N=3). Middle row, panel A: HL-60 T-cells (N=2). Bottom row, panel A: CCRF-CEM cells (N=2). CD4CAR NK cells eliminated primary T-cell leukemia cells from a patient with CD4+ T-cell lymphoma/Sézary syndrome (N=2) and CD4 expressing pediatric T-cell ALL (N=2). (C) Bar graph summarizing co-culture assay results for both 2:1 and 5:1 E:T ratios.

During 24-hour co-culture experiments, CD4CAR NK cells showed profound killing of CD4 positive leukemia/lymphoma cells at the low effector cell to target cell ratio (E:T) of 2:1 (FIG. 10A) and the standard 5:1 ratio (FIG. 10C). In co-culture cytotoxicity assays, target tumor cells were identified by the CD4$^+$, CD56$^-$ immunophenotype (labeled in blue on flow cytometry charts). As expected, vector control NK cells showed some non-specific tumor cell killing ability that is innate to NK cells, but as expected, were far less effective against CD4$^+$ tumor cells compared to CD4CAR NK cells. Analysis of Karpas 299 cells alone confirmed 99.1% CD4$^+$ expression (FIG. 1A upper panel). Strikingly, at an E:T ratio of 2:1, CD4CAR NK cells completely ablated 100% of Karpas 299 cells compared to vector control (N=2) (FIG. 10A upper panel and 10C). Similarly, analysis of HL-60 and CCRF-CEM cells alone confirmed high expression of CD4, 99.9% and 92.1%, respectively (FIG. 10A middle and lower panels). Likewise, at an E:T ratio of 2:1, CD4CAR NK cells robustly lysed 75% of HL-60 cells and 97% of CCRF-CEM cells, as compared to vector control (FIGS. 10A and 10C). Combined, these data show that CD4CAR NK cells specifically and potently target $CD4^+$ cells in addition to retaining non-specific anti-tumor cell activity intrinsic to NK cells.

Figure 10B:
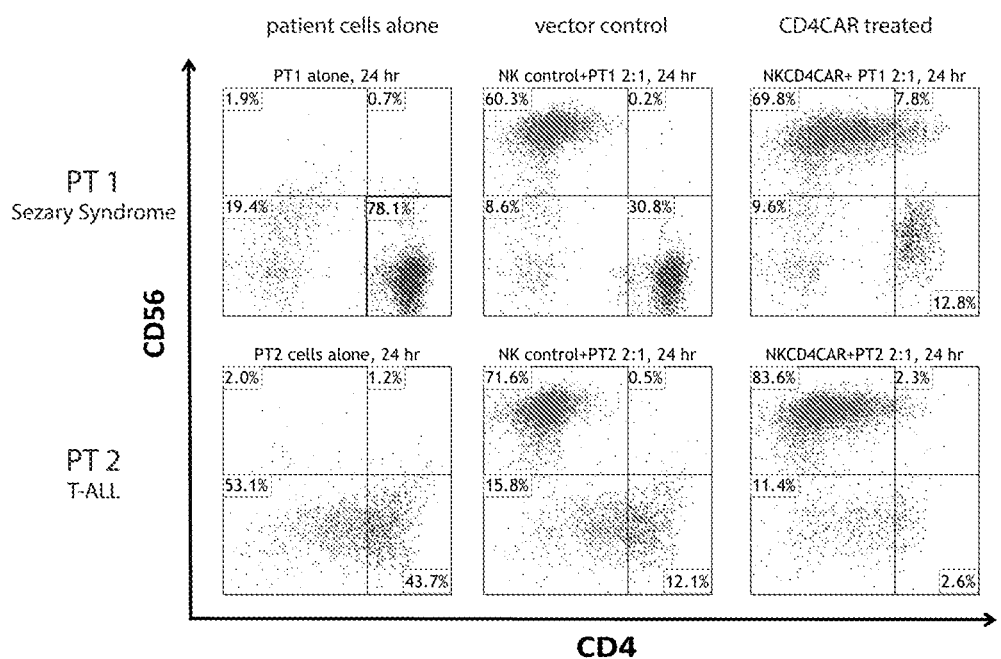

Co-culture studies were also conducted using patient samples (FIGS. 10B and 10C). Patient 1 presented with Sézary syndrome, an aggressive form of $CD4^+$ cutaneous T-cell lymphoma that did not respond to standard chemotherapy. Sézary syndrome is a subset of PTCL. Patient 1's leukemic cells were assessed to be 78.1% $CD4^+$ via flow cytometry (FIG. 10B). Patient 2 presented with a $CD4^+$ pediatric T-cell acute lymphoblastic leukemia (T-ALL). Analogously, Patient 2's cells were assessed to be 43.7% $CD4^+$ via flow cytometry (FIG. 10B). After 24 hours of co-culture at a low E:T ratio of 2:1, CD4CAR NK cells lysed 58% of $CD4^+$ Sézary syndrome cells from patient 1, and 78% of $CD4^+$ T-ALL cells from patient 2 (N=2). Furthermore, at an increased E:T ratio of 5:1, standard for CAR co-culture assays, CD4CAR NK cells lysed 82% of Sézary syndrome cells from patient 1, and 82% of T-ALL cells from patient 2 (N=2) (FIG. 10C and FIG. 14). These data strongly suggest a dose-dependent response and potent CD4CAR NK cell anti-tumor activity in a cell line and patient sample setting for both adult and pediatric $CD4^+$ T cell leukemias and lymphomas.

CD4CAR NK Cells Specifically Lyse CD4-Expressing Tumor Cell Lines in Dose Dependent Manner.

Figure 11:
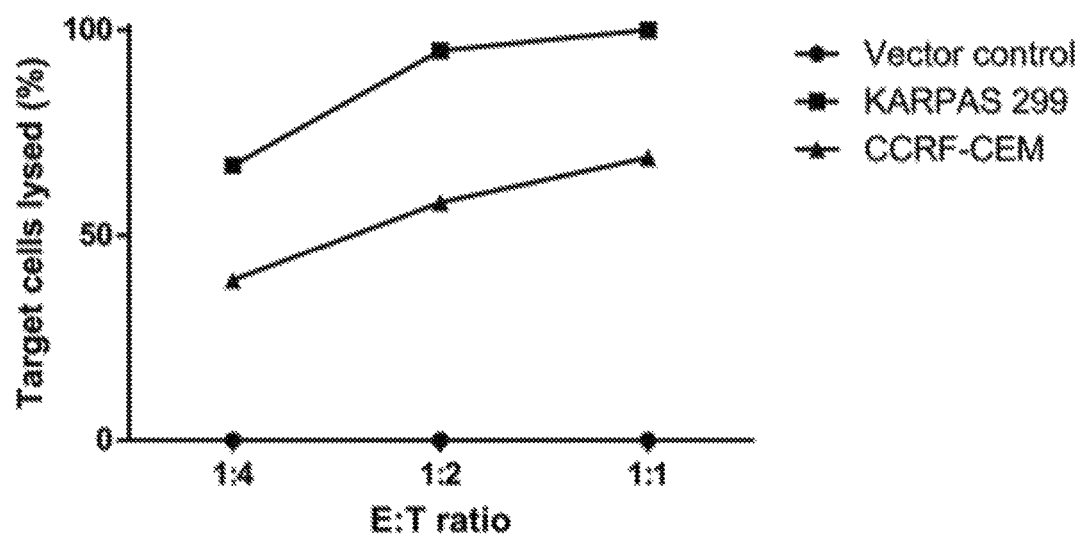
FIG. 11. Co-culture specificity and dose response killing curve. CD4CAR NK cells lyse CD4-expressing leukemic cell lines in a dose dependent and specific manner. CD4CAR NK and vector control cells were incubated with an equal ratio of CFSE-stained "on-target" (Karpas 299 or CCRF-CEM) cells and CMTMR-stained "off target" MOLT4 cells at 1:4, 1:2, and 1:1 effector to target ratios. After 24 hours, 7-AAD dye was added and remaining live cells were analyzed by flow cytometry. Percent killing of target cells was measured by comparing CD4+ Karpas 299 or CCRF-CEM cell survival in CD4CAR NK cell co-cultures relative to that in vector control NK cell co-cultures.
Figure 16A:
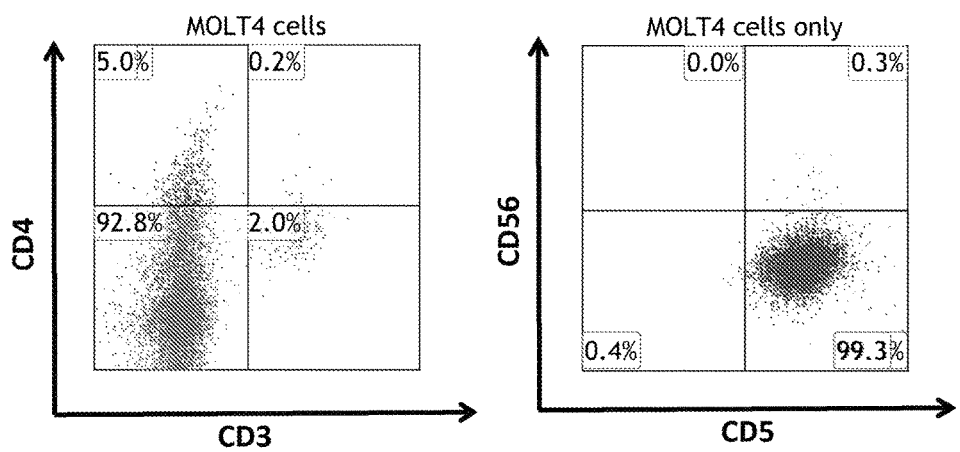
FIG. 16. CD4CAR NK cells did not lyse CD4−, CD5+ MOLT4 negative control. (A) MOLT4 cell immunophenotype was confirmed to be almost all CD4− and CD5+. (B) CD4CAR NK cells did not lyse MOLT4 cells at a 5:1 effector to target ratio at 0 h, 4 h, 8 h, and 24 h (lower panel) as assessed by comparison to vector control NK cell tumorlysis (upper panel). (C) Anti-CD4 CDCAR NK anti-tumor activity was confirmed at 4 h with a CD4+ Karpas 299 positive control at an 5:1 E:T ratio.
Figure 16B:
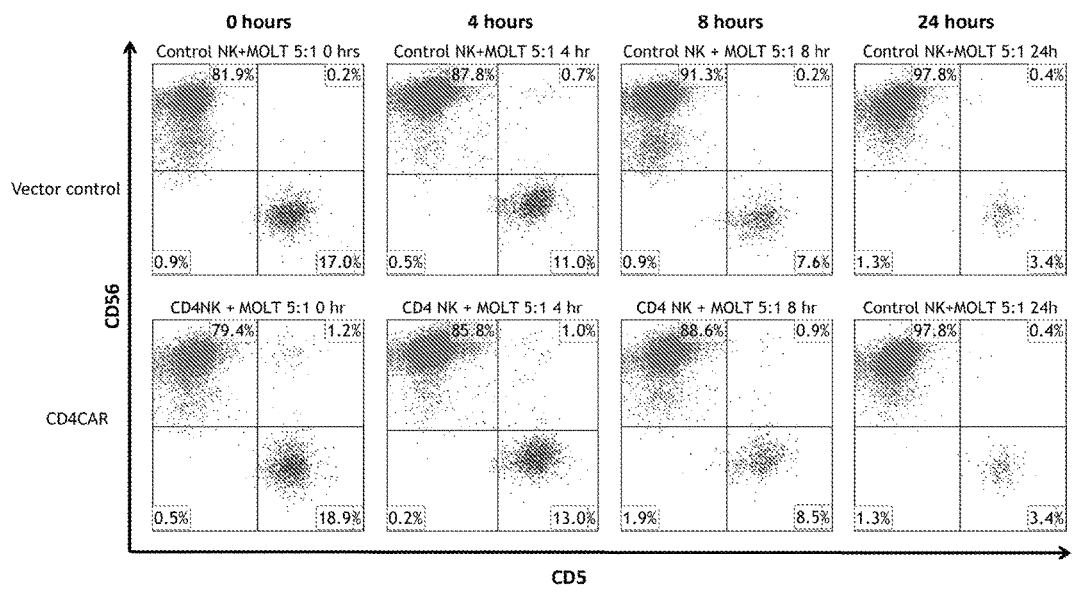
Figure 16C:
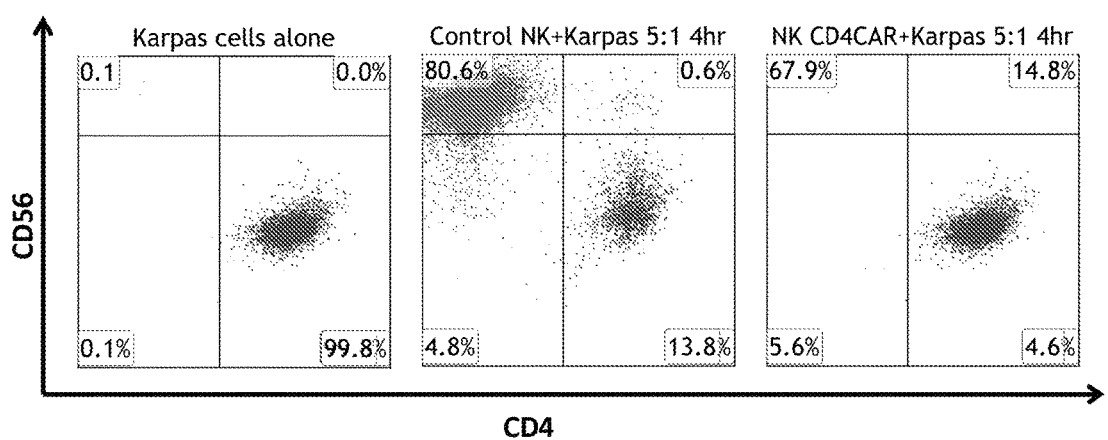

CD4CAR NK cells specifically lyse $CD4^+$ Karpas 299 and CCRF-CEM leukemic cell lines in vitro in a dose-dependent manner at effector: target ratios of 1:4, 1:2, and 1:1 (FIG. 11). For each co-culture E:T ratio, CD4CAR NK effector cells or vector control NK effector cells were incubated with tumor cells that were comprised of equal numbers of on-target $CD4^+$ cells, CFSE-stained Karpas 299 or CFSE-stained CCRF-CEM, and "off-target" CMTMR-stained $CD4^-$, $CD5^+$ MOLT4 acute lymphoblastic leukemia cells. The MOLT4 cells were included to account for variation in the starting cell numbers and for spontaneous target cell death. After 24 hours, live cells were analyzed by flow cytometry. Percent lysis of target cells was measured by comparing $CD4^+$ target cell survival in CD4CAR NK co-culture to vector control NK co-culture. Karpas 299 cells were eliminated at rates of 67%, 95%, and 100%, at effector to target ratios of 1:4, 1:2, and 1:1, respectively (FIG. 11). And CCRF-CEM cells were eliminated at rates of 39%, 58%, and 69% respectively at the same E:T ratios (FIG. 11). As expected, CD4CAR NK cells did not lyse CMTMR-labeled MOLT4 cells, confirmed to be <5% $CD4^+$ by flow cytometry analysis (FIG. 16A). Additional co-culture experiments confirmed that CD4CAR NK cells did not lyse MOLT4 cells at 0 h, 4 h, 8 h, and 24 h (FIG. 16B), whereas CD4CAR NK cells lysed Karpas 299 cells as detected by flow cytometry as early as 4 h (FIG. 16C). Combined, these data indicate that CD4CAR NK cell anti-tumor cytotoxicity is dose-dependent, rapid onset and highly specific to $CD4^+$ cells.

Figure 12A:
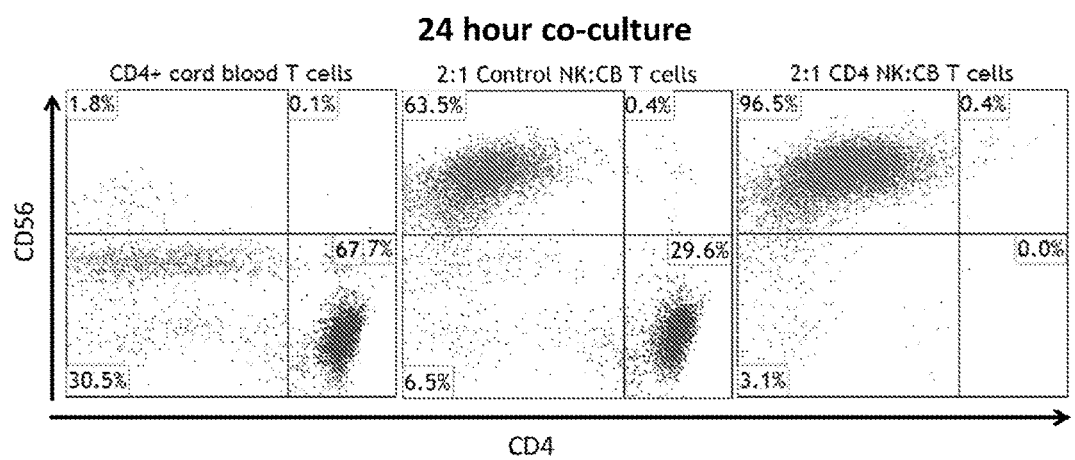
FIG. 12. CD4CAR NK cells eliminate CD4+ T-cells isolated from human cord blood at an effector to target ratio of 2:1, but do not affect hematopoietic stem cell/progenitor compartment output. (A) Co-culture assays were performed at an effector to target ratio of 2:1 for 24 hours, after which, cells were stained with mouse anti-human CD56 and CD4 antibodies. Target cells were incubated alone as a control (left). NK cells were transduced with either vector control (center) or CD4CAR (right) lentiviral supernatant and incubated with CD4+ T-cells obtained from human cord blood. (N=2) (B) CD4CAR NK cells were incubated at co-culture effector:target ratios of 2:1 and 5:1 respectively with 500 CD34+ cord blood cells for 24 hours in NK cell media supplemented with IL-2. Experimental controls used were CD34+ cells alone, and non-transduced NK cells were co-cultured at respective 2:1 and 5:1 effector:target ratios with CD34+CB cells. Hematopoietic compartment output was assessed via formation of erythroid burst-forming units (BFU-E) and number of granulocyte/monocyte colony-forming units (CFU-GM) at Day 16. CFU statistical analysis was performed via 2-way ANOVA with alpha set at 0.05.

Additional co-culture studies were conducted using $CD4^+$ T-cells isolated from cord blood. In these experiments, CD4CAR NK cells completely depleted $CD4^+$ T-cells at an effector:target ratio of 2:1 after 24 hours of co-culture, with remaining cells 0.0% $CD4^+$. As expected, after $CD4^+$ cord blood cell co-culture with corresponding vector control NK cells ($CD56^+$, $CD4^-$), the $CD4^+$ population remained largely intact (FIG. 12A), further confirming specific and robust CD4CAR NK-mediated depletion of $CD4^+$ populations on healthy tissue.

CD4CAR NK Cells do not Affect Stem Cell Output in Hematopoietic Compartment.

Figure 12B:
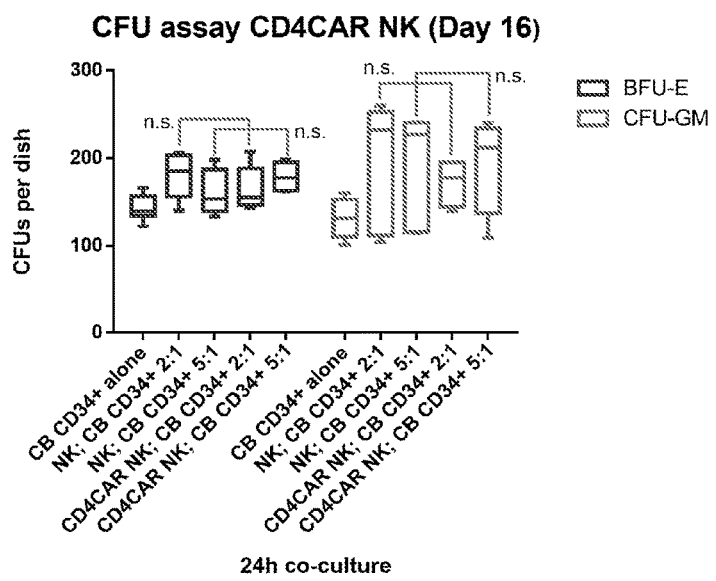

CFU (Colony-Forming-Unit) assay analysis revealed that CD4CAR NK cells did not significantly affect the CD34+ cord blood stem cell output of the hematopoietic compartment. Hematopoietic compartment output was assessed by the presence of erythroid progenitors and granulocyte/macrophage progenitors at Day 0, determined by number of erythroid burst-forming units (BFU-E) and number of granulocyte/monocyte colony-forming units (CFU-GM) at Day 16 (FIG. 12B). This finding is consistent with specific targeting of CD4, a mature T-cell marker, with limited impact on hematopoietic stem cells and early progenitors, and no evidence of lineage skewing, a measure of therapeutic safety.

CD4CAR NK Cells Exhibit Significant Anti-Tumor Activity In Vivo

Figure 13A:
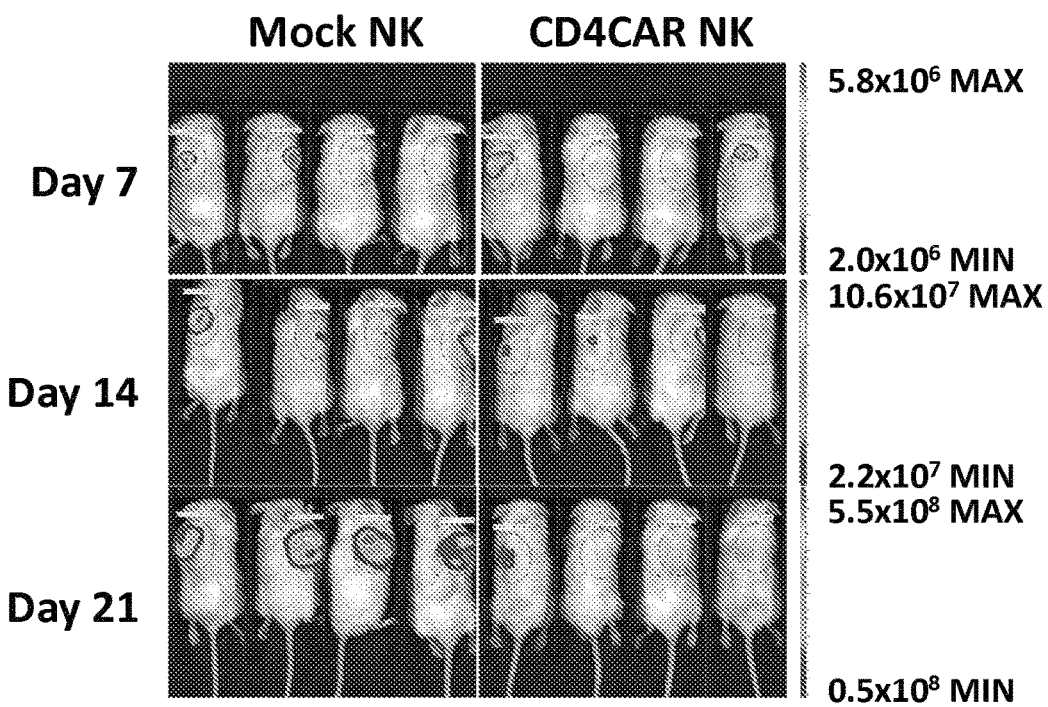
FIG. 13. CD4CAR NK cells demonstrate anti-leukemic effects in vivo. NSG mice were sublethally irradiated and intradermally injected with luciferase-expressing Karpas 299 cells (Day 0) to induce measurable tumor formation. On day 1 and every 5 days for a total of 6 courses, mice were intravenously injected with $5 \times 10^6$ CD4CAR NK cells or vector control NK control cells. (A) On days 7, 14, and 21, mice were injected subcutaneously with RediJect D-Luciferin and subjected to IVIS imaging. (B) Average light intensity measured for the CD4CAR NK injected mice was compared to that of vector control NK injected mice. (C) On day 1, and every other day after, tumor size area was measured and the average tumor size between the two groups was compared. (D) Percent survival of mice was measured and compared between the two groups.
Figure 13B:
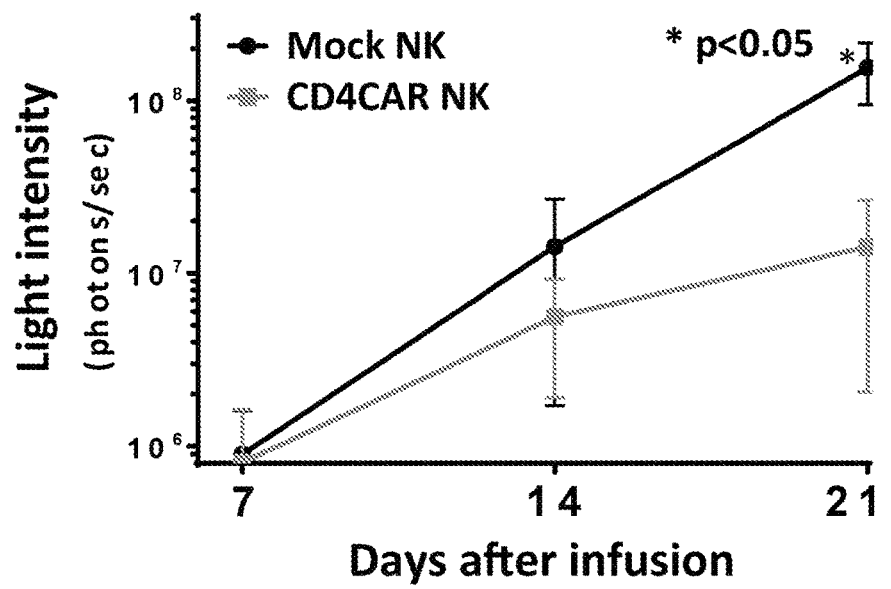
Figure 13C:
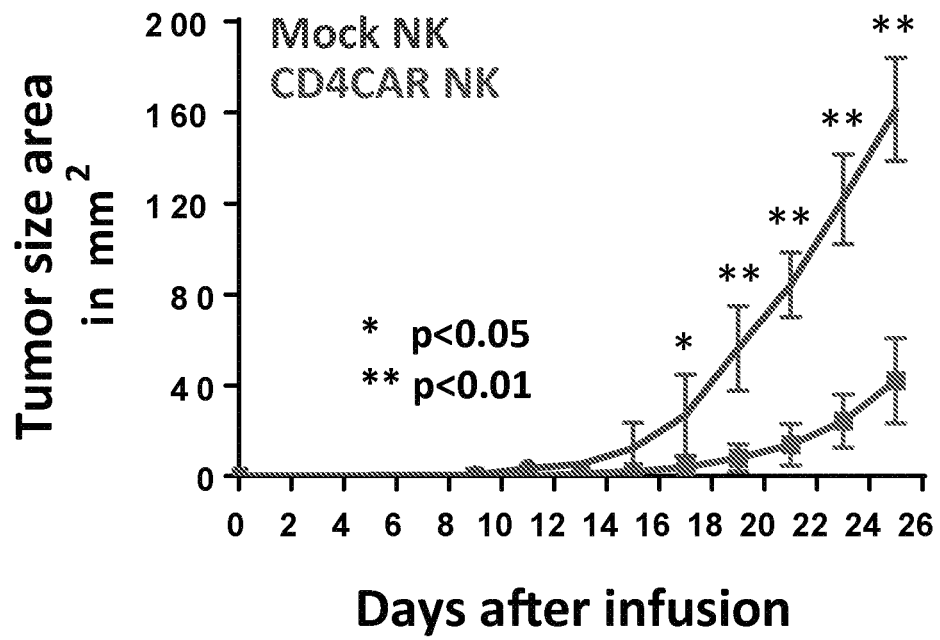
Figure 13D:
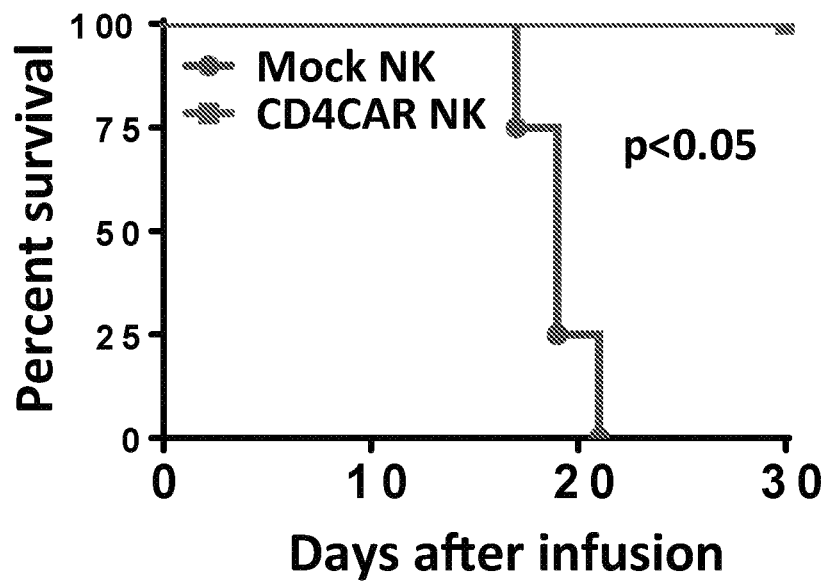

In order to evaluate the in vivo anti-tumor activity of CD4CAR NK cells, we developed a xenogeneic mouse model using NSG mice sublethally irradiated and intradermally injected with luciferase-expressing Karpas 299 cells to induce measurable tumor formation. On day 1, 24 hours following Karpas 299 cell injection, and every 5 days afterwards for a total of 6 courses, mice were intravenously injected with $5 \times 10^6$ CD4CAR NK cells or vector control NK control cells per administration. On days 7, 14, and 21, mice were injected subcutaneously with RediJect D-Luciferin and underwent IVIS imaging to measure tumor burden (FIG. 13A). Average light intensity measured for the CD4CAR NK injected mice was compared to that of vector control NK injected mice (FIG. 13B). By Day 21, the CD4CAR NK injected mice had significantly less light intensity and therefore thus less tumor burden compared to vector control ($p<0.01$). On day 1, and every other day afterwards, tumor size area was measured and the average tumor size between the two groups was compared (FIG. 13C). Unpaired student T test analysis revealed that the average tumor size of CD4CAR NK injected mice was significantly smaller than that of vector control NK injected mice starting on day 17 ($p<0.05$) and continuing on days 19-25 ($p<0.01$). Next, we compared mouse survival across the two groups (FIG. 13D). All of the CD4CAR NK injected mice survived past day 30. However, percent survival of vector control NK injected mice started to decrease on day 17 with no survival by day 23. In summary, these in vivo data indicate that CD4CAR NK cells significantly reduce tumor burden and prolong survival in Karpas 299-injected NSG mice.

Figure 17A:
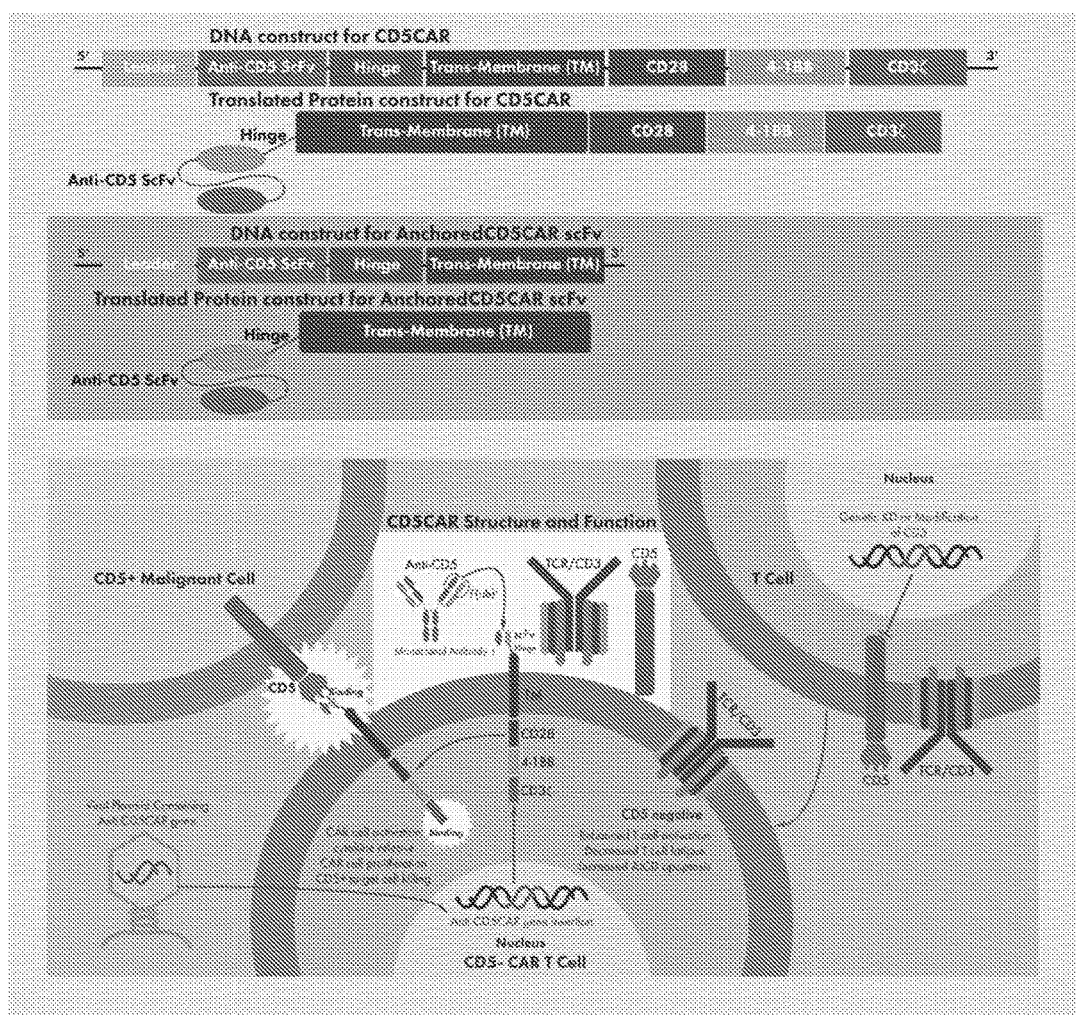
FIG. 17. Generation of CD5CAR. A. The DNA gene construct and the translated protein construct for CD5CAR, and anchored CD5 scFv antibody and a cartoon demonstrating the creation and function of CD5CAR. The DNA construct of the third generation CD5CAR construct from 5' to 3' reads: Leader sequence, the anti-CD5 extracellular single chain variable fragment (Anti-CD5 ScFv), the hinge region, the trans-membrane region, and the three intracellular signaling domains that define this construct as a 3rd generation car; CD28, 4-1BB and CD3ζ. The DNA construct of the anchored CD5 scFv antibody is the same as the CD5CAR construct without the intracellular signaling domains, as is the translated protein product for anchored CD5 scFv antibody. The translated protein constructs contain the anti-CD5 ScFv that will bind to the CD5 target, the hinge region that allows for appropriate positioning of the anti-CD5 ScFv to allow for optimal binding position, and the trans-membrane region. The complete CD5CAR protein also contains the two co-stimulatory domains and an intracellular domain of CD3 zeta chain. This construct is considered as a 3rd generation CAR: CD28, 4-1BB, and CD3ζ. B. Western blot analysis demonstrates the CD5CAR expression in HEK293 cells. HEK293 cells which had been transduced with GFP (as negative control) or CD5CAR lentiviruses for 48 h were used for Western blot analysis using CD3ζ antibody to determine the expression of CD5CAR. Left lane, the GFP control HEK293 cells, with no band as expected. The right lane showing a band at about 50 kDa, the molecular weight that we expected based on the CD5CAR construct. C. Flow cytometry analysis for CD5CAR expression on T cells surface for lentiviral transduced CD5CAR T cells. This analysis was performed on the double transduced CD5CAR T cells at day 8 after the second lentiviral transduction. Left: isotype control T cell population (negative control); right, transduced T cells expressing CD5 CAR showing 20.53% on T cells by flow cytometry using goat anti-mouse F(AB')2-PE.
Figure 17B:
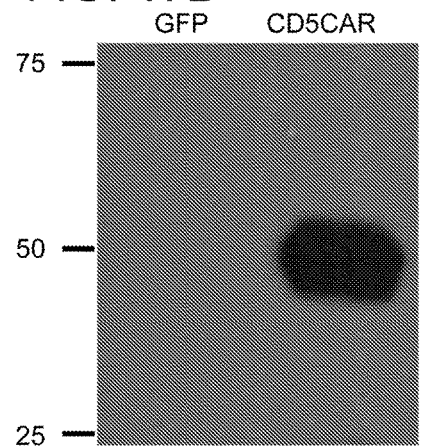
Figure 17C:
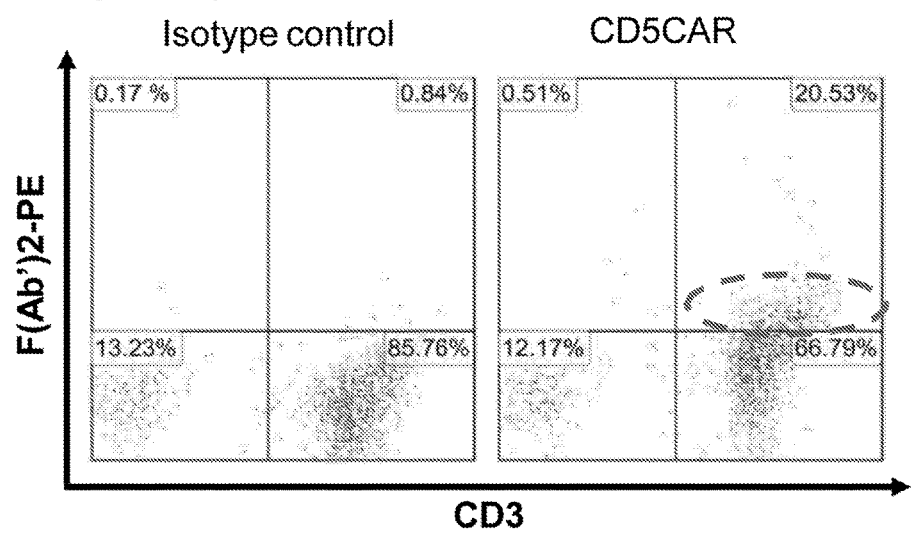

Anti-CD5 Chimeric Antigen Receptor (CD5CAR) T Cells Efficiently Target CD5 Positive Hematologic Malignancies Examples Results Generation of the Third Generation of CD5CAR The construct for CD5CAR, as well as anchored CD5 scFv antibody were designed to test the function and mechanism of CD5CAR T cells in terms of both the targeting and lysis of CD5 expressing cells and the ability of CD5CAR T cells to down-regulate CD5 expression within their own CD5CAR T-cell population (FIG. 17A). To confirm the CD5CAR construct, the generated CD5CAR lentiviruses were transduced into HEK293 cells. After 48 h treatment with CD5CAR or GFP-lentiviruses, the expression of CD5CAR in HEK293 cells was verified by Western blot analysis using CD3zeta antibody, which recognize C-terminal region of CD5CAR protein (FIG. 17B). The resulting band was the predicted size of CD5CAR protein in CD5CAR transduced HEK293 cells, but GFP transduced HEK293 cells did not exhibit any specific band by Western blot analysis. In order to evaluate the function of CD5CAR protein for future experiments, CD5CAR lentiviruses were transduced into activated human T cells. The expression of CD5CAR on surface of T cells was evaluated by flow cytometry analysis using goat anti-mouse F(ab') antibody, which recognizes scFv region of CD5CAR protein. Flow cytometric analysis showed that about 20% of CD5CAR expression was observed on CD5CAR transduced T-cells compared to isotype control (FIG. 17C). These results indicated that we successfully generated CD5CAR expression T cell for following experiments.

Down-Regulation of CD5 Expression for CAR Therapy

Figure 18A:
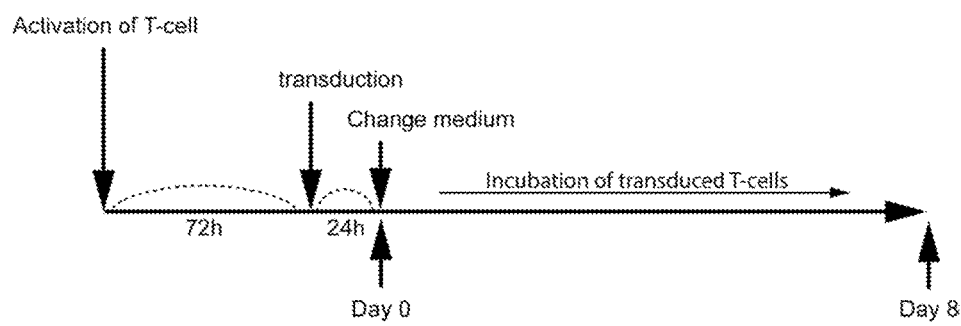
FIG. 18. Study Schema of the transduction of CD5CAR T-cells. A. Steps for generation of CD5 CAR T cells by single transduction. B. Steps for generation of CD5 CAR T cells by double transduction. C. Comparisons of single and double transductions with CD5 CAR lentiviruses in the down-regulation of surface CD5 expression on the T cells. The down-regulation of extracellular CD5 protein versus GFP T-cell control over 8 days following lentiviral transduction is analyzed. The single transduced CD5CAR T-cells do not show complete downregulation of CD5 from cell surface by day 8, with a maximum decrease in CD5 protein expression on day 6. In the double transduced population, we note the decrease in the absolute number of CD5+, CD3+ double positive CD5CAR T-cells over time, from 24.44% on day 0 to a near complete reduction of CD5 expression on day 4. In contrast, the GFP T-cell control maintains a CD5+, CD3+ double positive population above 95% from day 2 through day 8.
Figure 18B:
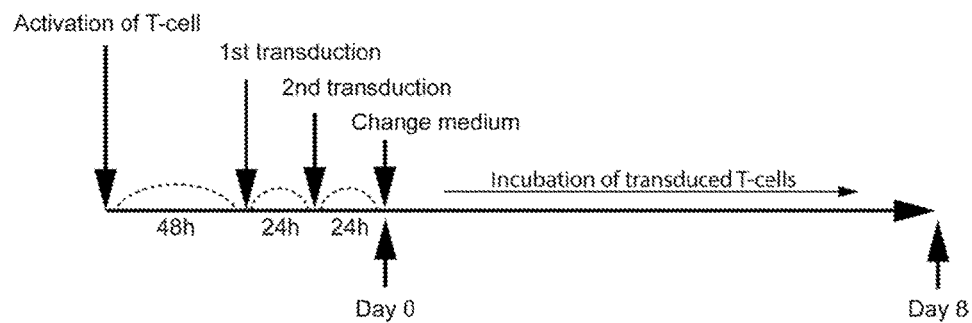
Figure 18C:
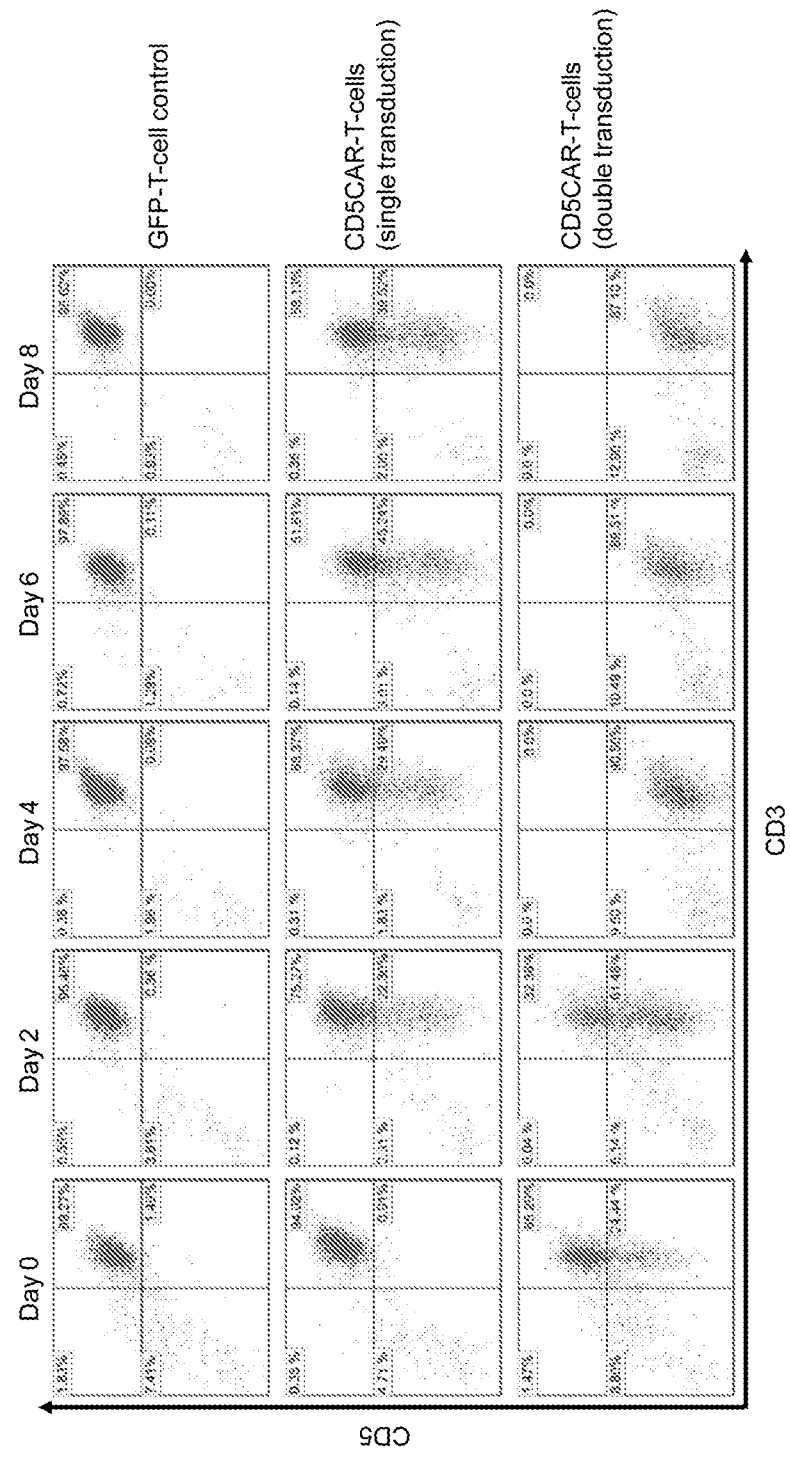

Prior to CD5CAR T cell co-culture and animal assays, the expression of CD5 on the surface of CD5CAR T cells is down regulated to avoid self-killing within the CD5CAR T population. The down-regulation of CD5 will prevent the self-killing of CAR T cells within the CAR T cell population, and the down-regulation of CD5 is associated with an increased killing ability of T-cells. A CAR that is produced within T-cells that has no CD5 expression could be a super-functional CAR, no matter the construct of the CAR itself. The steps for generation of CD5 CAR T cells and the comparison of CD5 down-regulation using single or double transduction of CD5 CAR lentiviuses are shown in FIGS. 18A and B. The single transduced CD5CAR T cells with un-concentrated lent-CD5 CAR viruses did not show complete downregulation of CD5 protein from cell surface by day 8, with a maximum CD5 negative population up to 46% on day 6 (FIG. 18C). In the double transduced population, about 90% of transduced T cells became CD5 negative on day 4-day incubation. In contrast, the GFP T-cell control maintains a CD5+, CD3+ double positive population above 95% from day 2 through day 8 (FIG. 18C).

Downregulation of CD5 Expression on T-Cells can be Accomplished by Transduction of Anchored CD5CAR scFv Lentiviruses.

Figure 19A:
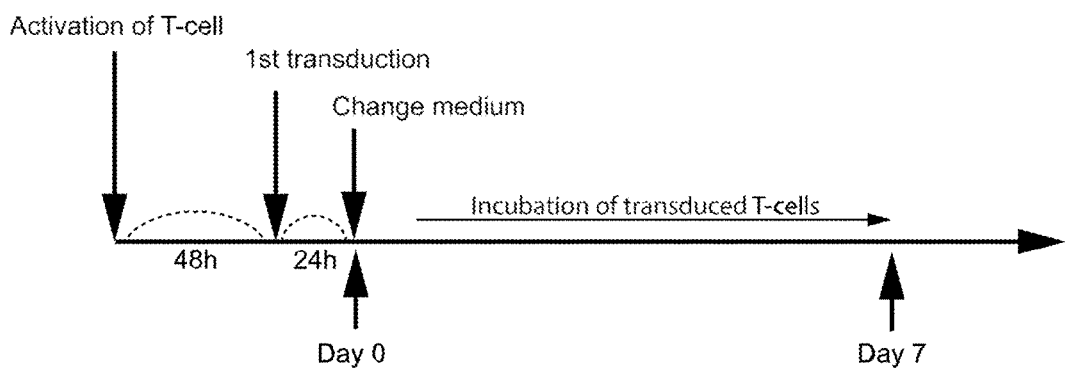
FIG. 19. Downregulation of CD5 expression on T-cells after lentiviral transduction of anchored CD5 scFv antibody after 7 days. A. Study schema for the transduction of anchored CD5 scFv lentiviruses, single transduction. B. Anchored CD5 scFv down-regulates or reduces the quantity of surface CD5 expression on T cells. Flow cytometry analysis demonstrating the significant decrease in CD5 protein expression (~32%) after single transduction of CD5 scFv and 7 day incubation. Elimination of CD5 expression is observed, but not complete after 7 days, and a follow up study is currently being completed for a double transduced anchored CD5 scFv antibody.
Figure 19B:
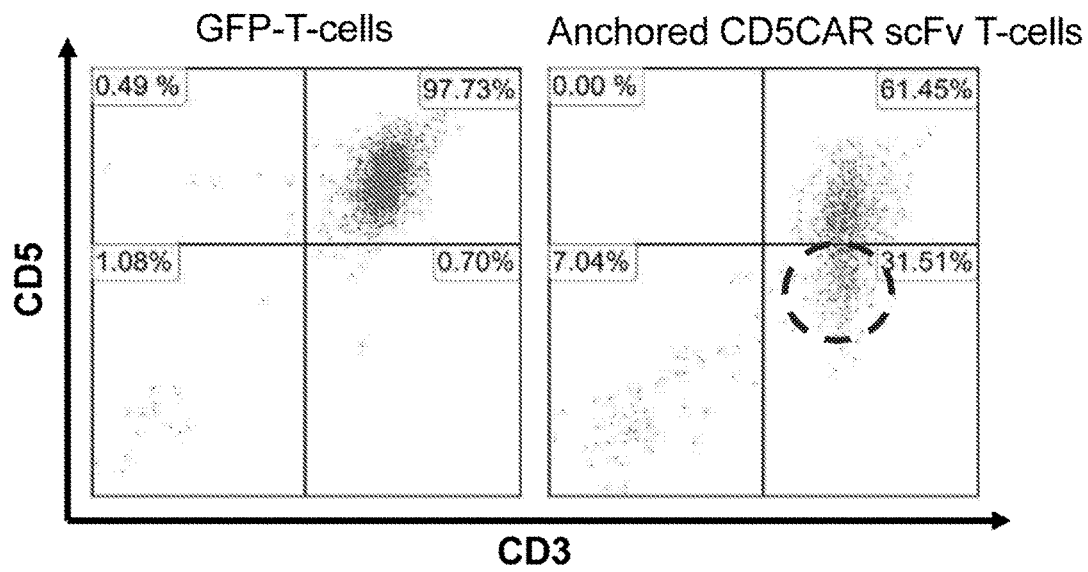

In order to further elucidate the mechanism by which CD5CAR down-regulates CD5 expression on T cells, a new construct was created entitled anchored CD5 scFv (SEQ ID NO. 7 (FIG. 17A). This construct includes an anti-CD5 scFv lined to a transmembrane domain via a hinge region, which allows CD5 scFv to anchor on the T cell surface. The anchored CD5 scFv polypeptide (SEQ ID NO. 16) binds to CD5 target without target cell lysis as observed with a functional CD5CAR. A single transduction and flow data analysis is shown in FIGS. 19A and 19B, with partial down-regulation of CD5 expression for T cells on day 7 of incubation. This is consistent with the partial down-regulation of CD5 expression seen for CD5CAR T-cells after a single transduction.

CD5CAR T Cells Effectively Lyse T-Cell ALL Cell Lines.

Figure 20A:
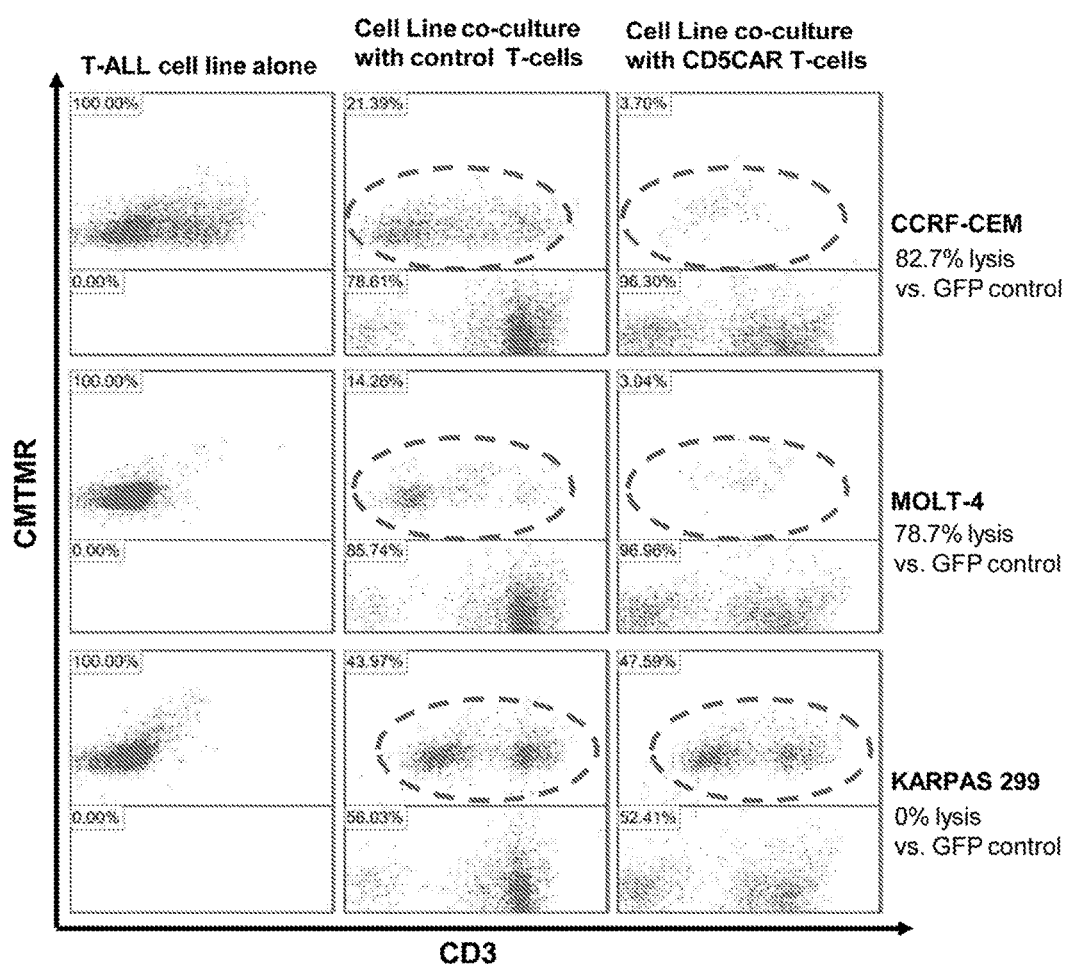
FIG. 20. CD5CAR cells effectively lyse T-ALL cell lines that express CD5, and do not lyse a T leukemic cell line that does not express CD5. A. Flow cytometry analysis of T-ALL cell lines alone (left column), in co-culture with GFP vector transduced T-cells (middle row) and in co-culture with CD5CAR transduced T-cells (right row). Each cell line is seen in each row, The CD5+ T-ALL cell lines in the top and middle rows (CCRF-CEM and Molt-4) with the CD5 negative cell line seen as the bottom row (KARPAS 299). KAEPAS 299 is a CD5 negative T cell lymphoma. The incubation time for all co-cultures was 24 hrs, with an effector:target cell ratio of 5:1. The cell lysis compared to GFP control was over 78% for both CD5 T ALL leukemic cell lines, compared to that for the GFP control. B. This bar graph denotes the T cell lysis achieved by the CD5CAR T-cells when compared to the GFP T-cells co-culture described in FIG. 20A. There was no lysis observed in CD5 CAR T cells co-cultures with KARPAS 299, which is CD5 negative (n=3 independent experiments done in duplicate).
Figure 20B:
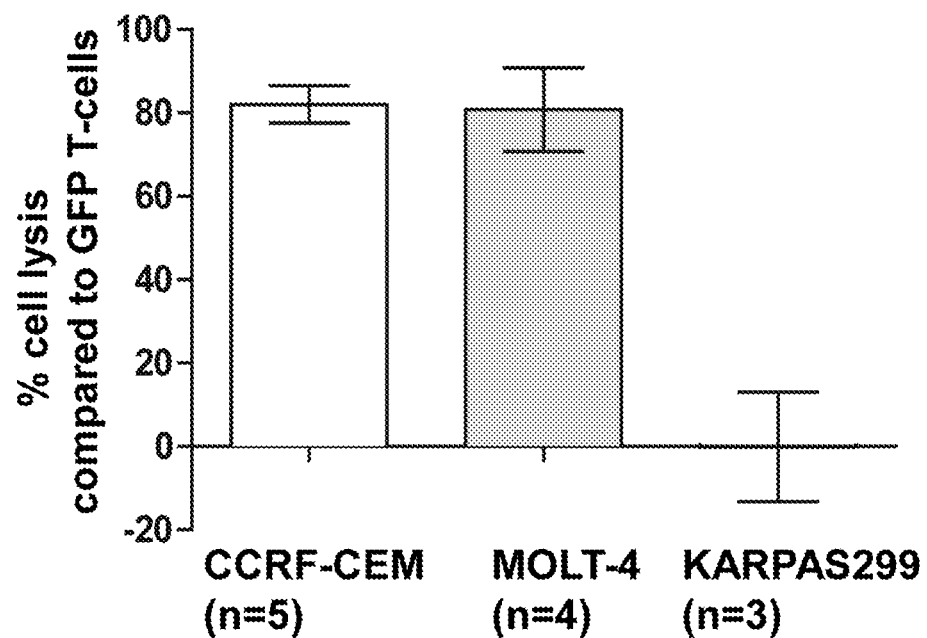

The killing ability of CD5CAR T cells was first tested against T-cell ALL established cell lines CCRF-CEM and MOLT-4, and an anaplastic large cell leukemic cell line KARPAS 299 as shown in FIGS. 20A and 20B. An avid killing ability was seen for the two CD5+ cell lines when compared to GFP control, with target cell lysis above 75% for both lines. 0% lysis was observed in an analplastic large cell line KARPAS 299, which is negative for CD5.

CD5CAR T Cells Effectively Lyse T-Cell ALL Cells from Human Samples.

Figure 21C:
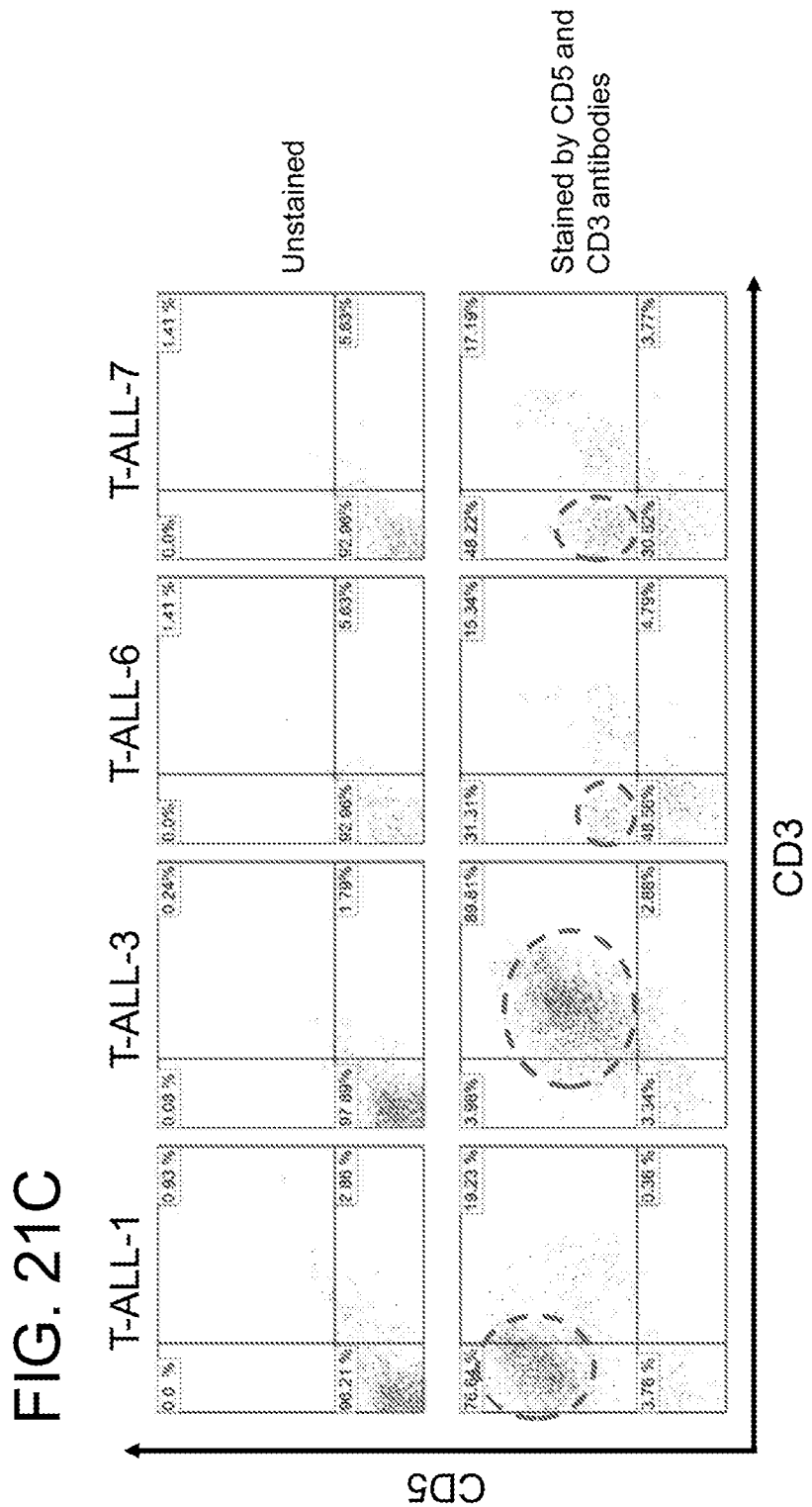
FIG. 21. CD5CAR cells effectively lyse T-cell acute lymphoblastic leukemic cells from patient samples that express CD5. A. Flow cytometry analysis of T-ALL cells alone (left column), in co-culture with GFP T-cells (middle row) and in co-culture with CD5CAR T-cells (right row). Each patient cells are given a row, and are numbered to maintain patient confidentiality. The incubation time for all co-cultures was 24 hrs, with an effector:target cell ratio of 5:1. The cell lysis compared to GFP control was over 71.3% for the T-ALL-1 compared to control. The rest of the cell lines demonstrated positive cell lysis as well, but to a lesser degree, between 33-47%. This may be related to the CD5 expression for each leukemic sample, which is discussed below. B. This bar graph denotes the T cell lysis achieved by the CD5CAR T-cells when compared to the GFP T-cell co-culture described in FIG. 21A. All experiments were done in duplicate. C. Flow cytometry analysis data demonstrating CD3 and CD5 expression levels for patient T cell ALL samples analyzed in FIG. 21A. We observe a different CD5 positivity for T-ALL 1 and T-ALL 3. D. Flow cytometry analysis of the levels of CD5 expression on a panel of four patient sample T-ALL cell populations. The difference of mean fluorescent intensity (MFI) was determined by flow cytometry analysis (FIG. 21C).
Figure 21D:
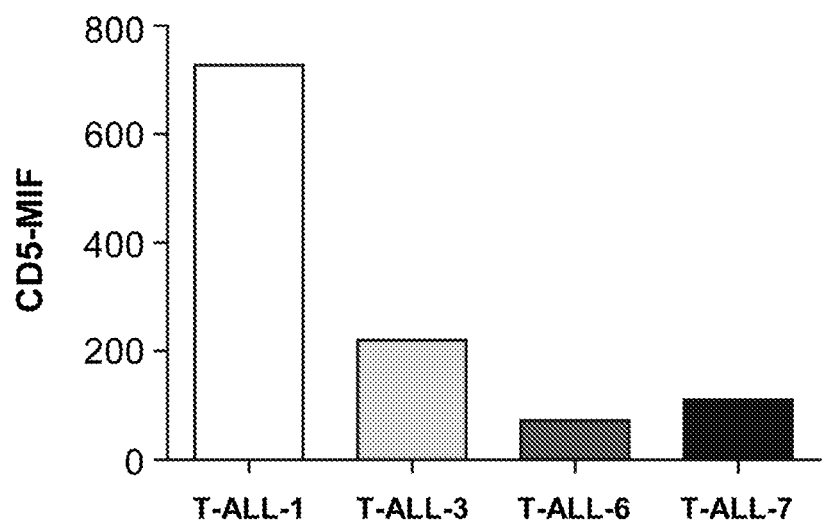
Figure 22:
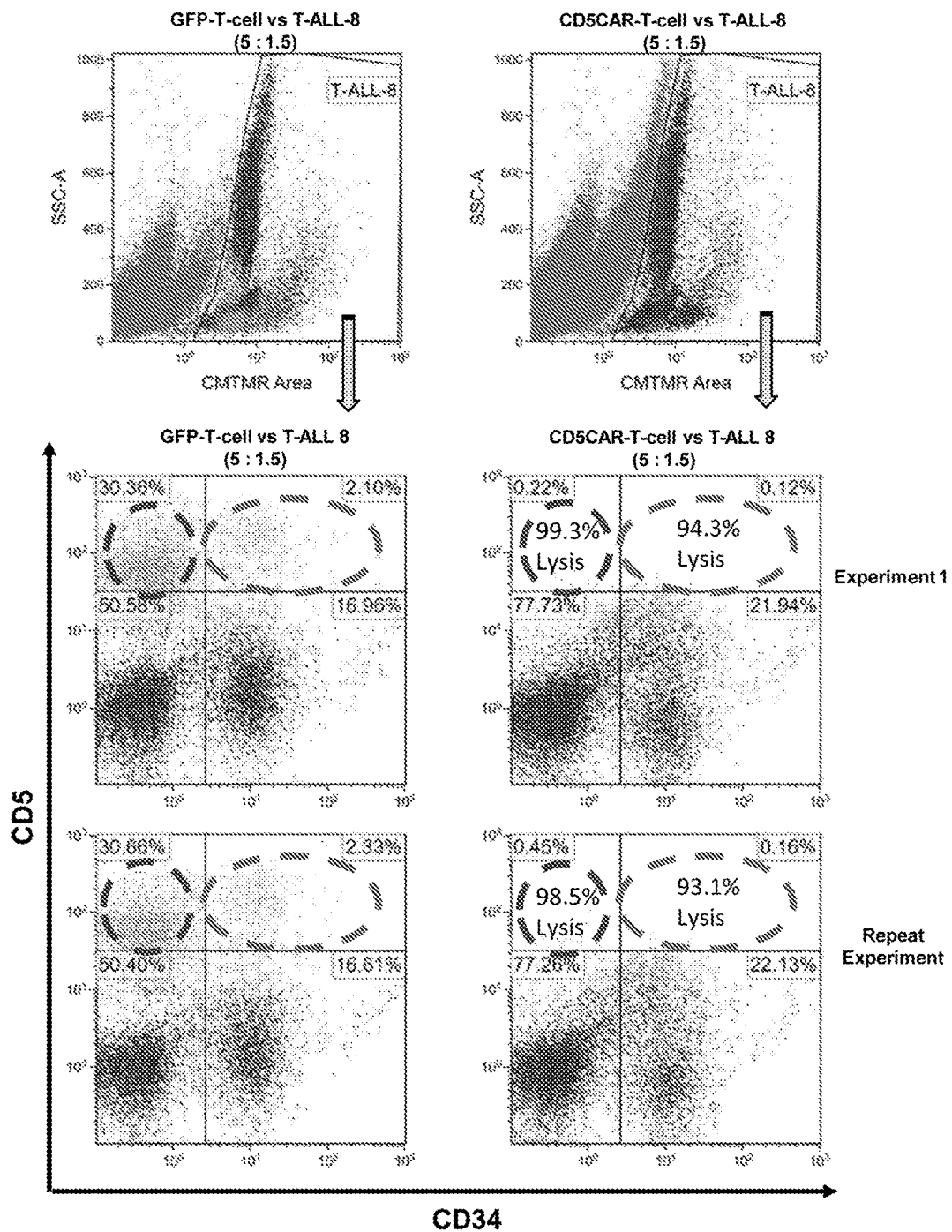
FIG. 22. Analysis of CD5CAR T-cell killing ability for patient T-ALL cells (T-ALL-8) in details. Flow cytometry analysis demonstrating CD5CAR T-cell killing ability for patient's T-ALL cells. The control GFP-T cell and T-ALL-8 cell co-culture are seen on the left, and the CD5CAR co-culture with T-ALL 8 is seen on the right. We note avid lysis of all CD5 positive cells, both CD34 positive (circled in red) and CD34 negative (circled in green, T cells), with no lysis noted for CD5 negative cells. When compared to GFP control, CD5CAR T cells lyse at minimum 93.1% of CD5 positive T-ALL-8 cells when compared to GFP control. Experiment was done in duplicate. In addition, CD5CAR T cells essentially eliminate the T cell population (CD5+ CD34-, circled in green).

The CD5CAR ability to lyse patient sample T-ALL cells was also assessed using multiple patient samples and CD5CAR cell co-cultures were shown in FIG. 21 and FIG. 22. While there was an avid cell killing noted for the T-ALL 1 patient leukemic cells that was similar to the CD5 target cell lysis seen when CD5CAR cells targeted T cell ALL cell lines, three other patient leukemic cells showed comparatively weaker lysis of target cells (FIG. 21A. and FIG. 21B.).

The ability of killing by CD5CAR on the patient leukemic cells correlated with the intensity of CD5 expression as shown in FIGS. 21A, 21B, and 21D. As shown in FIGS. 21C, and 21D, the CD5 expression for T-ALL-1, T-ALL 3, T-ALL 6 and T-ALL 7 through flow cytometry analysis was observed. The CD5 expression was significantly lower for the T-ALL patient samples, except for T-ALL-1 sample.

CD5CAR T Cells Exhibit the Specificity and Potent Target Cell Killing.

As a control, the CD5CAR T cells were also tested for their ability to ablate CD5 negative leukemic T cells. Anaplastic large T cell lymphoma line is the cell line that does not express CD5. Flow cytometry analysis showed that CD5CAR T cells were unable to lyse or eliminate KARPAS 299 cells, as shown in FIG. 21A, lower panel.

A patient sample (T-ALL-8) with a high level of CD5 expression was obtained from a patient with a minimal disease of T-ALL. Co-culture was performed with CD5CAR and analyzed in detail as shown in FIG. 22. Three population cells including CD5+ normal T cells, CD5+CD34+ T-ALL cells and CD5-CD34+ T-ALL cells were assessed by flow cytometry after co-culture. CD5CAR exhibited the specificity and potent target cell lysis ability with >93% of CD5 positive cell lysis for all CD5+ cell populations when compared to GFP control. The CD5CAR killed leukemic cells as efficiently as CD5 normal T cells. Killing was not observed in the CD5 negative population. CD5CAR T cells essentially eliminated the T cell population (CD5+CD34-).

CD5CAR T Cells Effectively Eliminate Normal T Cells.

Figure 23A:
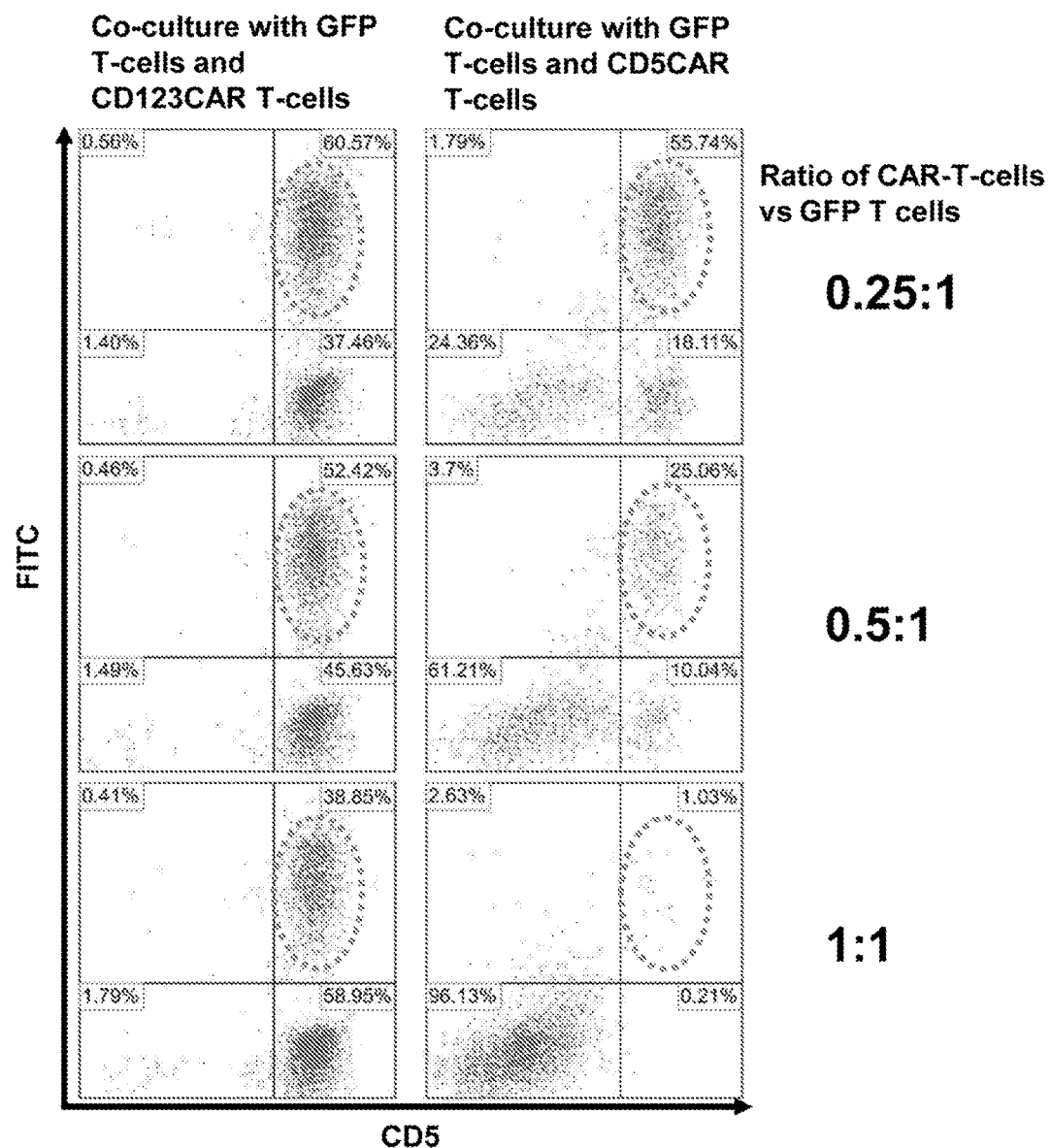
FIG. 23. CD5CAR T cells effectively eliminate normal GFP labeled T cells. A, CD5CAR T cells kill normal T cells in a dose dependent manner. CD5CAR T cells or CD123CAR T cells (control) were co-cultured with GFP labeled T cells at 0.25:1, 0.5:1 and 1:1 effector to target ratios. After 24 hours, remaining live GFP T cells were analyzed by flow cytometry. Percent killing of target cells was measured by comparing GFP T cell survival in CD5 co-cultures relative to that in control CD123CAR T cells as T cells do not express CD123. B, Co-culture killing curve based on the data from A.
Figure 23B:
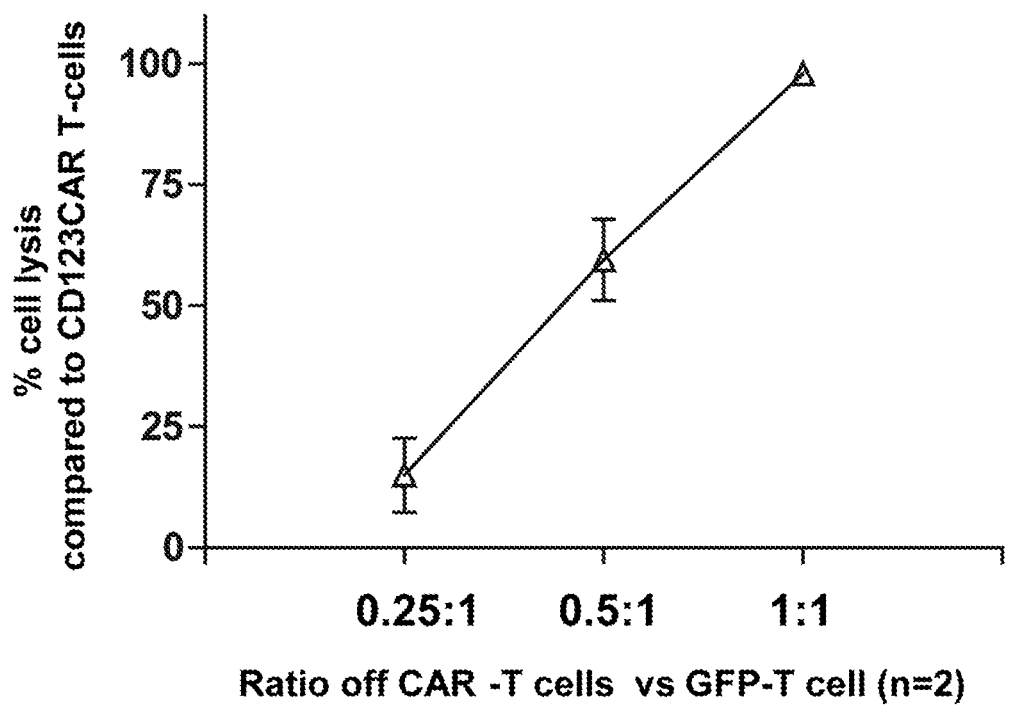

CD5CAR T cells demonstrated effective elimination of normal T cells in a dose dependent manner in a co-culture assay at low ratios (effector:target) of 0.25:1, 0.5:1 and 1:1 (FIG. 23). CD5CAR T cells or CD123CAR T (control) effector cells were incubated with GFP labeled T cells. Percent killing of target cells was measured by comparing GFP T cell survival in CD5CAR T co-culture relative to that in CD123CAR T control co-culture. Normal GFP T cells were eliminated in a dose-response fashion for CD5CAR T cells. CD5CAR T cells effectively eliminated all GFP T cells at effector to target ratio of 1:1 (FIG. 23). Since the CD5CAR T cells effectively eliminated all normal T cells, the feasibility of CD5CAR T therapy should depend on the ability to provide transient rather than permanent. CD5CAR T cells could be used as a novel conditioning regimen or a "bridge" for hematopoietic cell transplantation.

T Cells Maintained CD5 Expression when they were Co-Cultured with CD5CAR or Anchored CD5 scFv T Cells.

Figure 24A:
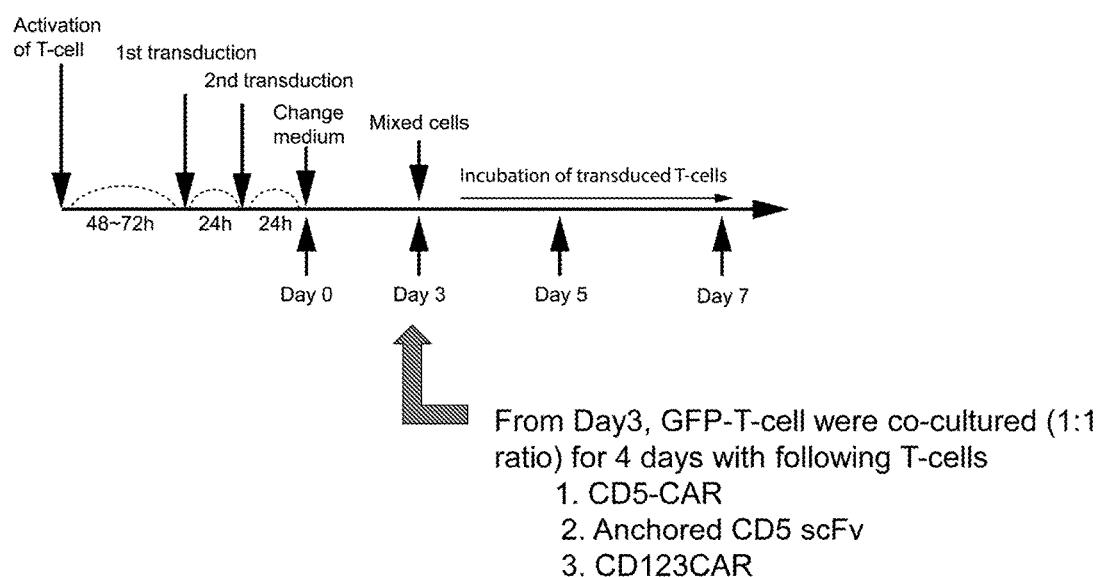
FIG. 24. T cells maintained CD5 expression when they were co-cultured with CD5CAR or anchored CD5 scFv T cells. A, Steps for generation of CD5CAR T cells or anchored CD5 scFv T cells and CD123 CAR T cells (control). B, CD5 expression levels on different CAR transduced T-cells (Day 3 after $2^{nd}$ transduction). Activated T cells were transduced with lentiviruses expressing CD5CAR or anchored CD5 scFv and CD123CAR. After 3 day transduction, CD5 expression was analyzed by flow cytometry.

One of CD5 properties is its internalization after binding by an antibody. As a result, targeting cells lose a targeted antigen, which may cause an antigen escape. This phenomenon has been reported as a cause of failure in clinical studies using CAR T-cell based therapies. We next investigate the issue if CD5 CAR or anchored CD5 scFv T cells affect the CD5 expression on CD5 positive T or leukemic cells using a co-culture assay. Steps for generation of CD5CAR T cells or anchored CD5 scFv T cells and CD123 CAR T cells (control) were shown in FIG. 24A. After the second T cell transduction with lenti-CD5CAR or anchored CD5 scFv and CD123CAR viruses on day 3, transduced T cells were analyzed with the expression of CD5 by flow cytometry. T cells transduced either CD5CAR or anchored CD5 scFv lentiviruses displayed essentially complete down-regulation of the surface CD5 protein (FIG. 24B). In contrast, the CD123 CAR transduced-T cell control maintained the CD5 expression.

Figure 25A:
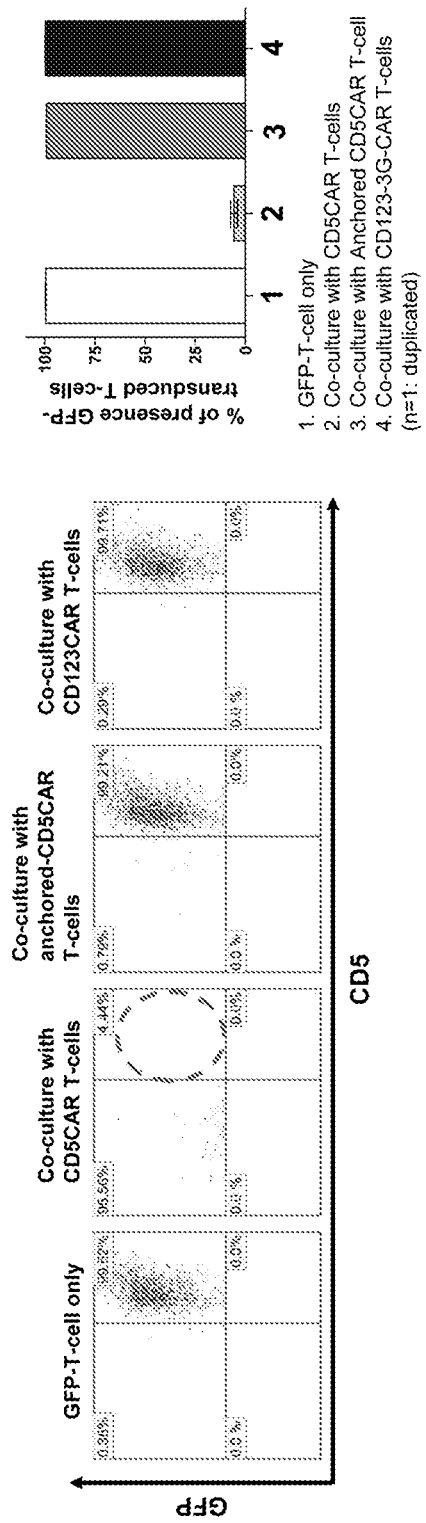
FIG. 25. Co-culture assays were performed to determine if normal T cells maintained CD5 expression when they were co-cultured with CD5CAR or anchored CD5 scFv T cells or CD123CAR (control) for 2 days (FIG. 25A) or 4 days (FIG. 25B) at a ratio of 1:1. CD5CAR T cells or anchored CD5 scFv T cells or CD123CAR T (control) cells were incubated with GFP labeled T cells and the co-cultured GFP labeled T cells were then analyzed for CD5 expression and live cells by flow cytometry. C (FIG. 25C), CD5CAR- or anchored CD5 scFv transduced CCRF-CEM or Molt-4 T ALL cells showed downregulation of CD5 expression. CCRF-CEM or Molt-4 T ALL cells were transduced with lentiviruses expressing CD5CAR or anchored CD5 scFv. After the second transduction, the transduced leukemic cells were analyzed for CD5 expression by flow cytometry.

We then co-cultured transduced CD5CAR or CD5 anchored scFv and CD123CAR T cells with GFP-labeled T cells at the ratio of 1:1 (E:T) for 2 or 4 days. As shown in FIGS. 25A and B, CD5CAR T cells effectively eliminated all GFP-T cells. As expected, transduced CD5 anchored scFv or CD123CAR T cells were unable to lyse GFP T cells. In addition, GFP T cells still expressed CD5 when co-cultured with transduced CD5 anchored scFv or CD123CAR T cells. These studies indicate that CD5 antigen escape is unlikely to occur when employing CD5CAR for immunotherapy.

Down-Regulation of CD5 Expression in the T ALL Cells when they were Transduced with Lenti-CD5CAR or CD5 Anchored scFv Viruses.

Figure 25C:
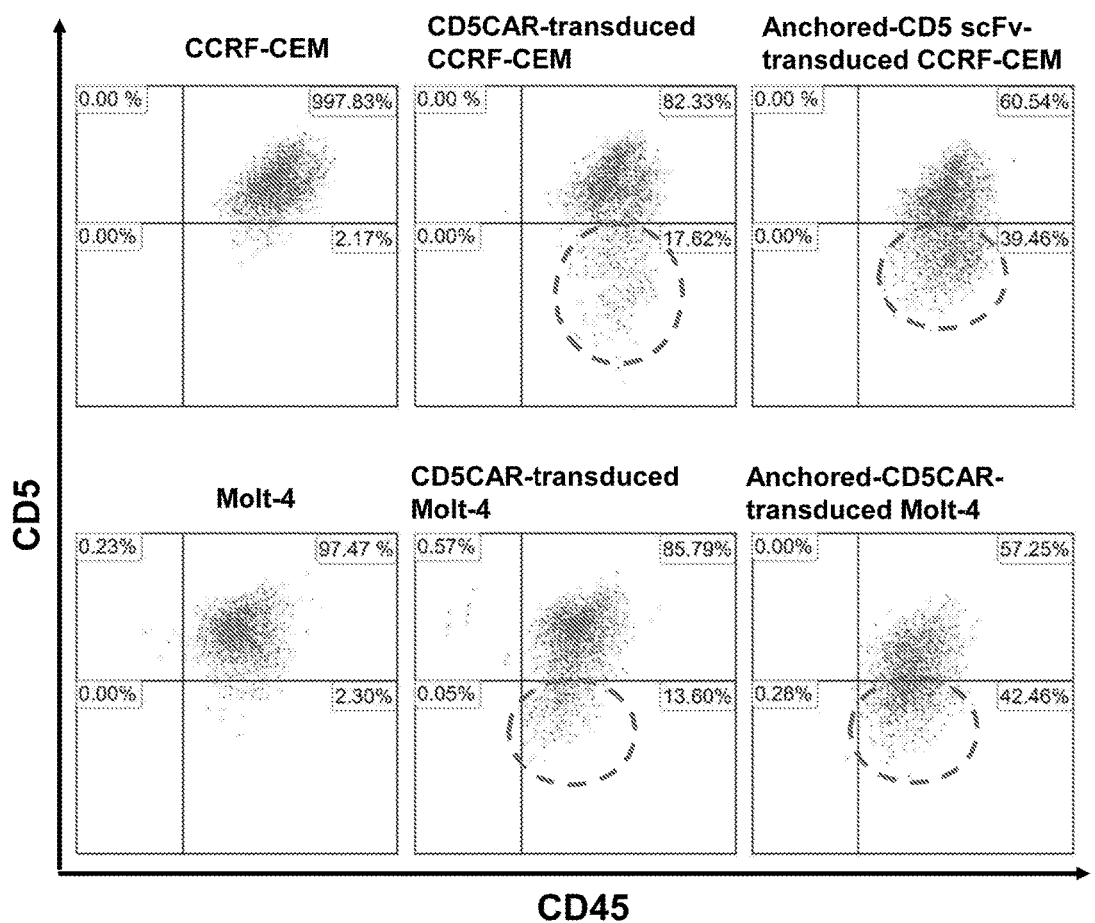

We next tested if transduction of CD5CAR- or anchored CD5CAR lentiviruses on T ALL cells results in the down-regulation of CD5 expression. CCRF-CEM and MOLT-4 T-ALL cells were transduced with CD5CAR- or anchored CD5 scFv lentiviruses. CD5CAR or anchored CD5 scFv significantly down-regulated or reduced the quantity of surface CD5 expression on these leukemic cells (FIG. 25C). In contrast, the T cells maintained CD5 expression when these cells were used to co-culture with transduced anchored CD5 scFv T cells (FIGS. 24A and B).

CD5CAR T Cells Exhibit Profound Anti-Tumor Activity In Vivo.

Figure 26A:
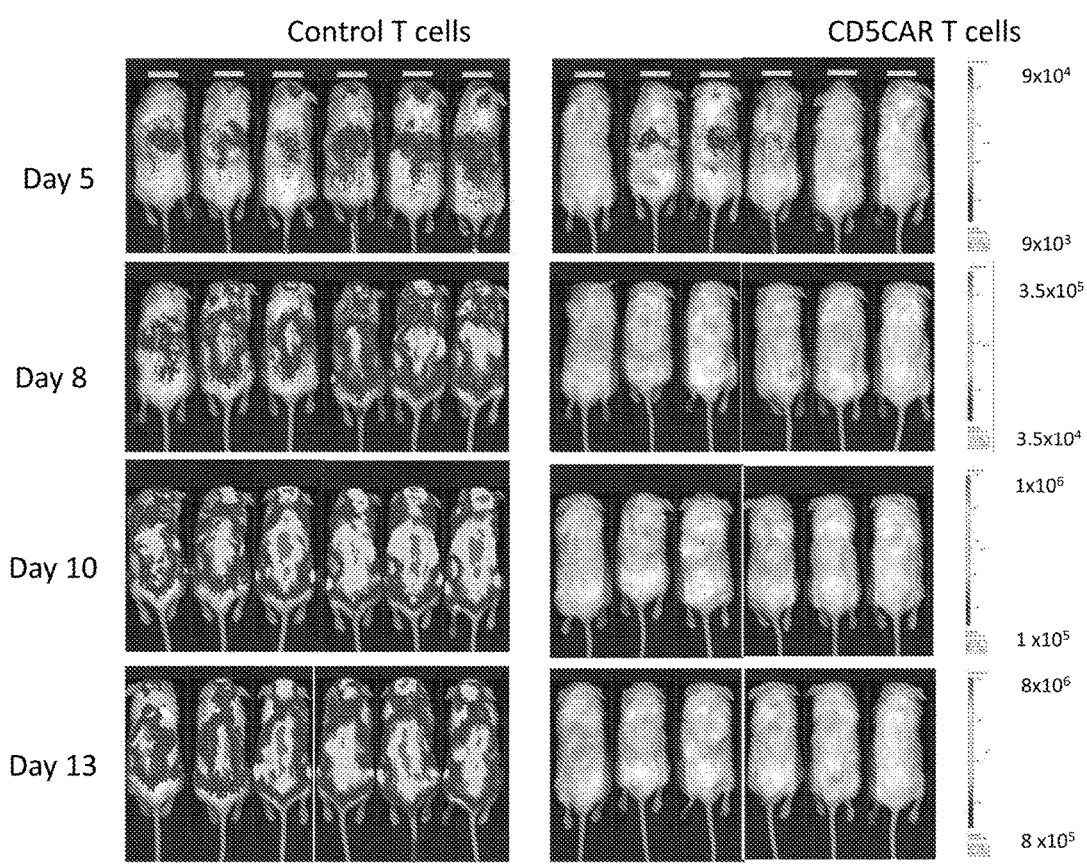
FIG. 26. CD5CAR T cells demonstrate profound antileukemic effects in vivo. NSG mice were sublethally irradiated and, after 24 hours, intravenously injected with $1\times10^6$ luciferase-expressing CCRF-CEM cells (Day 0) to induce measurable tumor formation. On day 3 and 4, mice were intravenously injected with $5\times10^6$ CD5CAR T cells or vector control T cells. These injections were repeated on Days 6 and 7, for a total of $2.0\times10^7$ cells per mouse. A, On days 5, 8, 10 and 13, mice were injected subcutaneously with RediJect D-Luciferin and subjected to IVIS imaging. B, Average light intensity measured for the CD5CAR T injected mice was compared to that of vector control T injected mice. C, Percentage of tumor cells killed in mice treated with CD5CAR T cells relative to control. D, Peripheral blood was drawn from mice on Day 15 and percentages of leukemic cells were determined and compared to that of vector control or normal injected mice.
Figure 26B:
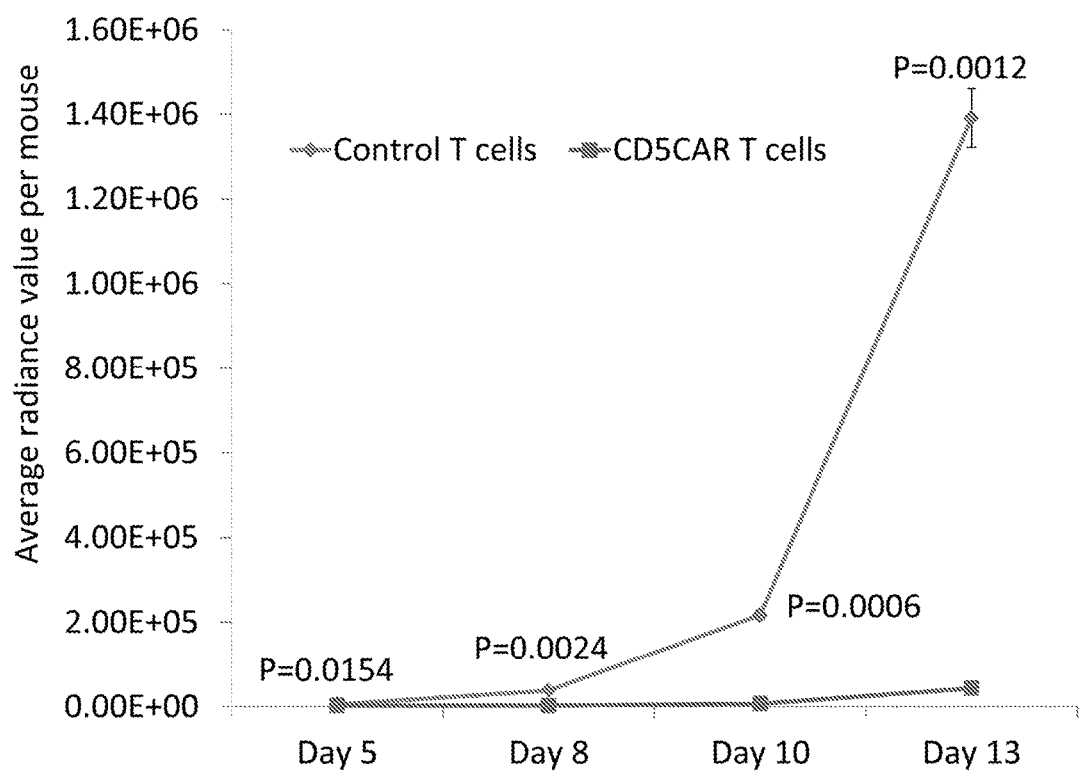
Figure 26C:
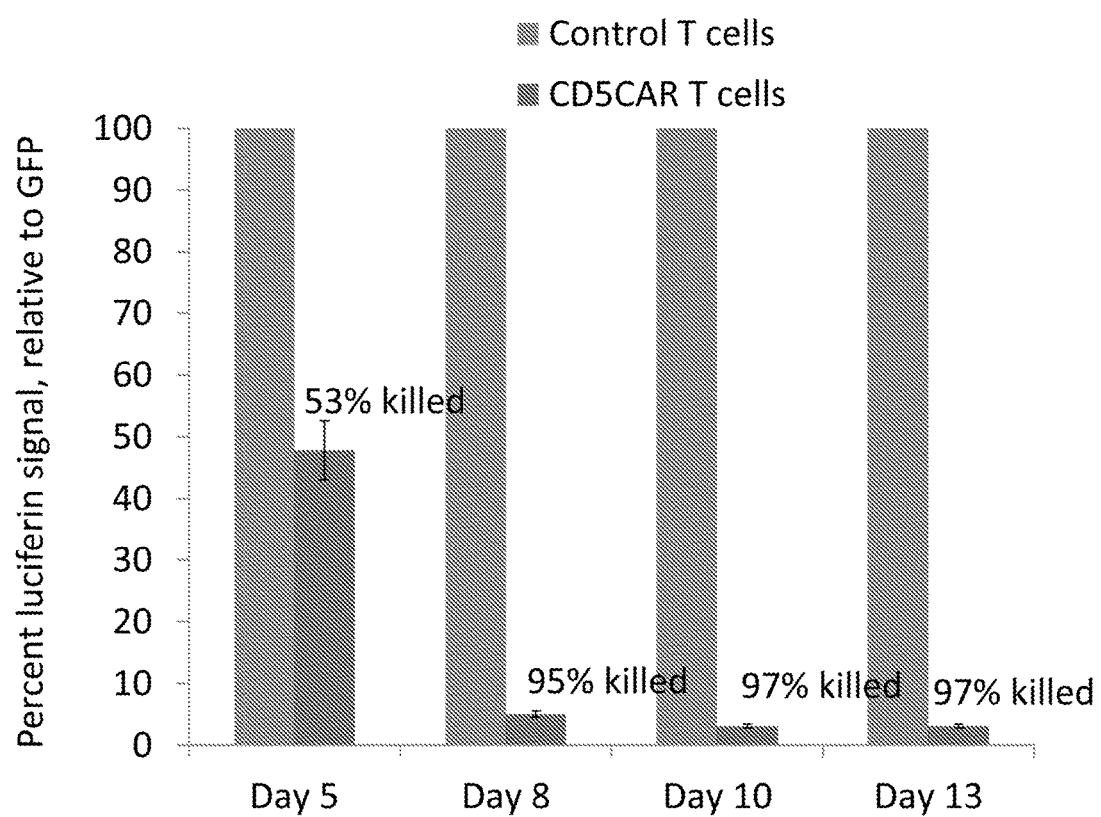

In order to evaluate the in vivo anti-tumor activity of CD5CAR T cells as a predictor of their therapeutic efficacy in patients, we developed a xenograft mouse model using NSG mice sublethally (2.0 Gy) irradiated and intravenously injected with $1.0 \times 10^6$ firefly luciferase-expressing CCRF-CEM cells (CD5+) to induce measurable tumor formation. On day 3 days following CCRF-CEM-Luc+ cell injection, mice were intravenously injected with $5 \times 10^6$ CD5CAR T cells or vector control T cells. These injections were repeated on Day 4, Day 6, and Day 7, for a total of $20 \times 10^6$ T cells per mouse. On days 5, 8, 10 and 13, mice were injected subcutaneously with RediJect D-Luciferin (Perkin-Elmer) and subjected to IVIS imaging (Caliper Life-Sciences) to measure tumor burden (FIG. 26A). Average light intensity measured for the CD5CAR T cell injected mice was compared to that of vector control T injected mice (FIG. 26B). Paired T test analysis revealed a very highly significant difference between the two groups by day 13 with less light intensity and thus less tumor burden in the CD5CAR T injected group compared to control (p<0.0012). Further analysis showed that by Day 5, mice treated with CD5CAR T cells only 3 days previously had 53% lower tumor burden compared to control mice, and that percentage improved to 95% by Day 8 (FIG. 26C.) Tumor burden remained at near background levels for treated mice through Day 13. On Day 15, a small amount of peripheral blood was drawn from each mouse including 2 mice which were not injected with wither CCRF-CEM or T cells (to serve as background controls), and analyzed by flow cytometry for the presence of transplanted CCRF-CEM cells (CD5+). Results mirrored the imaging perfectly as percentage of tumor cells in CD5CAR T cell-treated mice dropped to near background levels (<1%), while mice given control T cells had between 28-43% CCRF-CEM tumor cells (FIG. 26D). In summary, these in vivo data indicate that CD5CAR T cells robustly reduce tumor burden and prolong survival in CCRF-CEM-injected NSG mice when compared to vector control T cells.

Anti-CD5 Chimeric Antigen Receptor (CD5CAR) NK Cells Efficiently Eliminate CD5 Positive Hematologic Malignancies.

Examples

Results
Generation of the CD5NK-CAR

The anti-CD5 molecule is a modular design, comprising of a single-chain variable fragment (scFv) in conjunction with CD28 and 4-1BB domains fused to the CD3zeta signaling domain to improve signal transduction making it a third generation CAR. A strong spleen focus forming virus promoter (SFFV) was used for efficient expression of the CD5CAR molecule on the NK cell surface and the CD8 leader sequence was incorporated into the construct. The anti-CD5 scFv is attached to the intracellular signaling domains via a CD8-derived hinge (H) and transmembrane (TM) regions. This CD5CAR construct was then cloned into a lentiviral plasmid.

Generation of CD5CAR NK Cells

The transduction efficiency of the CD5CAR was determined by flow cytometry analysis. To enrich for CD5CAR+ NK cells, the highest expressing NK cells were harvested using flow cytometry. Following sorting, the expression of the CD5CAR$^{high}$ NK was expanded for efficacy studies in vitro and vivo.

CD5CAR NK Cells Effectively Eliminate Human T-Cell Acute Lymphomblastic Leukemia (T-ALL) Cell Lines CD5CAR NK cells were tested for anti-T-ALL activity in vitro using CCRF-CEM, MOLT-4 and Jurkat cell lines. All these T-ALL cell lines highly expressed CD5.

Figure 27A:
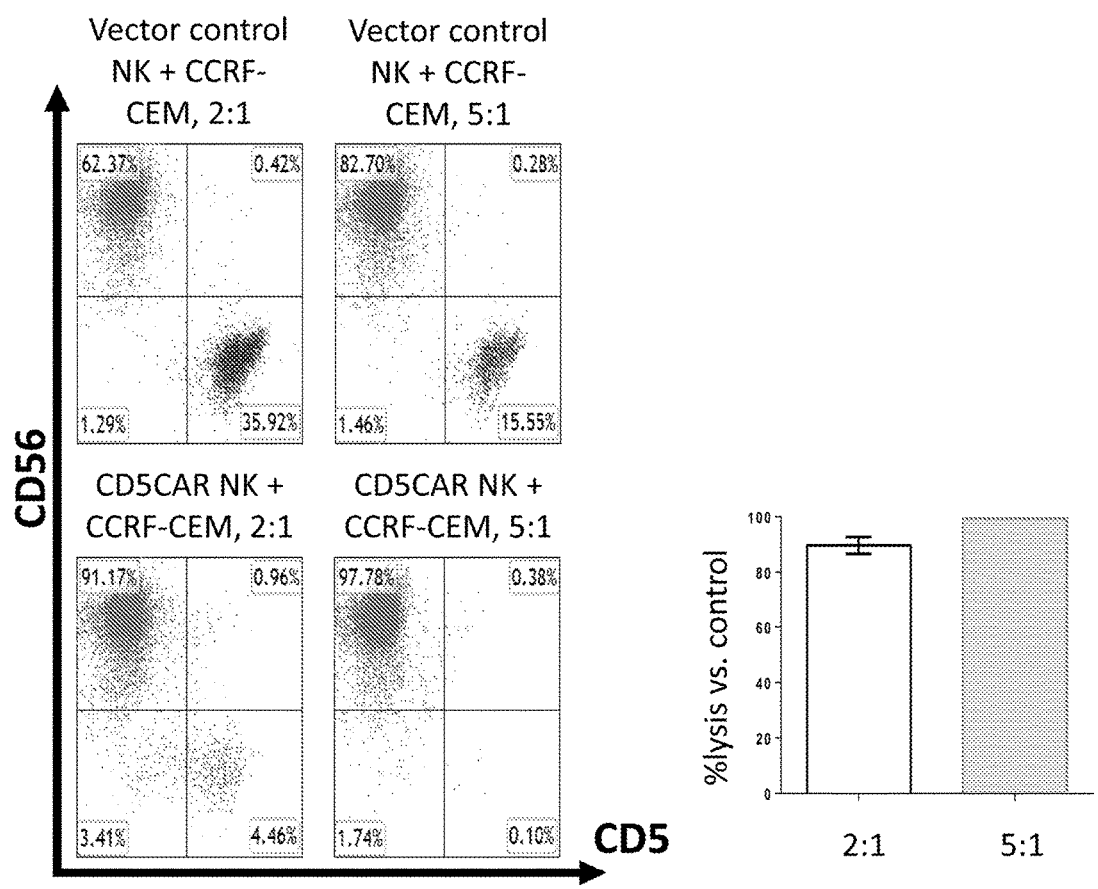
FIG. 27. The CD5 CAR NK cells (NK-92) effectively eliminate CCRF-CEM T-ALL cell line in vitro. A and B, T-lymphoblast cell line CCRF-CEM expressing CD5 was co-cultured with CD5 CAR NK cells in the indicated E:T (effector:target) cell ratios for 24 hours. Target populations were quantified with flow cytometry using CD56 and CD5 to separate the NK-CAR and target cell population respectively. Cell survival is expressed relative to transduced vector control NK cells and each bar graph represents the average statistics for duplicate samples with N=2. C, CD5CAR NK cells eliminate CCRF-CEM cells in a dose-dependent manner. T-lymphoblast cell line, CCRF-CEM expressing CD5 was co-cultured with CD5CAR NK cells in the indicated E:T (effector:target) cell ratios with the lower bound of the E:T ratio reduced. Saturation is achieved with an E:T ratio of 2:1 and co-culturing under reduced ratios results in a dosage-dependent manner of CD5 elimination. Complete elimination of CCRF-CEM was achieved at 5:1.
Figure 27B:
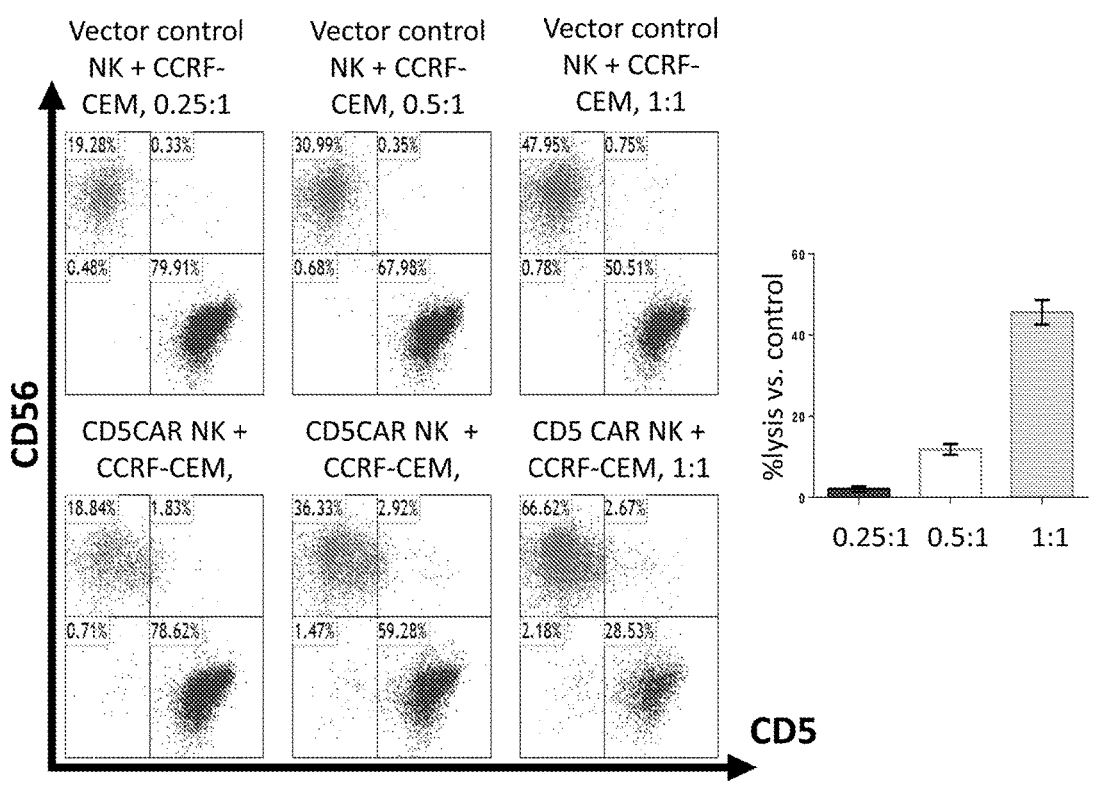
Figure 27C:
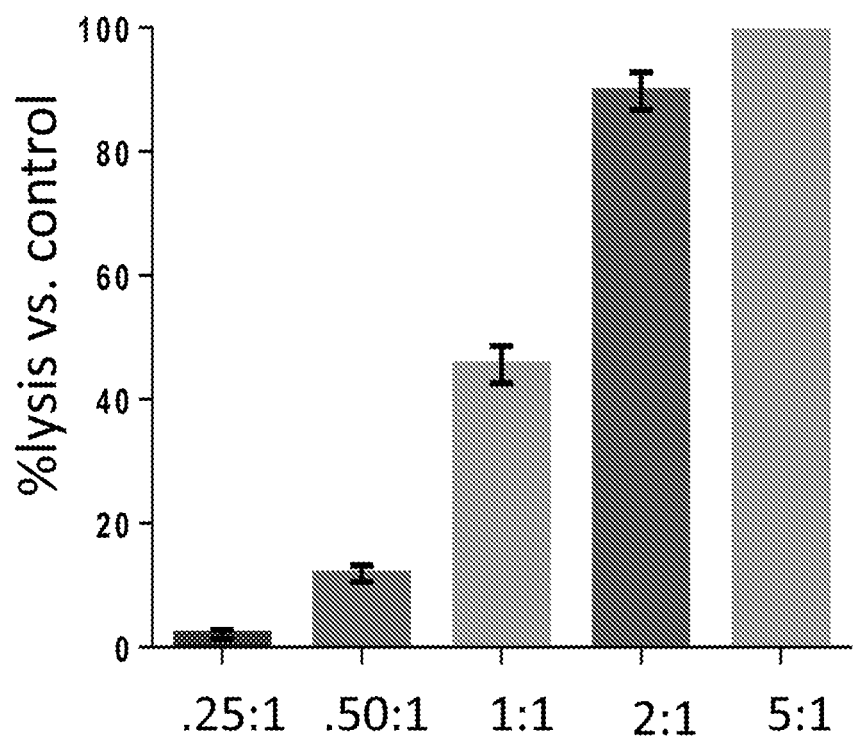
Figure 28A:
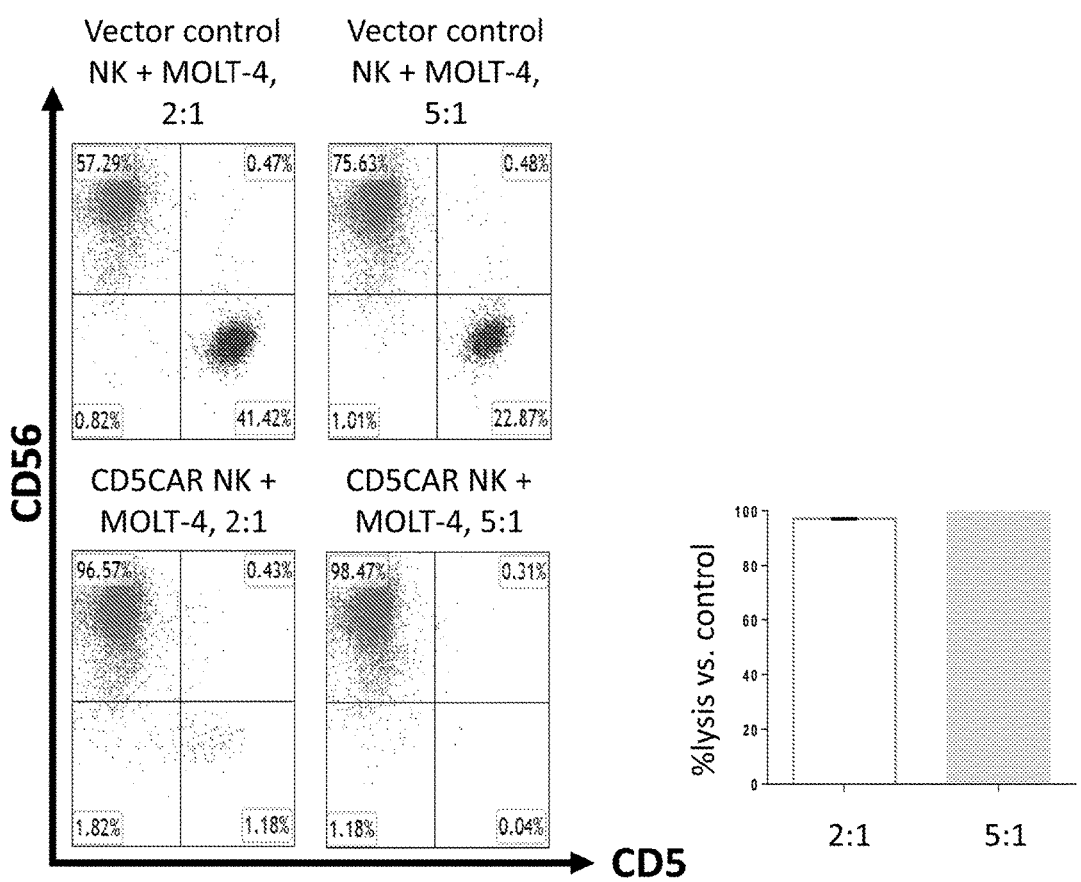
FIG. 28. CD5CAR NK cells effectively lyse two CD5+ T-ALL lines, MOLT-4 and Jurkat. A, CD5CAR NK cells were co-cultured with MOLT-4 cells in the indicated E:T (effector:target) cell ratios for 24 hours. Cell survival is expressed relative to transduced vector control NK cells and each bar graph represents the average statistics for duplicate samples with N=2 experiments. B, CD5CAR NK cells are co-cultured with Jurkat cells in the indicated E:T (effector:target) cell ratios for 24 hours. Cell survival is expressed relative to transduced vector control NK cells and each bar graph represents the average statistics for duplicate samples with N=2 experiments.
Figure 28B:
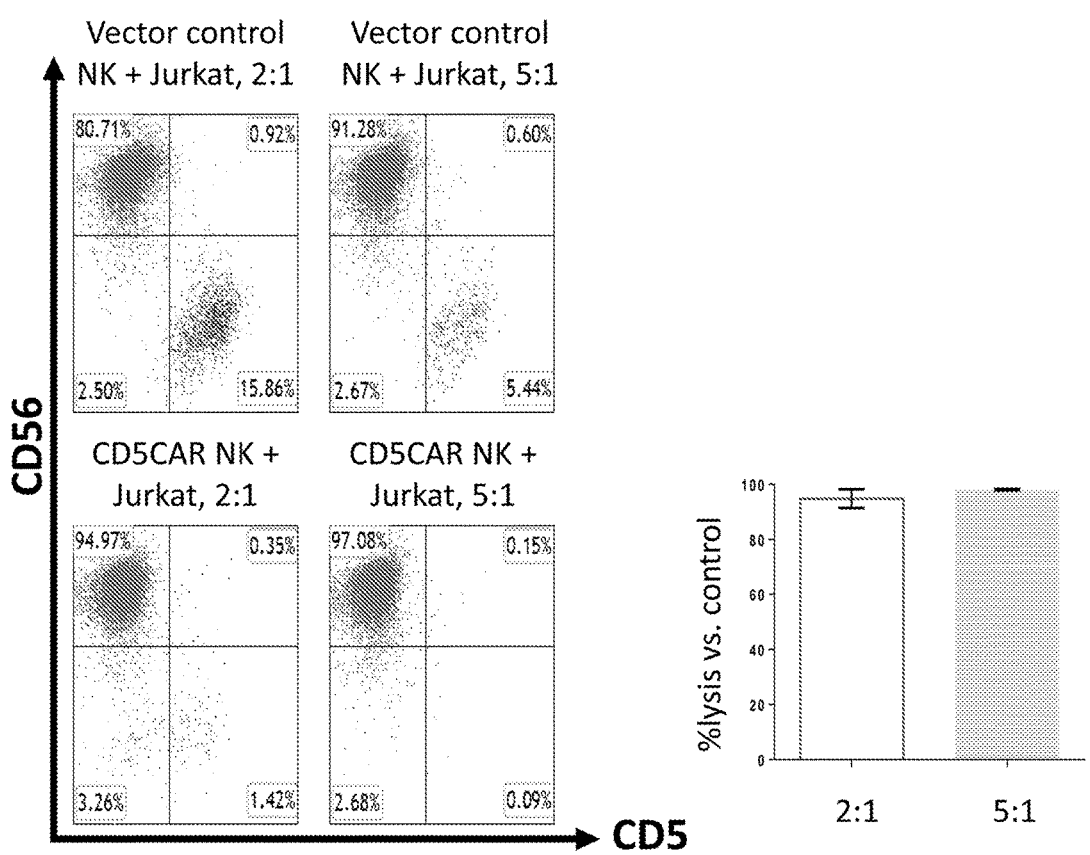

During co-culture experiments, CD5CAR NK cells demonstrated profound killing of CCRF-CEM at the low effector cell to target cell ratio (E:T) of 2:1 and 5:1. At these ratios, CD5CAR NK cells virtually eliminated CCRF-CEM cells (FIG. 27A). CD5CAR NK cells lysed CCRF-CEM leukemic cells in vitro in a dose-dependent manner at effector: target ratios of 0.25:1, 0.5:1, 1:1, 2:1 and 5:1 (FIGS. 27B and 27C). Additional two T-ALL cells, MOLT-4 and Jurkat were used to test the anti-leukemic activity for CD5NK cells. Co-culture studies of these two cell lines were conducted with CD5CAR NK cells. CD5CAR NK cells essentially eliminated MOLT-4 and Jurkat cells at a low effector: target ratio of 2:1 (FIGS. 28A and B).

Figure 29A:
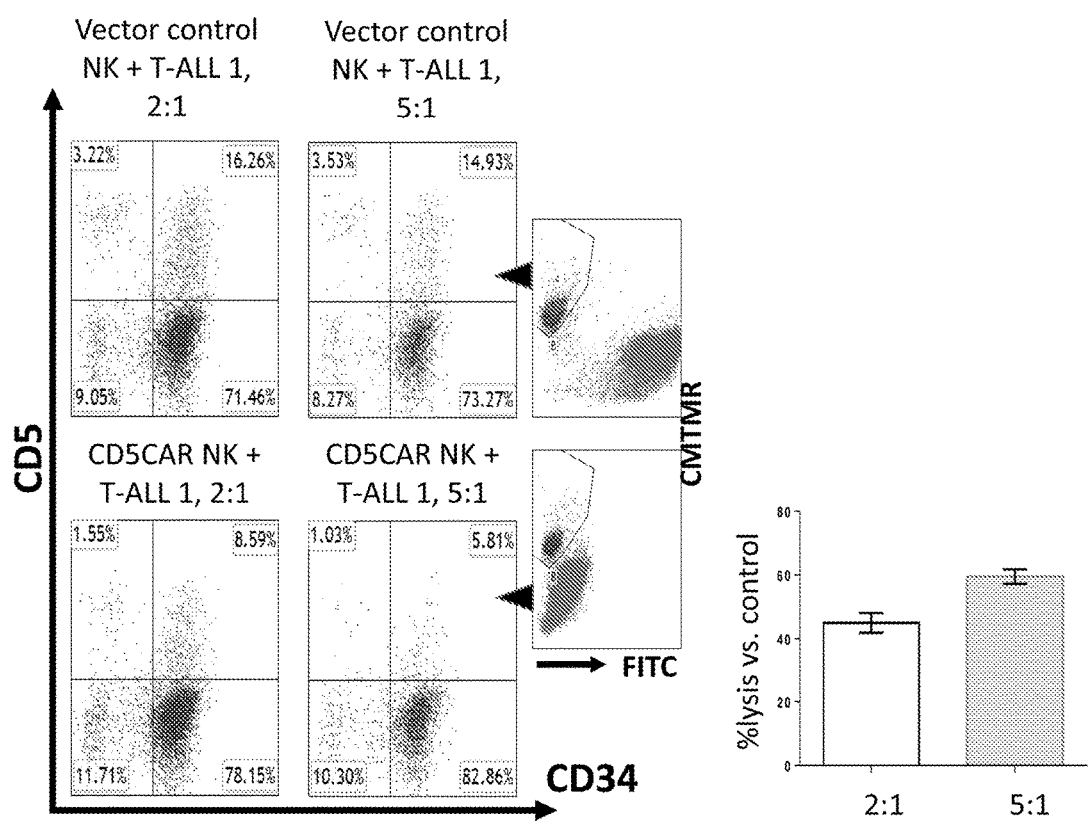
FIG. 29. CD5CAR NK cells effectively eliminate aggressive CD5+ T-ALL cells using human samples. A, T-ALL cells from patient, T-ALL #1 were co-cultured with CD5CAR NK cells in the indicated E:T (effector:target) cell ratios for 24 hours. B, T-ALL cells from patient, T-ALL #2 were co-cultured with CD5CAR NK cells in the indicated E:T (effector:target) cell ratios for 24 hours. Target populations were gated and quantified with flow cytometry using cell cytotracker dye (CMTMR) to screen T-ALL patient samples. Data represents the average statistics for duplicate samples. Target CD5+CD34+ cell populations were gated against an isotype control. Cell survival is expressed relative to transduced vector control NK cells and each bar graph. From left to right, the bar graph shows the data for CD34+ CD5+ on the left and CD5+cd34− on the right, for each ratio. CD5CAR NK shows almost complete lysis of the highly expressing CD5+ target population with activity against the low CD5+CD34+ potential tumor stem cell population. Saturation is achieved at a ratio of 2:1, signifying a need for dilution of E:T ratios.
FIGS. 29C and 29D, leukemic cells from patient #3 (PTCLs) and patient #4 (Sezary Syndrome) were co-cultured with CD5CAR NK cells, respectively in the indicated E:T (effector:target) cell ratios for 24 hours.
Figure 29B:
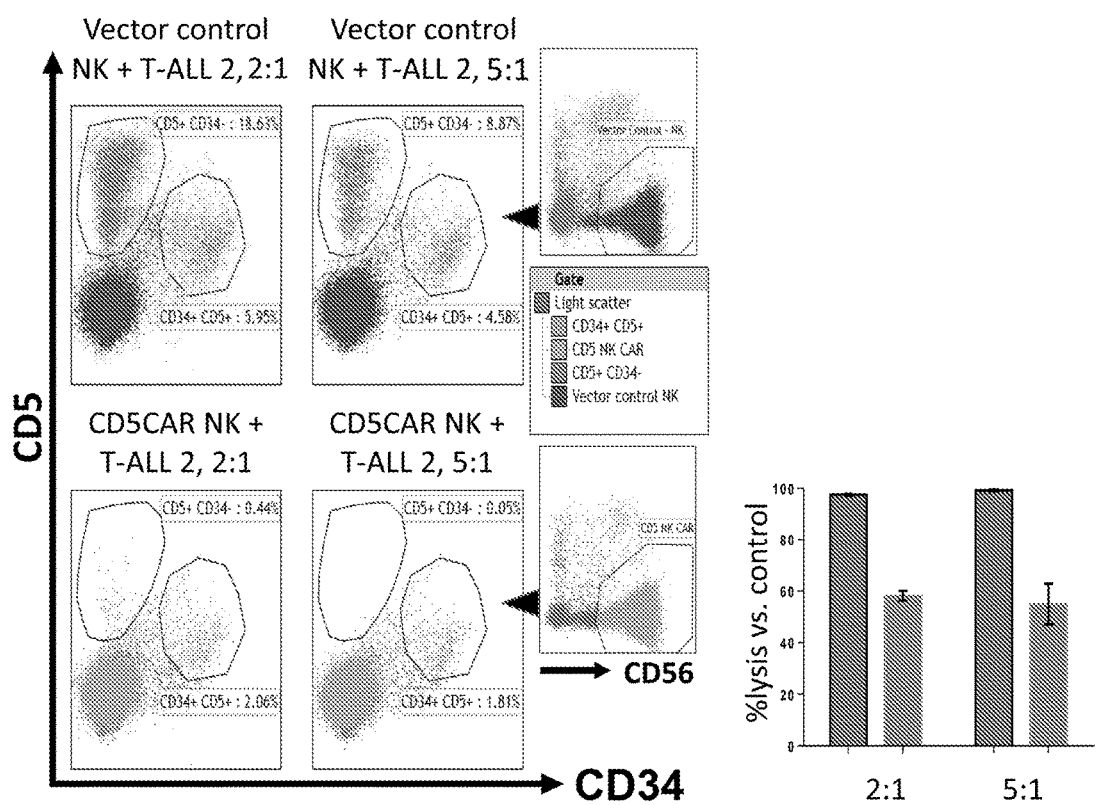

CD5CAR NK Cells Effectively Eliminate Aggressive CD5+ T-ALL Cells Using Human Samples Co-culture experiments were also conducted using patient samples (FIG. 29A, B). Both patient 1 and 2 were T-ALL that did not respond to standard chemotherapy. Patient 1 (T-ALL #1) had a small subset of T-ALL cells positive for CD5. Leukemic cells from this patient were co-cultured with CD5CAR NK cells. Target populations were gated and quantified with flow cytometry using cell cytotracker dye (CMTMR) to label patient's cells. Target CD5+CD34+ cell populations were gated against an isotype control. CD5CAR NK cells lysed about 60% of CD34+CD5+ leukemic cells at an E:T ratio of 5:1. Importantly, CD5CAR NK cells showed no any activity against CD5– cell populations, implying specific and directed activity against (selective for) target antigen epitopes. Patient 2 had a T-ALL population, which was virtually positive for CD5, and co-cultured with CD5CAR NK cells. CD5CAR NK cells showed almost complete lysis of the highly expressing CD5+ target population with potent activity against the dim CD5+CD34+ population (FIG. 29B).

CD5CAR NK Cells Effectively Eliminate Aggressive CD5+ Peripheral T Cell Lymphoma (PTCL) Cells Using Human Samples.

Figure 29C:
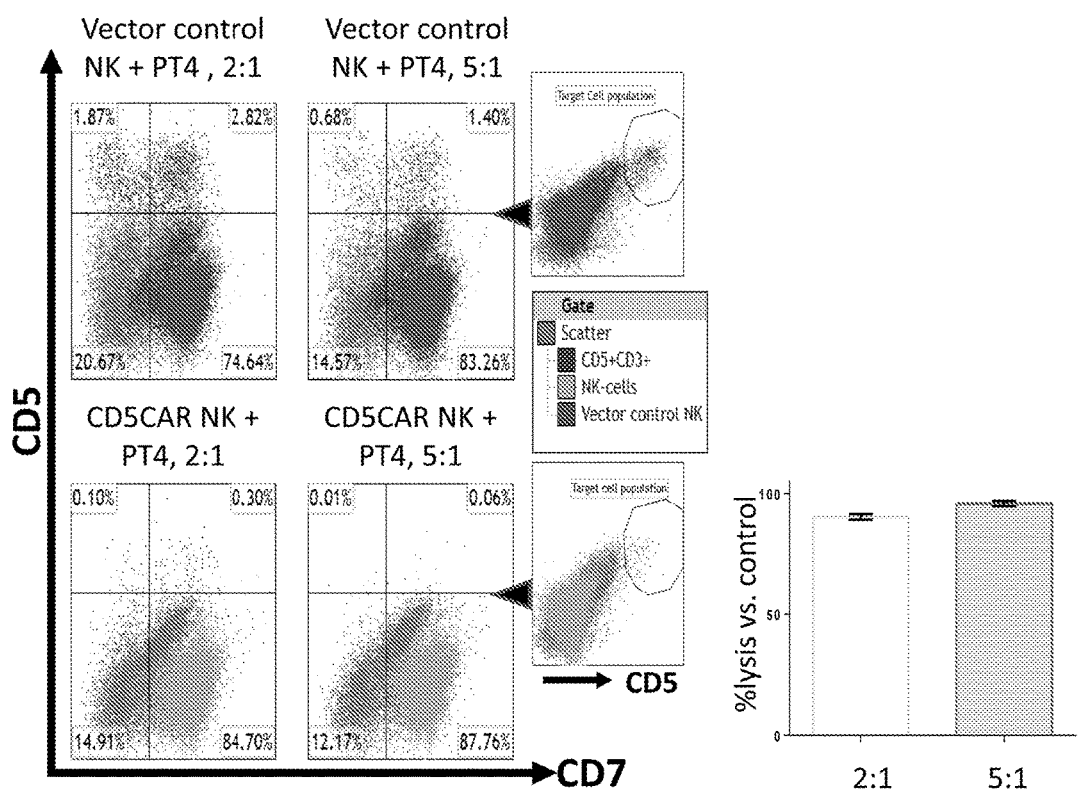

Patient 3 presented a CD4+ PTCL (unclassified type) and patient 4 presented with Sézary syndrome, an aggressive form of PTCLs that did not respond to a standard chemotherapy. Lymphoma cells from patient 3 were co-cultured with CD5CAR NK cells for 24 hours. Leukemic cells were CD5+CD7− positive and the CD5+CD7− population was gated and quantified by flow cytometry. Target CD5+CD7− population was analyzed and cell survival was expressed relative to transduced vector control NK cells. CD5CAR NK displayed almost complete lysis of the leukemic CD5+CD7− target population, with complete lysis across the entire CD5+ population including normal T cells expressing CD5 (FIG. 29C).

Figure 29D:
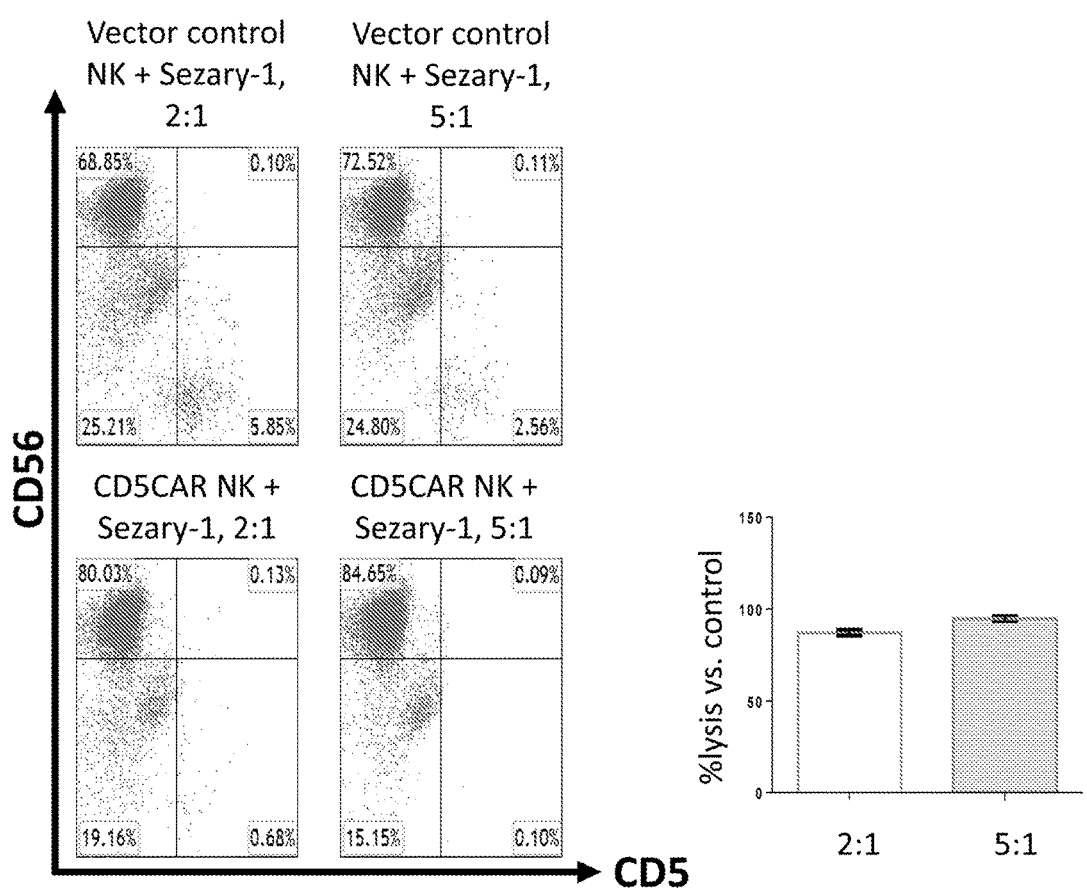

Leukemic cells from patient #4 with Sézary syndrome were co-cultured with CD5CAR NK cells at E:T ratios of 2:1 and 5:1 after 24 hours. CD5CAR NK cells demonstrated a potent anti-leukemic acidity with over 90% lysis of Sézary syndrome cells (FIG. 29D). Saturation was achieved at 2:1 E:T ratio where leukemic cells were virtually eliminated.

CD5CAR NK Cells Effectively Deplete Normal T Cells.

Figure 30:
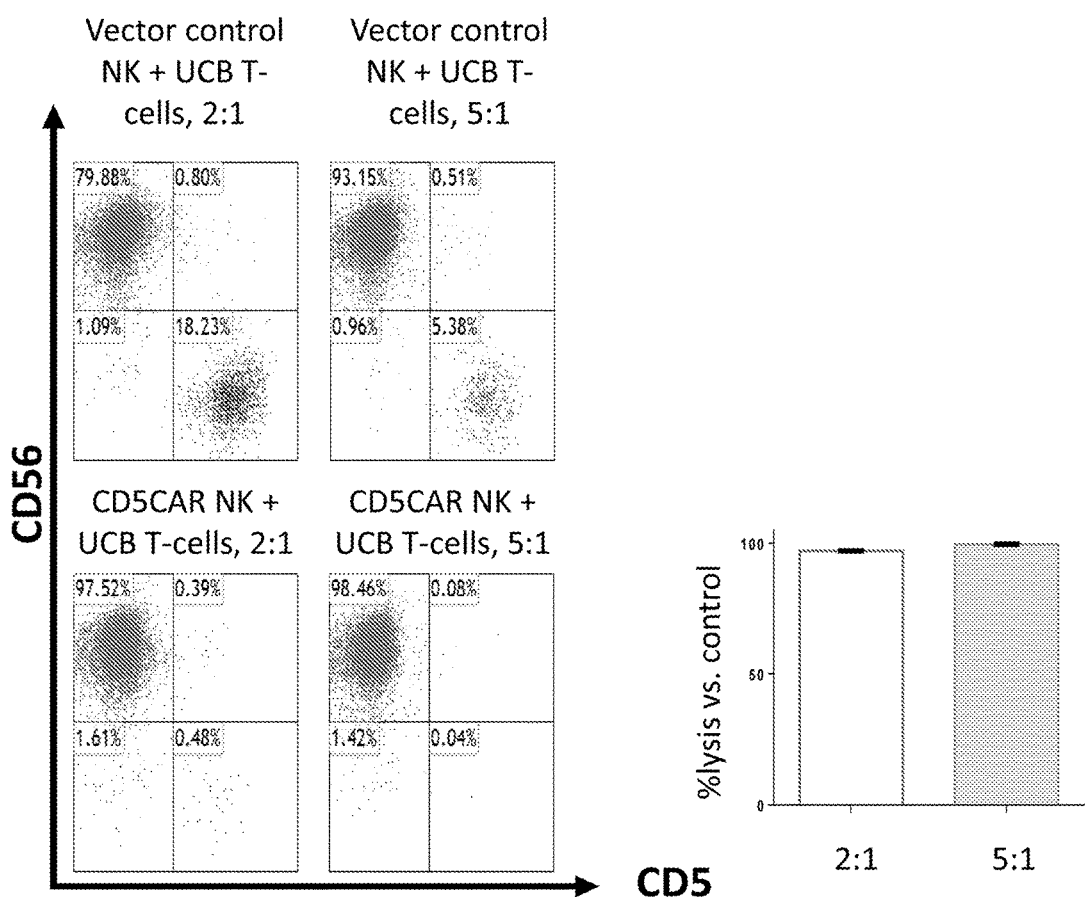
FIG. 30. CD5NK-CAR specifically eliminates umbilical cord blood T-cells. T cells are isolated from umbilical cord blood (UCB) T-cells and co-cultured with CD5CAR NK cells in the indicated E:T (effector:target) cell ratios for 24 hours. Target populations were quantified with flow cytometry using CD56 and CD5 to separate the NK-CAR and T-cell population respectively. Cell survival is expressed relative to transduced vector control NK cells and each bar graph represents the average statistics for duplicate samples.

T cells were isolated from cord blood and used to co-culture with CD5CAR NK cells. As shown in FIG. 30, CD5CAR NK cells completely depleted T cells at a low effector:target ratio of 2:1 after 24 hours of co-culture (FIG. 30). As compared to that of the GFP control, the T cell population remained largely intact.

CD5CAR NK Cells Effectively Lyse CD5+ B-Cell Malignancies Including Mantle Cell Lymphoma (MCL) and Chronic Lymphocytic Lymphoma (CLL).

Figure 31A:
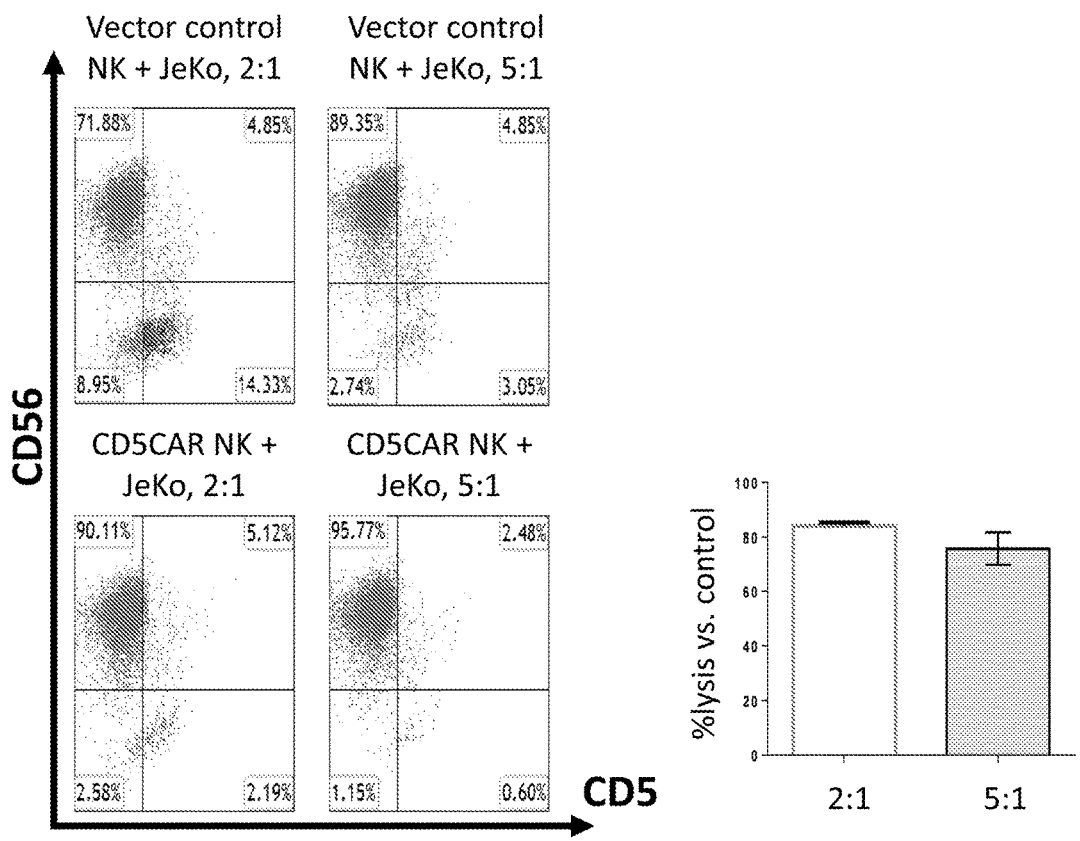
FIG. 31. CD5CAR NK cells effectively eliminate CD5+ mantle cell lymphoma and chronic lymphocytic leukemia. CD5CAR NK cells were co-cultured with Jeko cells (FIG. 31A) and leukemic cells from patients with mantle cell lymphoma (FIG. 31B) and chronic lymphocytic leukemia (FIG. 31C). Mantle cell line lymphoma derived cell line JeKo expressing a major subset of CD5 was co-cultured with CD5CAR NK cells in the indicated E:T (effector:target) cell ratios for 6 hours. For mantle cell lymphoma or CLL, co-cultures were conducted for 24 hours. Target populations were gated and quantified with flow cytometry as illustrated in figures. CD5CAR NK cells specifically targets the CD5+ CD19+ leukemia population and the CD5+CD19− T-cell population. Cell survival is expressed relative to transduced vector control NK cells and each bar graph represents the average statistics for duplicate samples.
Figure 31B:
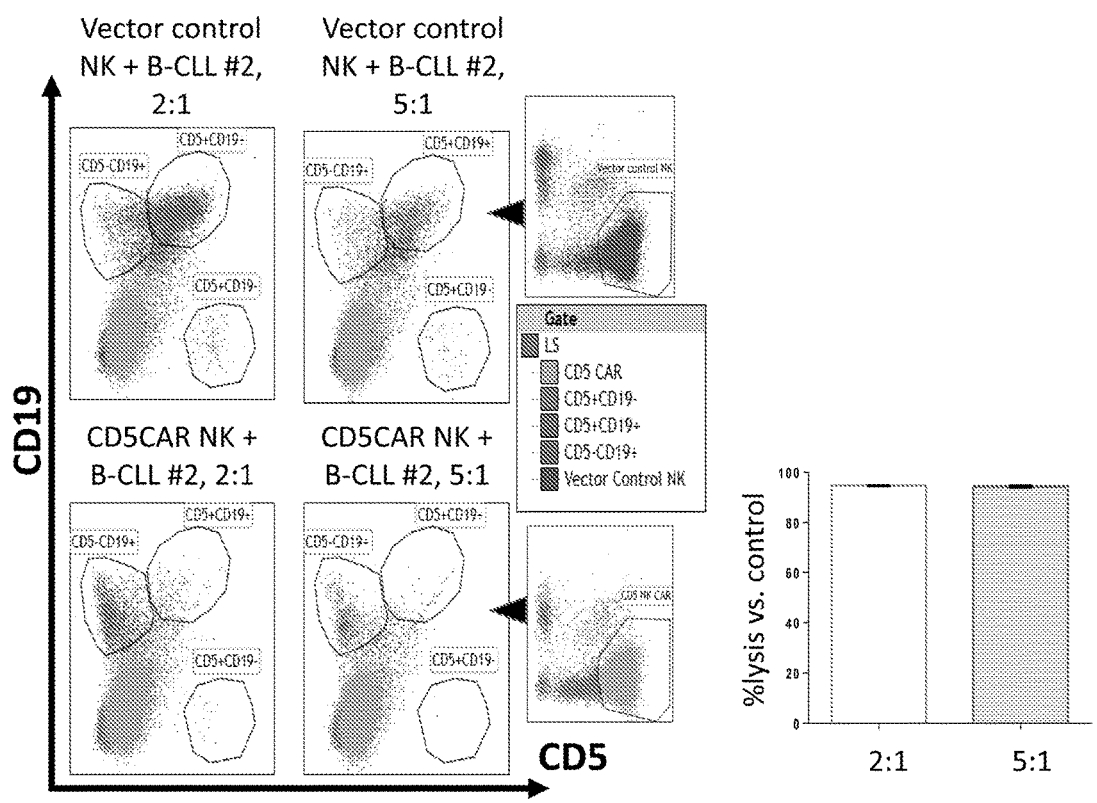
Figure 32:
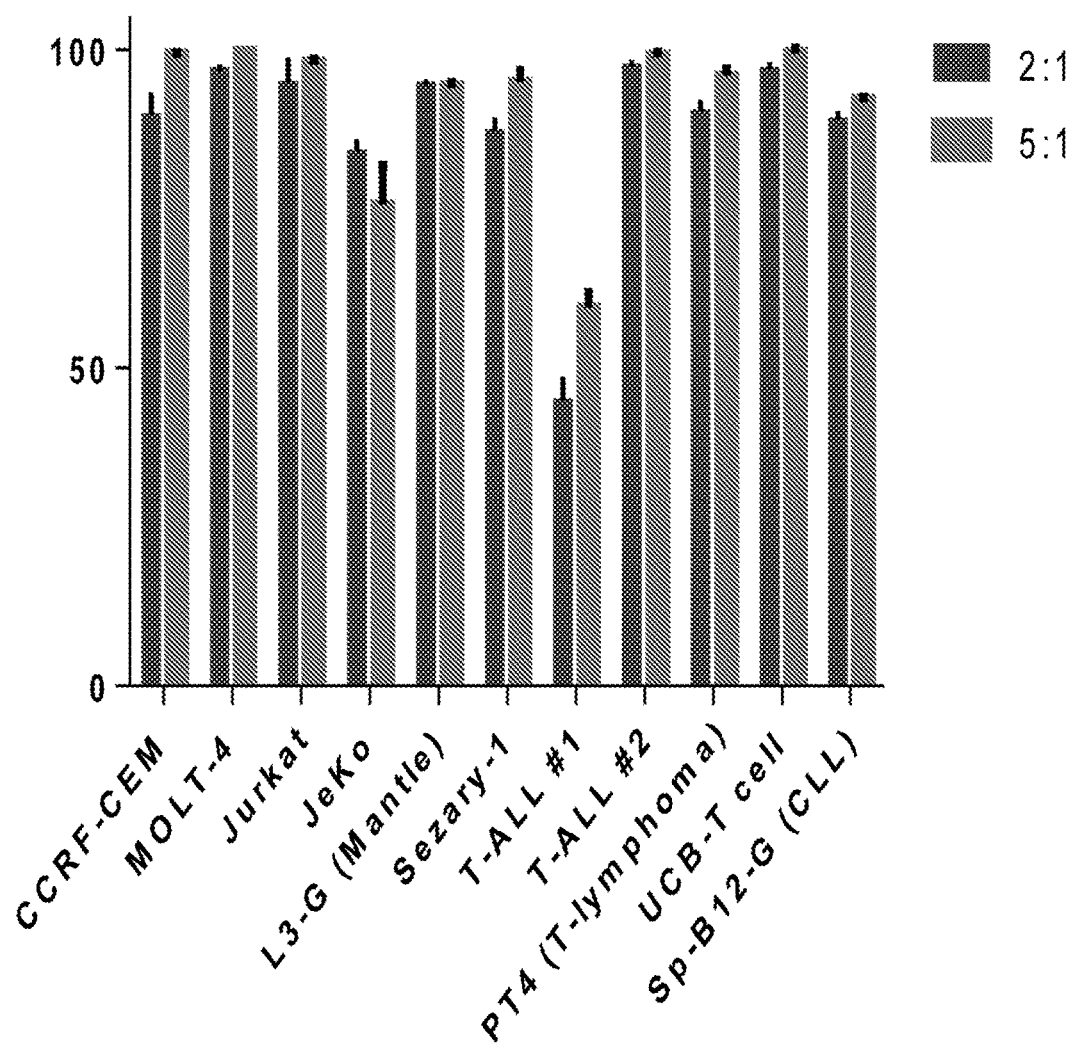
FIG. 32. Bars graph summarizing the CD5CAR NK cell co-cultures studies.

Additional co-culture studies were conducted with CD5+ Jeko lymphoma cell line and lymphoma cells from patients with (MCL) and CLL. The JeKo-1 MCL cell line was established from peripheral blood mononuclear cells of a patient with a large cell variant of MCL. In co-culture studies at a low E:T of 2:1, CD5CAR NK cells effectively lysed approximately 80% of Jeko cells (FIG. 31A). Cells isolated from a patient samples with MCL was also co-cultured with CD5CAR NK cells. Target populations were gated and live cells were quantified by flow cytometry. CD5CAR NK cells virtually eliminated both populations, which were CD5+CD19+ leukemia population and CD5+ CD19− T-cell population (FIG. 31B). Cells from a patient with B-cell CLL were also co-cultured with CD5CAR NK cells. CD19 was used to gate the leukemic population with flow cytometry. CD5+CD19+ CLL cells were virtually eliminated by CD5CAR NK cells (FIG. 31C). These studies strongly suggest that CD5CAR NK cells include a biological property of profound anti-tumor activity in leukemic cell lines and patient leukemic samples (FIG. 32) including for T-ALL, PTCLs and B-cell lymphomas expressing CD5.

CD5CAR NK Cells Demonstrate a Potent Anti-Leukemic Activity In Vivo.

Figure 33A:
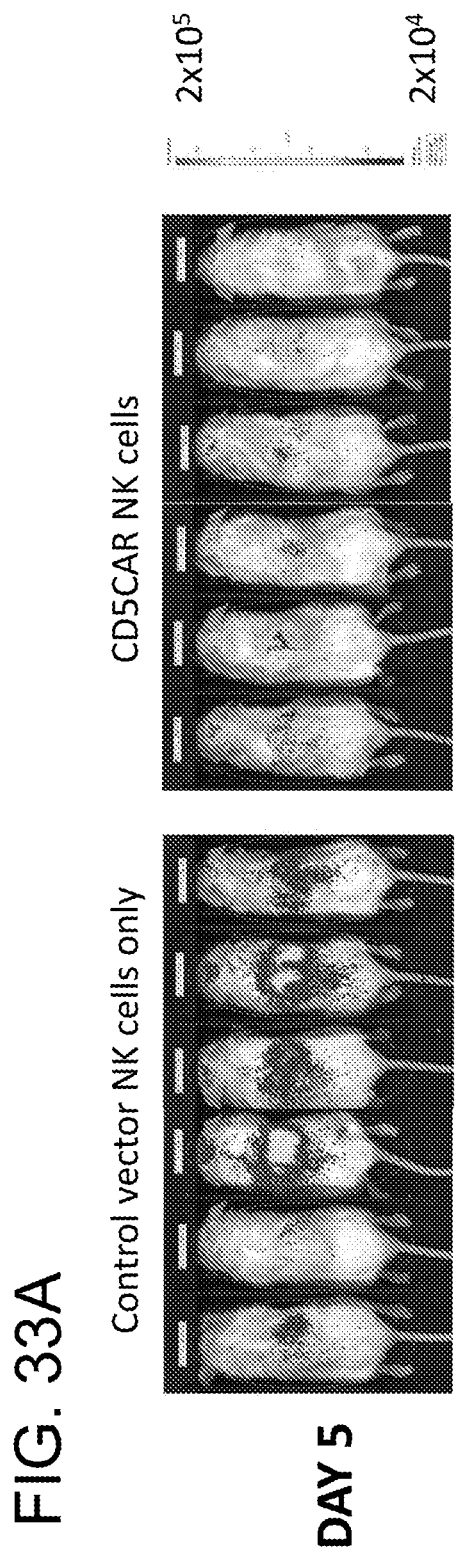
FIG. 33. CD5CAR NK cells demonstrate potent anti-leukemic effects in vivo. NSG mice were sublethally irradiated and, after 24 hours, intravenously injected with $1 \times 10^6$ luciferase-expressing CCRF-CEM cells (Day 0) to induce measurable tumor formation. On day 3 and 4, mice were intravenously injected with $5 \times 10^6$ CD5CAR NK cells or vector control NK cells. These injections were repeated on Days 6 and 7, for a total of $2.0 \times 10^7$ cells per mouse. A, on day 5, mice were injected subcutaneously with RediJect D-Luciferin and subjected to IVIS imaging. B, Percentage of tumor cells killed in mice treated with CD5CAR NK cells relative to control.
Figure 33B:
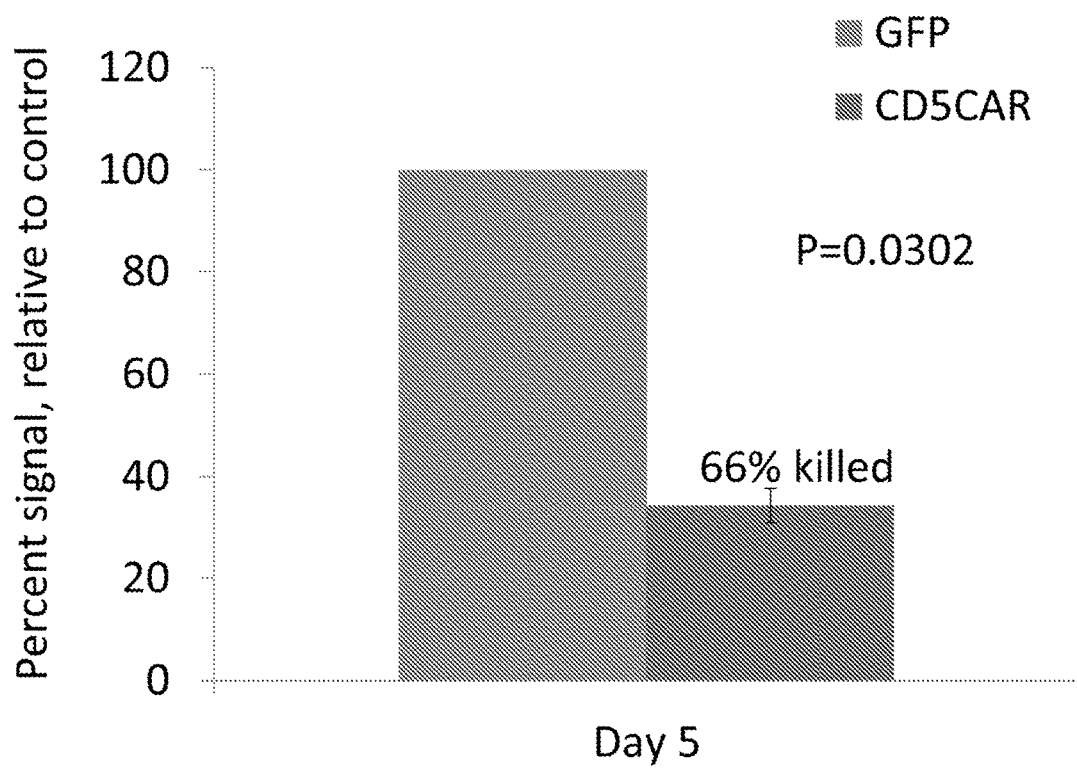

A similar strategy for CD5CAR T cells, animal studies were employed to determine the in vivo anti-tumor activity of CD5CAR NK cells. Sublethally irradiated NSG mice were intravenously injected with $1.0 \times 10^6$ firefly luciferase-expressing CCRF-CEM cells to induce measurable tumor formation. 3 days following CCRF-CEM-Luc+ cell injection, mice were intravenously injected with $5 \times 10^6$ CD5CAR NK cells or vector control T cells. These injections were repeated on Day 4 for a total of $10 \times 10^6$ T cells per mouse. On day 5, mice were injected subcutaneously with RediJect D-Luciferin and subjected to IVIS imaging to measure tumor burden (FIG. 33A). Average light intensity measured for the CD5CAR NK cell injected mice was compared to that of vector control NK cell injected mice (FIG. 33B). Tumor burden was two thirds lower for treated mice on day 5 after tumor injection. Paired T test analysis revealed a very highly significant difference (P=0.0302) between the two groups. These in vivo data indicate that CD5CAR NK cells significantly reduce tumor burden in CCRF-CEM-injected NSG mice in a rapid manner when compared to vector control NK cells.

Figure 34A:
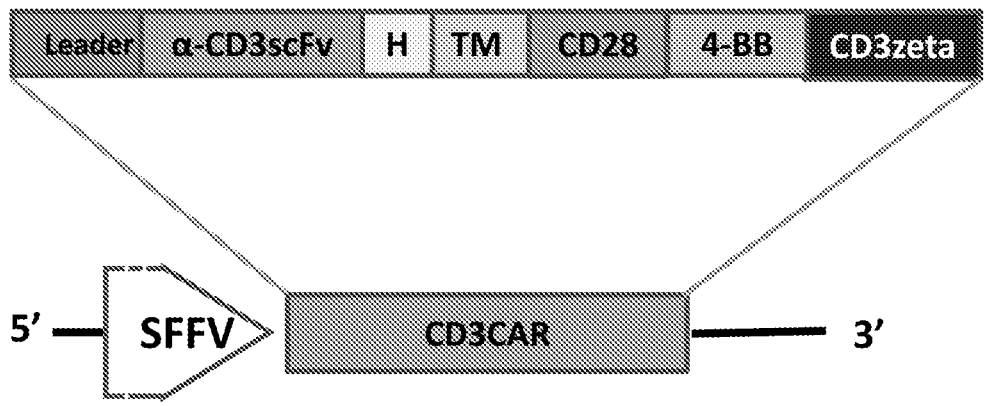
FIG. 34, Organization of CD3CAR and its expression. A, Schematic representation of the organization of CD3CAR in lentiviral vectors. CAR expression is driven by a SFFV (spleen focus-forming virus) promoter and as a $3^{rd}$ generation construct, contains a leader sequence, the anti-CD3scFv, a hinge domain (H), a transmembrane domain (TM), two co-stimulatory domains of CD28 and 4-BB and the intracellular signaling domain of CD3 zeta. B, HEK-293FT cells were transduced with lentiviral plasmids for GFP (lane 1) and CD3CAR (lane 2) for Western blot analysis at 48 h post transduction and probed with mouse anti-human CD3zeta antibody.

Anti-CD3 Chimeric Antigen Receptor (CD3CAR) NK Cells Efficiently Lyse CD3 Positive Hematologic Malignancies Examples Results Generation of the CD3CAR The anti-CD3 molecule is a modular design, comprising of a single-chain variable fragment (scFv) in conjunction with CD28 and 4-1BB domains fused to the CD3zeta signaling domain to improve signal transduction making it a third generation CAR. A strong spleen focus forming virus promoter (SFFV) was used for efficient expression of the CD3CAR molecule on the NK cell (NK-92) surface and the CD8 leader sequence was incorporated into the construct. The anti-CD3 scFv is attached to the intracellular signaling domains via a CD8-derived hinge (H) and transmembrane (TM) regions (FIG. 34A). This CD3CAR construct was then cloned into a lentiviral plasmid.

Characterization of CD3CAR

Figure 34B:
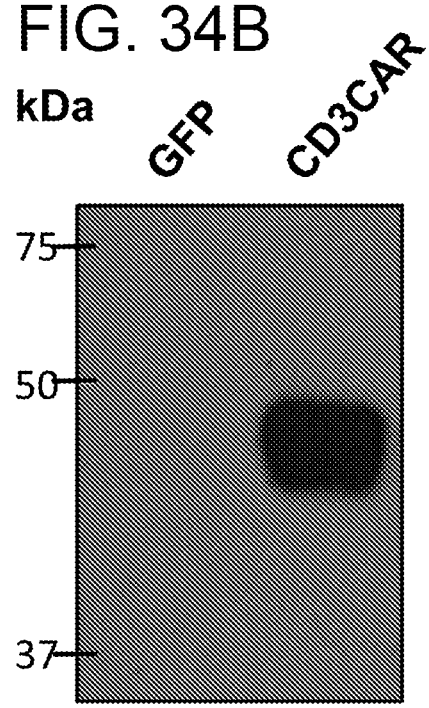

Western blot analysis was performed on HEK293-FT cells transfected with CD3CAR lentiviral plasmid and vector control plasmid. Immunoblots with anti-CD3zeta monoclonal antibody show bands of predicted size for the CD3CAR-CD3zeta fusion protein (FIG. 34B) versus no bands for the vector control protein.

Generation of CD3CAR NK Cells Using NK-92 Cells

The transduction efficiency of the CD3CAR was determined by flow cytometry analysis. To enrich for CD3CAR NK cells, the highest expressing NK cells were harvested using fluorescence-activated cell sorting (FACS). Following sorting, NK cells with relatively high expression of CD3CAR was obtained. Expression of CD3CAR following flow cytometry sorting was stable around 30% of CAR expression for subsequent NK cell expansion and cryo-preservation.

CD3CAR NK Cells Effectively Lyse Human T-ALL Cell Lines

Figure 35A:
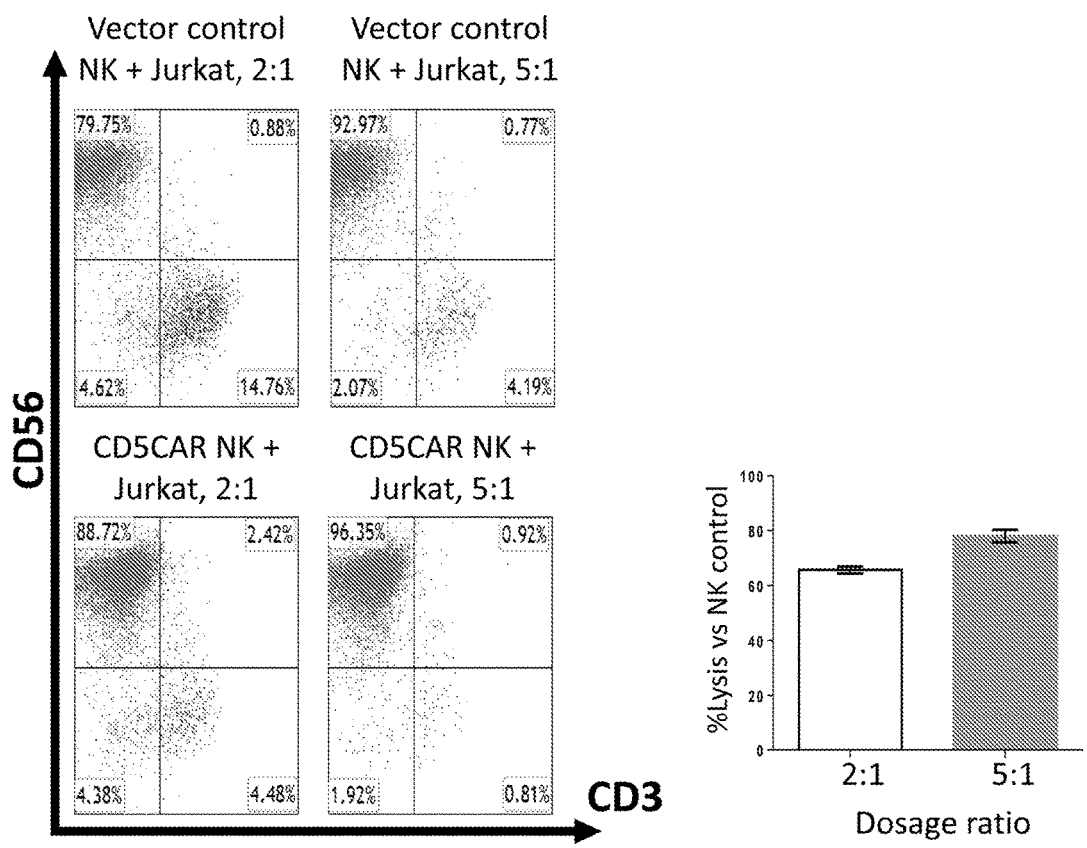
FIG. 35. CD3CAR NK cells eliminate CD3-expressing T-ALL cell lines in vitro. A, T-lymphoblast cell line Jurkat expressing approximately 80% CD3 was co-cultured with CD3CAR NK cells in the indicated E:T (effector:target) cell ratios for 6 hours. B, Sorted (CCRF-CD3) or unsorted CCRF-CEM (CCRF-CEM) cells were co-cultured with CD3CAR NK cells for 24 hours. Target populations were quantified with flow cytometry using CD56 and CD3 to separate the NK-CAR and target cell population respectively. Cell survival is expressed relative to transduced vector control NK cells and each bar graph represents the average statistics for duplicate samples with N=2 experiments.
Figure 35B:
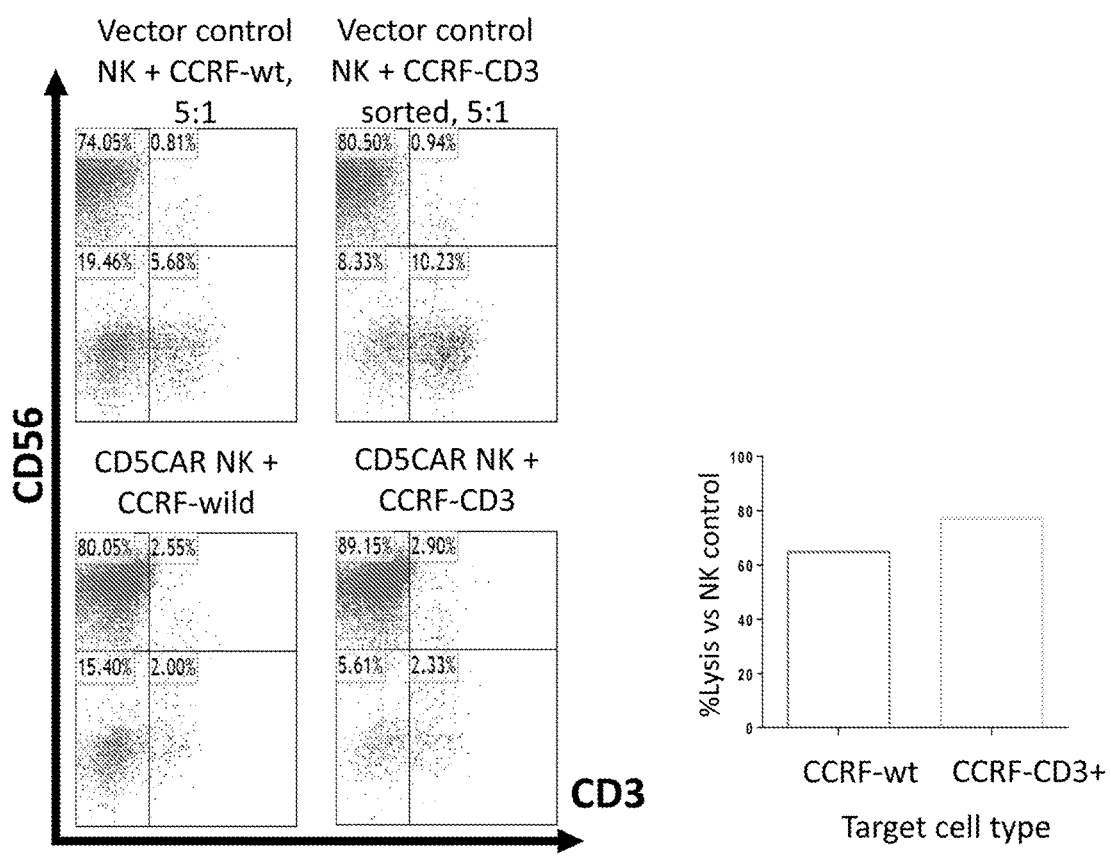

To determine the efficacy for CD3CAR NK cells, we conducted co-culture assays using CD3+ T-ALL cell lines, Jurkat, and CCRF-CEM. CD3 positive cells in Jurkat and CCRF-CEM cells are approximately 80% and 10% positive for CD3, respectively. CD3+ cells from the CCRF-CEM cell line were then sorted for highly expressed CD3 cells, and CD3 expression in sorted CCRF-CEM cells were about 50%. During co-culture with Jurkat and CCRF-CEM cells, CD3CAR NK cells demonstrated profound leukemic cell killing abilities (FIG. 35). At 6 hour incubation and at a low E:T ratio of 2:1, CD3CAR NK cells effectively lysed over 60% of Jurkat cells (FIG. 35A). We next compared the killing ability of relative highly expressed CD3 CCRF-CEM cells (sorted) with that of unsorted CCRF-CEM cells. The CD3 CAR NK cells appeared to be more efficacious against a higher CD3 expressing population in sorted CCRF-CEM than a lower CD3 expressing unsorted CCRF-CEM (FIG. 35B) population.

CD3CAR NK Cells Effectively Eliminate CD3+ Leukemic Cells from Human Samples

Figure 36A:
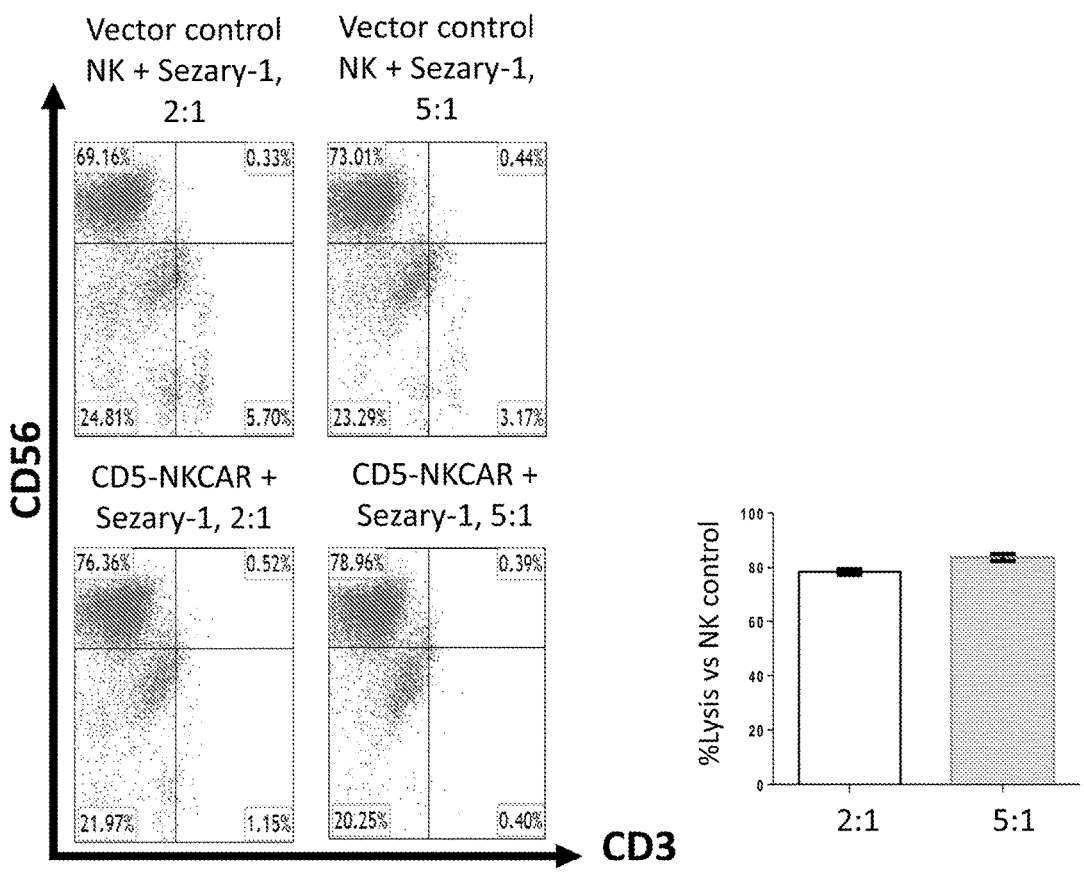
FIG. 36. The CD3CAR NK cells display robust killing ability for primary CD3+ leukemic cells from patient samples. A, SPT-1 (Sezary syndrome) patient cells were CD3 positive and were co-cultured with CD3CAR NK cells in the indicated E:T (effector:target) cell ratios for 24 hours. Target populations were quantified with flow cytometry using CD56 and CD3 to separate the NK-CAR and target cell population respectively. While SPT-1 is a heterogenous cell population, the broad CD3+ expressing population is eliminated by the CD3NK-CAR. B, PT4 (unclassified PTCLs) patient cells were CD3+CD7−, and were co-cultured with CD3CAR NK cells in the indicated E:T (effector:target) cell ratios for 24 hours. Target populations were gated and quantified as seen in figure. PT4 leukemia cells are typed CD3+CD7- and are effectively eliminated by the CD3CAR NK cells. The broad CD3+ population is also affected by the CD3CAR NK cells.
Figure 36B:
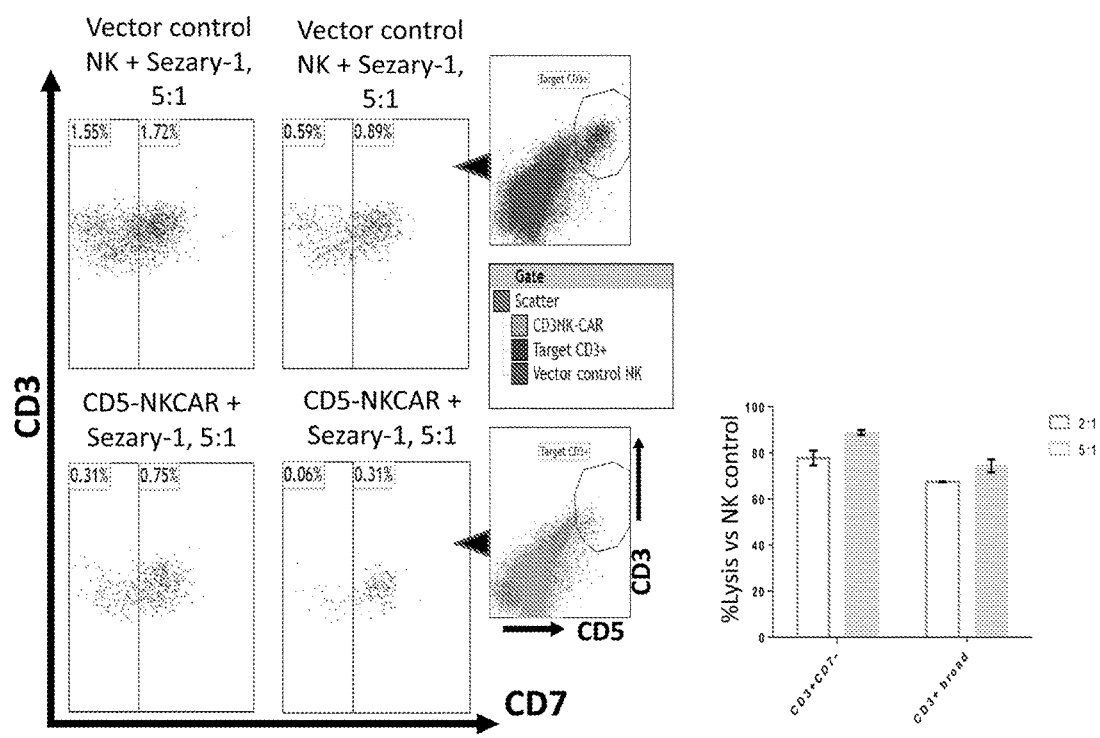

The killing ability of CD3CAR NK cells was also tested using patient samples. Flow cytometry analysis of both patient samples revealed strong and uniform CD3 expression. As analyzed by flow cytometry, co-culture of Sezary syndrome patient sample with CD3CAR T cells effectively resulted in lysis of approximately 80% of leukemic cells at a low E:T ratio of 2:1 (FIG. 36A). Co-culture of patient sample, unclassified PTCLs with CD3CAR NK cells for 24 hours resulted in virtual ablation of CD3+ malignant cells (FIG. 36B). The CD3CAR NK cells also affected the broad CD3+ population.

CD3CAR NK Cells are Able to Deplete Normal T Cells.

Figure 37:
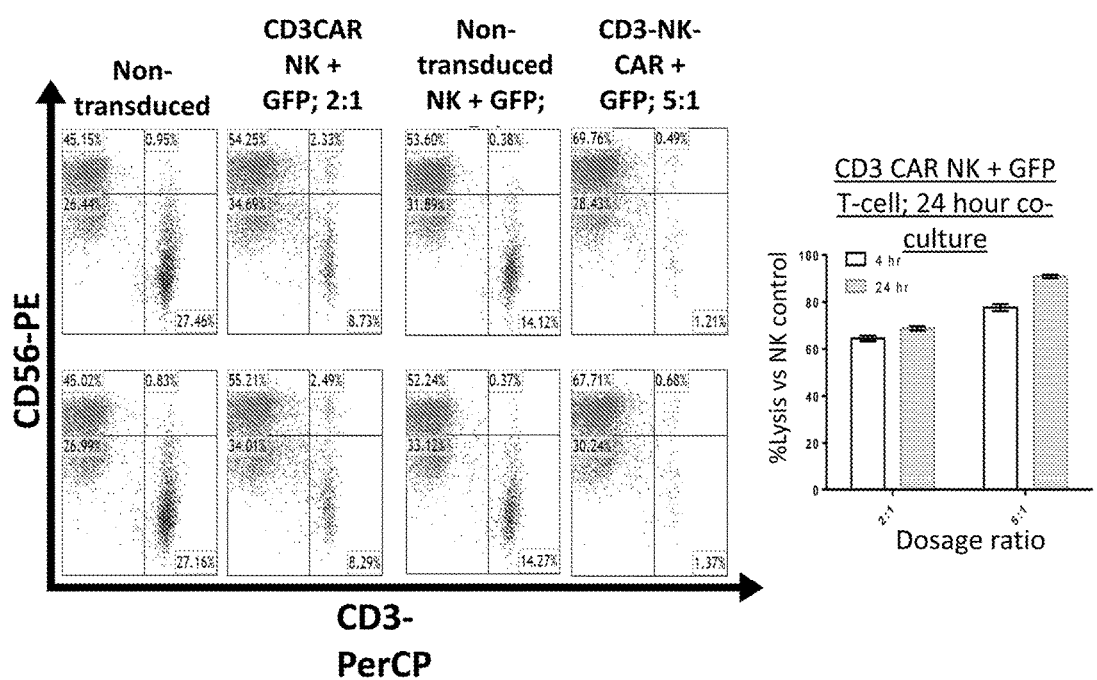
FIG. 37, CD3CAR NK cells are able to lyse normal T cells as expected. Normal T cells were isolated from umbilical cord blood and transduced with lentiviruses expressing GFP. The transduced GFP T cells were used to co-culture with CD3CAR NK cells. Co-culture conditions were carried out in NK cell media with 2.5% serum. Co-cultures were incubated for 24 hours and labeled for flow cytometry analysis. The ability of CD3CAR NK cells to lyse target T cells was evaluated by comparing the amount of residual CD3+ GFP T-cells after co-culture. Importantly, with an increased incubation period, target CD3+ GFP T-cells were shown to be lysed with over 80% efficiency at a dosage of 5:1 effector to target cell ratio.

GFP transduced normal T cells were used to co-culture CD3CAR NK cells. As shown in FIG. 37, CD3CAR NK cells depleted a substantial portion of normal T cells after 4 or 24-hour incubation.

CD3CAR NK Cells Exhibit Profound Anti-Leukemic Activity In Vivo

Figure 38A:
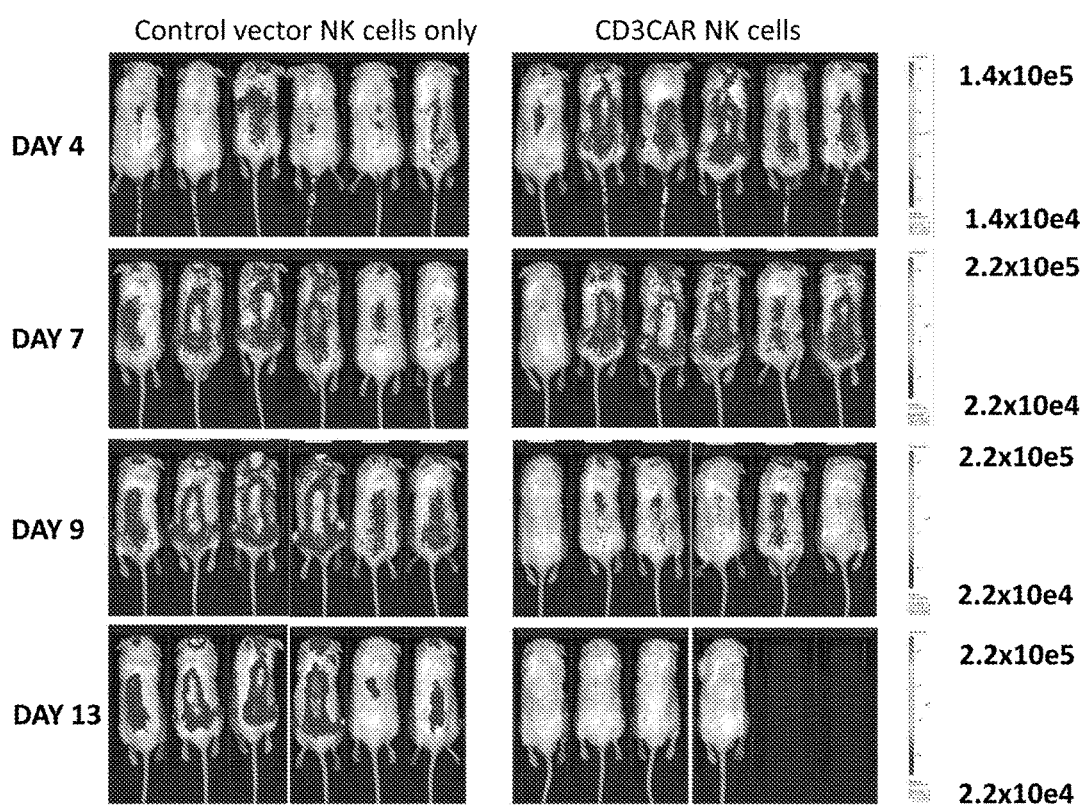
FIG. 38. CD3CAR NK cells demonstrate profound anti-leukemic effects in vivo. A, NSG mice were sublethally irradiated and, after 24 hours, intravenously injected with $1\times10^6$ luciferase-expressing Jurkat cells (Day 0) to induce measurable tumor formation. On day 3 and 4 mice were intravenously injected with $5\times10^6$ CD3CAR NK cells or vector control NK cells each day. These injections were repeated on Days 6 and 7, and again on Day 10, for a total of $2.5\times10^7$ cells per mouse. (A) On days 4, 7, 9, and 13, mice were injected subcutaneously with RediJect D-Luciferin and subjected to IVIS imaging. B, Average light intensity measured for the CD3CAR NK injected mice was compared to that of vector control NK cell injected mice. C, Percentage of tumor cells killed in mice treated with CD3CAR NK cells relative to control.

To determine the in vivo anti-tumor efficacy of CD3CAR NK cells, sublethally irradiated NSG mice were intravenously injected with $1.0 \times 10^6$ firefly luciferase-expressing Jurkat cells, which are CD3 positive (~80%), and measurable tumor formation was detected by Day 3 or 4. Three days following Jurkat-Luc+ cell injection, mice were intravenously injected with $5 \times 10^6$ CD3CAR NK cells or vector control NK cells per mouse, 6 per group. These injections were repeated on Day 3, 6, 7 and 10 for a total of $25 \times 10^6$ T cells per mouse. On days 4, 7, 9 and 13 mice were subjected to IVIS imaging to measure tumor burden (FIG. 38A). Two treated mice died due to injection procedure on day 13. Average light intensity measured for the CD3CAR NK cell injected mice was compared to that of vector control NK injected mice (FIG. 38B). After an initial lag period, tumor burden then dropped to approximately two-thirds lower for treated mice by Day 9 and just 13% on Day 13 (FIG. 38C). Paired T test analysis revealed a highly significant difference (P=0.0137) between the two groups. We conclude that these in vivo data demonstrate that CD3CAR NK cells significantly reduce tumor burden and prolong survival in Jurkat-injected NSG mice when compared to vector control NK cells.

CRISPR/Cas Nucleases Target to CD2, CD3, CD5 and CD7 Expressed on T or NK Cells.

T or NK cells appear to share some of surface antigens, such as CD2, CD3, CD5 and CD7 with leukemia or lymphoma. CD2, CD3, CD5, and CD7 could be good targets for T and NK cells as they are expressed in most of T cell leukemia/lymphoma.

Therefore, when one of surface antigens, CD2, CD3, CD5, and CD7 is selected as a target, this antigen is needed to delete or down-regulate in T or NK cells used to generate CAR if they share this antigen, to avoid self-killing within the CAR T or NK cell population.

Steps for generation of CAR T or NK cell targeting T-cell lymphomas or T-cell leukemia are described in FIG. 39. Three pairs of sgRNA were designed with CHOPCHOP to target CD2, CD3, CD5, and CD7. Gene-specific sgRNAs (FIG. 40) were then cloned into the lentiviral vector (Lenti U6-sgRNA-SFFV-Cas9-puro-wpre) expressing a human Cas9 and puromycin resistance genes linked with an E2A self-cleaving linker. The U6-sgRNA cassette is in front of the Cas9 element. The expression of sgRNA and Cas9puro is driven by the U6 promoter and SFFV promoter, respectively.

Examples

Results

CRISPR/Cas Nucleases Target to CD5 on T Cell Lines.

Figure 41A:
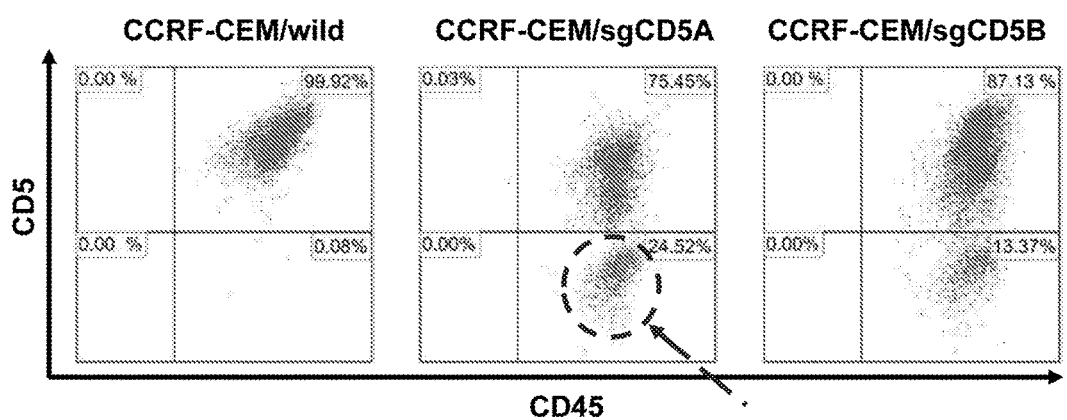
FIG. 41. Generation of stable CD5-deficient CCRF-CEM and MOLT-4 T cells using CRISPR/Cas9 lentivirus system. A. Flow cytometry analysis demonstrating the loss of CD5 expression in CCRF-CEM T-cells with CRISPR/Cas9 KD using two different sgRNAs, Lenti-U6-sgCD5a-SFFV-Cas9puro (sgCD5A) and Lenti-U6-sgCD5b-SFFV-Cas9puro (sgCD5B) after puromycin selection. Wild type control is seen in the left most scatter plot. Because the CRISPR/Cas9 KD technique with sgRNA CD5A was more successful at CD5 protein downregulation, this population (denoted by the blue circle and arrow) was selected for sorting, purification and analysis in FIG. 41B. B. Flow cytometry analysis data indicating the percentage of purely sorted stable CD5 negative CCRF-CEM cells transduced using the scCD5A CRISPR/Cas9 technique. We note the >99% purity of CD45 positive, CD5 negative CCRF sgCD5A T-cells. C. Flow cytometry analysis demonstrating the loss of CD5 expression in MOLT-4 T-cells with CRISPR/Cas9 KD using two different sgRNA sequences (sequence CD5A and CD5B, middle and right columns) after puromycin treatment. Wild type control is seen in the leftmost scatter plot. Because the CRISPR/Cas9 KD technique with primer CD5A was more successful at CD5 protein downregulation, this population (denoted by the blue circle and arrow) was selected for sorting, purification and analysis in FIG. 4D. D. Flow cytometry analysis data indicating the percentage of purely sorted stable CD5 negative MOLT-4 cells transduced using the scCD5A CRISPR/Cas9 technique. We note the >99% purity of CD45 positive, CD5 negative MOLT-4 sgCD5A T-cells.
Figure 41B:
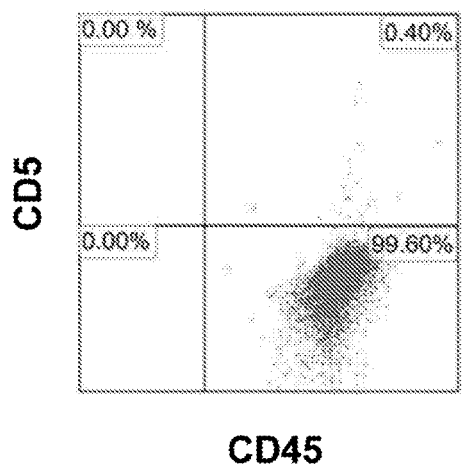
Figure 41C:
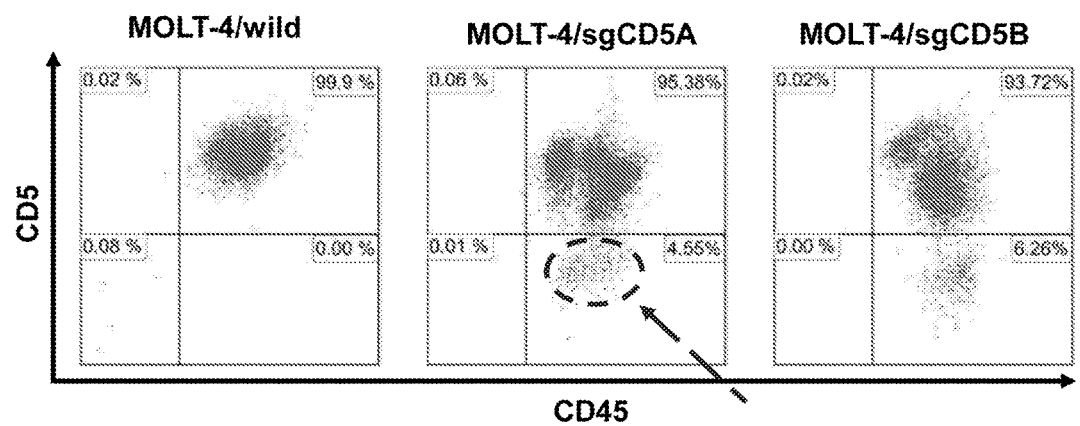
Figure 41D:
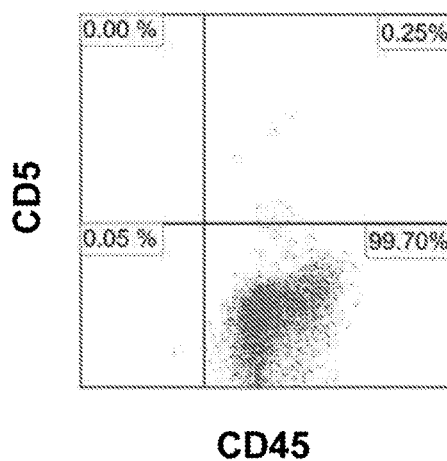
Figure 42A:
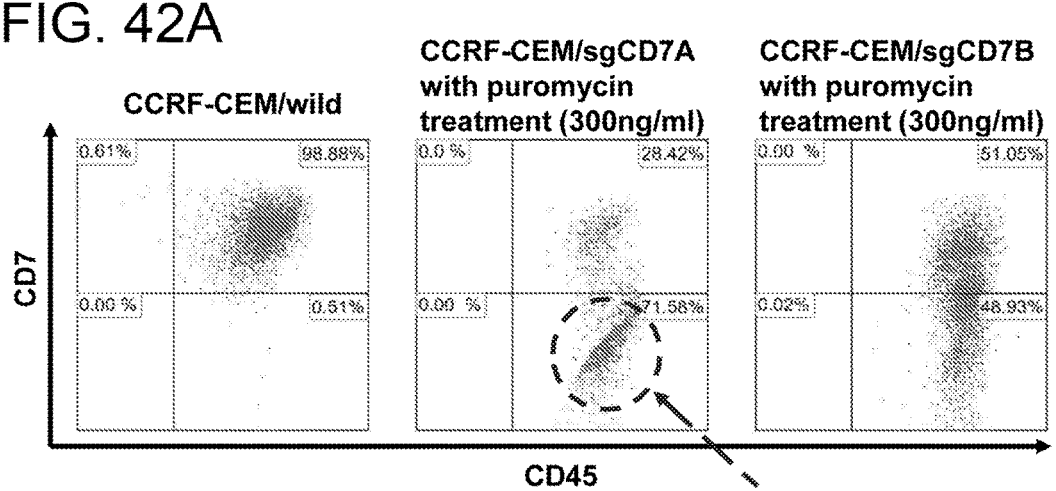
FIG. 42. Generation and cell sorting of stable CD7 loss in CCRF-CEM cells or NK-92 cells using CRISPR/Cas9 lentivirus system. The percentage of CD7 loss in CCRF-CEM (FIGS. 42A and B) or NK-92 (FIGS. 42C and D) using sgCD7A (Lenti-U6-sgCD7a-SFFV-Cas9-puro) and sgCD7B (Lenti-U6-sgCD7b-SFFV-Cas9-puro) was determined by flow cytometric analysis with CD45 and CD7 antibodies after puromycin treatment. The values of insert in figures showed percentage of positive and negative expressing CD45 or CD7 among analysis. Right panel indicated the percentage purity of sorted stable CD7 negative cells in CCRF-CEM (B) or in NK-92 cells (D) prepared from CD7 negative cells transduced using sgCD7A or sgCD7D CRISPR lentiviruses.
Figure 42B:
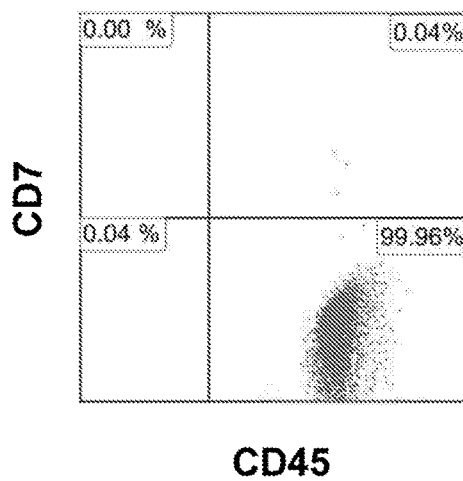
Figure 42C:
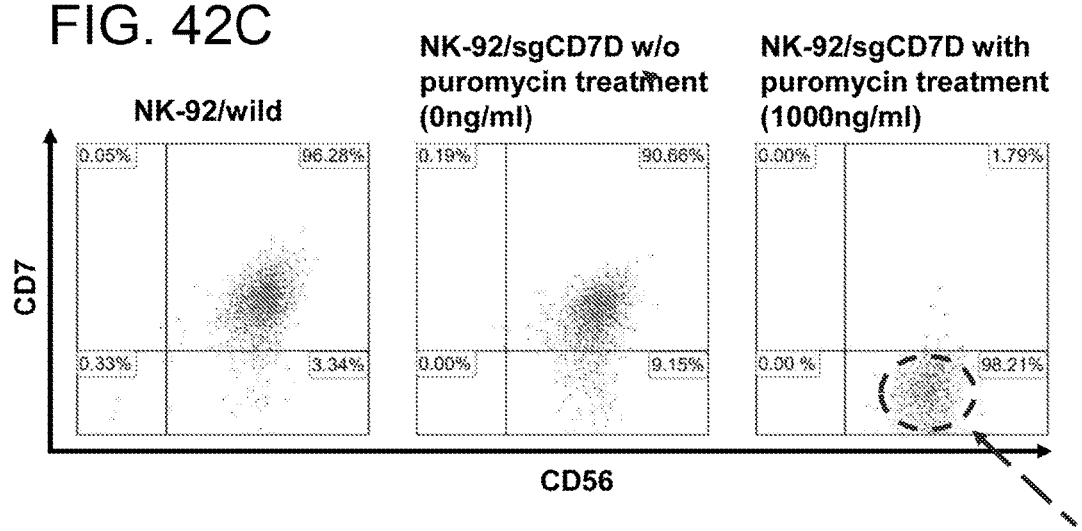
Figure 42D:
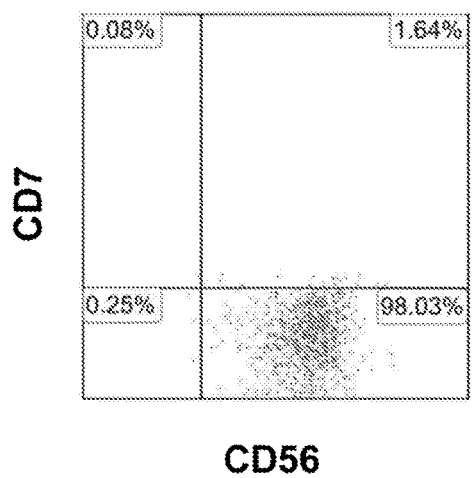

Lentiviruses carried gene-specific sgRNAs were used to transduce CCRF-CEM and MOLT cells. Initially, the loss of CD5 expression was observed in both of these T cell lines using two different two CDISPR/Cas9 sgRNA sequences (FIGS. 41A and 41C). The most successful population in terms of the loss of CD5 expression was chosen for each cell line, and these cells were sorted, expanded normally and found to be of >99% purity CD45+ and CD5-(FIGS. 41B and 41D).

CRISPR/Cas Nucleases Target to CD7 on T Cell Lines and NK Cells.

Lentiviruses carried gene-specific sgRNAs were used to transduce CCRF-CEM, MOLT cells and NK cells (FIG. 42). Flow cytometry analysis demonstrated the loss of CD7 expression in CCRF-CEM and NK-92 cells with CRISPR/Cas9 approach using two different sgRNAs (FIGS. 42A and 42B). The population (denoted by the blue circle and arrow) was selected for sorting, expansion and analysis in FIG. 42B. The loss of CD5 expression by flow cytometry analysis was also seen in NK-92 cells using a similar approach described above with CRISPR/Cas nucleases targeting to CD7 (FIGS. 42C and 42D) The sorted CD7 negative NK-92 cells (FIG. 42D) were expanded and used to generate CD7CAR NK cells to eliminate CD7 positive leukemic cells.

CD7CAR $NK^{7-}$-92 Cells have a Robust Anti-Leukemic Activity

Figure 43A:
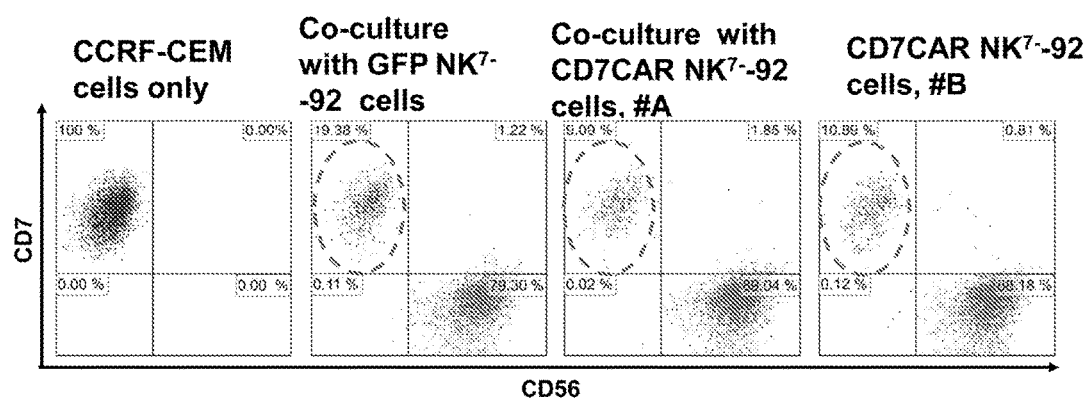
FIG. 43. CD7CAR $NK^{7-}$-92 cells effectively lyse T cell ALL cell line T cells that express CD7. To avoid self-killing, CD7 deficient NK-92 ($NK^{7-}$-92) cells were generated and transduced with CD7CAR. Two transduced preparations of CD7CAR $NK^{7-}$-92 cells, #A and #B were used to test their killing ability. A, Flow cytometry analysis of CCRF-CEM cells alone (left column), in co-culture with GFP $NK^{7-}$-92 cells (middle column), and in co-culture with CD7CAR-NK-92-cells, #A and B# (right columns). B, bar graphs based on data obtained from A.
Figure 43B:
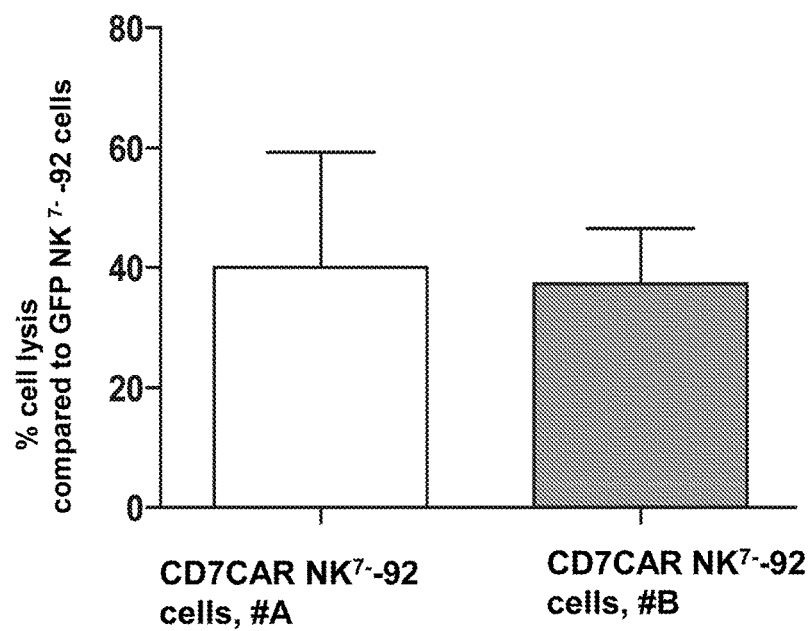

CD7 is expressed in both NK and T-ALL leukemic cells. To avoid self-killing within the CD7CAR NK-92 population, CD7 expression first needs to be inactivated. CD7 deficient NK-92 cells ($NK^{7-}$-92 cells) were generated as described in (FIG. 42D) and expanded. The expanded $NK^{7-}$-92 cells were transduced with lentivirus expressing a CD7CAR. CD7CAR includes an anti-CD7 scFV in conjunction with CD28 and 4-BB domains fused to CD3zeta signaling domain making it a third generation CAR. CD7CAR $NK^{7-}$-92 cells were used to test their lysis ability of leukemic cells expressing CD7. As shown in FIG. 43, CD7CAR $NK^{7-}$-92 cells displayed a potent anti-leukemic activity against a T-ALL cell line, CCRF-CEM. As analyzed by flow cytometry, co-culture of CCRF-CEM cells effectively resulted in the lysis of approximately 50% of leukemic cells at E:T ratio of 5:1 (FIGS. 43A and 43B).

Figure 44:
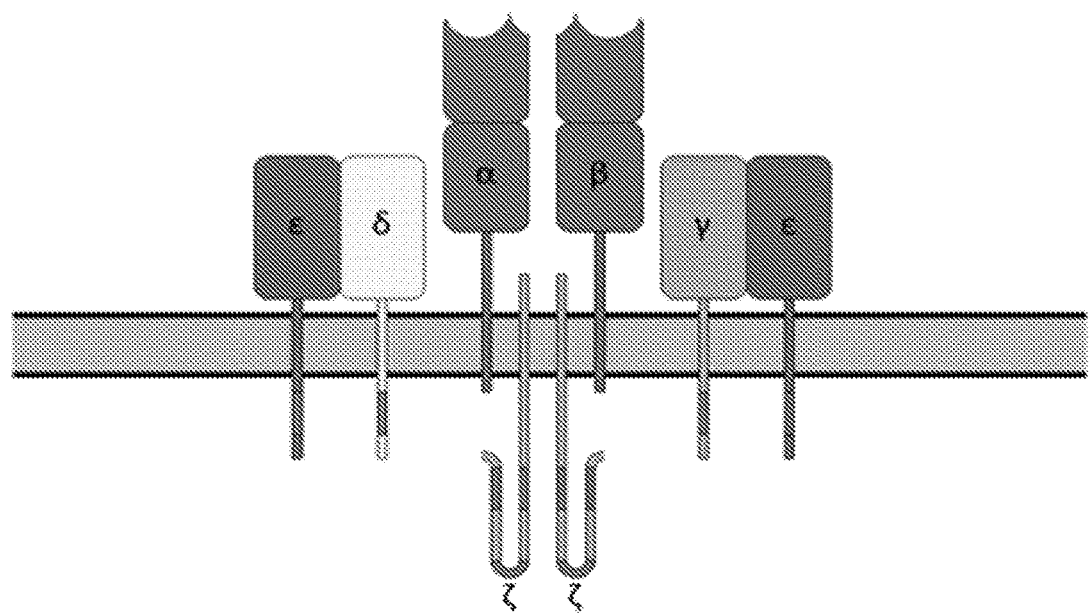
FIG. 44. CD3 multimeric protein complex. CD3 includes a protein complex and is composed of four distinct chains as described the figure above. The complex includes a CD3δ chain, a CD3γ chain, and two CD3ε chains. These chains associate with the T-cell receptor (TCR) composing of αβ chains.

CD3 multimeric protein complex is elucidated in FIG. 44. The complex includes a CD3δ chain, a CD3γ chain, and two CD3ε chains. These chains associate with the T-cell receptor (TCR) composing of αβ chains.

CD3CAR is Used for Graft-Versus-Host Disease (GvHD).

CD3CAR is administered to a patient prior to or after a stem cell transplant. The patient is tested for elevated levels of white blood cells.

CD3CAR is administered to a patient prior to or after a bone marrow transplant. The patient is tested for elevated levels of white blood cells.

CD3CAR is administered to a patient prior to or after a tissue graft. The patient is tested for elevated levels of white blood cells.

Organ Transplant

CD3CAR is administered to an organ transplant patient before organ transplant surgery. The patient is tested for organ rejection. The following histological signs are determined: (1) infiltrating T cells, in some cases accompanied by infiltrating eosinophils, plasma cells, and neutrophils, particularly in telltale ratios, (2) structural compromise of tissue anatomy, varying by tissue type transplanted, and (3) injury to blood vessels.

CD3CAR is administered to an organ transplant patient after organ transplant surgery. The patient is tested for organ rejection. The following histological signs are determined: (1) infiltrating T cells, in some cases accompanied by infiltrating eosinophils, plasma cells, and neutrophils, particularly in telltale ratios, (2) structural compromise of tissue anatomy, varying by tissue type transplanted, and (3) injury to blood vessels.

The invention claimed is:

1. An in vitro method of reducing the number of CD4 positive T cell leukemia cells or CD4 positive T cell lymphoma cells, the method comprising the steps of:
 (i) contacting a plurality of cells comprising CD4 positive T cell leukemia cells or CD4 positive T cell lymphoma cells with an effective amount of engineered cells comprising a polynucleotide that encodes for a chimeric antigen receptor (CAR) polypeptide comprising: a signal peptide, a CD4 antigen recognition domain, a hinge region, a transmembrane domain, at least one co-stimulatory domain, and a signaling domain; said polynucleotide comprises the nucleotide of SEQ ID NO:4 or SEQ ID NO:5, wherein the CD4 antigen recognition domain specifically recognizes CD4 in a target cell population; and
(ii) optionally, assaying for CD4 positive T cell leukemia cells or CD4 positive lymphoma cells;
wherein the engineered cells comprise at least one of CD8 T-cells, Natural Killer cells, and Natural Killer T cells (NKT cells); and wherein the number of CD4 positive T cell leukemia cells or CD4 positive T cell lymphoma cells are reduced by at least 5% as compared to the number of CD4 positive T cell leukemia cells or CD4 positive T cell lymphoma cells prior to the contacting of step (i).

2. The method of reducing the number of CD4 positive T cell leukemia cells or CD4 positive T cell lymphoma cells according to claim 1, wherein said engineered cells are Natural Killer cells or Natural Killer T cells (NKT cells).

3. A method of treating a CD4 associated cell proliferative disease in a human patient in need thereof, the method comprising the steps of:
(i) obtaining T cells from said human patient;
(ii) transforming said T cells with a polynucleotide encoding a CD4CAR polypeptide comprising a signal peptide, a CD4 antigen recognition domain that specifically recognizes CD4 in a target cell population, a hinge region, a transmembrane domain, at least one co-stimulatory domain, and a signaling domain; to provide engineered cells that express a chimeric antigen receptor (CAR);
(iii) administering to said human patient in need thereof a therapeutically effective amount of the engineered cells of step (ii);
(iv) reducing the tumor burden of CD4 associated cell proliferative disease cells; and
(v) optionally, assaying for CD4 positive cells associated with the cell proliferative disease;
wherein the human patient in need thereof comprises a human patient who is suffering from a CD4 associated cell proliferative disease; and wherein the engineered cells comprise at least one of CD8 T-cells, and Natural Killer T cells (NKT cells); and said polynucleotide comprises the nucleotide of SEQ ID NO:4 or SEQ ID NO:5.

4. The method of treating a CD4 associated cell proliferative disease in a human patient in need thereof according to claim 3, wherein the CD4 associated cell proliferative disease is selected from the group consisting of CD4 positive leukemia and CD4 positive lymphoma.

5. The method of treating a CD4 associated cell proliferative disease according to claim 4, wherein said CD4 associated cell proliferative disease is CD4 positive acute myeloid leukemia.

6. The method of treating a CD4 associated cell proliferative disease according to claim 5, wherein said CD4 positive acute myeloid leukemia is acute myeloid leukemia M4 or acute myeloid leukemia M5.

7. The method of treating a CD4 associated cell proliferative disease according to claim 3 wherein said engineered cells are Natural Killer T cells (NKT cells).

8. The method of treating a CD4 associated cell proliferative disease according to claim 3, wherein the method further comprises administration in conjunction with one or more of chemotherapy, radiation, immunosuppressive agents, and antiviral therapy.

9. A method of treating a CD4 associated cell proliferative disease in a human patient in need thereof, the method comprising the steps of:
administering to said human patient in need thereof a therapeutically effective amount of an engineered Natural Killer cell comprising:
a polynucleotide encoding a CD4CAR polypeptide comprising a signal peptide, a CD4 antigen recognition domain, a hinge region, a transmembrane domain, at least one co-stimulatory domain, and a signaling domain, wherein the CD4 antigen recognition domain specifically recognizes CD4 in a target cell population, and said polynucleotide comprises the nucleotide sequences of SEQ ID NO. 4 or SEQ ID NO. 5;
wherein the patient in need thereof comprises a patient who is suffering from a CD4 associated cell proliferative disease; and wherein the number of CD4 associated cell proliferative disease cells are reduced by at least 5% as compared to the number of CD4 associated cell proliferative disease cells prior to administering said engineered Natural Killer cell.

10. The method of treating a CD4 associated cell proliferative disease in a patient in need thereof according to claim 9, wherein the CD4 associated cell proliferative disease is selected from the group consisting of CD4 positive leukemia and CD4 positive lymphoma.

11. The method of treating a CD4 associated cell proliferative disease according to claim 9, wherein said CD4 associated cell proliferative disease is CD4 positive acute myeloid leukemia.

12. The method of treating a CD4 associated cell proliferative disease according to claim 11, wherein said CD4 positive acute myeloid leukemia is acute myeloid leukemia M4 or acute myeloid leukemia M5.

13. The method of treating a CD4 associated cell proliferative disease according to claim 3, wherein said CD4 associated cell proliferative disease is selected from the group consisting of: CD4 expressing acute myelomonocytic leukemia, CD4 expressing acute monoblastic leukemia, CD4 expressing monocytic leukemia, and CD4 expressing chronic myelomonocytic leukemia.

14. The method of treating a CD4 associated cell proliferative disease according to claim 9, wherein said CD4 associated cell proliferative disease is selected from the group consisting of: CD4 expressing acute myelomonocytic leukemia, CD4 expressing acute monoblastic leukemia, CD4 expressing monocytic leukemia, and CD4 expressing chronic myelomonocytic leukemia.

15. The method of treating a CD4 associated cell proliferative disease according to claim 9, wherein the number of CD4 associated cell proliferative disease cells are reduced by at least 50% as compared to the number of CD4 associated cell proliferative disease cells prior to administering said engineered cell.

16. The method of treating a CD4 associated cell proliferative disease according to claim 9, wherein the CD4CAR polypeptide comprises at least two co-stimulatory domains.

17. The method of treating a CD4 associated cell proliferative disease according to claim 9, wherein said polynucleotide comprises SEQ ID NO. 4.

18. The method of treating a CD4 associated cell proliferative disease according to claim 9, wherein said polynucleotide comprises SEQ ID NO. 5.

19. The method of treating a CD4 associated cell proliferative disease according to claim 9, wherein said engineered Natural Killer cell is an engineered NK-92 cell.

20. The method of reducing the number of CD4 positive T cell leukemia cells or CD4 positive T cell lymphoma cells according to claim 1, wherein said engineered cell is a Natural Killer cell.

* * * * *